(12) United States Patent
Bogen et al.

(10) Patent No.: US 8,859,776 B2
(45) Date of Patent: Oct. 14, 2014

(54) SUBSTITUTED PIPERIDINES THAT INCREASE P53 ACTIVITY AND THE USES THEREOF

(75) Inventors: Stephane L. Bogen, Somerset, NJ (US); Yao Ma, Lexington, MA (US); Yaolin Wang, Short Hills, NJ (US); Brian Robert Lahue, Millbury, MA (US); Latha G. Nair, Edison, NJ (US); Manami Shizuka, Lexington, MA (US); Matthew Ernst Voss, Nassau, NY (US); Margarita Kirova-Snover, Troy, NY (US); Weidong Pan, Somerset, NJ (US); Yuan Tian, Newton, MA (US); Bheemashankar A. Kulkarni, Bangalore (IN); Craig R. Gibeau, Natick, MA (US); Yuan Liu, Belmont, MA (US); Giovanna Scapin, Staten Island, NY (US); Diane Rindgen, North Plainfield, NJ (US); Ronald J. Doll, Convent Station, NJ (US); Timothy J. Guzi, Sudbury, MA (US); Danny J. Hicklin, Montclair, NJ (US); Amin Nomeir, Milford, NJ (US); Gerald W. Shipps, Jr., Stoneham, MA (US); Malcolm MacCoss, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 276 days.

(21) Appl. No.: 13/501,685

(22) PCT Filed: Oct. 5, 2010

(86) PCT No.: PCT/US2010/051403
§ 371 (c)(1),
(2), (4) Date: Apr. 12, 2012

(87) PCT Pub. No.: WO2011/046771
PCT Pub. Date: Apr. 21, 2011

(65) Prior Publication Data
US 2012/0208844 A1 Aug. 16, 2012

Related U.S. Application Data

(60) Provisional application No. 61/251,603, filed on Oct. 14, 2009, provisional application No. 61/252,468, filed on Oct. 16, 2009.

(51) Int. Cl.
*C07D 401/00* (2006.01)
*A01N 43/40* (2006.01)
*C07D 401/14* (2006.01)
*C07D 409/14* (2006.01)

(52) U.S. Cl.
CPC ............ *C07D 409/14* (2013.01); *C07D 401/14* (2013.01)
USPC .......................................... 546/187; 514/316

(58) Field of Classification Search
CPC ..................................................... C07D 401/14
USPC ............................................ 546/187; 514/316
See application file for complete search history.

(56) References Cited

U.S. PATENT DOCUMENTS

| | | | |
|---|---|---|---|
| 6,403,584 B1 | 6/2002 | de Laszlo et al. | |
| 6,645,987 B2 | 11/2003 | Chackalamannil et al. | |
| 7,807,672 B2 | 10/2010 | Deng et al. | |
| 7,851,626 B2 | 12/2010 | Ding et al. | |
| 7,884,107 B2 | 2/2011 | Ma et al. | |
| 2004/0180887 A1 | 9/2004 | Branch et al. | |
| 2004/0197893 A1 | 10/2004 | Schubert | |
| 2004/0259867 A1 | 12/2004 | Fotouhi | |
| 2004/0259884 A1 | 12/2004 | Haley | |
| 2005/0037383 A1 | 2/2005 | Taremi | |
| 2005/0272751 A1 | 12/2005 | McKerracher et al. | |
| 2008/0004286 A1 | 1/2008 | Wang | |
| 2008/0004287 A1* | 1/2008 | Ma et al. ................... | 514/253.13 |
| 2008/0039409 A1 | 2/2008 | Nakajima et al. | |

FOREIGN PATENT DOCUMENTS

| | | |
|---|---|---|
| EP | 0 947 494 A1 | 10/1999 |
| JP | 09 249566 A | 9/1997 |
| WO | WO 00/15657 A1 | 3/2000 |
| WO | WO 03/051359 A1 | 6/2003 |

(Continued)

OTHER PUBLICATIONS

Barak et al., "mdm2 expression is induced by wild type p53 activity", *The EMBO Journal*, 12(2): 461-468 (1993).

(Continued)

*Primary Examiner* — John Mabry
(74) *Attorney, Agent, or Firm* — Li Su; Laura M. Ginkel

(57) ABSTRACT

The present invention provides a compound of Formula 1

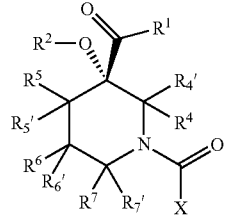

Formula 1 as described herein or a pharmaceutically acceptable salt, solvate or ester thereof. The compounds are useful as inhibitors of the HDM2 protein. Also disclosed are pharmaceutical compositions comprising the above compounds and methods of treating cancer using the same.

44 Claims, No Drawings

(56) References Cited

FOREIGN PATENT DOCUMENTS

| WO | WO 2004/080460 A1 | 9/2004 |
|---|---|---|
| WO | WO 2005/110996 A1 | 11/2005 |
| WO | 2006069287 A1 | 6/2006 |
| WO | WO 2007/070398 A1 | 6/2007 |
| WO | 2008005268 A1 | 1/2008 |
| WO | 2009121914 A1 | 10/2009 |
| WO | WO 2011/023677 A1 | 3/2011 |
| WO | WO 2011/098398 A1 | 8/2011 |

OTHER PUBLICATIONS

Blaydes et al., "Tolerance of high levels of wild-type p53 in transformed epithelial cells dependent on auto-regulation by mdm-2", *Oncogene*, 14:1859-1868 (1997).
Bottger et al., "Identification of novel mdm2 binding peptides by phage display", *Oncogene*, 13:2141-2147 (1996).
Chene, "Inhibition of the p53-MDM2 interaction: Targeting a protein-protein Interface", *Molecular Cancer Research*, 2:20-28 (Jan. 2004).
Chene, "Inhibiting the p53-MDM2 interaction: An important target for cancer therapy", *Nature Reviews*, 3:102-109 (Feb. 2003).
Ding et al., "Structure-Based Design of Potent Non-Peptide MDM2 Inhibitors", *J. Am. Chem. Soc.*, 127(29):10130-10131 (2005).
Ding et al., "Structure-Based Design of Spiro-oxindoles as Potent, Specific Small-Molecule Inhibitors of the MDM2-p53 Interaction", *Journal of Medicinal Chemistry*, 49(12): 3432-3435 (2006).
Donehower et al., "Mice deficient for p53 are developmentally normal but susceptible to spontaneous tumours", *Nature*, 356:215-221 (Mar. 19, 1992).
Duncan et al., "Isolation and Structure Elucidation of chlorofusin, a Novel p53-MDM2 Antagonist from a *Fusarium* sp.", *J. Am. Chem. Soc.*, 123(4):554-560 (2001).
Fotouhi et al., "Small Molecule Inhibitors of p53/MDM2 Interaction", *Current Topics in Medicinal Chemistry*, 5(2): 159-165 (2005).
Freedman et al., "Nuclear Export Is Required for Degradation of Endogenous p53 by MDM2 and Human Papillomavirus E6", *Molecular and Cellular Biology*, 18(12): 7288-7293 (Dec. 1988).
Galatin et al., "A Nonpeptidic Sulfonamide Inhibits the p53—mdm2 Interaction and Activates p53-Dependent Transcription in mdm2-Overexpressing Cells", *J. Med. Chem.*, 47(17): 4163-4165 (2004).
Grasberger et al., "Discovery and Cocrystal Structure of Benzodiazepinedione HDM2 Antagonists that Activate p53 in Cells", *J. Med. Chem.*, 48(4): 909-912 (2005).
Hainaut et al., "Database of p53 gene somatic mutations in human tumors and cell lines: updated compilation and future prospects", *Nucleic Acids Research*, 25(1):151-157 (1997).
Hall et al., "Genetic Alterations of Cyclins, Cyclin-Dependent Kinases, and Cdk Inhibitors in Human Cancer", *Advances in Cancer Research*, 68:67-108 (1996).
Honda et al., "Oncoprotein MDM2 is a ubiquitin ligase E3 for tumor suppressor p53", *FEBS Letters*, 420:25-27 (1997).
Honda et al., "Activity of MDM2, a ubiquitin ligase, toward p53 or itself is dependent on the Ring finger domain of the ligase", *Oncogene*, 19:1473-1476 (2000).
Ko et al., "p53: puzzle and paradigm", *Genes & Development*, 10: 1054-1072 (1996).
Kojima et al., "MDM2 antagonists induce p53-dependent apoptosis in AML: implications for leukemia therapy", *Blood*, 106(9):3150-3159 (Nov. 1, 2005).
Kussie et al., "Structure of the MDM2 Oncoprotein Bound to the p53 Tumor Suppressor Transactivation Domain", *Science*, 274:948-953 (Nov. 8, 1996).
Levine, "p53, the Cellular Gatekeeper for Growth and Division", *Cell*, 88:323-331 (Feb. 7, 1997).
Lu et al., "Discovery of a Nanomolar Inhibitor of the Human Murine Double Minute 2 (MDM2)—p53 Interaction through an Integrated, Virtual Database Screening Strategy", *Journal of Medicinal Chemistry*, 49(13):3759-3762 (2006).

May et al., "Twenty years of p53 research: structural and functional aspects of the p53 protein", *Oncogene*, 18:7621-7636 (1999).
Momand et al., "MDM2—master regulator of the p53 tumor suppressor protein", *Gene*, 242 15-29 (2000).
Momand et al., "The mdm-2 Oncogene Product Forms a Complex with the p53 Protein and Inhibits p53—Mediated Transactivation", *Cell*, 69:1237-1245 (Jun. 26, 1992).
Oliner et al., "Oncoprotein MDM2 conceals the activation domain of tumour suppressor p53", *Letters to Nature*, 362:857-860 (Apr. 29, 1993).
Oren, "Decision making by p53: life, death and cancer", *Cell Death and Differentiation*, 10:431-442 (2003).
Roth, "Nucleo-cytoplasmic shuttling of the hdm2 oncoprotein regulates the levels of the p53 protein via a pathway used by the human immunodeficiency virus rev protein", *The EMBO Journal*, 17(2):554-564 (1998).
Sherr, "The Pezcoller Lecture: Cancer Cell Cycles Revisited", *Cancer Research*, 60:3689-3695 (Jul. 15, 2000).
Stoll et al., "Chalcone Derivatives Antagonize Interactions between the Human Oncoprotein MDM2 and p53", *Biochemistry*, 40(2):336-344 (2001).
Tao et al., "Nucleocytoplasmic shuttling of oncoprotein Hdm2 is required for Hdm2-mediated degradation of p53", *Proc. Natl. Acad. Sci. USA*, 96:3077-3080 (Mar. 1999).
Vassilev, "p53 Activation by Small Molecules: Application in Oncology", *Journal of Medicinal Chemistry*, 48(14):4491-4499 (Jul. 14, 2005).
Vassilev et al., "In Vivo Activation of the p53 Pathway by Small-Molecule antagonists of MDM2", *Science*, 303: 844-848 (Feb. 6, 2004).
Wu et al., "The p53-mdm-2 autoregulatory feedback loop", *Genes & Development*, 7:1126-1132 (1993).
Zheleva et al., "The p53-Mdm2 Pathway: Targets for the Development of New Anticancer Therapeutics", *Mini Reviews in Medicinal Chemistry*, 3(3): 257-270 (2003).
Cannon, J.G. *Burger's Medicinal Chemistry and Drug Discovery*, Chapter Nineteen. Fifth Ed., vol. 1: Principles and Practice. Wiley-Interscience; pp. 783-802 (1995).
Ding et al., "Emerging cancer therapeutic opportunities target DNA-repair systems." *Trends in Pharmacological Sciences*, 27(6):338-344 (2006).
Dörwald, F. Z., "Side reactions in organic synthesis". A guide to Successful Synthesis Design, Weinheim: Wiley-VCH, Verlag, GmbH & Co. KGaA, 2005, Preface.
Horig et al., "Review: From bench to clinic and back: Perspective on the 1st IQPC Translational Research conference", *Journal of Translational Medicine* 2:44 (2004) (BioMed Central pp. 1-8).
Jordan, V.C., Tamoxifen: A most unlikely pioneering medicine, *Nature Reviews/Drug Discovery*, 2:205-213 (2003).
Schafer, S. et al., "Failure is an option: learning from unsuccessful proof-of-concept trial". *Drug Discovery Today*, 13(21/22):913-916 (2008).
Vippagunta, S.R., et al., Crystalline Solids, *Advanced Drug Delivery Reviews*, 48:3-26 (2001).
Wolff, M.E. (Editor); *Burger's Medicinal Chemistry and Drug Discovery*, vol. 1: Principle and Practice; pp. 975-977 (1995); Fifth Ed., New York: John Wiley & Sons.
Yang Y. et al., "Small molecule inhibitors of HDM2 ubiquitin ligase activity stabilize and activate p53 in cells", *Cancer Cell*, 7:547-559 (Jun. 2005).
USPTO, Office Action dated Dec. 30, 2008 in U.S. Appl. No. 11/769,030.
USPTO, Office Action dated May 28, 2009 in U.S. Appl. No. 11/769,030.
USPTO, Office Action dated Jan. 27, 2010 in U.S. Appl. No. 11/769,030.
Kussie, P.H., "Structure of the MDM2 Oncoprotein Bound to the p53 Tumor Suppressor Transactivation Domain", Science, 274:948-953 (1996).

* cited by examiner

SUBSTITUTED PIPERIDINES THAT INCREASE P53 ACTIVITY AND THE USES THEREOF

FIELD OF THE INVENTION

The present invention relates to novel compounds useful as Human Double Minute 2 ("HDM2") protein inhibitors, regulators or modulators, pharmaceutical compositions containing the compounds and methods of treatment using the compounds and compositions to treat diseases such as, for example, cancer, diseases involving abnormal cell proliferation, and diseases caused by inadequate p53 levels. This invention specifically discloses substituted piperidines as inhibitors of the HDM2 protein.

BACKGROUND OF THE INVENTION

The tumor suppressor protein p53 plays a central role in maintaining the integrity of the genome in a cell by regulating the expression of a diverse array of genes responsible for DNA repair, cell cycle and growth arrest, and apoptosis [May et al., *Oncogene* 18 (53) (1999) p. 7621-7636; Oren, *Cell Death Differ.* 10 L (2003) p. 431-442, Hall and Peters, *Adv. Cancer Res.*, 68: (1996) p. 67-108; Hainaut et al., *Nucleic Acid Res.*, 25: (1997) p. 151-157; Sherr, *Cancer Res.*, 60: (2000) p. 3689-95]. In response to oncogenic stress signals, the cell triggers the p53 transcription factor to activate genes implicated in the regulation cell cycle, which thereby initiates either apoptosis or cell cycle arrest. Apoptosis facilitates the elimination of damaged cells from the organism, while cell cycle arrest enables damaged cells to repair genetic damage [reviewed in Ko et al., *Genes & Devel.* 10: (1996) p. 1054-1072; Levine, *Cell* 88: (1997) p. 323-331]. The loss of the safeguard functions of p53 predisposes damaged cells to progress to a cancerous state. Inactivating p53 in mice consistently leads to an unusually high rate of tumors [Donehower et al., *Nature,* 356: (1992) p. 215-221].

The p53 transcription factor promotes the expression of a number of cell cycle regulatory genes, including its own negative regulator, the gene encoding the Mouse Double Minute 2 (MDM2) protein [Chene, *Nature Reviews Cancer* 3: (2003) p. 102-109; Momand, *Gene* 242 (1-2): (2000) p. 15-29; Zheleva et al. *Mini. Rev. Med. Chem.* 3 (3): (2003) p. 257-270]. The MDM2 protein (designated HDM2 in humans) acts to down-regulate p53 activity in an auto-regulatory manner [Wu et al, *Genes Dev.*, 7: (1993) p. 1126-1132; Bairak et al., *EMBO J,* 12: (1993) p. 461-468]. In the absence of oncogenic stress signals, i.e., under normal cellular conditions, the MDM2 protein serves to maintain p53 activity at low levels [Wu et al, *Genes Dev.*, 7: (1993) p. 1126-1132; Barak et al., *EMBO J,* 12: (1993) p. 461-468]. However, in response to cellular DNA damage or under cellular stress, p53 activity increases helping to prevent the propagation of permanently damaged clones of cells by induction of cell cycle and growth arrest or apoptosis.

The regulation of p53 function relies on an appropriate balance between the two components of this p53-MDM2 auto-regulatory system. Indeed, this balance appears to be essential for cell survival. There are at least three ways that MDM2 acts to down-regulate p53 activity. First, MDM2 can bind to the N-terminal transcriptional activation domain of p53 to block expression of p53-responsive genes [Kussie et al., *Science,* 274: (1996) p. 948-953; Oliner et al., *Nature,* 362: (1993) p. 857-860; Momand et al, *Cell,* 69: (1992) p. 1237-1245]. Second, MDM2 shuttles p53 from the nucleus to the cytoplasm to facilitate the proteolytic degradation of p53 [Roth et al, *EMBO J,* 17: (1998) p. 554-564; Freedman et al., *Mol Cell Biol,* 18: (1998) p. 7288-7293; Tao and Levine, *Proc. Natl. Acad. Sci.* 96: (1999) p. 3077-3080]. Finally, MDM2 possesses an intrinsic E3 ligase activity for conjugating ubiquitin to p53 for degradation within the ubiquitin-dependent 26S proteosome pathway [Honda et al., *FEBS Lett,* 420: (1997) p. 25-27; Yasuda, *Oncogene* 19: (2000) p. 1473-1476]. Thus, MDM2 impedes the ability of the p53 transcription factor to promote the expression of its target genes by binding p53 in the nucleus. Attenuating the p53-MDM2 auto-regulatory system can have a critical effect on cell homeostasis. Consistently, a correlation between the overexpression of MDM2 and tumor formation has been reported [Chene, *Nature* 3: (2003) p. 102-109]. Functional inactivation of wild type p53 is found in many types of human tumors. Restoring the function of p53 in tumor cells by anti-MDM2 therapy would result in slowing the tumor proliferation and instead stimulate apoptosis. Not surprisingly then, there is currently a substantial effort being made to identify new anticancer agents that hinder the ability of HDM2 to interact with p53 [Chene, *Nature* 3: (2003) p. 102-109]. Antibodies, peptides, and antisense oligonucleotides have been demonstrated to destroy the p53-MDM2 interaction, which would release p53 from the negative control of MDM2, leading to activation of the p53 pathway allowing the normal signals of growth arrest and/or apoptosis to function, which offers a potential therapeutic approach to treating cancer and other diseases characterized by abnormal cell proliferation. [See, e.g., Blaydes et al., *Oncogene* 14: (1997) p. 1859-1868; Bottger et al., *Oncogene* 13 (10): (1996) p. 2141-2147].

U.S. Pub. No. 2005/0037383 A1 describes modified soluble HDM2 protein, nucleic acids that code for this HDM2 protein, the crystals of this protein that are suitable for X-ray crystallization analysis, the use of the proteins and crystals to identify, select, or design compounds that may be used as anticancer agents, and some of the compounds themselves that bind to modified HDM2. (Schering-Plough Corp.).

Small molecules, said to antagonize the p53-MDM2 interaction, have been described. WO 00/15657 (Zeneca Limited) describes piprizine-4-phenyl derivatives as inhibitors of the interaction between MDM2 and p53. Grasberger et al. (*J. Med. Chem.*, 48 (2005) p. 909-912) (Johnson & Johnson Pharmaceutical Research & Development L.L. C.) describes discovery and co-crystal structure of benzodiazepinedione as HDM2 antagonists that activate p53 in cells. Galatin et al. (*J. Med. Chem.* 47 (2004) p. 4163-4165) describes a nonpeptidic sulfonamide inhibitor of the p53-MDM2 interaction and activator of p53 dependent transcription in MDM2-overexpressing cells.

Vassilev (*J. Med. Chem. (Perspective) Vol.* 48 No. 14, (2005) p. 1-8) (Hoffmann-LaRoche Inc.) describes several small molecule p53 activators as an application in oncology, including the following formulas:

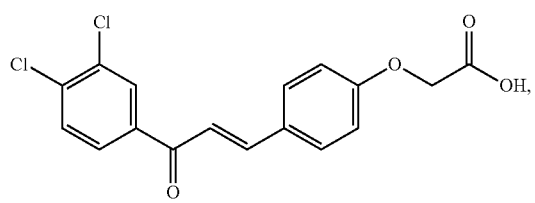

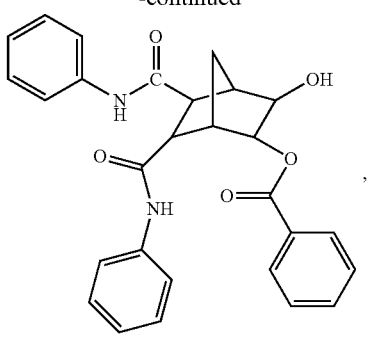

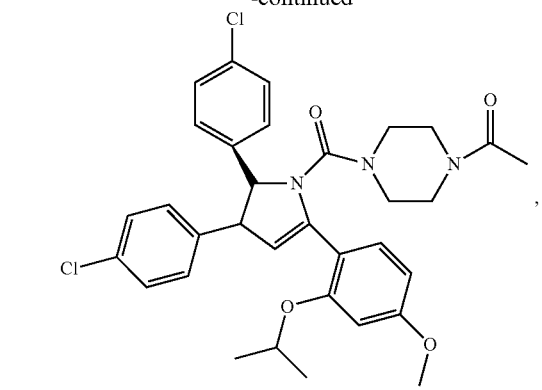

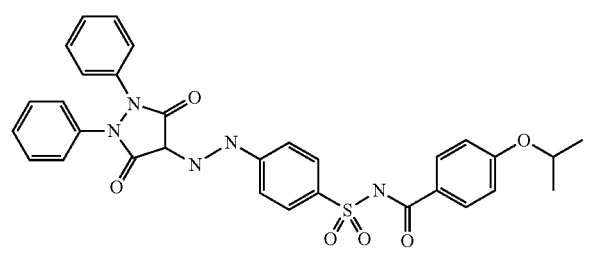

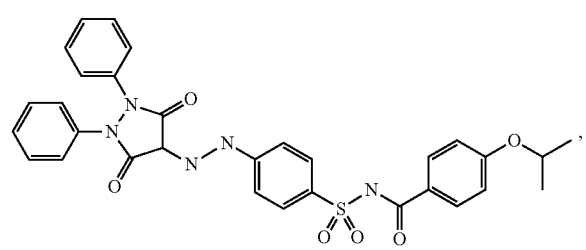

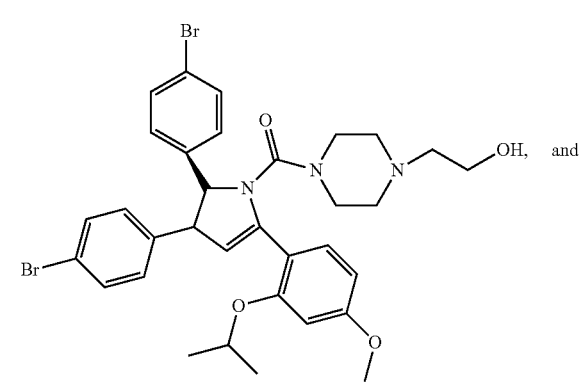

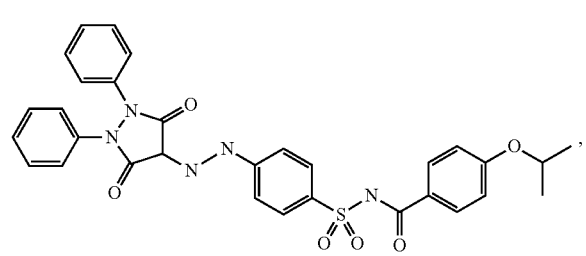

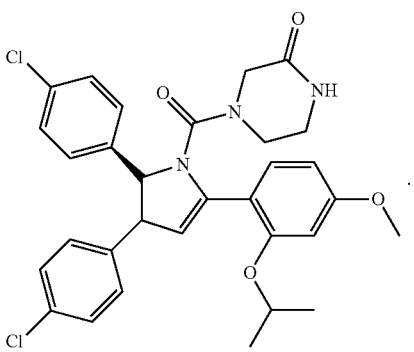

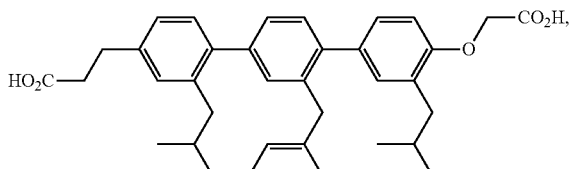

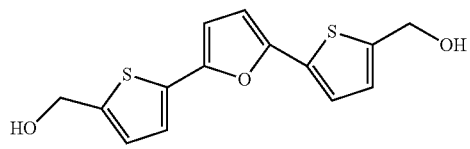

The first four compounds listed above were also described in Totouhi et al. (*Current Topics in Medicinal Chemistry Vol. 3, No.* 2 (2005) p. 159-166, at 161) (Hoffmann La Roche Inc.). The last three compounds listed above were also described in Vassilev et al. (*Science Vol.* 303 (2004): p. 844-848) (Hoffmann La Roche Inc.) and their implications on leukemia activity were investigated in Kojima et al. (*Blood, Vol.* 108 *No.* 9 (November 2005) p. 3150-3159).

Ding et. al. (*J. Am. Chem. Soc. Vol.* 127 (2005): 10130-10131) and (*J. Med. Chem. Vol.* 49 (2006): 3432-3435) describes several spiro-oxindole compounds as MDM2-p53 inhibitors.

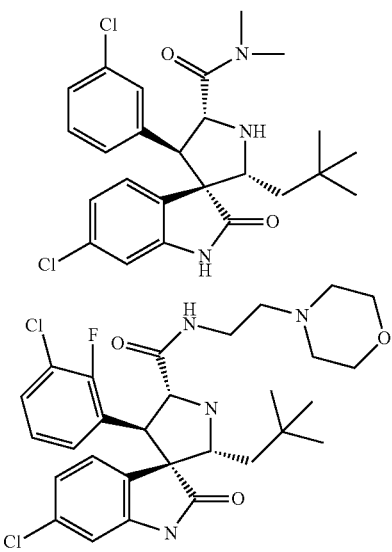

Lu, et. al. (*J. Med. Chem. Vol.* 49 (2006): 3759-3762) described 7-[anilino(phenyl)methyl]-2-methyl-8-quinolinol as a small molecule inhibitor of MDM2-p53 interaction.

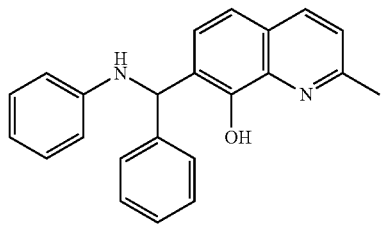 [SMILES: Cc1ccc2ccc(C(Nc3ccccc3)c3ccccc3)c(O)c2n1]

Chène (*Molecular Cancer Research Vol.* 2: (January 2006) p. 20-28) describes inhibition of the p53-MDM2 interaction by targeting the protein-protein interface. U.S. Pub. No. 2004/0259867 A1 and 2004/0259884 A1 describes Cis-imidazoles (Hoffmann La Roche Inc.) and WO2005/110996A1 and WO 03/051359 describes Cis-Imidazolines (Hoffmann La Roche Inc.) as compounds that inhibit the interaction of MDM2 with p53-like peptides resulting in antiproliferation. WO 2004/080460 A1 describes substituted piperidine compounds as MDM2-p53 inhibitors for treating cancer (Hoffmann La Roche Inc.). EP 0947494 A1 describes phenoxy acetic acid derivatives and phenoxy methyltetrazole that act as antagonists of MDM2 and interfere with the protein-protein interaction between MDM2 and p53, which results in anti-tumor properties (Hoffmann La Roche Inc.). Duncan et al., *J. Am. Chem. Soc.* 123 (4): (2001) p. 554-560 describes a p-53-MDM2 antagonist, chlorofusin, from a Fusarium Sp. Stoll et al., *Biochemistry* 40 (2) (2001) p. 336-344 describes chalcone derivatives that antagonize interactions between the human oncoprotein MDM2 and p53.

There is a need for effective inhibitors of the HDM2 or MDM2 protein in order to treat or prevent cancer, other disease states associated with cell proliferation, diseases associated with HDM2, or diseases caused by inadequate p53 activity. The present application discloses compounds that have potency in inhibiting or antagonizing the HDM2-p53 and MDM2-p53 interaction and/or activating p53 proteins in cells.

In its many embodiments, the present invention provides novel compounds having HDM2 or MDM2 antagonist activity, methods of preparing such compounds, pharmaceutical compositions comprising one or more of such compounds, methods of preparing pharmaceutical formulations comprising one or more of such compounds, methods of treatment or prevention of one or more diseases associated with HDM2, MDM2, p53, or p53 peptides by administering such compounds or pharmaceutical compositions.

WO2008/005268 (equivalent of US Patent Publication US 2008/0004287 A1) discloses substituted piperidine compounds as HDM2 inhibitors.

SUMMARY OF THE INVENTION

In its many embodiments, the present invention provides a novel class of substituted piperidine compounds, pharmaceutical compositions comprising one or more said compounds, and methods for using said compounds for treating or preventing a disease associated with the HDM2 protein.

Accordingly, in one aspect the present invention provides a compound of Formula 1

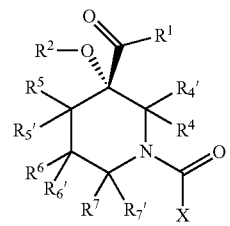

Formula 1 or a pharmaceutically acceptable salt thereof, wherein:
$R^1$ is:

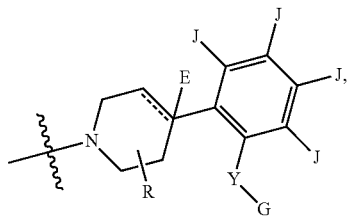

wherein:

E is either present or absent, and when present is selected from the group consisting of H, halo, OH, CN, —O($C_1$-$C_6$) alkyl, —($C_1$-$C_6$)alkyl, —C(O)OH, —C(O)N$R^8R^{8'}$, —($C_1$-$C_6$)alkyl-C(O)OH, —($C_1$-$C_6$)alkyl-OH, —($C_1$-$C_6$)alkyl-C(O)N$R^8R^{8'}$, ($C_2$-$C_6$)alkenyl, —($C_2$-$C_6$)alkynyl, heterocyclyl, and heteroaryl;

each J independently is selected from the group consisting of H and halogen;

G, Y and R may or may not be present, wherein: when Y is not present, G is not present; when Y is present, it is selected from the group consisting of O, S, N$R^8$, $SO_2$, and $CR^8R^{8'}$;

R when present is one or more moieties independently selected from the group consisting of —($C_1$-$C_6$)alkyl, and —($CR^8R^{8'}$)$_n$—C(O)OH;

G when present is selected from the group consisting of —($CR^8R^{8'}$)$_n$—C(O)OH, —($CR^8R^{8'}$)$_n$—C(O)N$R^8R^9$, —($CR^8R^{8'}$)$_n$—($C_3$-$C_8$)Cycloalkyl-C(O)N$R^8R^9$, —($CR^8R^{8'}$)$_n$— —($C_3$-$C_8$)cycloalkyl-($CR^8R^{8'}$)$_n$—C(O)OH, —($CR^8R^{8'}$)$_n$—

—O—(CR$^8$R$^{8'}$)$_n$—(C$_3$-C$_8$)cycloalkyl-(CR$^8$R$^{8'}$)$_n$—C(O)OH, —(CR$^8$R$^{8'}$)$_n$—O—(CR$^8$R$^{8'}$)$_n$—C(O)OH, —(CR$^8$R$^{8'}$)$_n$—S—(CR$^8$R$^{8'}$)$_n$—C(O)OH, C(O)OH, —(CR$^8$R$^{8'}$)$_n$—NH—(CR$^8$R$^{8'}$)$_n$—C(O)OH, —(CR$^8$R$^{8'}$)$_n$—O—(CR$^8$R$^{8'}$)$_n$—CH$_3$, —(CR$^8$R$^{8'}$)$_n$—S—(CR$^8$R$^{8'}$)$_n$—CH$_3$, —(CR$^8$R$^{8'}$)$_n$—NH—(CR$^8$R$^{8'}$)$_n$—CH$_3$, —(CR$^8$R$^{8'}$)$_n$—CH$_3$, —(CR$^8$R$^{8'}$)$_n$-heteroaryl, —(CR$^8$R$^{8'}$)$_n$—P(O)OR$^8$OR$^{8'}$, —(CR$^8$R$^{8'}$)$_n$—P(O)O$_2$, and —(CR$^8$R$^{8'}$)$_n$—OH; wherein:

each R$^8$ and R$^{8'}$ is independently selected from the group consisting of H, D, and (C$_1$-C$_6$)alkyl; or wherein R$^8$ and R$^{8'}$ together with the carbon to which each is attached form (C$_3$-C$_8$)cycloalkyl;

each R$^9$ independently is SO$_2$(C$_1$-C$_6$)alkyl or SO$_2$(C$_3$-C$_8$)cycloalkyl;

each n independently is 0-10; providing that when n is 0, any oxygen, nitrogen or sulfur atom of Y is not directly linked to any oxygen, nitrogen, sulfur or phosphorus atom of G;

==== represents a single or a double bond, providing that when E is present, ==== represents a single bond;

R$^2$ is

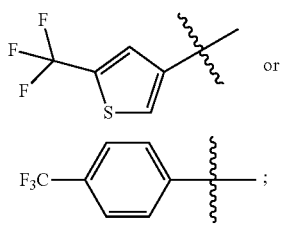

R$^4$, R$^{4'}$, R$^5$, R$^{5'}$, R$^6$, R$^{6'}$, R$^7$, and R$^{7'}$ independently are selected from the group consisting of hydrogen and (C$_1$-C$_6$)alkyl; and X is

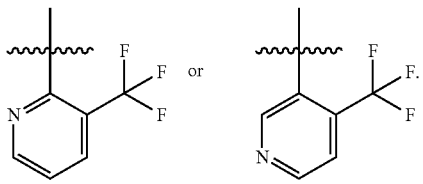 [SMILES: *c1ncccc1C(F)(F)F ; "or" ; *c1cnccc1C(F)(F)F]

In another aspect, the present invention provides a compound represented by Formula 2 below:

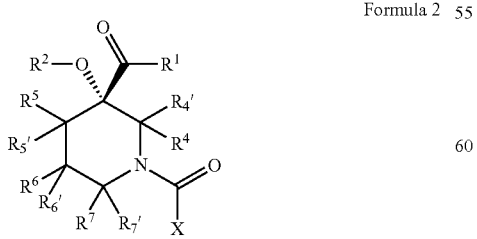

Formula 2 wherein R$^1$, R$^2$, R$^{4'}$ R$^4$, R$^5$, R$^{5'}$, R$^6$, R$^{6'}$, R$^7$, R$^{7'}$ and X, are selected independently of each other and wherein R$^1$ is:

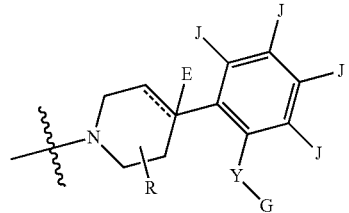

wherein E is selected from the group consisting of H, halo, OH, CN, —O—(C$_1$-C$_6$)alkyl, (C$_1$-C$_6$)alkyl, —C(O)OH, —C(O)NR$^8$R$^{8'}$, —(C$_1$-C$_6$)alkyl-C(O)OH, —(C$_1$-C$_6$)alkyl-C(O)NR$^8$R$^{8'}$, —(C$_2$-C$_6$)alkenyl, —(C$_2$-C$_6$)alkynyl and heterocyclyl, J is independently selected from the group consisting of H and halogen, G, Y and R may or may not be present,
wherein when Y is not present, G is not present,
when Y is present it is selected from the group consisting of O, S, NR$^8$, SO$_2$, and CR$^8$R$^{8'}$,
further wherein, when R is present, it is one or more moieties independently selected from the group consisting of halogen, —CN, —OH, —SH, (C$_1$-C$_6$)alkoxy, —(C$_2$-C$_6$)alkenoxy, -(C$_1$-C$_6$)alkyl, —(C$_2$-C$_6$)alkenyl, haloalkoxy, —C(O)NR$^{10}$R$^{11}$, —C(O)OR$^{10}$, —OC(O)R$^{10}$, —NR$^{11}$C(O)R$^{11}$, —NR$^{10}$R$^{11}$, —S-alkyl, —S-alkenyl, —S-haloalkyl, (C$_2$-C$_6$)alkynyl, haloalkyl, haloalkenyl-, —(CR$^8$R$^{8'}$)$_n$—C(O)OH, —(CR$^8$R$^{8'}$)$_n$-heteroaryl, —(CR$^8$R$^{8'}$)$_n$—C(O)NR$^8$R$^9$, —(CR$^8$R$^{8'}$)$_n$—(C$_3$-C$_8$)Cycloalkyl-C(O)NR$^8$R$^9$, —(CR$^8$R$^{8'}$)$_n$—(C$_3$-C$_8$)cycloalkyl-(CR$^8$R$^{8'}$)$_n$—C(O)OH, —(CR$^8$R$^{8'}$)$_n$—O—(CR$^8$R$^{8'}$)$_n$—C(O)OH, —(CR$^8$R$^{8'}$)$_n$—S—(CR$^8$R$^{8'}$)$_n$—C(O)OH, —(CR$^8$R$^{8'}$)$_n$—NH—(CR$^8$R$^{8'}$)$_n$—C(O)OH, —(CR$^8$R$^{8'}$)$_n$—O—(CR$^8$R$^{8'}$)$_n$—CH$_3$, —(CR$^8$R$^{8'}$)$_n$—S—(CR$^8$R$^{8'}$)$_n$—CH$_3$, —(CR$^8$R$^{8'}$)$_n$—NH—(CR$^8$R$^{8'}$)$_n$—CH$_3$, —(CR$^8$R$^{8'}$)$_n$—CH$_3$, —(CR$^8$R$^{8'}$)$_n$-heteroaryl, —(CR$^8$R$^{8'}$)$_n$—P(O)OR$^8$OR$^{8'}$, —(CR$^8$R$^{8'}$)$_n$—P(O)O$_2$, and —(CR$^8$R$^{8'}$)$_n$—OH, G is selected from the group consisting of —(CR$^8$R$^{8'}$)$_n$—C(O)OH, —(CR$^8$R$^{8'}$)$_n$-heteroaryl, —(CR$^8$R$^{8'}$)$_n$—C(O)NR$^8$R$^9$, —(CR$^8$R$^{8'}$)$_n$—(C$_3$-C$_8$)cycloalkyl-C(O)NR$^8$R$^9$, —(CR$^8$R$^{8'}$)$_n$—(C$_3$-C$_8$)Cycloalkyl-(CR$^8$R$^{8'}$)$_n$—C(O)OH, —(CR$^8$R$^{8'}$)$_n$—O—(CR$^8$R$^{8'}$)$_n$—C(O)OH, —(CR$^8$R$^{8'}$)$_n$—S—(CR$^8$R$^{8'}$)$_n$—C(O)OH, C(O)OH, —(CR$^8$R$^{8'}$)$_n$—NH—(CR$^8$R$^{8'}$)$_n$—C(O)OH, —(CR$^8$R$^{8'}$)$_n$—O—(CR$^8$R$^{8'}$)$_n$—CH$_3$, —(CR$^8$R$^{8'}$)$_n$—S—(CR$^8$R$^{8'}$)$_n$—CH$_3$, —(CR$^8$R$^{8'}$)$_n$—NH—(CR$^8$R$^{8'}$)$_n$—CH$_3$, —(CR$^8$R$^{8'}$)$_n$—CH$_3$, —(CR$^8$R$^{8'}$)$_n$-heteroaryl, —(CR$^8$R$^{8'}$)$_n$—P(O)OR$^8$OR$^{8'}$, —(CR$^8$R$^{8'}$)$_n$—P(O)O$_2$, —(CR$^8$R$^{8'}$)$_n$—OH, wherein each R$^8$ and R$^{8'}$ is independently selected from the group consisting of H and (C$_1$-C$_6$)alkyl, or further wherein R$^8$ and R$^{8'}$ together with the carbon to which each is attached can cyclicize to form (C$_3$-C$_8$)spirocycloalkyl, R$^9$ is SO$_2$(C$_1$-C$_6$)alkyl or SO$_2$(C$_3$-C$_8$)cycloalkyl, n is 0-10, providing that when n is 0, G is not attached to Y such that O is linked to O, S, N, or SO$_2$, further providing that when n is 0, G is not attached to Y such that N is linked to O, S or N, and still further providing that when n is 0, G is not attached to Y such that S is linked to O, N or SO$_2$, further wherein, any spirocycloalkyl or cycloalkyl in Formula 2, can be unsubstituted or substituted with one or more $(C_1\text{-}C_6)$alkyl groups, still further wherein, any Hydrogen atom that is substituted on any alkyl, cycloalkyl, heterocycloalkyl or spirocycloalkyl, in Formula 2, can be replaced by a Deuterium atom, wherein said ----- represents an optional double bond, providing that when E is present, ----- represents a single bond, $R^2$ is

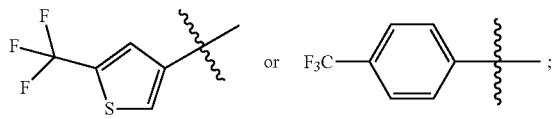 [SMILES: *c1csc(C(F)(F)F)c1 ; *c1ccc(C(F)(F)F)cc1]

$R^4$ or $R^{4'}$, which may be the same or different, are independently selected from the group consisting of hydrogen, alkyl, alkenyl, alkynyl, heteroalkyl, heteroalkenyl, hydroxyalkyl, -alkylCO$_2$R$^{12}$, alkylOCOR$^{12}$, -alkylNR$^{10}$COR$^{12}$, hydroxyalkenyl, alkoxyalkyl, alkoxyalkenyl, aminoalkyl, aminoalkenyl, alkylNR$^{10}$R$^{11}$, alkenylNR$^{10}$R$^{11}$, cycloalkylalkyl, cycloalkylalkenyl, cyclenylalkyl, cyclenylalkenyl, cycloalkylalkynyl, cyclenylalkynyl, heterocyclylalkyl, heterocyclylalkenyl, heterocylenylalkyl, heterocyclenylalkenyl, arylalkyl, arylalkenyl, heteroarylalkyl, and heteroarylalkenyl, wherein each of said alkyl, alkenyl, alkynyl, heteroalkyl, heteroalkenyl, hydroxyalkyl, -alkylCO$_2$R$^{12}$, alkylOCOR$^{12}$, -alkylNR$^{10}$COR$^9$, hydroxyalkyl, hydroxyalkenyl, alkoxyalkyl, alkoxyalkenyl, aminoalkyl, aminoalkenyl, alkylNR$^{10}$R$^{11}$, alkenylNR$^{10}$R$^{11}$, cycloalkylalkyl, cycloalkylalkenyl, cyclenylalkyl, cyclenylalkenyl, cycloalkylalkynyl, cyclenylalkynyl, heterocyclylalkyl, heterocyclylalkenyl, heterocylenylalkyl, heterocyclenylalkenyl, arylalkyl, arylalkenyl, heteroarylalkyl, and heteroarylalkenyl can be unsubstituted or substituted with one or more moieties, which can be the same or different, independently selected from the group consisting of trihaloalkyl, dihaloalkyl, monohaloalkyl, trihaloalkenyl, dihaloalkenyl, monohaloalkenyl, halogen, CN, hydroxyl, thiohydroxyl, amine, alkoxy, alkenoxy, aryloxy, cyclenyloxy, cycloalkyloxy, heteroaryloxy, heterocyclenyloxy, heterocyclyloxy, alkyl, alkenyl, trifluoroalkoxy, difluoroalkoxy, monofluoroalkoxy, heteroalkyl, heteroalkenyl, carboxyl, —CONR$^{11}$R$^{11}$, —COOR$^{12}$, —OCOR$^{12}$, —NR$^{10}$COR$^{12}$, cycloalkyl, heterocyclyl, —NR$^{11}$R$^{11}$, —S-alkyl, —S-alkenyl, —S-cycloalkyl, —S-cyclenyl, —S-aryl, —S-heterocyclyl, —S-heterocyclenyl, —S-heteroaryl, —S-trifluoroalkyl, —S-difluoroalkyl, —S-monofluoroalkyl, cyclenyl, heterocyclenyl, aryl, heteroaryl, and alkynyl;

or wherein $R^4$ and $R^{4'}$ or $R^5$ and $R^{5'}$ or $R^6$ and $R^{6'}$ or $R^7$ and $R^{7'}$, together with the carbon to which each is attached, independently form a spirocyclic group, wherein said spirocyclic group can be unsubstituted or substituted with one or more moieties, which can be the same or different, independently selected from the group consisting of trihaloalkyl, dihaloalkyl, monohaloalkyl, trihaloalkenyl, dihaloalkenyl, monohaloalkenyl, halogen, CN, hydroxyl, thiohydroxyl, amine, alkoxy, alkyl, alkenyl, trifluoroalkoxy, difluoroalkoxy, monofluoroalkoxy, heteroalkyl, heteroalkenyl, carboxyl, —CONR$_{10}$R$^{11}$, —COOR$^{12}$, —OCOR$^{12}$, —NR$^{10}$COR$^{12}$, cycloalkyl, heterocyclyl, —NR$^{10}$R$^{11}$, alkylthio, trifluoroalkylthio, difluoroalkylthio, monofluoroalkylthio, cyclenyl, heterocyclenyl, aryl, heteroaryl, and alkynyl;

$R^5$, $R^{5'}$, $R^7$ or $R^{7'}$, which may be the same or different, are independently selected from the group consisting of hydrogen, alkyl, alkenyl, alkynyl, alkoxyl, —S-alkyl, heteroalkyl, hydroxyalkyl, alkoxyalkyl, aminoalkyl, alkylNR$^{10}$R$^{11}$, trihaloalkyl, dihaloalkyl, monohaloalkyl, aryl, heteroaryl, cycloalkyl, cyclenyl, heterocyclyl, heterocyclenyl, arylalkyl, heteroarylalkyl, cycloalkylalkyl, cyclenylalkyl, heterocyclylalkyl, or heterocyclenylalkyl, wherein each of said aryl, heteroaryl, cycloalkyl, cyclenyl, heterocyclyl, heterocyclenyl, arylalkyl, heteroarylalkyl, cycloalkylalkyl, cyclenylalkyl, heterocyclylalkyl, heterocyclenylalkyl can be unsubstituted or substituted with one or more moieties, which can be the same or different, independently selected from the group consisting of alkyl, alkenyl, hydroxyl, —SH, —NH$_2$, halogen, trifluoroalkyl, difluoroalkyl, and monofluoroalkyl;

$R^6$ or $R^{6'}$, which may be the same or different, are independently selected from the group consisting of hydrogen, alkyl, alkenyl, alkoxyl, trihaloalkyl, dihaloalkyl, and monohaloalky;

$R^6$ and $R^7$ or $R^5$ and $R^6$ or $R^5$ and $R^7$ together with the carbon to which each is attached, can independently cyclicize to form a fused cycloalkyl, cyclenyl, heterocyclyl, or heterocyclenyl together with the parent ring;

X is or N

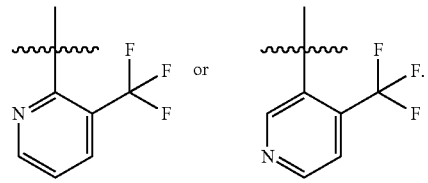 [SMILES: *c1ncccc1C(F)(F)F ; "or" ; *c1cnccc1C(F)(F)F]

$R^{10}$ and $R^{11}$, which can be the same or different, are independently selected from the group consisting of hydrogen, alkyl, alkenyl, alkynyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, alkoxyalkyl, alkenoxyalkyl, alkynoxyalkyl, cycloalkoxyalkyl, cycloalkenoxyalkyl, aryloxyalkyl, heterocycloalkoxyalkyl, heterocycloalkenoxyalkyl, heteroaryloxyalkyl, cycloalkylalkoxyalkyl, cyclenylalkoxyalkyl, arylalkoxyalkyl, heterocyclylalkoxyalkyl, heterocyclenylalkoxyalkyl, heteroarylalkoxyalkyl, -alkyl-S-alkyl, -alkyl-S-alkenyl, -alkyl-S-alkynyl, -alkyl-S-cycloalkyl, -alkyl-S-cyclenyl, -alkyl-S-aryl, -alkyl-S-heterocyclyl, -alkyl-S-heterocyclenyl, -alkyl-S-heteroaryl, -alkyl-S-cycloalkylalkyl, -alkyl-S-cyclenylalkyl, -alkyl-S-arylalkyl, -alkyl-S-heterocyclylalkyl, -alkyl-S-heterocyclenylalkyl, -alkyl-S-heteroarylalkyl, hydroxyalkyl, hydroxyalkenyl, -alkyl-SH, -alkenyl-SH, -alkylNH$_2$, -alkenylNH$_2$, —COR$^{12}$, —CO$_2$alkyl, —CO$_2$alkenyl, -alkylN(alkoxy)$_2$, -alkylNHalkoxy, —CONHSO$_2$alkyl, —CONHSO$_2$alkenyl, —CONalkylSO$_2$alkyl, —CONHalkyl, —CONHalkenyl, -alkylCO$_2$alkyl, -alkylCONHalkyl, -alkylCONH$_2$, -alkylCON(alkyl)$_2$, -alkylCON(alkenyl)$_2$, -alkylCO$_2$H, -alkylN(alkyl)$_2$, -alkylNHalkyl, -alkyl-NH$_2$, -alkenyl-N(alkyl)$_2$, -alkyl-N(alkenyl)$_2$, -alkyl-Nalkyl(alkenyl), -alkenyl-NH$_2$, wherein each of said cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkoxyalkyl, cycloalkenoxyalkyl, aryloxyalkyl, heterocycloalkoxyalkyl, heterocycloalkenoxyalkyl, heteroaryloxyalkyl, cycloalkylalkoxyalkyl, cyclenylalkoxyalkyl, arylalkoxyalkyl, heterocyclylalkoxyalkyl, heterocyclenylalkoxyalkyl, heteroarylalkoxyalkyl, can be unsubstituted or substituted with one or more moieties, which may be the same or different, each moiety being independently selected from the group consisting of alkyl, alkenyl, alkynyl, —CN, hydroxyl, —SH, —NH$_2$, —N(alkyl)$_2$, —N(alkenyl)$_2$, —N(alkoxyalkyl)$_2$, trifluoroalkyl, difluoroalkyl, monofluoroalkyl, alkoxy, —S-alkyl, halogen, hydroxyalkyl, hydroxyalkenyl, -alkylSH, —COR$^{12}$, —SO$_2$R$^{12}$, heteroalkyl, alkoxyalkoxy, —S-alkyl-S-alkyl, -alkylNH$_2$, -alkyl-N(alkyl)$_2$, and -alkylNHalkyl, further wherein, in any —NR$^{10}$R$^{11}$ in Formula 2, said R$^{10}$ and R$^{11}$ can optionally be joined together with the N of said —NR$^{10}$R$^{11}$ to form a cyclic ring;

R$^{12}$ is selected from the group consisting of hydrogen, hydroxyl, —NH$_2$, —N(alkyl)$_2$, —N(alkenyl)$_2$, —NHalkyl, —NHalkenyl, —NH-alkyl-O-alkyl, —NH-alkenyl-O-alkyl, -alkyl-S-alkyl, -alkyl-O-alkyl, -alkenyl-O-alkyl, -alkyl-O-alkenyl, -alkenyl-S-alkyl, -alkenyl-S-alkenyl, trifluoroalkyl, difluoroalkyl, monofluoroalkyl, alkoxy, —S-alkyl, -alkyl-S-alkyl, alkoxyalkyl, alkyl, alkenyl, alkynyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, heteroalkyl, heteroalkenyl, -alkylN(alkyl)$_2$, -alkylNHalkyl, -alkyl-NH$_2$, -alkenyl-N(alkyl)$_2$, -alkyl-N(alkenyl)$_2$, -alkyl-Nalkyl(alkenyl), -alkenyl-NH$_2$, hydroxyalkyl, hydroxyalkenyl, -alkyl-SH, -alkenyl-SH, -alkylCO$_2$H, -alkylCO$_2$alkyl, -alkylCONHalkyl, -alkylCONH$_2$, -alkylCON(alkyl)$_2$, -alkylCON(alkenyl)$_2$, wherein each of said cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, heteroalkyl, heteroalkenyl can be unsubstituted or substituted with one or more moieties, which can be the same or different, independently selected from the group consisting of alkyl, heteroalkyl, heteroalkenyl, alkenyl, alkynyl, alkoxyalkoxy, —S-alkyl-S-alkyl, hydroxyalkyl, -alkylSH, hydroxyalkenyl, -alkyl-NH$_2$, -alkyl-N(alkyl)$_2$, and -alkylNHalkyl.

In the assay for HDM2 inhibitory activity (fluorescence polarization assay) [Zhang et al., J. Analytical Biochemistry 331: 138-146 (2004)] the compounds of the present invention exhibit FP IC$_{50}$, values of less than 0.5 μM. Also, the cytochrome P450 3A4 enzyme inhibition studies of the compounds of the present invention indicate that these compounds have an IC$_{50}$ CYP3A4 (pre and co incubation) of more than 1 μM. The compounds of the present invention by themselves or in combination with one or more other suitable agents disclosed later in this application can be useful as HDM2 or MDM2 inhibitors and can be useful in the treatment and prevention of proliferative diseases such as cancers.

Such treatment or prevention can be done with the inventive compound as well as with pharmaceutical compositions or formulations comprising the compound.

DETAILED DESCRIPTION OF THE INVENTION

In one embodiment, the present invention provides compounds illustrated as Formula 1, as described above, or pharmaceutically acceptable salts, solvates, esters, or prodrugs thereof, wherein the various moieties are as described above.

In another embodiment, in Formula 1, R is absent and E is present, i.e., R$^1$ in Formula 1 is

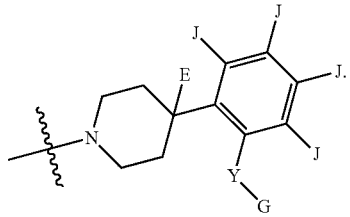

In another embodiment, in Formula 1, both R and E are absent, i.e., R$^1$ in Formula 1 is

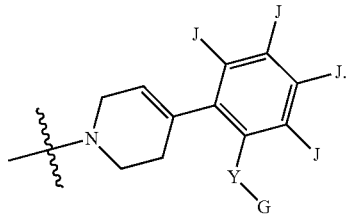

In another embodiment, in Formula 1, each n independent is 0, 1, 2, 3, 4, 5, 6, 7, 8, 9, or 10.

In another embodiment, in Formula 1, E is present and is selected from the group consisting of H, halo, OH, CN, —O(C$_1$-C$_6$)alkyl, (C$_1$-C$_6$)alkyl, —C(O)OH, —C(O)NR$^8$R$^{8'}$, —(C$_1$-C$_6$)alkyl-C(O)OH, —(C$_1$-C$_6$)alkyl-OH, —(C$_1$-C$_6$)—C(O)NR$^8$R$^{8'}$, and heteroaryl.

In another embodiment, in Formula 1, E is present and is selected from the group consisting of H, halo, OH, CN, —O(C$_1$-C$_6$)alkyl, (C$_1$-C$_6$)alkyl, —C(O)OH, —C(O)NR$^8$R$^{8'}$, —(C$_1$-C$_6$)alkyl-C(O)OH, —(C$_1$-C$_6$)alkyl-OH, —(C$_1$-C$_6$)—C(O)NR$^8$R$^{8'}$, and heteroaryl; wherein —(C$_1$-C$_6$)alkyl-OH is hydroxymethyl; said —(C$_1$-C$_6$)alkyl-C(O)NR$^8$R$^{8'}$ is —C(O)NH$_2$; said —(C$_1$-C$_6$)alkyl-C(O)OH is —(CH$_2$)$_4$C(O)OH; said halo is —F; said —O(C$_1$-C$_6$)alkyl is methoxy; said —(C$_1$-C$_6$)alkyl is methyl; and said heteroaryl is tetrazolyl.

In another embodiment, in Formula 1, each J independently is H or Fluoro.

In another embodiment, in Formula 1, Y is present and is selected from the group consisting of O, S, SO$_2$, and CR$^8$R$^{8'}$.

In another embodiment, in Formula 1, Y is CR$^8$R$^{8'}$, wherein R$^8$ and R$^8$ are both H, i.e., Y is CH$_2$.

In another embodiment, in Formula 1, G is present, and is selected from the group consisting of —(CR$^8$R$^{8'}$)$_n$—C(O)OH, —(CR$^8$R$^{8'}$)$_n$—C(O)NR$^8$R$^9$, —(CR$^8$R$^{8'}$)$_n$—(C$_3$-C$_8$)cycloalkyl-C(O)NR$^8$R$^9$, —(CR$^8$R$^{8'}$)$_n$—(C$_3$-C$_8$)cycloalkyl-(CR$^8$R$^{8'}$)$_n$—C(O)OH, —(CR$^8$R$^{8'}$)—O—(CR$^8$R$^{8'}$)$_n$—(C$_3$-C$_8$)cycloalkyl-(CR$^8$R$^{8'}$)$_n$—C(O)OH, —(CR$^8$R$^{8'}$)$_n$—O—(CR$^8$R$^{8'}$)$_n$—C(O)OH, —(CR$^8$R$^{8'}$)$_n$—NH—(CR$^8$R$^{8'}$)$_n$—C(O)OH, —(CR$^8$R$^{8'}$)$_n$—O—(CR$^8$R$^{8'}$)$_n$—CH$_3$, —(CR$^8$R$^{8'}$)$_n$—CH$_3$, —(CR$^8$R$^{8'}$)$_n$-heteroaryl, —(CR$^8$R$^{8'}$)$_n$—P(O)OR$^8$OR$^{8'}$, and —(CR$^8$R$^{8'}$)$_n$—OH.

In another embodiment, in Formula 1, G is present and is —(CR$^8$R$^{8'}$)$_n$—C(O)OH, wherein n is 1-6, and in one embodiment, 1, 2, 3, 4, 5, or 6.

In another embodiment, in Formula 1, G is present and is —(CR$^8$R$^{8'}$)$_n$—C(O)OH, which is selected from the group consisting of —(CH$_2$)$_{1-5}$C(O)OH, —CH(CH$_3$)—(CH$_2$)$_{2-3}$—C(O)OH, —(CH$_2$)$_{1-3}$C(CH$_3$)$_2$C(O)OH, —(CH$_2$)$_3$CH(CH $(CH_3)_2)$—C(O)OH, —$(CD_2)_3$C(O)OH, —$(CH_2)_{1-2}$—CH$(CH_3)$—$(CH_2)_{1-2}$—C(O)OH, CH$(CH_3)$—$(CH_2)_{2-3}$—C(O)OH,

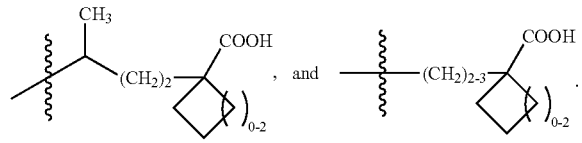

Here,

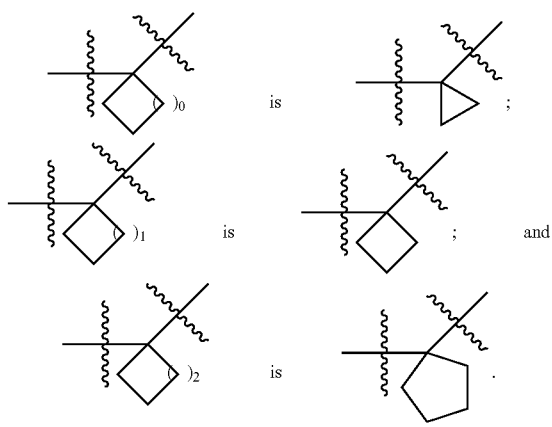

In another embodiment, in Formula 1, G is present and is —$(CR^8R^{8'})_n$—C(O)NR$^8$R$^9$ wherein n is 1-6, and in one embodiment, 1, 2, 3, 4, 5, or 6.

In another embodiment, in Formula 1, G is present and is —$(CR^8R^{8'})_n$—C(O)NR$^8$R$^9$ which is —$(CH_2)_{1-4}$—C(O)NH—S(O)$_2$CH$_3$ or —$(CH_2)_{3-4}$—C(O)NH—S(O)$_2$-cyclopropyl.

In another embodiment, in Formula 1, G is present and is —$(CR^8R^{8'})_n$—$(C_3$-$C_8)$cycloalkyl-C(O)NR$^8$R$^9$ wherein said $(C_3$-$C_8)$cycloalkyl is unsubstituted $(C_3$-$C_8)$cycloalkyl or $(C_3$-$C_8)$cycloalkyl that is substituted with an alkyl group. In another embodiment, said —$(CR^8R^{8'})_n$—$(C_3$-$C_8)$cycloalkyl-C(O)NR$^8$R$^9$ is

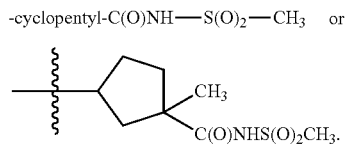

In another embodiment, in Formula 1, G is present and is —$(CR^8R^{8'})_n$—$(C_3$-$C_8)$cycloalkyl-$(CR^8R^{8'})_n$—C(O)OH wherein each n is independently 0 or 1. In another embodiment, said —$(CR^8R^{8'})_n$—$(C_3$-$C_8)$cycloalkyl-$(CR^8R^{8'})_n$—C(O)OH is selected from the group consisting of —CH$_2$-cyclopentyl-C(O)OH, -cyclobutyl-C(O)OH, -cyclopentyl-C(O)OH, -cyclohexyl-C(O)OH, and -cyclopentyl-CH$_2$—C(O)OH.

In another embodiment, in Formula 1, G is present and is —$(CR^8R^{8'})_n$—O—$(CR^8R^{8'})_n$—$(C_3$-$C_8)$cycloalkyl-$(CR^8R^{8'})_n$—C(O)OH wherein each n is 0. In another embodiment, said —$(CR^8R^{8'})_n$—O—$(CR^8R^{8'})_n$—$(C_3$-$C_8)$cycloalkyl-$(CR^8R^{8'})_n$—C(O)OH is —O-cyclopenyl-C(O)OH or —O-cyclobutyl-C(O)OH.

In another embodiment, in Formula 1, G is present and is —$(CR^8R^{8'})_n$—O—$(CR^8R^{8'})_n$—C(O)OH wherein the first n is 0 or 1, and the second n is 3. In another embodiment, said —$(CR^8R^{8'})_n$—O—$(CR^8R^{8'})_n$—C(O)OH is selected from the group consisting of —CH$_2$—O—$(CH_2)_3$—C(O)OH, —O—$(CH_2)_2$—C(CH$_3$)$_2$—C(O)OH, and —O—$(CH_2)_3$—C(O)OH.

In another embodiment, in Formula 1, G is present and is —$(CR^8R^{8'})_n$—NH—$(CR^8R^{8'})_n$—C(O)OH wherein the first n i 0 and the second n is 3. In another embodiment, said —$(CR^8R^{8'})_n$—NH—$(CR^8R^{8'})_n$—C(O)OH is —NH(CH$_2$)$_3$C(O)OH.

In another embodiment, in Formula 1, G is present and is —$(CR^8R^{8'})_n$—O—$(CR^8R^{8'})_n$—CH$_3$ wherein the first n is 0 and the second n i s 0. In another embodiment, said —$(CR^8R^{8'})_n$—O—$(CR^8R^{8'})_n$—CH$_3$ is —$(CH_2)_2$—O—CH$_3$.

In another embodiment, in Formula 1, G is present and is —$(CR^8R^{8'})_n$—CH$_3$ wherein n is 0. In another embodiment, said —$(CR^8R^{8'})_n$—CH$_3$ is —CH$_3$.

In another embodiment, in Formula 1, G is present and is —$(CR^8R^{8'})_n$-heteroaryl wherein said n is 2. In another embodiment, said heteroaryl is pyrazolyl which is unsubstituted or substituted with an alkyl. In another embodiment, said —$(CR^8R^{8'})_n$-heteroaryl is —$(CH_2)_2$-(alkyl substituted pyrazolyl).

In another embodiment, in Formula 1, G is present and is —$(CR^8R^{8'})_n$—P(O)OR$^8$OR$^{8'}$ wherein said n is 3. In another embodiment, said —$(CR^8R^{8'})_n$—P(O)OR$^8$OR$^{8'}$ is —$(CH_2)_3$P(O)(OH)(OH) or —$(CH_2)_3$P(O)(OCH$_3$)(OCH$_3$).

In another embodiment, in Formula 1, G is present and is —$(CR^8R^{8'})_n$—OH wherein n is 2. In other embodiment, said —$(CR^8R^{8'})_n$—OH is —$(CH_2)_2$—OH.

In another embodiment, in Formula 1, Y is O and G is selected from the group consisting of —$(CR^8R^{8'})_n$—C(O)OH, —$(CR^8R^{8'})_n$—C(O)NR$^8$R$^9$, —$(CR^8R^{8'})_n$—$(C_3$-$C_8)$cycloalkyl-C(O)NR$^8$R$^9$, —$(CR^8R^{8'})_n$—$(C_3$-$C_8)$cycloalkyl-$(CR^8R^{8'})_n$—C(O)OH, —$(CR^8R^{8'})_n$—O—$(CR^8R^{8'})_n$—CH$_3$, —$(CR^8R^{8'})_n$—CH$_3$, —$(CR^8R^{8'})_n$-heteroaryl, and —$(CR^8R^{8'})_n$—P(O)OR$^8$OR$^{8'}$.

In another embodiment, in Formula 1, Y is S and G is —$(CR^8R^{8'})_n$—C(O)OH or —$(CR^8R^{8'})_n$—$(C_3$-$C_8)$Cycloalkyl-$(CR^8R^{8'})_n$—C(O)OH.

In another embodiment, in Formula 1, Y is SO$_2$ and G is —$(CR^8R^{8'})_n$—NH—$(CR^8R^{8'})_n$—C(O)OH.

In another embodiment, in Formula 1, Y is CR$^8$R$^{8'}$ and G is selected from the group consisting of —$(CR^8R^{8'})_n$—O—$(CR^8R^{8'})_n$—C(O)OH, —$(CR^8R^{8'})_n$—O—$(CR^8R^{8'})_n$—$(C_3$-$C_8)$cycloalkyl-$(CR^8R^{8'})_n$—C(O)OH, —$(CR^8R^{8'})_n$—C(O)OH, —$(CR^8R^{8'})_n$—OH, —$(CR^8R^{8'})_n$-heteroaryl, and —$(CR^8R^{8'})_n$—C(O)NR$^8$R$^9$.

In another embodiment, in Formula 1, R$^4$ is hydrogen and R$^{4'}$ is 1-propyl, such that Formula 1 is represented by Formula 1A:

Formula 1A

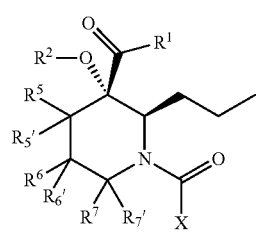

wherein $R^1$, $R^2$, $R^5$, $R^{5'}$, $R^6$, $R^{6'}$, $R^7$, $R^{7'}$, and X are as set forth in Formula 1.

In another embodiment, in Formula 1A, $R^5$, $R^{5'}$, $R^6$, $R^{6'}$, $R^7$, and $R^{7'}$ are all hydrogen, i.e., Formula 1 or 1A is represented by Formula 1B:

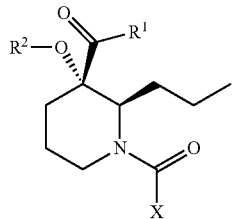

Formula 1B

In another embodiment, in Formula 1B, $R^1$ is

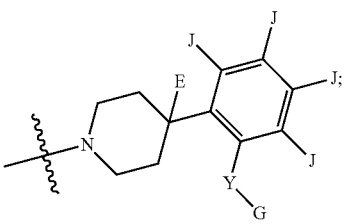

$R^2$ is

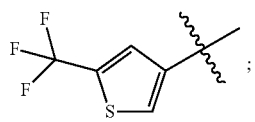 [SMILES: *c1csc(C(F)(F)F)c1]

and either (i) each J in $R^1$ is H, or (ii) one J in $R^1$ is halo, and the remaining three Js are H, i.e., Formula 1, 1A, or 1B is represented by Formula 1C or 1D as set forth below:

Formula 1C

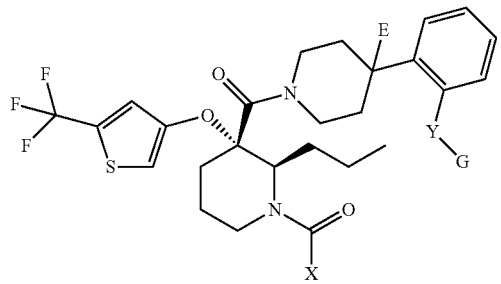

Formula 1D

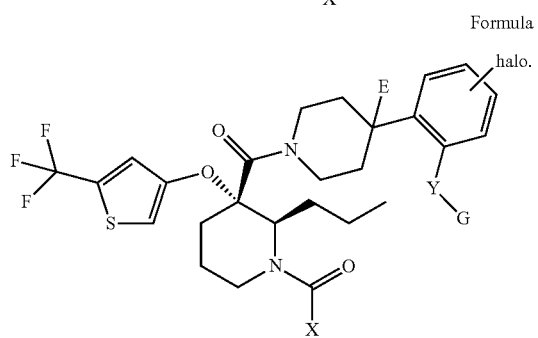

In another embodiment, in Formula 1B, $R^1$ is

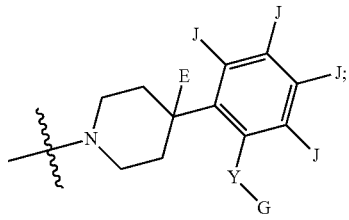

$R^2$ is

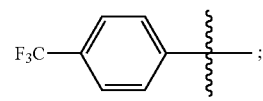 [SMILES: *c1ccc(C(F)(F)F)cc1]

and each J in $R^1$ is H; i.e., i.e., Formula 1, 1A, or 1B is represented by Formula 1E as set forth below:

Formula 1E

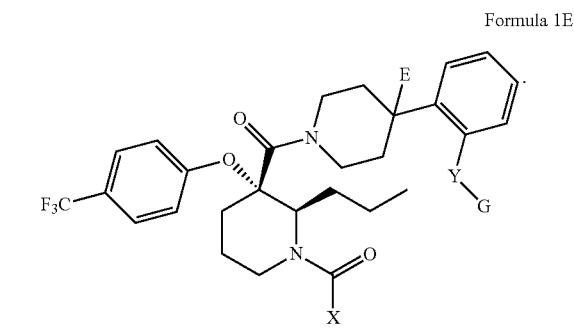

Non-limiting examples of compounds of Formula 1 include:

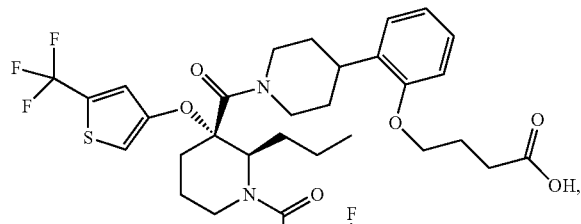

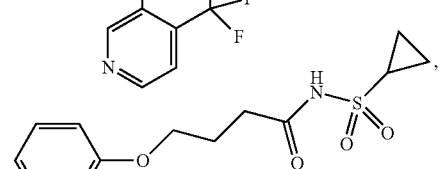

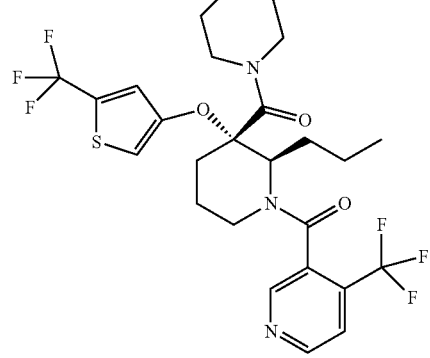

-continued
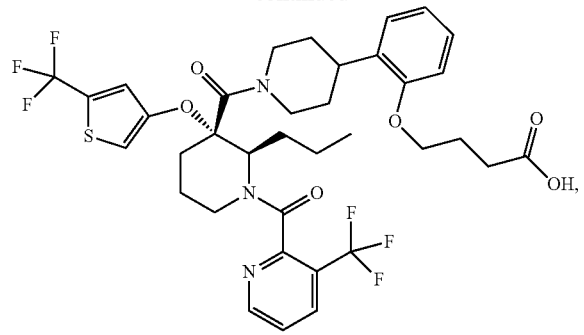
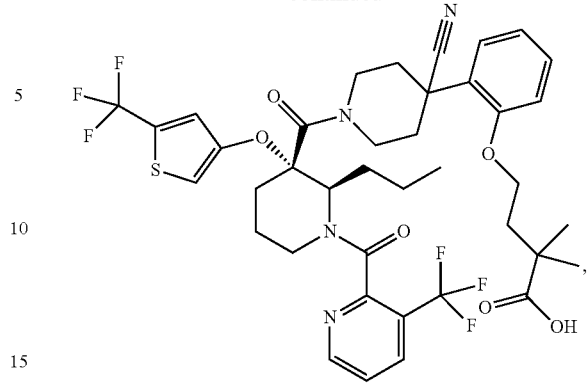
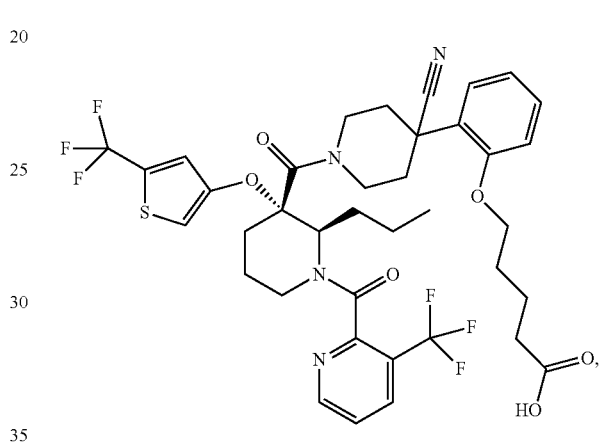
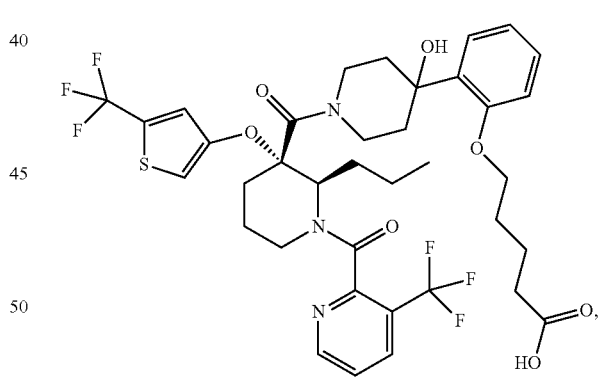
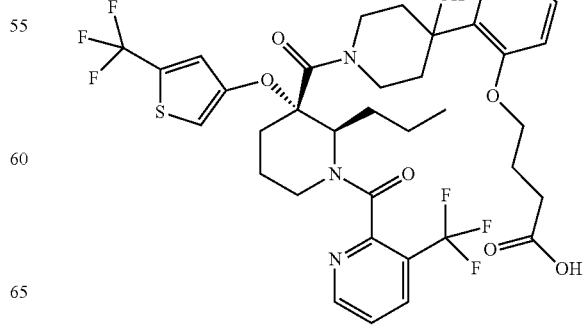

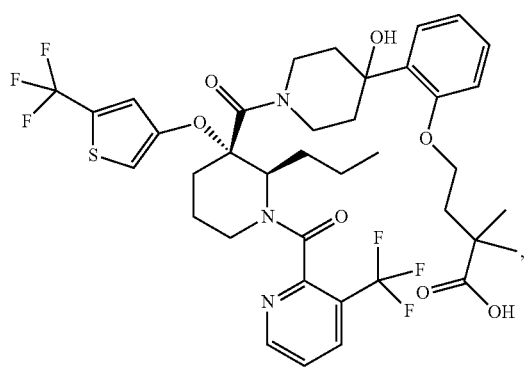
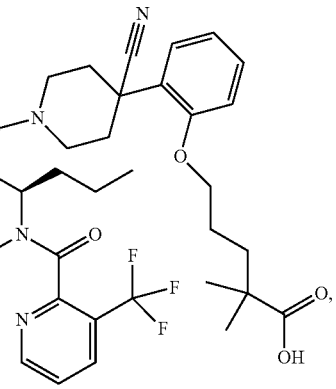
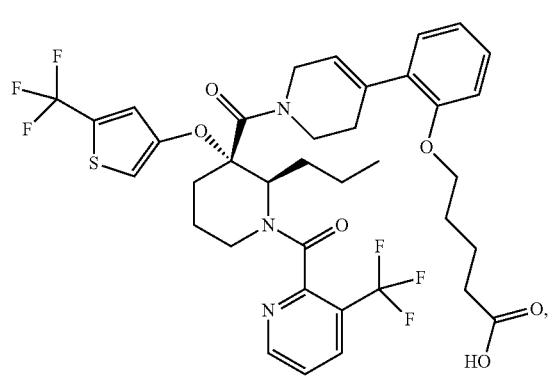
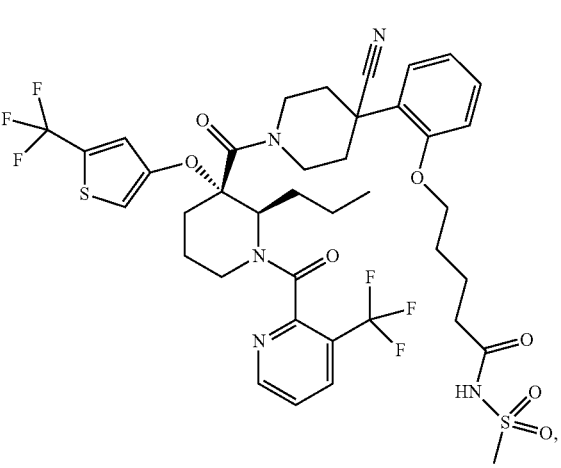
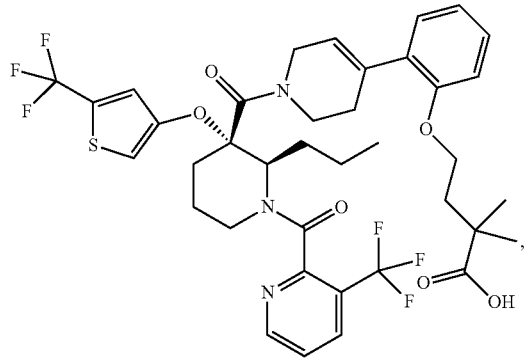
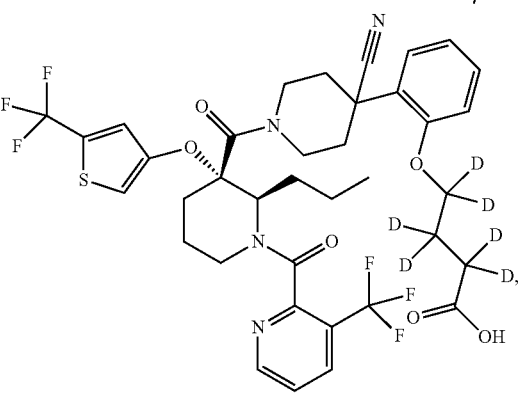
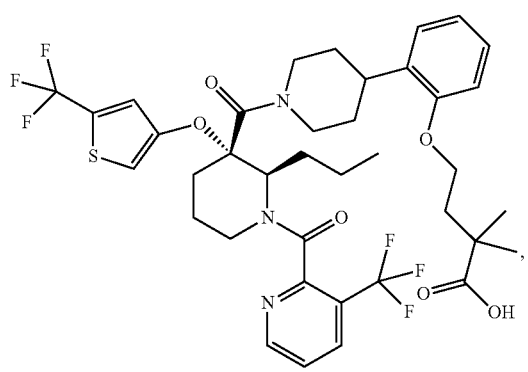

21
-continued
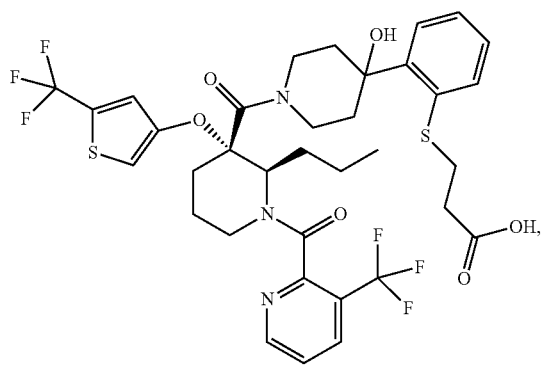
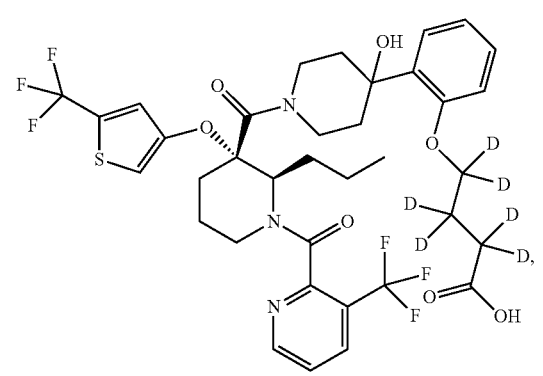
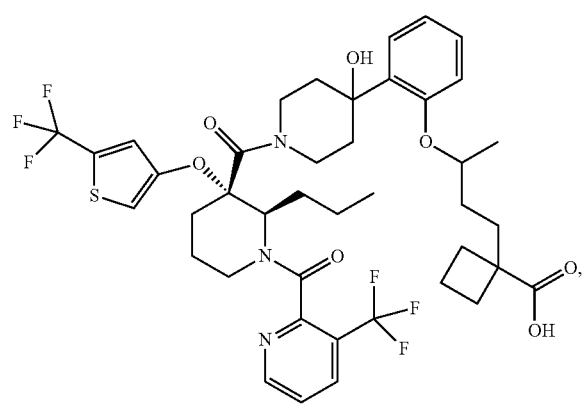
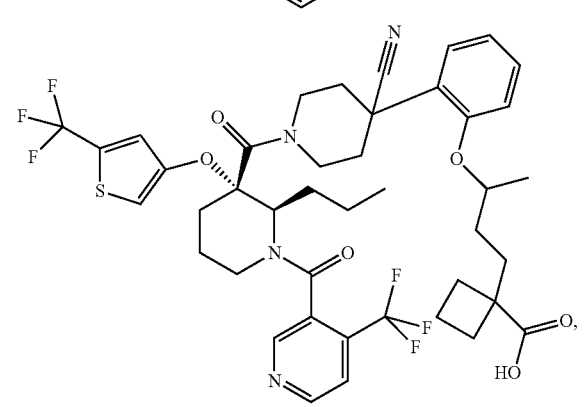
22
-continued
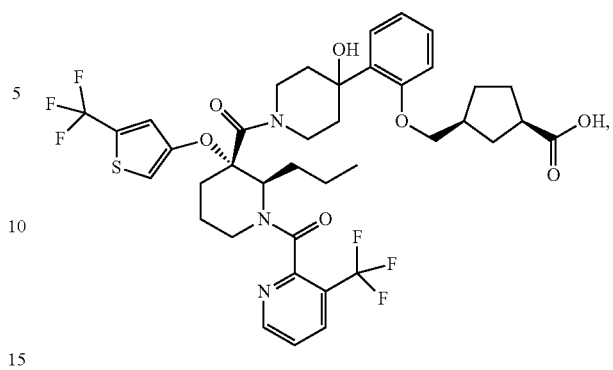
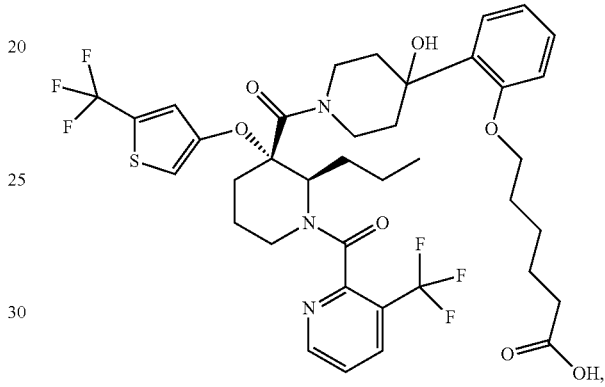
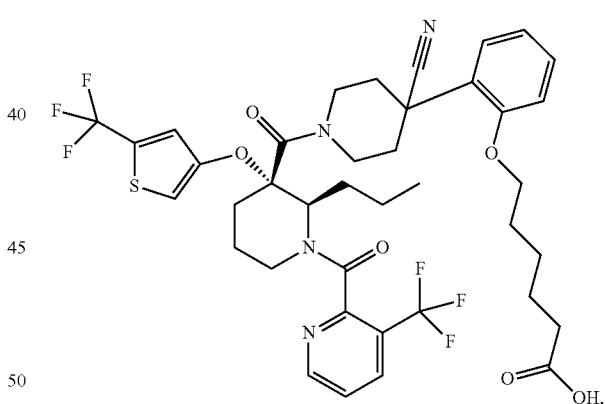
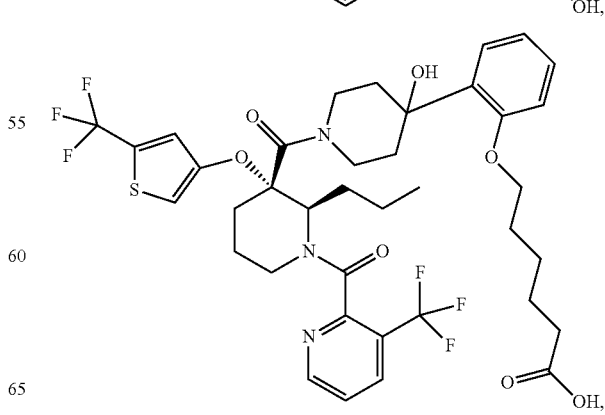

23
-continued
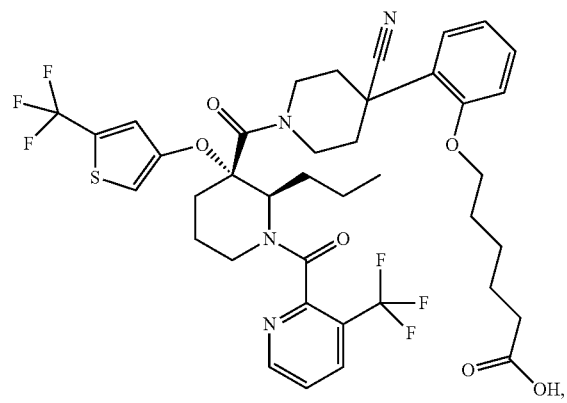
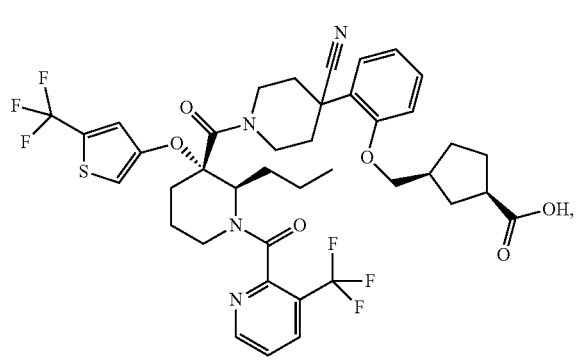
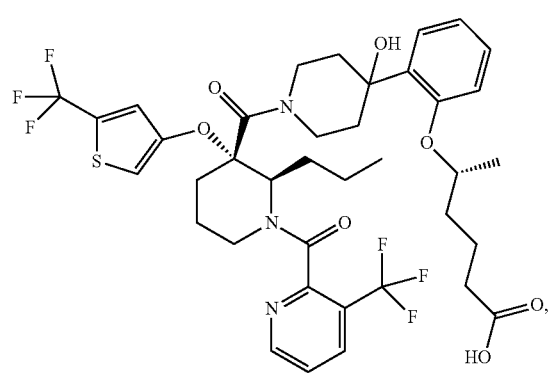
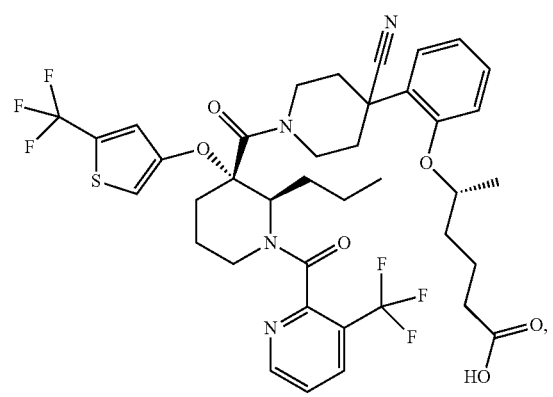
24
-continued
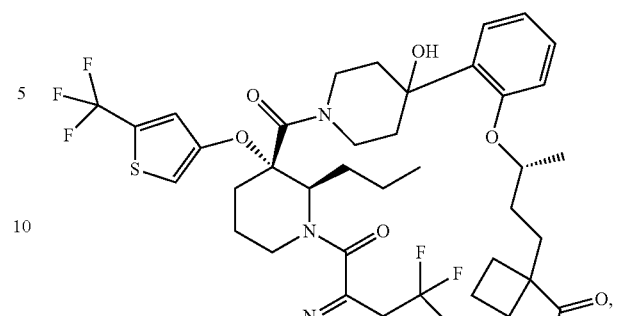
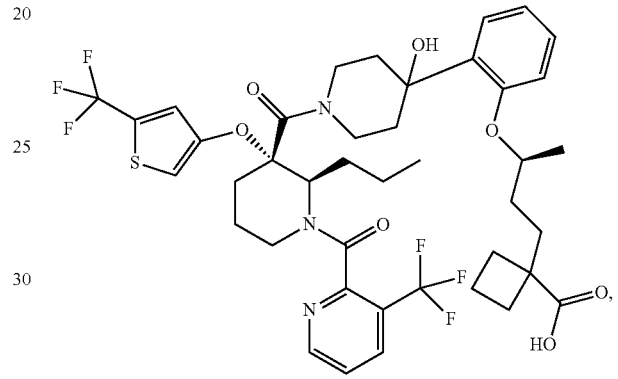
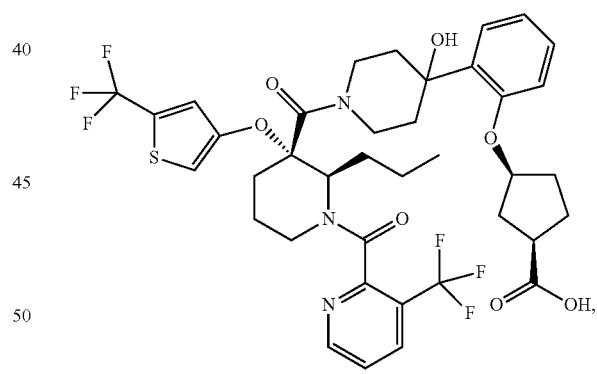
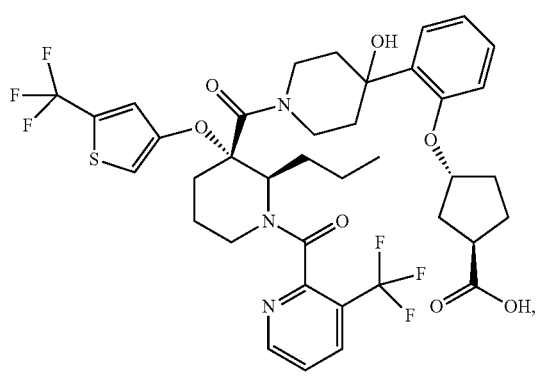

| 25 -continued | 26 -continued |
|---|---|
| 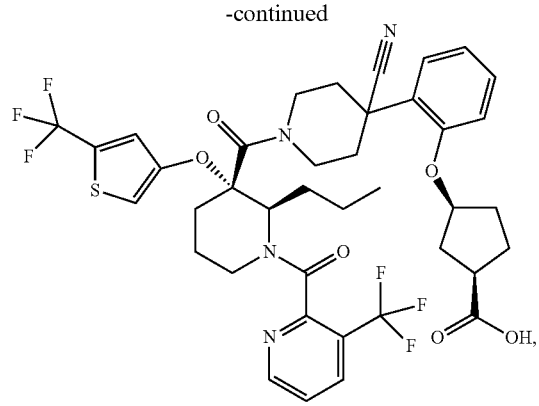 | 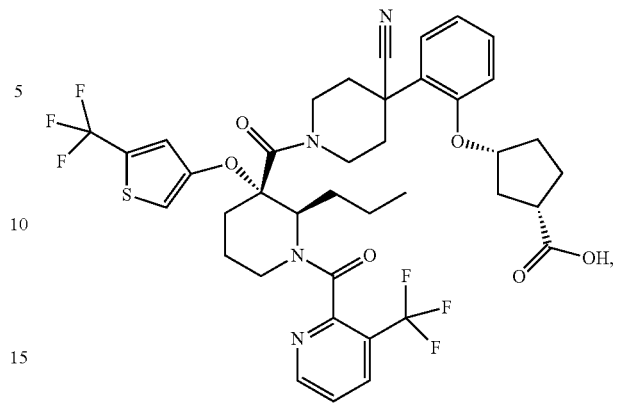 |
| 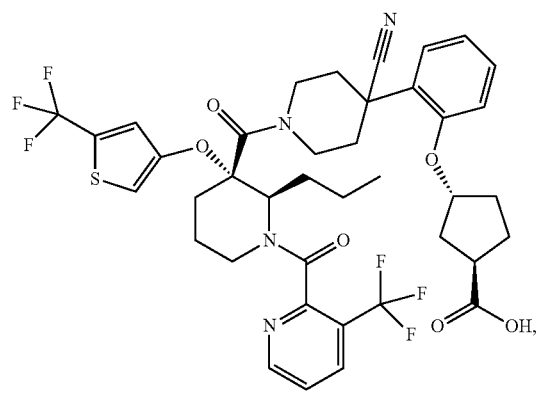 | 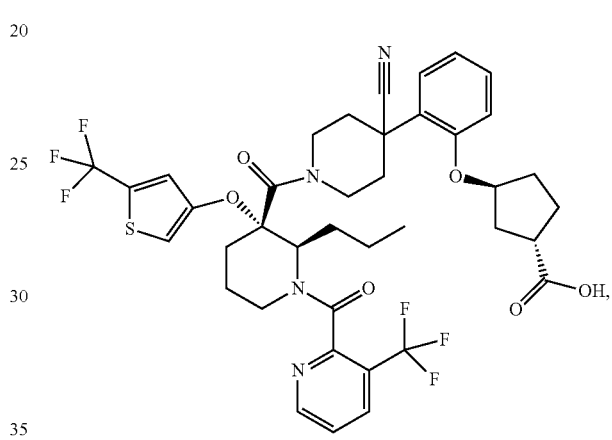 |
| 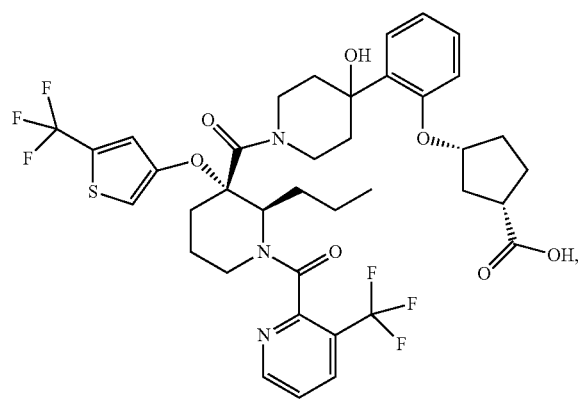 | 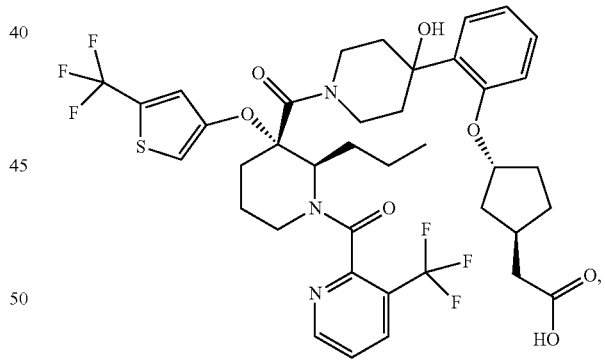 |
| 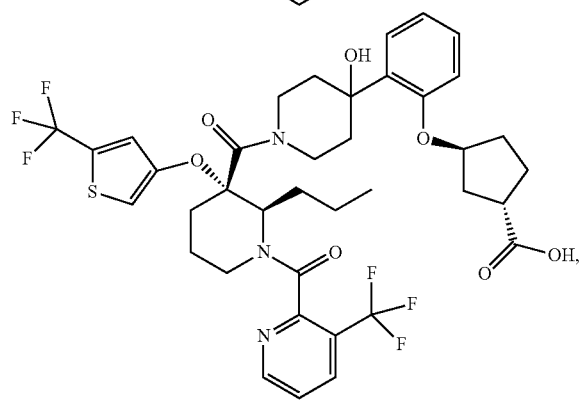 | 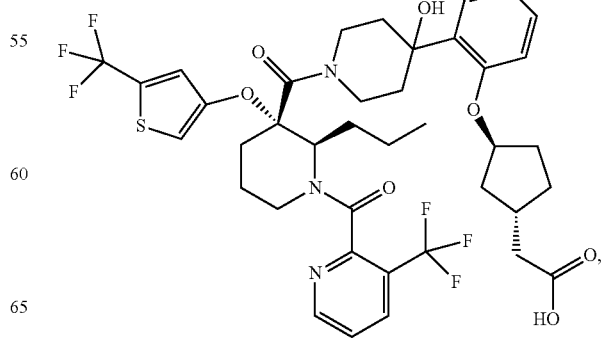 |

27
-continued
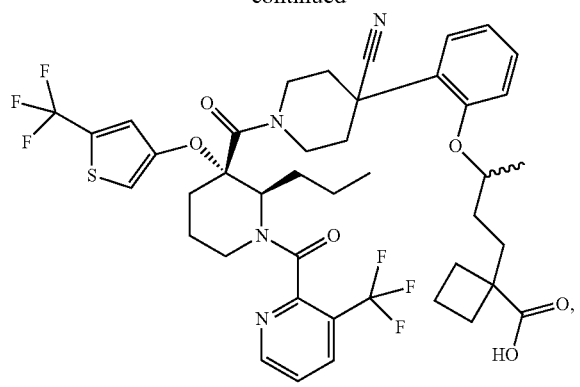
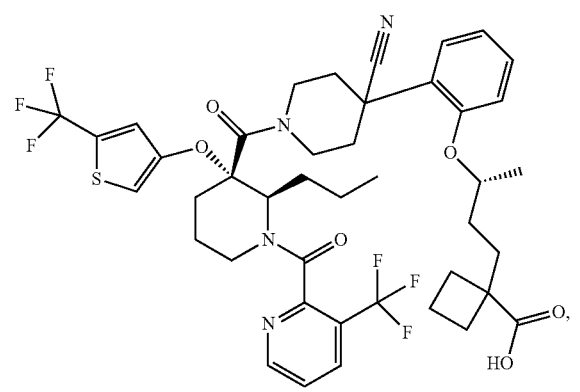
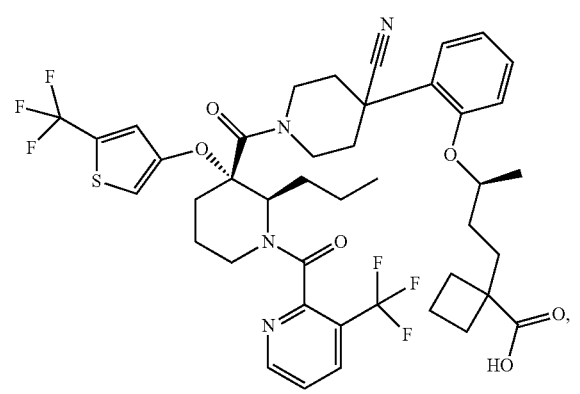
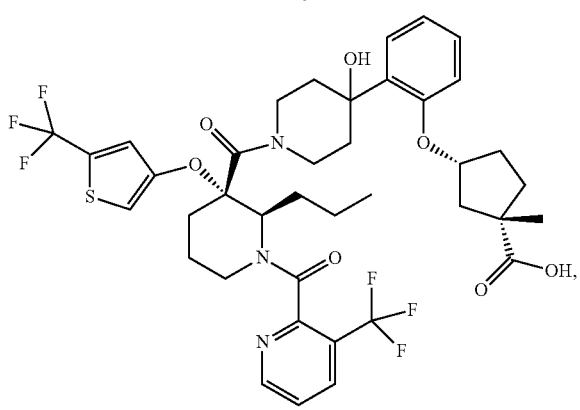
28
-continued
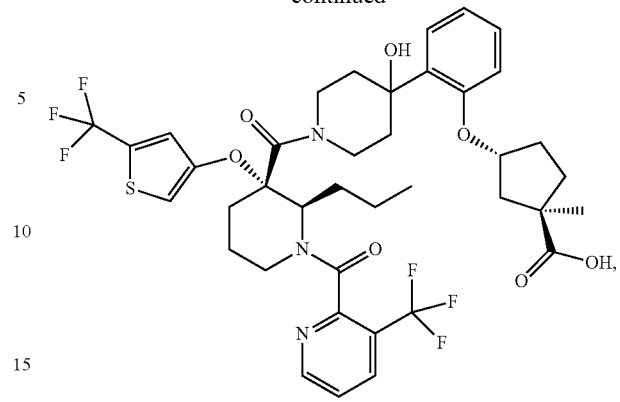
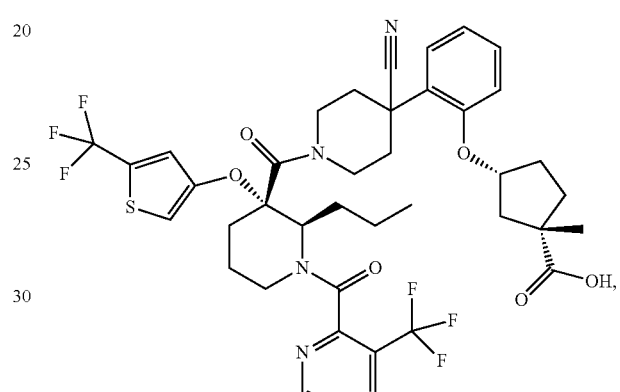
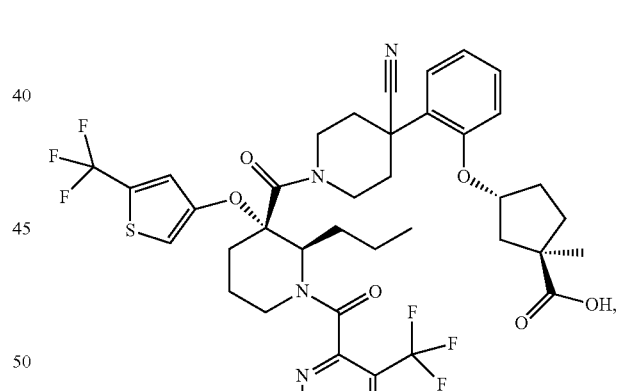
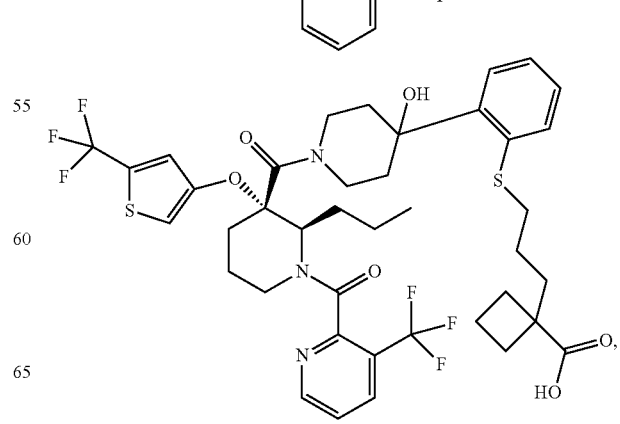

29
-continued
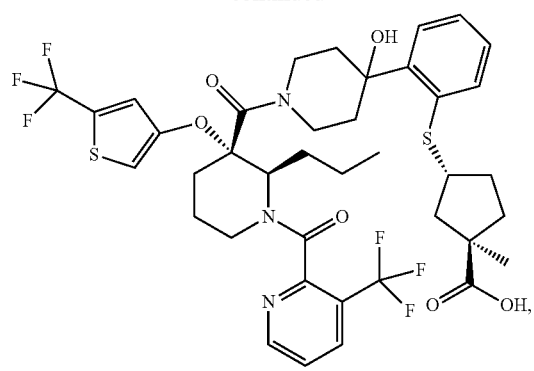
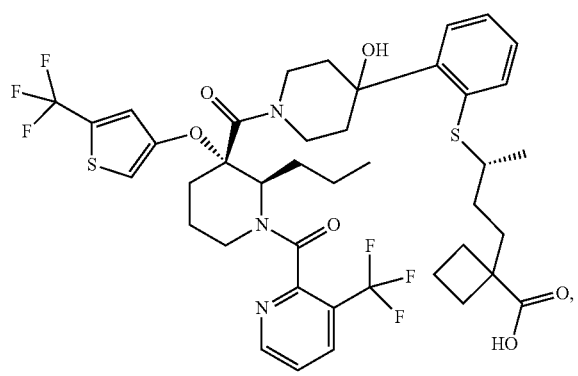
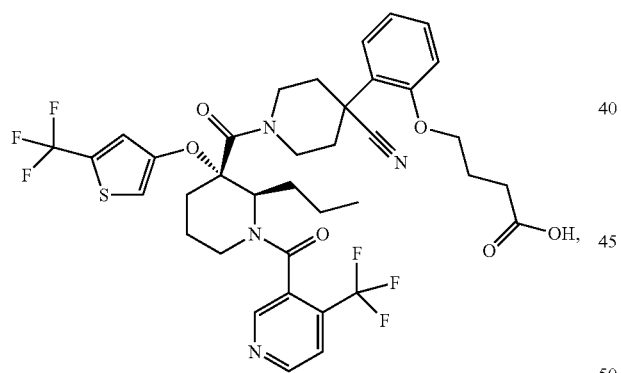
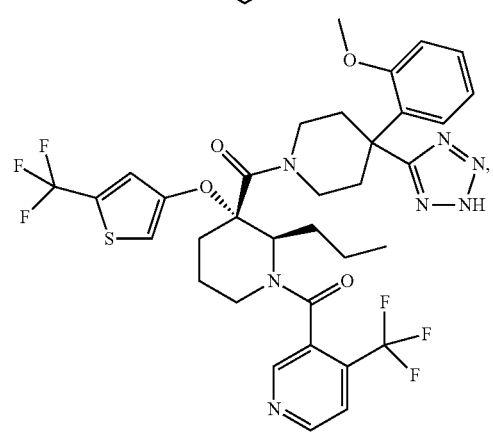
30
-continued
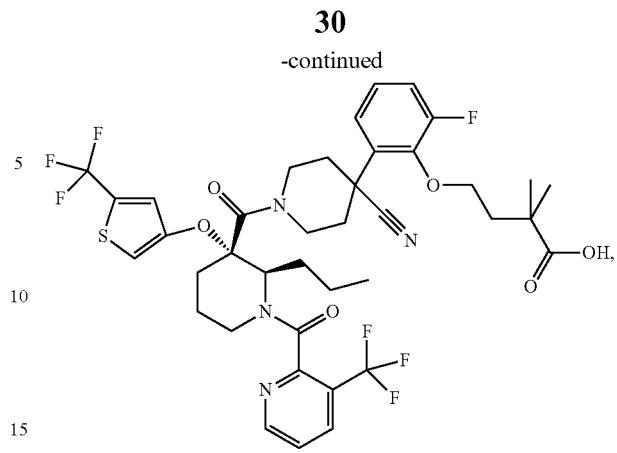
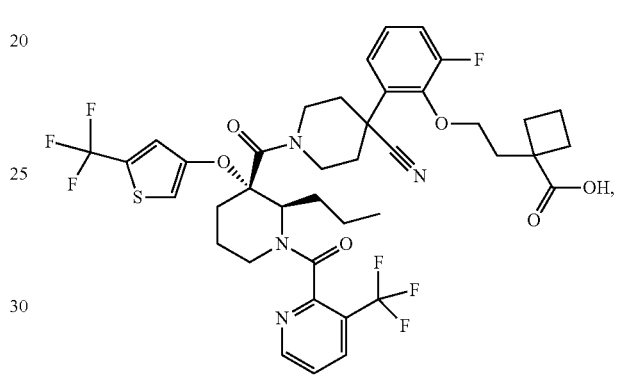
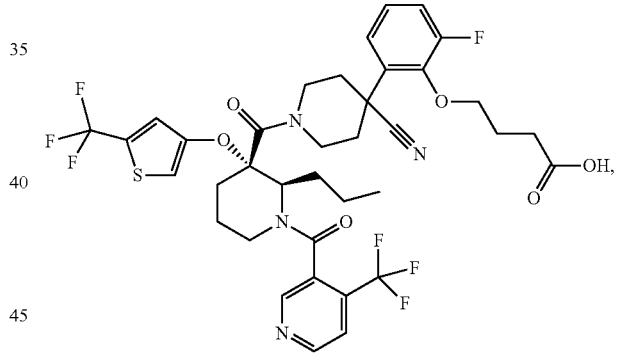
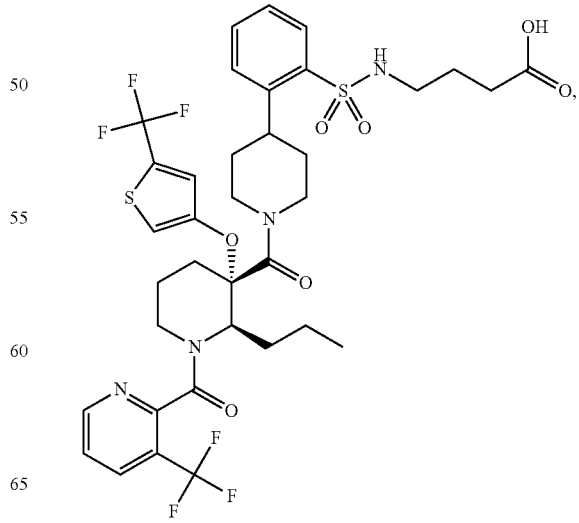

31
-continued
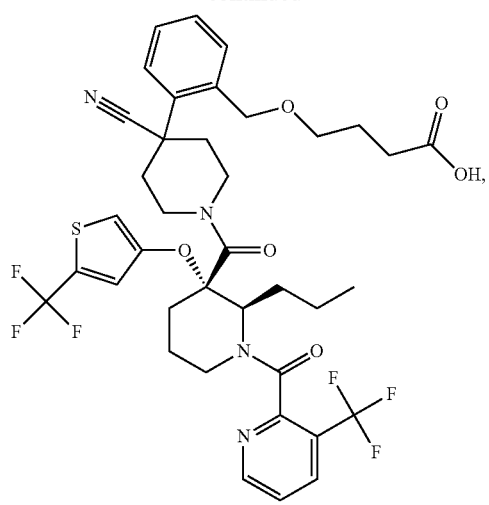
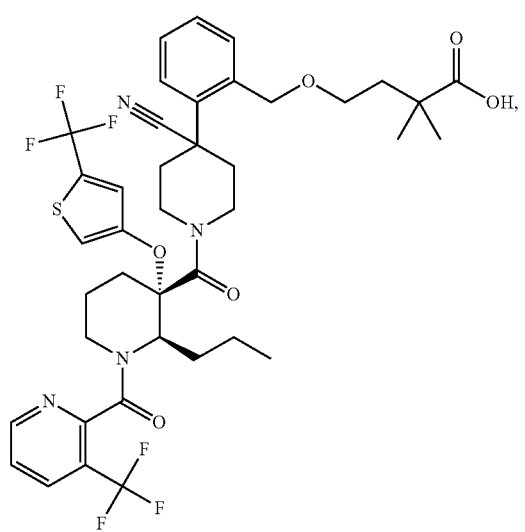
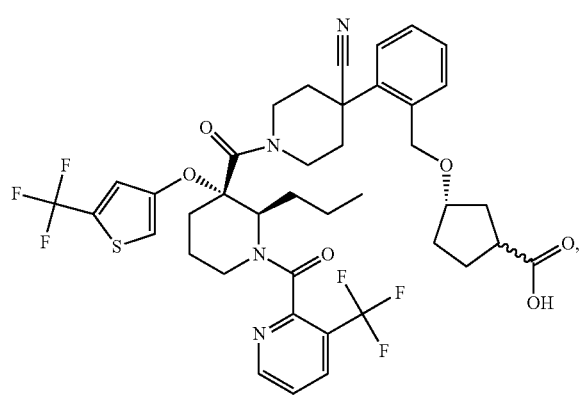
32
-continued
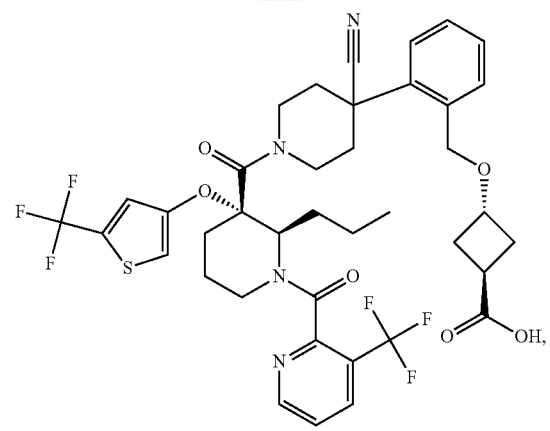
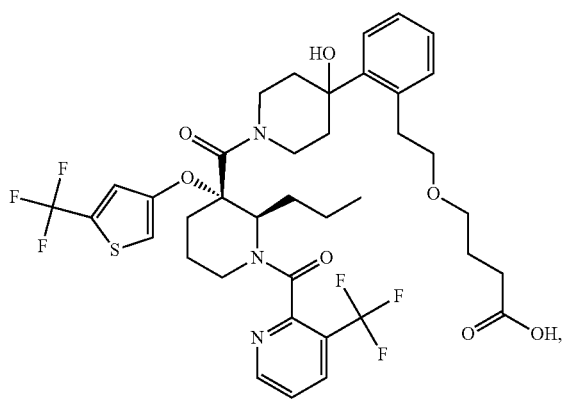
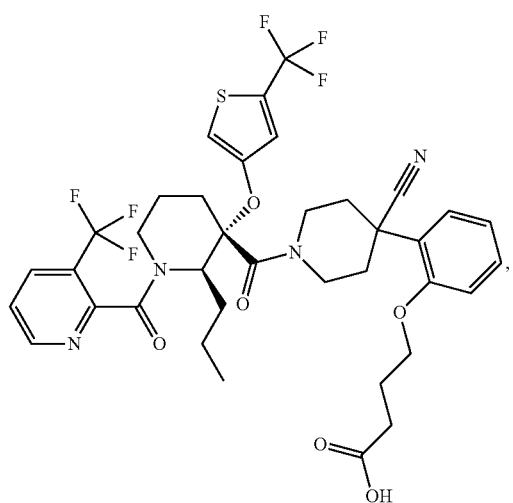

33
-continued
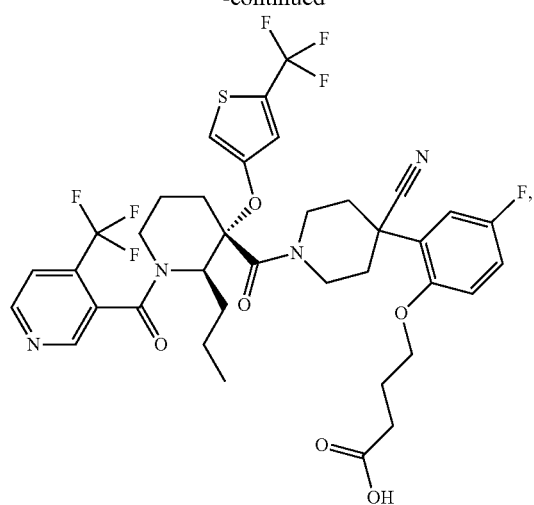
34
-continued
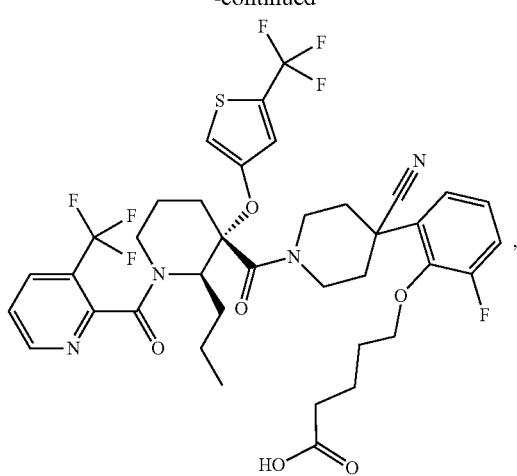
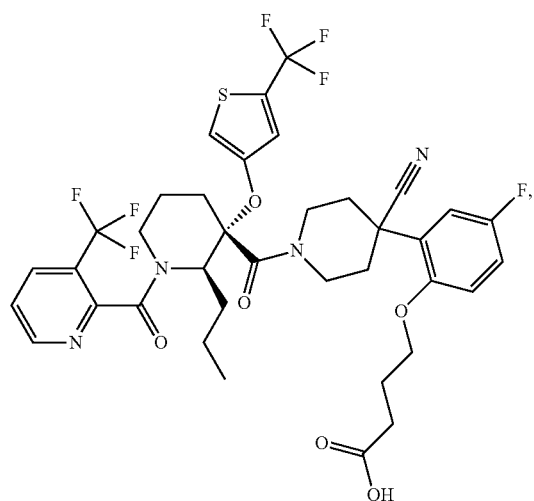
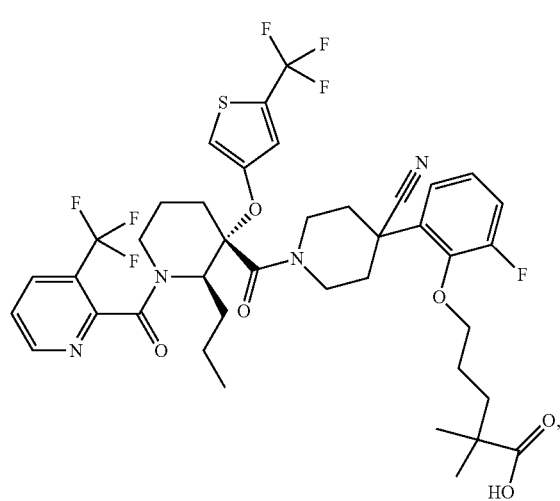
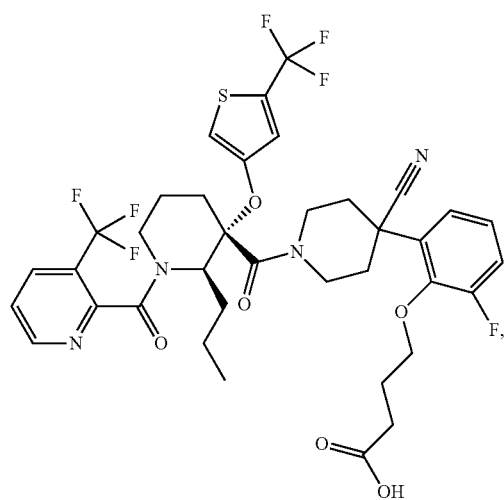
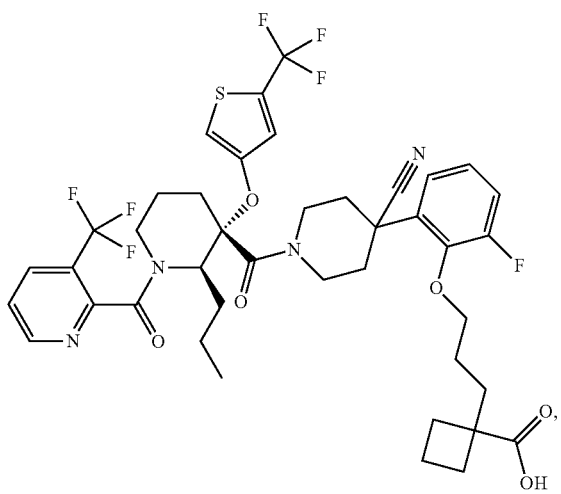

35
-continued
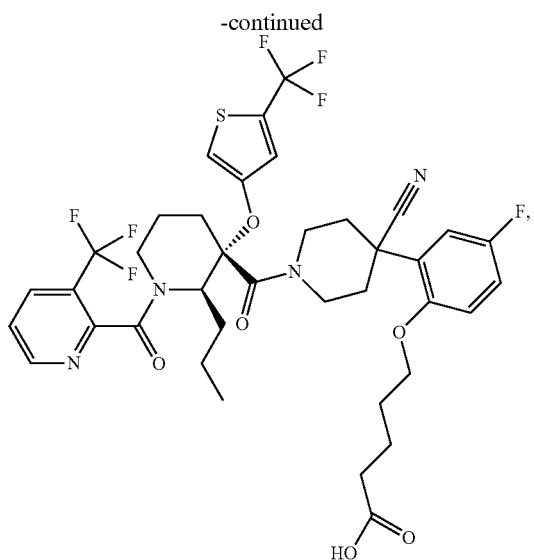
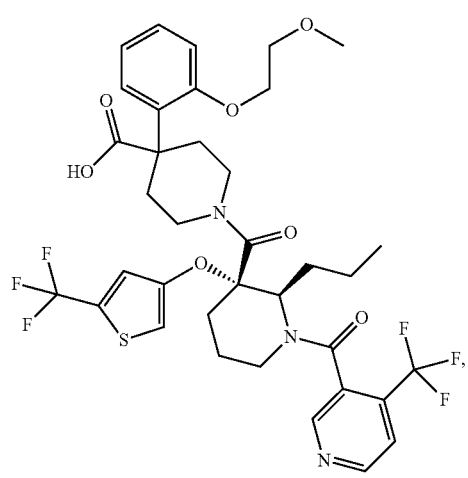 [SMILES: CCC[C@H]1N(C(=O)c2cnccc2C(F)(F)F)CCC[C@@]1(Oc1csc(C(F)(F)F)c1)C(=O)N1CCC(C(=O)O)(c2ccccc2OCCOC)CC1]
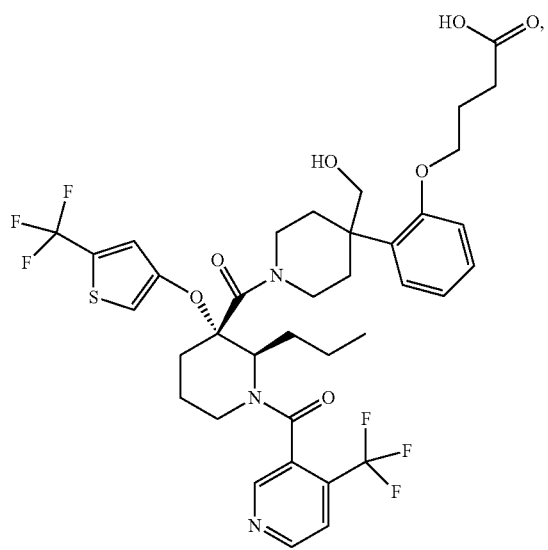 [SMILES: CCC[C@H]1N(C(=O)c2cnccc2C(F)(F)F)CCC[C@@]1(Oc1csc(C(F)(F)F)c1)C(=O)N1CCC(CO)(c2ccccc2OCCCC(=O)O)CC1]
36
-continued
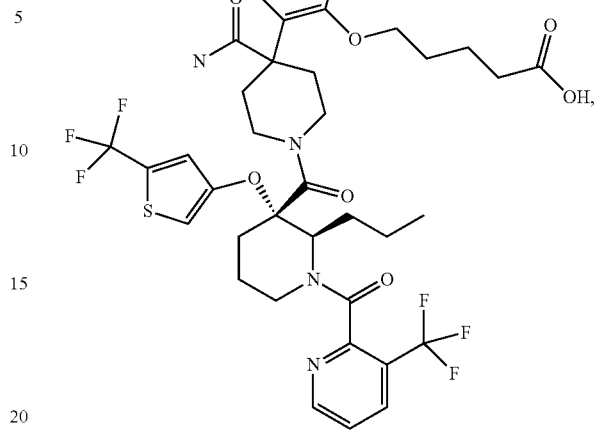
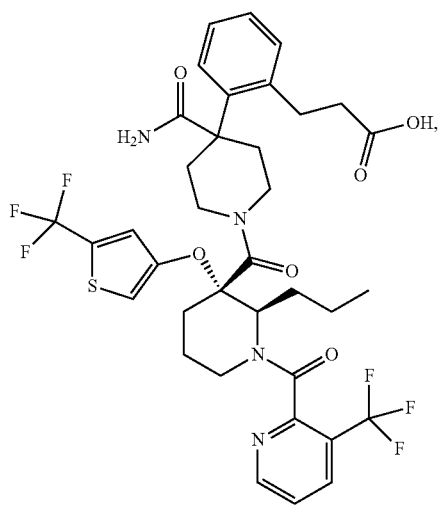
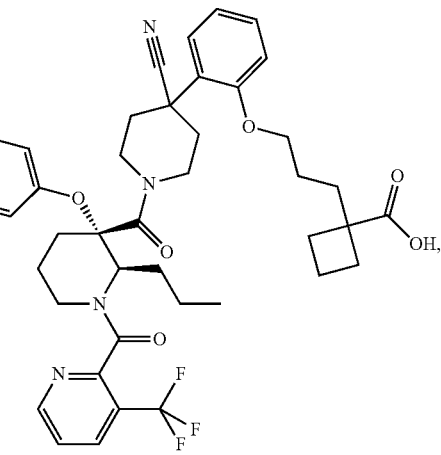

37
-continued
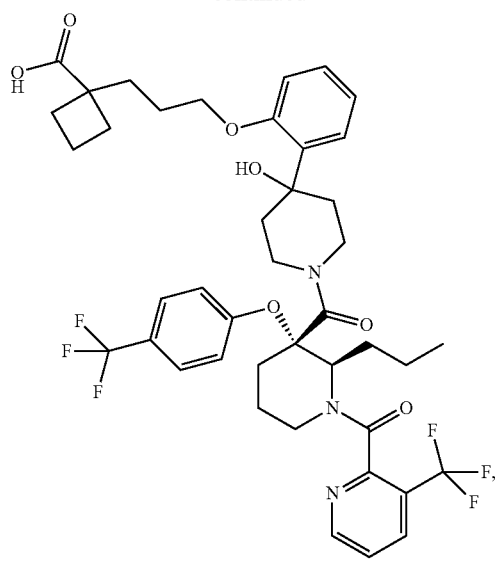
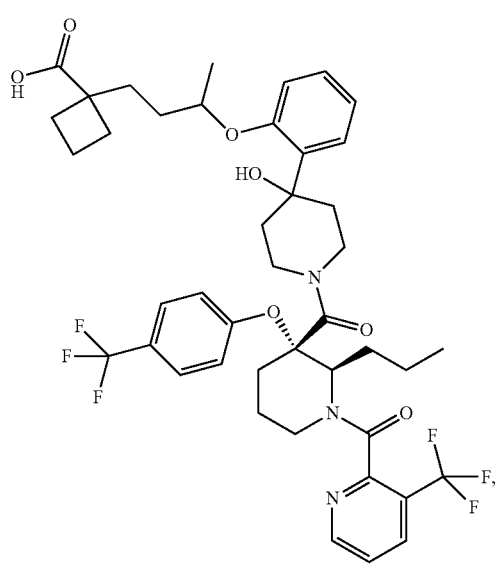
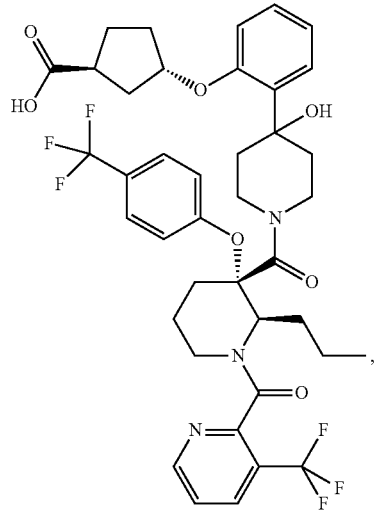
38
-continued
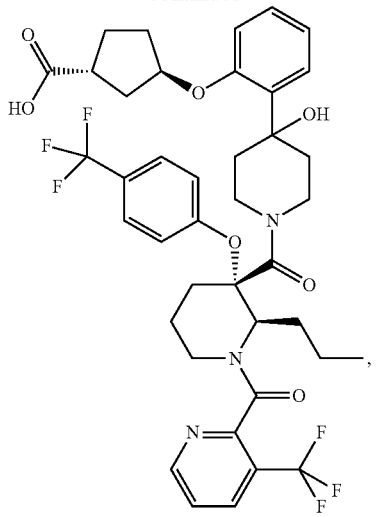
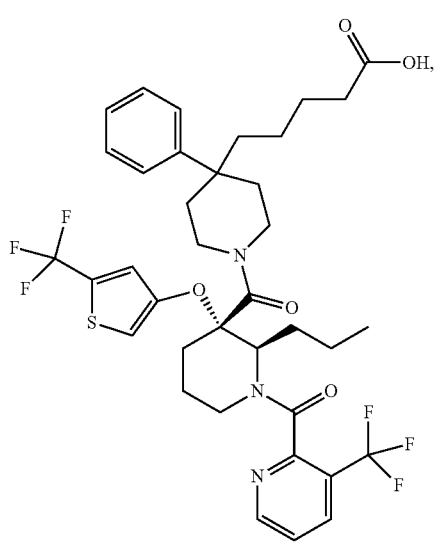
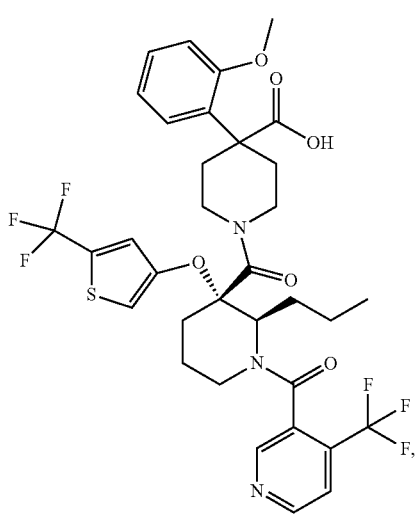

39
-continued
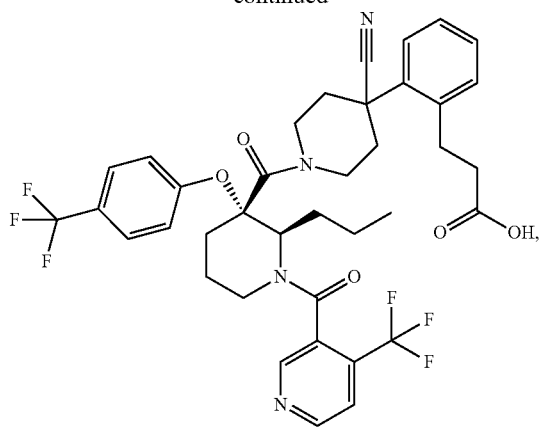
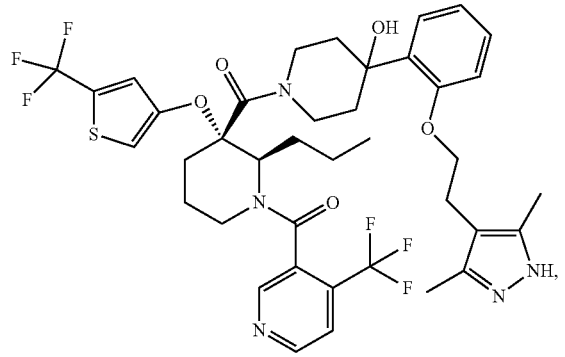
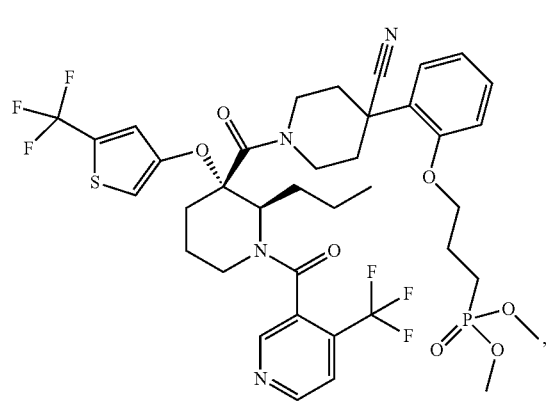
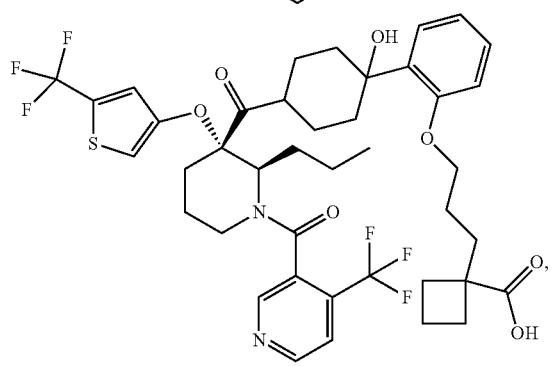
40
-continued
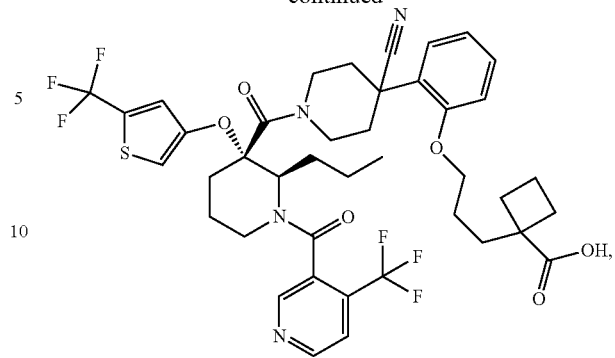
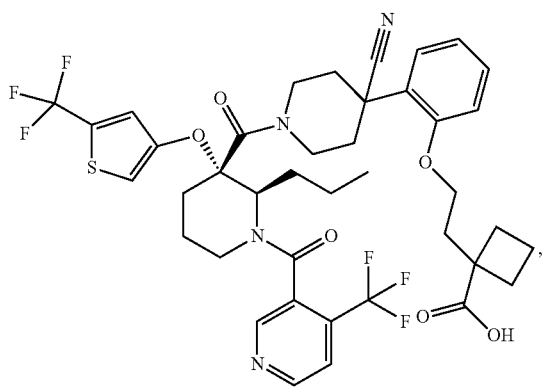
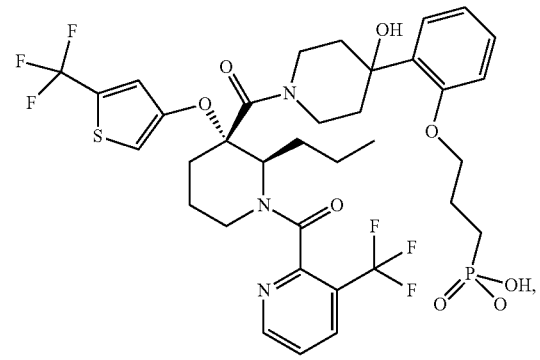
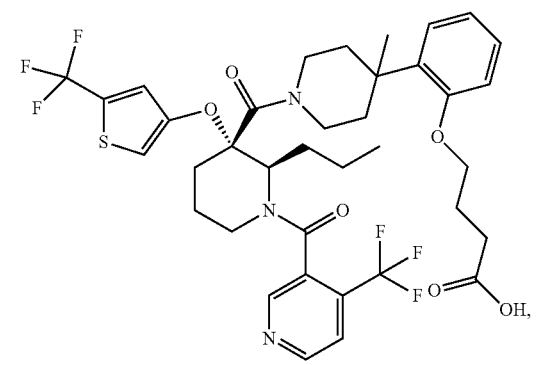

41
-continued
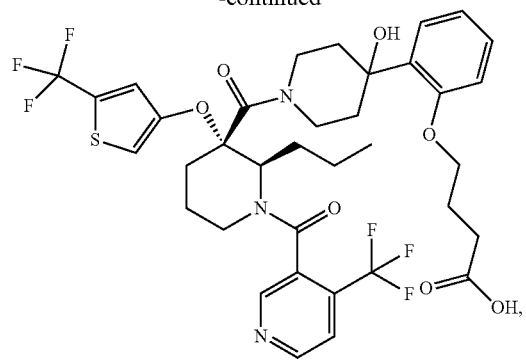
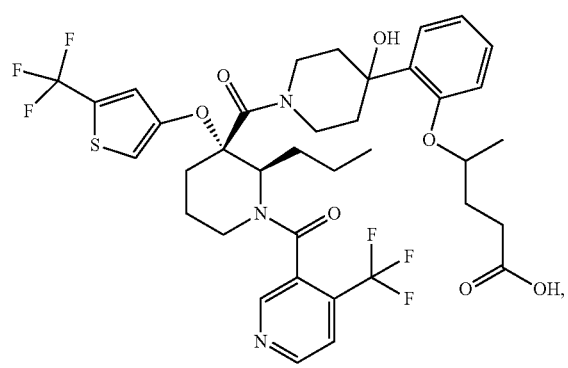
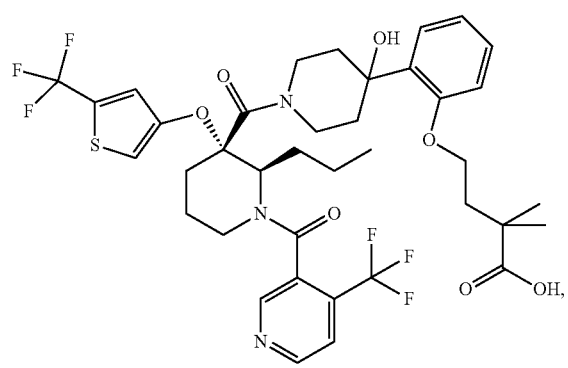
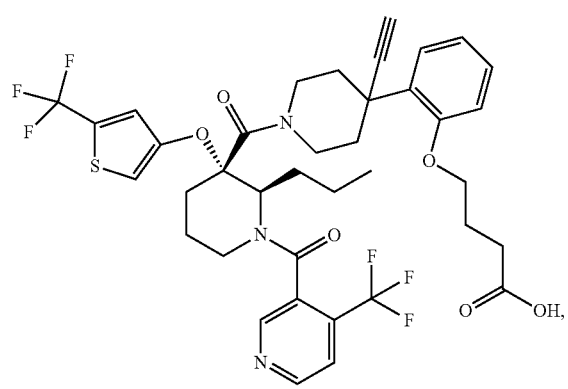
42
-continued
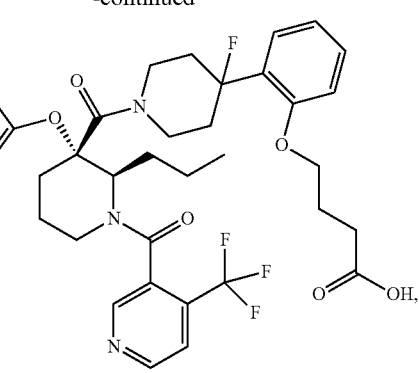
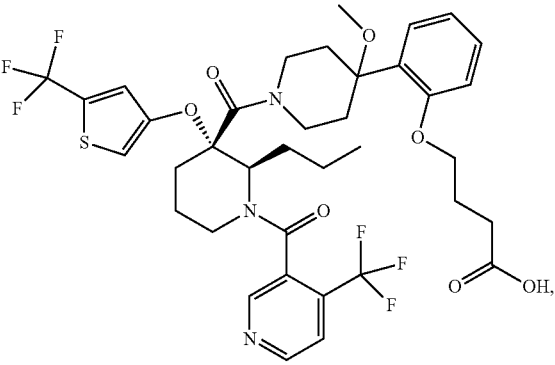
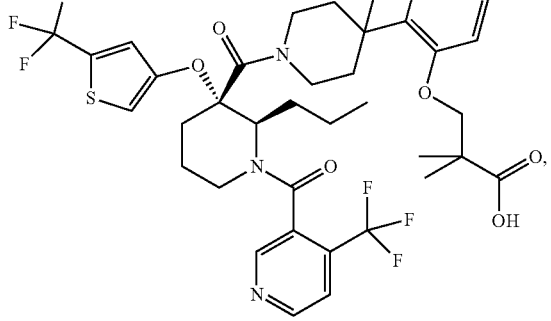
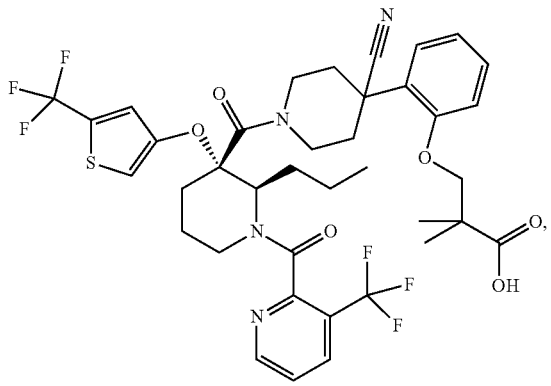

43
-continued
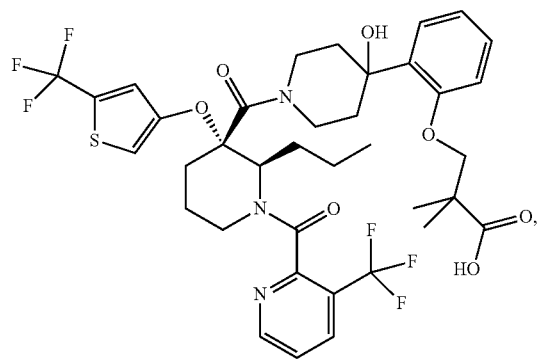
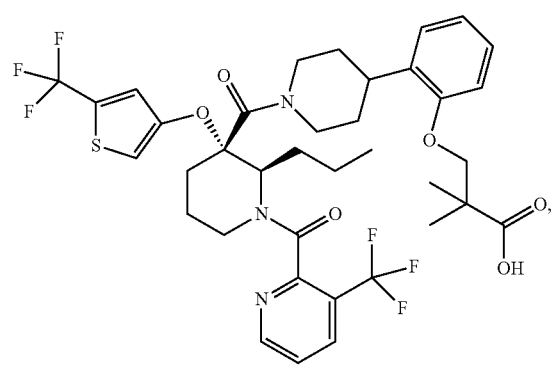
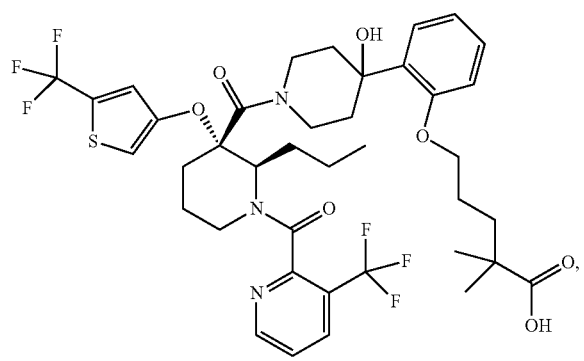
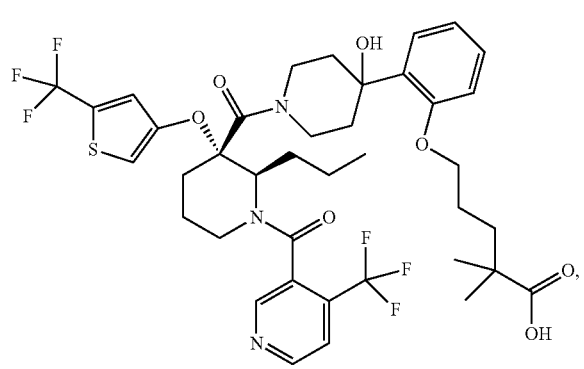
44
-continued
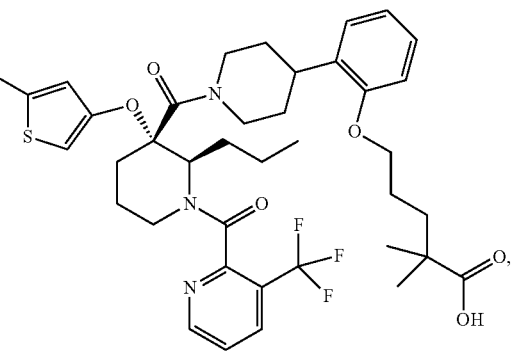
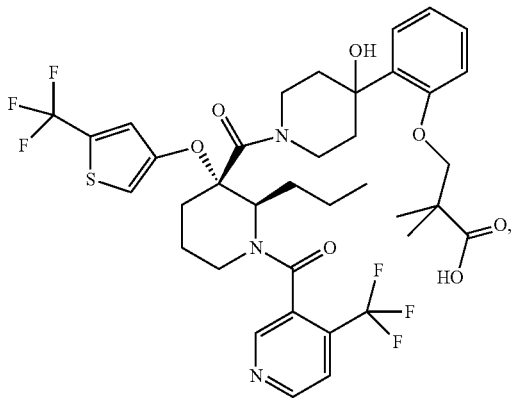
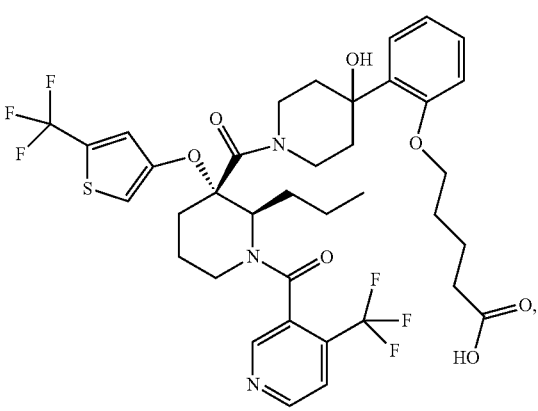

45
-continued
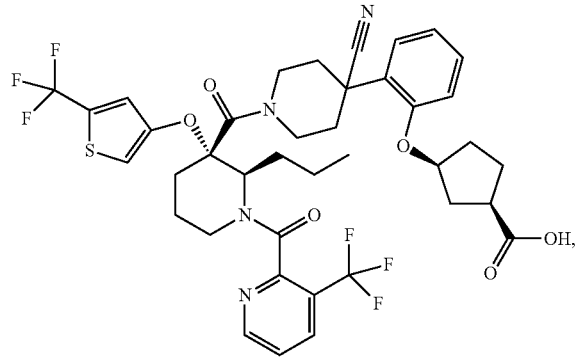
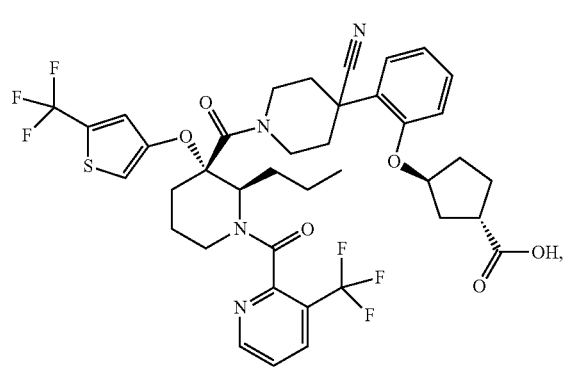
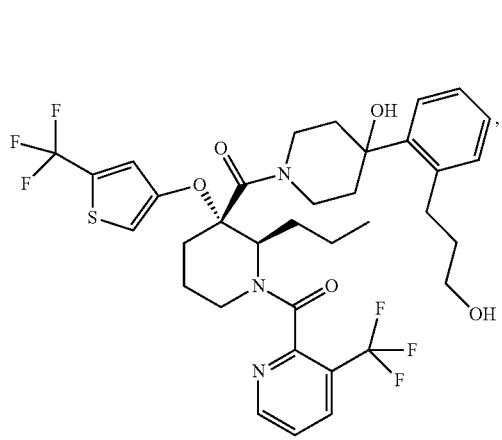
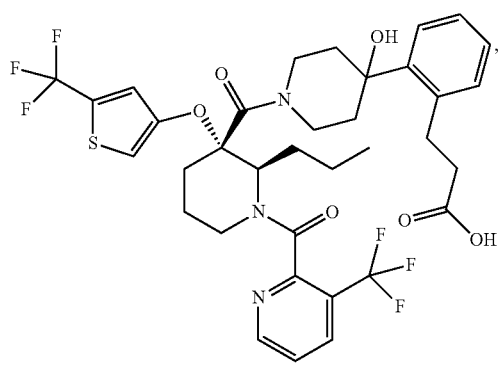
46
-continued
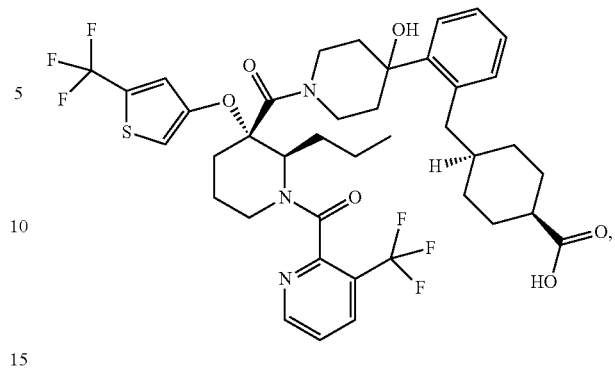
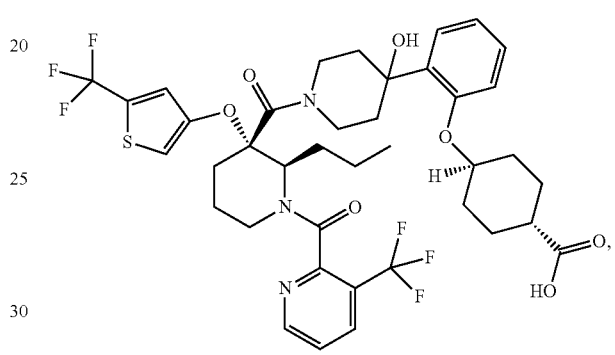
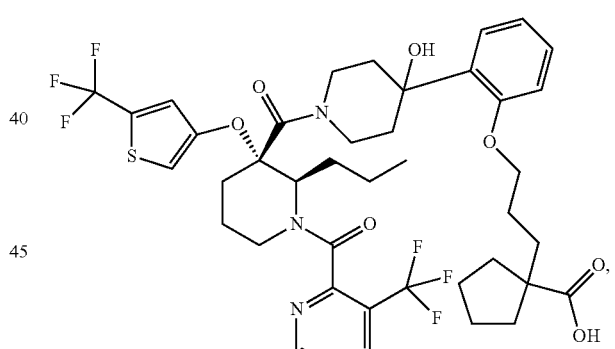
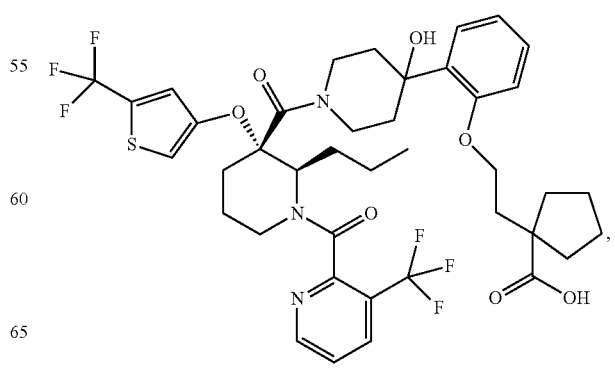

47
-continued
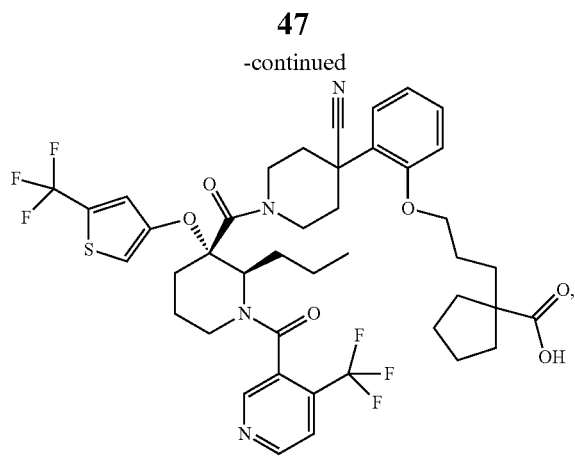
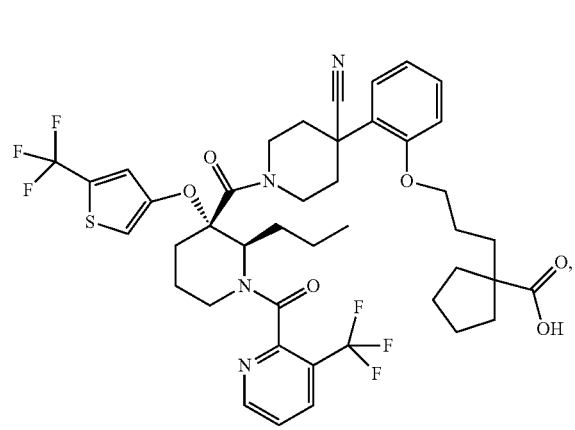
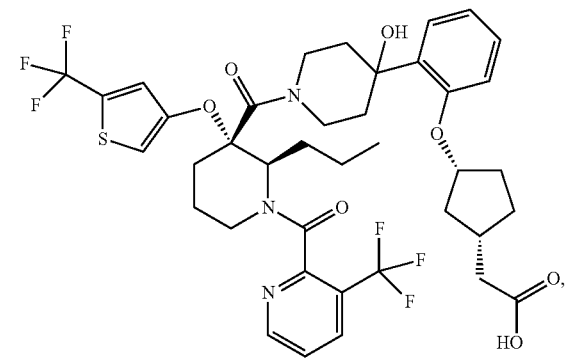
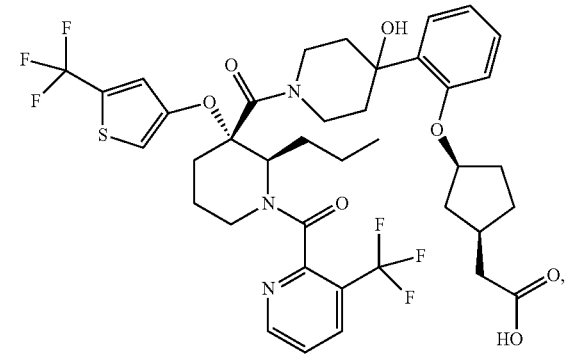
48
-continued
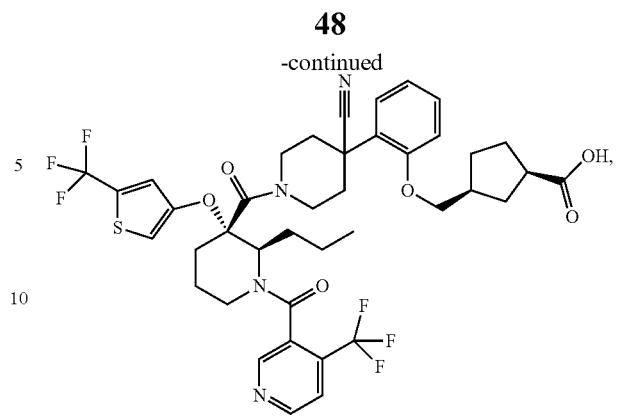
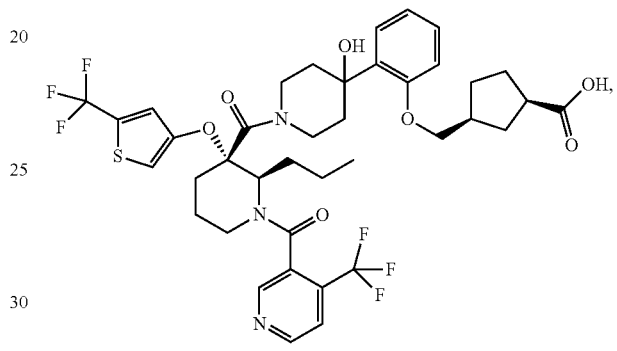
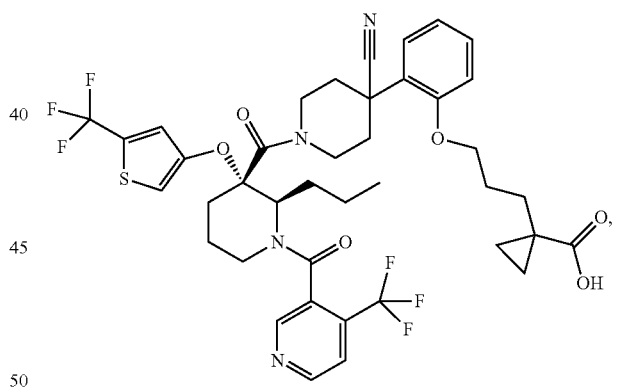
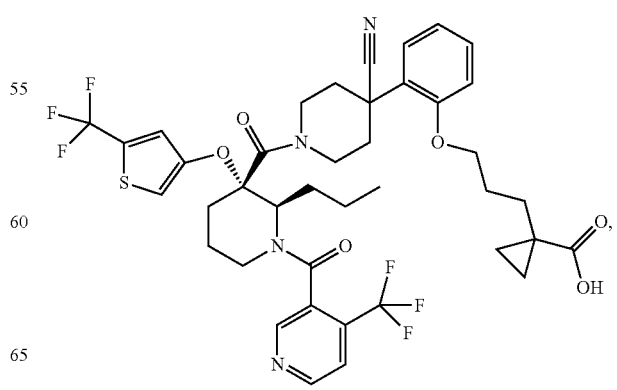

49
-continued
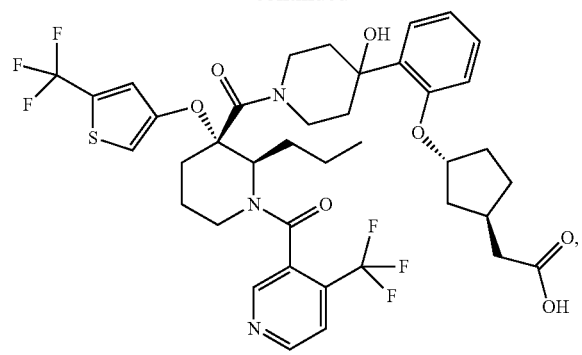
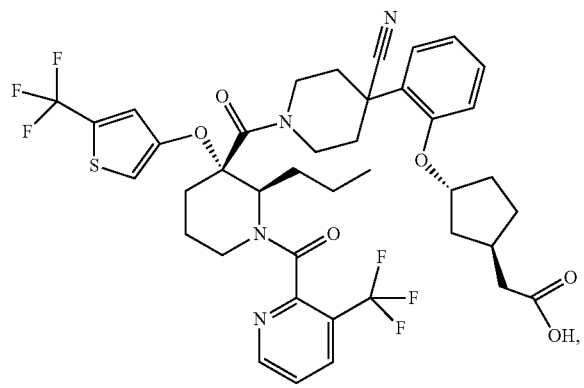
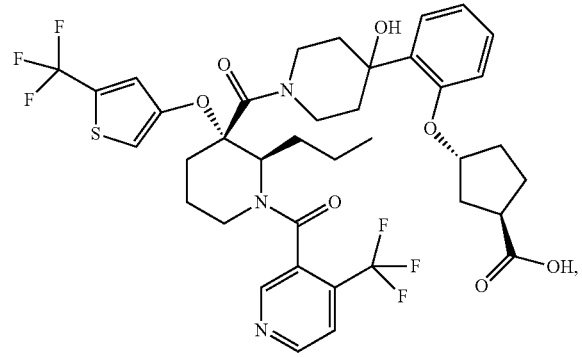
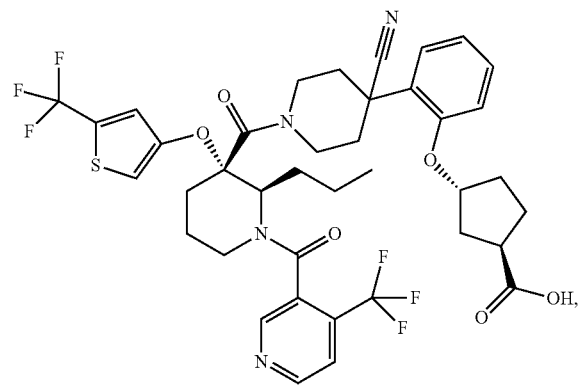
50
-continued
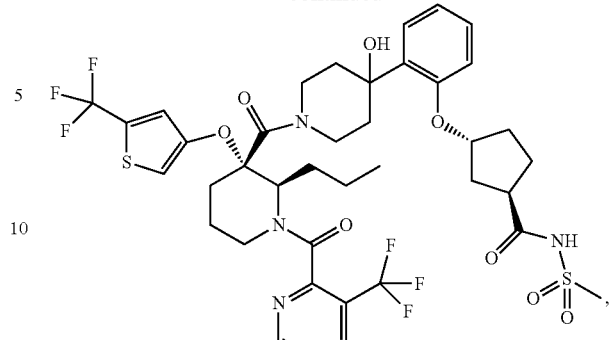
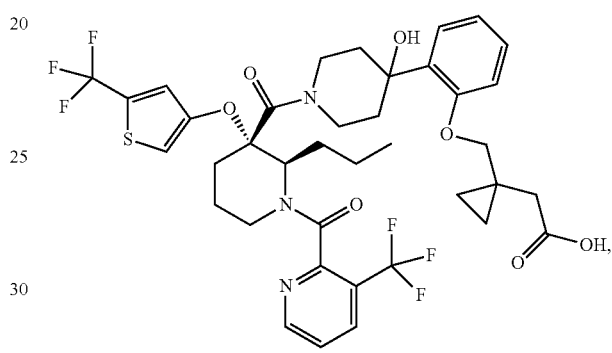
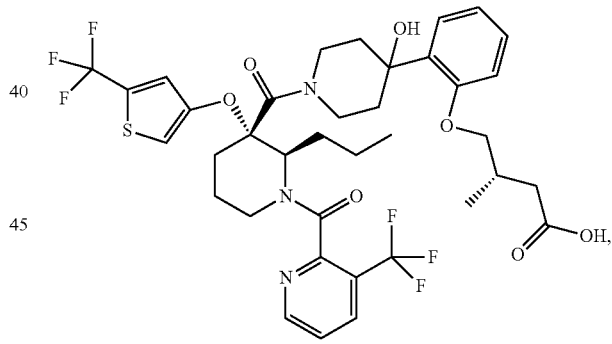
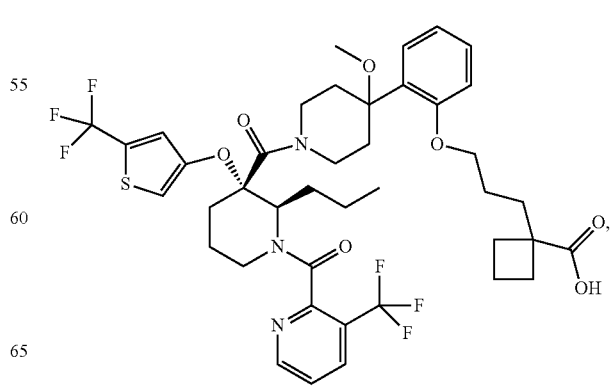

51
-continued
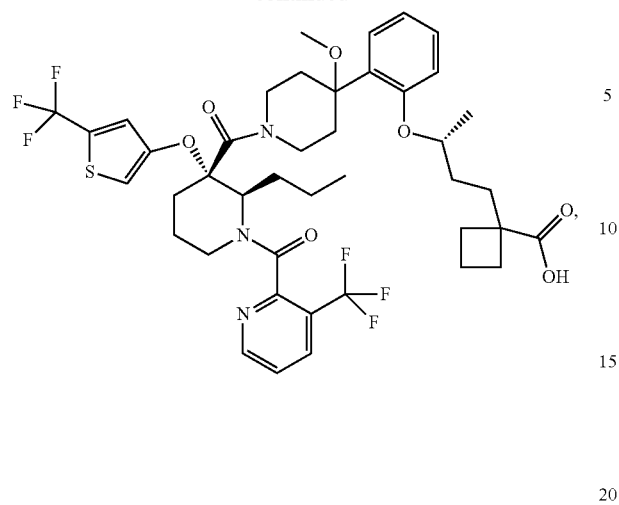
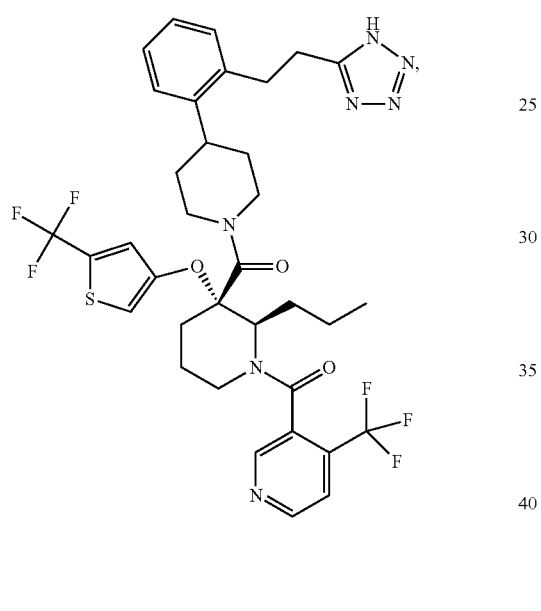
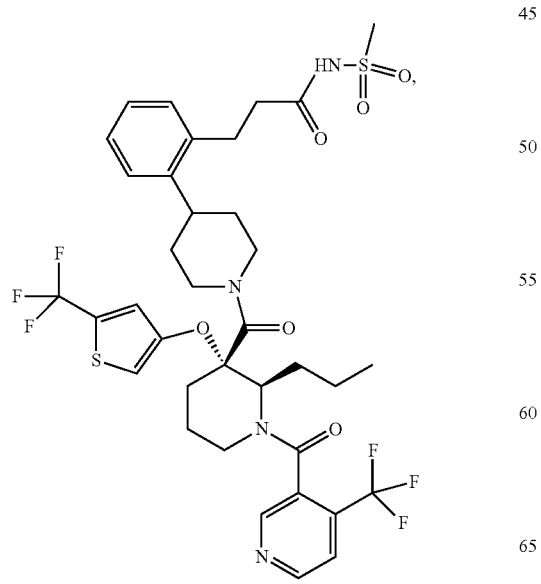
52
-continued
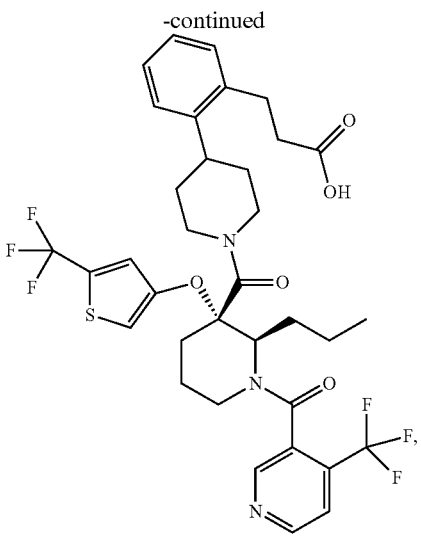
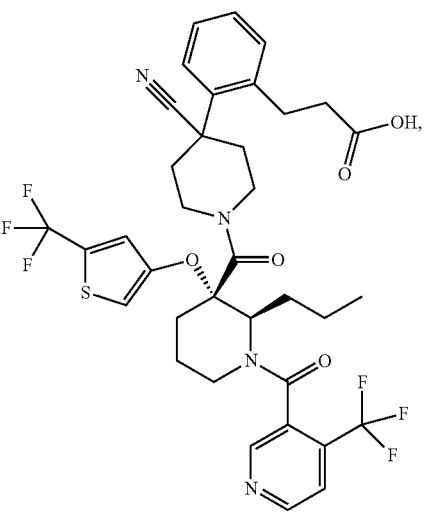
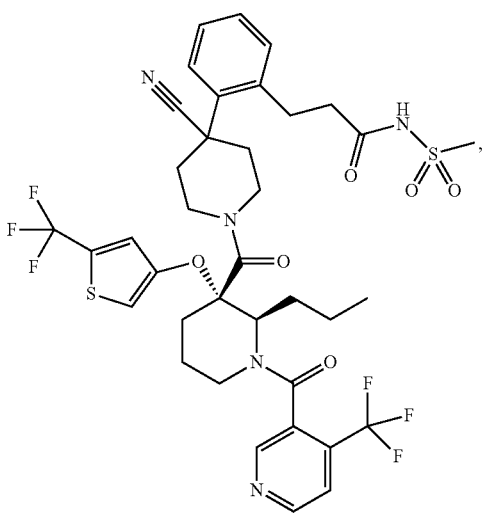

53
-continued
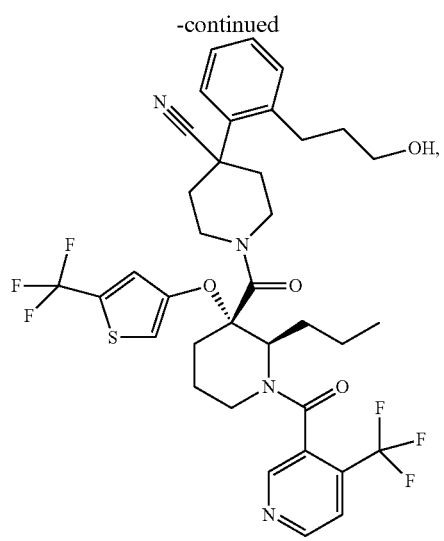
54
-continued
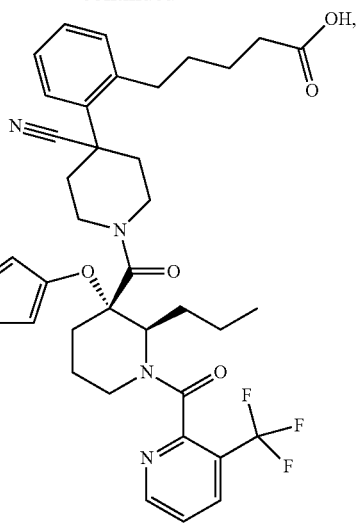
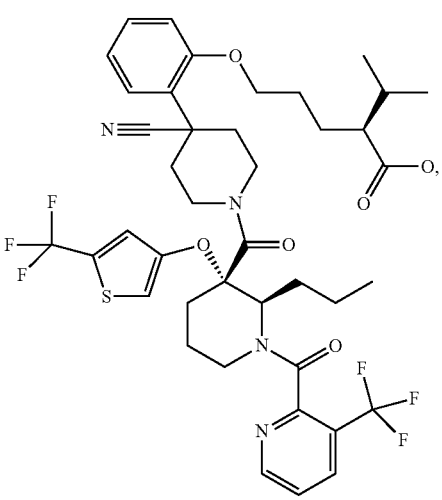
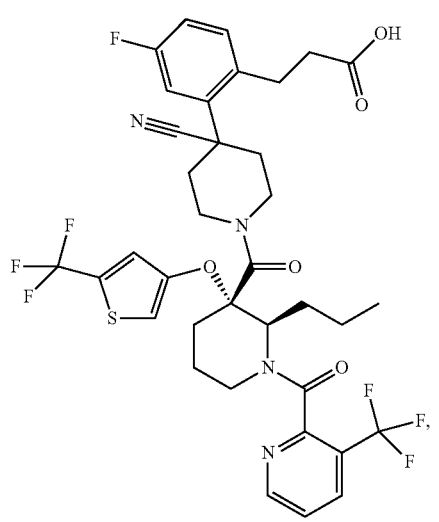
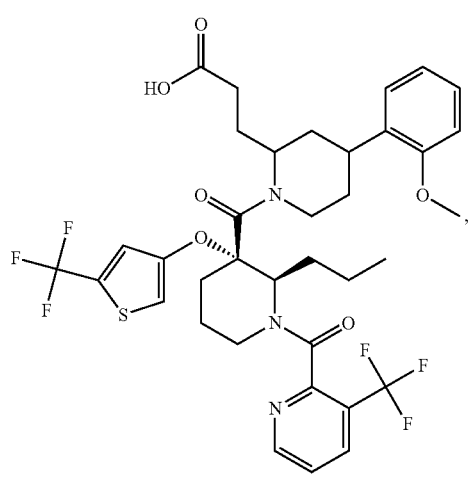

-continued

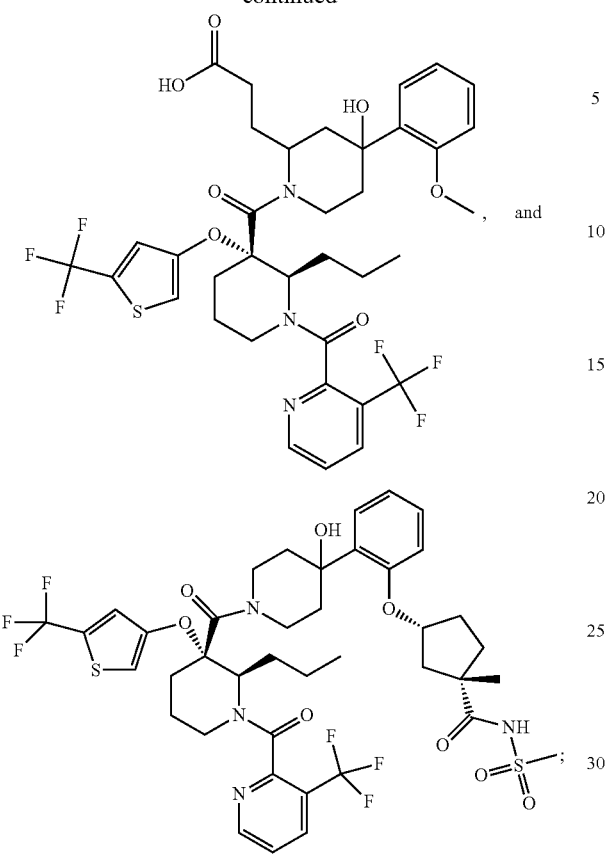

or a pharmaceutically acceptable salt thereof.

In another embodiment, the present invention provides compounds illustrated as Formula 2, as described above, or pharmaceutically acceptable salts, solvates, esters, or prodrugs thereof, wherein the various moieties are as described above.

In another embodiment the compound of Formula 2 wherein $R^4$ or $R^{4'}$, which may be the same or different, are independently selected from the group consisting of hydrogen and alkyl, In another embodiment the compound of Formula 2, wherein $R^5$, $R^{5'}$, $R^6$, $R^{6'}$, $R^7$ and $R^{7'}$ are each independently H.

In another embodiment the compound of Formula 2, wherein J may or may not be present, when J is present it is halo.

In another embodiment the compound of Formula 2, G is selected from the group consisting of —$(CR^8R^{8'})_n$—C(O)OH, —$(CR^8R^{8'})_n$-heteroaryl, —$(CR^8R^{8'})_n$—C(O)NR$^8$R$^9$, —$(CR^8R^{8'})_n$—$(C_3$-$C_8)$Cycloalkyl-C(O)NR$^8$R$^9$, —$(CR^8R^{8'})_n$—$(C_3$-$C_8)$cycloalkyl-$(CR^8R^{8'})_n$—C(O)OH, —$(CR^8R^{8'})_n$—O—$(CR^8R^{8'})_n$—C(O)OH, —$(CR^8R^{8'})_n$—S—$(CR^8R^{8'})_n$—C(O)OH, C(O)OH, —$(CR^8R^{8'})_n$—NH—$(CR^8R^{8'})_n$—C(O)OH, —$(CR^8R^{8'})_n$—O—$(CR^8R^{8'})_n$—CH$_3$, —$(CR^8R^{8'})_n$—S—$(CR^8R^{8'})_n$—CH$_3$, —$(CR^8R^{8'})_n$—NH—$(CR^8R^{8'})_n$—CH$_3$, —$(CR^8R^{8'})_n$—CH$_3$, —$(CR^8R^{8'})_n$-heteroaryl, —$(CR^8R^{8'})_n$—P(O)OR$^8$OR$^{8'}$, —$(CR^8R^{8'})_n$—P(O)O$_2$, —$(CR^8R^{8'})_n$—OH, wherein each $R^8$ and $R^{8'}$ is independently selected from the group consisting of H and $(C_1$-$C_6)$alkyl, or further wherein $R^8$ and $R^{8'}$ together with the carbon to which each is attached can cyclicize to form $(C_3$-$C_8)$spirocycloalkyl, $R^9$ is SO$_2$(C$_1$-C$_6$)alkyl or SO$_2$(C$_3$-C$_8$)cycloalkyl, n is 0-10, providing that when n is 0, G is not attached to Y such that O is linked to O, S, N, or SO$_2$, further providing that when n is 0, G is not attached to Y such that N is linked to O, S or N, and still further providing that when n is 0, G is not attached to Y such that S is linked to O, N or SO$_2$, further wherein, any spirocycloalkyl or cycloalkyl in Formula 2, can be unsubstituted or substituted with one or more (C$_1$-C$_6$)alkyl groups, still further wherein, any Hydrogen atom that is substituted on any alkyl, cycloalkyl, heterocycloalkyl or spirocycloalkyl, in Formula 2, can be replaced by a Deuterium atom.

In another embodiment the compound of Formula 2, wherein $R^8$ and $R^{8'}$ are independently H or (C$_1$-C$_6$)alkyl.

In another embodiment the compound of Formula 2, wherein $R^9$ is SO$_2$(C$_1$-C$_6$)alkyl or SO$_2$(C$_3$-C$_8$)cycloalkyl.

In another embodiment the compound of Formula 2, wherein G is selected from the group consisting of:

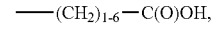

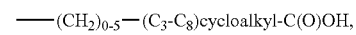
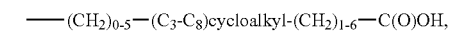

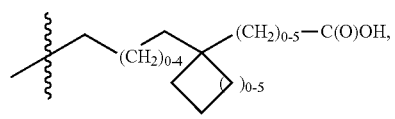

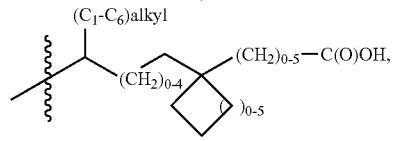

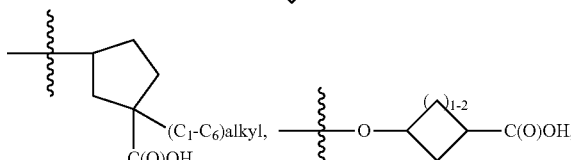

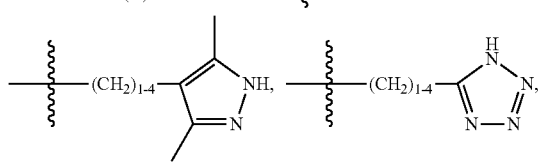

-continued

—(CH₂)₁₋₆—O—(C₁-C₆)alkyl, —(C₁-C₆)alkyl,

—NH—(CH₂)₁₋₃—C(O)OH, —O—(C₃-C₈)cycloalkyl-C(O)OH,

—(CH₂)₁₋₆—O—(CH₂)₁₋₄—C(O)OH,

—(CH₂)₁₋₅—(O)O((C₁-C₆)alkyl)₂, —(CH₂)₁₋₆—OH, (C₃-C₈)(cycloalkyl)-C(O)—N(SO₂)(C₁-C₆)alkyl, and —(C₃-C₈)cycloalkyl providing that G is not attached to Y such that O is linked to O, S, N, or SO₂, further providing that G is not attached to Y such that N is linked to O, S or N, and still further providing that G is not attached to Y such that S is linked to O, N or SO₂.

In another embodiment the compound of Formula 2, wherein J is F.

In another embodiment the compound of Formula 2, wherein R is selected from the group consisting of halogen, —CN, —OH, —SH, (C₁-C₆)alkoxy, —(C₂-C₆)alkenoxy, —(C₁-C₆)alkyl, —(C₂-C₆)alkenyl, haloalkoxy, —C(O)NR¹⁰R¹¹, —C(O)OR¹⁰, —OC(O)R¹⁰, —NR¹⁰C(O)R¹¹, —NR¹⁰R¹¹, —S-alkyl, —S-alkenyl, —S-haloalkyl, (C₂-C₆) alkynyl, haloalkyl, haloalkenyl-, G is selected from the group consisting of —(CR⁸R⁸')ₙ—C(O)OH, —(CR⁸R⁸')ₙ-heteroaryl, —(CR⁸R⁸')ₙ—C(O)NR⁸R⁹, —(CR⁸R⁸')ₙ—(C₃-C₈)cycloalkyl-C(O)NR⁸R⁹, —(CR⁸R⁸')ₙ—(C₃-C₈)cycloalkyl-(CR⁸R⁸')ₙ—C(O)OH, —(CR⁸R⁸')ₙ—O—(CR⁸R⁸')ₙ—C(O)OH, —(CR⁸R⁸')ₙ—S—(CR⁸R⁸')ₙ—C(O)OH, —(CR⁸R⁸')ₙ—NH—(CR⁸R⁸')ₙ—C(O)OH, —(CR⁸R⁸')ₙ—O—(CR⁸R⁸')ₙ—CH₃, —(CR⁸R⁸')ₙ—S—(CR⁸R⁸'R⁸')ₙ—CH₃, —(CR⁸R⁸')ₙ—NH—(CR⁸R⁸')ₙ—CH₃, —(CR⁸R⁸')ₙ—CH₃, —(CR⁸R⁸')ₙ- heteroaryl, —(CR⁸R⁸')ₙ—P(O)OR⁸OR⁸', —(CR⁸R⁸')ₙ—P(O)O₂, —(CR⁸R⁸')ₙ—OH, wherein each R⁸ and R⁸' is independently selected from the group consisting of H and (C₁-C₆)alkyl; or further wherein R⁸ and R⁸' together with the carbon to which each is attached can cyclicize to form (C₃-C₈)spirocycloalkyl, R⁹ is SO₂(C₁-C₆)alkyl or SO₂(C₃-C₈)cycloalkyl, n is 0-10, further wherein, any spirocycloalkyl or cycloalkyl in Formula 2, can be unsubstituted or substituted with one or more (C₁-C₆)alkyl groups.

In another embodiment, in Formula 2, R¹ is

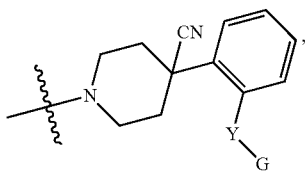

wherein Y is selected from the group consisting of O, S, NR⁸, SO₂ and CH₂ and G is selected from the group consisting of —(CR⁸R⁸')ₙ—C(O)OH, —(CR⁸R⁸')ₙ-heteroaryl, —(CR⁸R⁸')ₙ—C(O)NR⁸R⁹, —(CR⁸R⁸')ₙ—(C₃-C₈)cycloalkyl-C(O)NR⁸R⁹, —(CR⁸R⁸')ₙ—(C₃-C₈)cycloalkyl-(CR⁸R⁸')ₙ—C(O)OH, —(CR⁸R⁸')ₙ—O—(CR⁸R⁸')ₙ—C(O)OH, —(CR⁸R⁸')ₙ—S—(CR⁸R⁸')ₙ—C(O)OH, C(O)OH, —(CR⁸R⁸')ₙ—NH—(CR⁸R⁸')ₙ—C(O)OH, —(CR⁸R⁸')ₙ—O—(CR⁸R⁸')ₙ—CH₃, —(CR⁸R⁸')ₙ—S—(CR⁸R⁸')ₙ—CH₃, —(CR⁸R⁸')ₙ—NH—(CR⁸R⁸')ₙ—CH₃, —(CR⁸R⁸')ₙ—CH₃, —(CR⁸R⁸')ₙ-heteroaryl, —(CR⁸R⁸')ₙ—P(O)OR⁸OR⁸', —(CR⁸R⁸')ₙ—P(O)O₂, —(CR⁸R⁸')ₙ—OH, wherein each R⁸ and R⁸' is independently selected from the group consisting of H and (C₁-C₆)alkyl, or further wherein R⁸ and R⁸' together with the carbon to which each is attached can cyclicize to form (C₃-C₈)spirocycloalkyl, R⁹ is SO₂(C₁-C₆)alkyl or SO₂(C₃-C₈)cycloalkyl, n is 0-10, providing that when n is 0, G is not attached to Y such that O is linked to O, S, N, or SO₂, further providing that when n is 0, G is not attached to Y such that N is linked to O, S or N, and still further providing that when n is 0, G is not attached to Y such that S is linked to O, N or SO₂, further wherein, any spirocycloalkyl or cycloalkyl in Formula 2, can be unsubstituted or substituted with one or more (C₁-C₆)alkyl groups, still further wherein, any Hydrogen atom that is substituted on any alkyl, cycloalkyl, heterocycloalkyl or spirocycloalkyl, in Formula 2, can be replaced by a Deuterium atom.

In another embodiment, in Formula 2, R¹ is

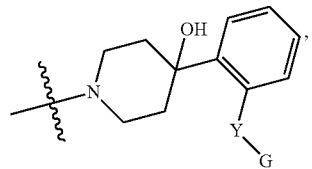

wherein Y is selected from the group consisting of O, S, NR⁸, SO₂ and CH₂ and G is selected from the group consisting of —(CR⁸R⁸')ₙ—C(O)OH, —(CR⁸R⁸')ₙ-heteroaryl, —(CR⁸R⁸')ₙ—C(O)NR⁸R⁹, —(CR⁸R⁸')ₙ—(C₃-C₈)cycloalkyl-C(O)NR⁸R⁹, —(CR⁸R⁸')ₙ—(C₃-C₈)cycloalkyl-(CR⁸R⁸')ₙ—C(O)OH, —(CR⁸R⁸')ₙ—O—(CR⁸R⁸')ₙ—C(O)OH, —(CR⁸R⁸')ₙ—S—(CR⁸R⁸')ₙ—C(O)OH, —(CR⁸R⁸')ₙ—NH—(CR⁸R⁸')ₙ—C(O)OH, —(CR⁸R⁸')ₙ—O—(CR⁸R⁸')ₙ—CH₃, —(CR⁸R⁸')ₙ—S—(CR⁸R⁸')ₙ—CH₃, —(CR⁸R⁸')ₙ—NH—(CR⁸R⁸')ₙ—CH₃, —(CR⁸R⁸')ₙ—CH₃, —(CR⁸R⁸')ₙ-heteroaryl, —(CR⁸R⁸')ₙ—P(O)OR⁸OR⁸', —(CR⁸R⁸')ₙ—P(O)O₂, —(CR⁸R⁸')ₙ—OH, wherein each R⁸ and R⁸' is independently selected from the group consisting of H and (C₁-C₆)alkyl, or further wherein R⁸ and R⁸' together with the carbon to which each is attached can cyclicize to form (C₃-C₈)spirocycloalkyl, R⁹ is SO₂(C₁-C₆)alkyl or SO₂(C₃-C₈)cycloalkyl, n is 0-10, providing that when n is 0, G is not attached to Y such that O is linked to O, S, N, or SO₂, further providing that when n is 0, G is not attached to Y such that N is linked to O, S or N, and still further providing that when n is 0, G is not attached to Y such that S is linked to O, N or SO₂, further wherein, any spirocycloalkyl or cycloalkyl in Formula 2, can be unsubstituted or substituted with one or more (C₁-C₆)alkyl groups, still further wherein, any Hydrogen atom that is substituted on any alkyl, cycloalkyl, heterocycloalkyl or spirocycloalkyl, in Formula 2, can be replaced by a Deuterium atom.

In another embodiment, in Formula 2, $R^1$ is

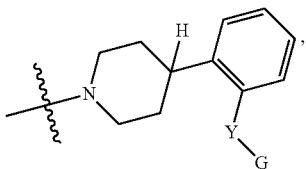

wherein Y is selected from the group consisting of O, S, $NR^8$, $SO_2$ and $CH_2$ and G is selected from the group consisting of —$(CR^8R^{8'})_n$—C(O)OH, —$(CR^8R^{8'})_n$-heteroaryl, —$(CR^8R^{8'})_n$—C(O)$NR^8R^9$, —$(CR^8R^{8'})_n$—($C_3$-$C_8$)cycloalkyl-C(O)$NR^8R^9$, —$(CR^8R^{8'})_n$—($C_3$-$C_8$)cycloalkyl-$(CR^8R^{8'})_n$—C(O)OH, —$(CR^8R^{8'})_n$—O—$(CR^8R^{8'})_n$—C(O)OH, —$(CR^8R^{8'})_n$—S—$(CR^8R^{8'})_n$—C(O)OH, C(O)OH, —$(CR^8R^{8'})_n$—NH—$(CR^8R^{8'})_n$—C(O)OH, —$(CR^8R^{8'})_n$—O—$(CR^8R^{8'})_n$—$CH_3$, —$(CR^8R^{8'})_n$—S—$(CR^8R^{8'})_n$—$CH_3$, —$(CR^8R^{8'})_n$—NH—$(CR^8R^{8'})_n$—$CH_3$, —$(CR^8R^{8'})_n$—$CH_3$, —$(CR^8R^{8'})_n$-heteroaryl, —$(CR^8R^{8'})_n$—P(O)$OR^8OR^{8'}$, —$(CR^8R^{8'})_n$—P(O)$O_2$, —$(CR^8R^{8'})_n$—OH, wherein each $R^8$ and $R^{8'}$ is independently selected from the group consisting of H and ($C_1$-$C_6$)alkyl, or further wherein $R^8$ and $R^{8'}$ together with the carbon to which each is attached can cyclicize to form ($C_3$-$C_8$)spirocycloalkyl, $R^9$ is $SO_2$($C_1$-$C_6$)alkyl or $SO_2$($C_3$-$C_8$)cycloalkyl, n is 0-10, providing that when n is 0, G is not attached to Y such that O is linked to O, S, N, or $SO_2$, further providing that when n is 0, G is not attached to Y such that N is linked to O, S or N, and still further providing that when n is 0, G is not attached to Y such that S is linked to O, N or $SO_2$, further wherein, any spirocycloalkyl or cycloalkyl in Formula 2, can be unsubstituted or substituted with one or more ($C_1$-$C_6$)alkyl groups, still further wherein, any Hydrogen atom that is substituted on any alkyl, cycloalkyl, heterocycloalkyl or spirocycloalkyl, in Formula 2, can be replaced by a Deuterium atom.

In another embodiment, in Formula 2, $R^1$ is

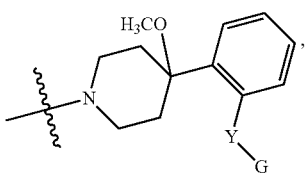

wherein Y is selected from the group consisting of O, S, $NR^8$, $SO_2$ and $CH_2$ and G is selected from the group consisting of —$(CR^8R^{8'})_n$—C(O)OH, —$(CR^8R^{8'})_n$-heteroaryl, —$(CR^8R^{8'})_n$—C(O)$NR^8R^9$, —$(CR^8R^{8'})_n$—($C_3$-$C_8$)cycloalkyl-C(O)$NR^8R^9$, —$(CR^8R^{8'})_n$—($C_3$-$C_8$)cycloalkyl-$(CR^8R^{8'})_n$—C(O)OH, —$(CR^8R^{8'})_n$—O—$(CR^8R^{8'})_n$—C(O)OH, —$(CR^8R^{8'})_n$—S—$(CR^8R^{8'})_n$—C(O)OH, C(O)OH, —$(CR^8R^{8'})_n$—NH—$(CR^8R^{8'})_n$—C(O)OH, —$(CR^8R^{8'})_n$—O—$(CR^8R^{8'})_n$—$CH_3$, —$(CR^8R^{8'})_n$—S—$(CR^8R^{8'})_n$—$CH_3$, —$(CR^8R^{8'})_n$—NH—$(CR^8R^{8'})_n$—$CH_3$, —$(CR^8R^{8'})_n$—$CH_3$, —$(CR^8R^{8'})_n$-heteroaryl, —$(CR^8R^{8'})_n$—P(O)$OR^8OR^{8'}$, —$(CR^8R^{8'})_n$—P(O)$O_2$, —$(CR^8R^{8'})_n$—OH, wherein each $R^8$ and $R^{8'}$ is independently selected from the group consisting of H and ($C_1$-$C_6$)alkyl, or further wherein $R^8$ and $R^{8'}$ together with the carbon to which each is attached can cyclicize to form ($C_3$-$C_8$)spirocycloalkyl, $R^9$ is $SO_2$($C_1$-$C_6$)alkyl or $SO_2$($C_3$-$C_8$)cycloalkyl, n is 0-10, providing that when n is 0, G is not attached to Y such that O is linked to O, S, N, or $SO_2$, further providing that when n is 0, G is not attached to Y such that N is linked to O, S or N, and still further providing that when n is 0, G is not attached to Y such that S is linked to O, N or $SO_2$, further wherein, any spirocycloalkyl or cycloalkyl in Formula 2, can be unsubstituted or substituted with one or more ($C_1$-$C_6$)alkyl groups, still further wherein, any Hydrogen atom that is substituted on any alkyl, cycloalkyl, heterocycloalkyl or spirocycloalkyl, in Formula 2, can be replaced by a Deuterium atom.

In another embodiment, in Formula 2, $R^1$ is

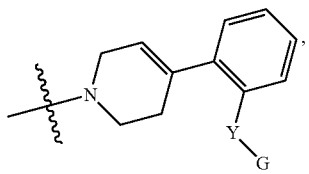

wherein Y is selected from the group consisting of O, S, $NR^8$, $SO_2$ and $CH_2$ and G is selected from the group consisting of —$(CR^8R^{8'})_n$—C(O)OH, —$(CR^8R^{8'})_n$-heteroaryl, —$(CR^8R^{8'})_n$—C(O)$NR^8R^9$, —$(CR^8R^{8'})_n$—($C_3$-$C_8$)cycloalkyl-C(O)$NR^8R^9$, —$(CR^8R^{8'})_n$—($C_3$-$C_8$)cycloalkyl-$(CR^8R^{8'})_n$—C(O)OH, —$(CR^8R^{8'})_n$—O—$(CR^8R^{8'})_n$—C(O)OH, —$(CR^8R^{8'})_n$—S—$(CR^8R^{8'})_n$—C(O)OH, C(O)OH, —$(CR^8R^{8'})_n$—NH—$(CR^8R^{8'})_n$—C(O)OH, —$(CR^8R^{8'})_n$—O—$(CR^8R^{8'})_n$—$CH_3$, —$(CR^8R^{8'})_n$—S—$(CR^8R^{8'})_n$—$CH_3$, —$(CR^8R^{8'})_n$—NH—$(CR^8R^{8'})_n$—$CH_3$, —$(CR^8R^{8'})_n$—$CH_3$, —$(CR^8R^{8'})_n$-heteroaryl, —$(CR^8R^{8'})_n$—P(O)$OR^8OR^{8'}$, —$(CR^8R^{8'})_n$—P(O)$O_2$, —$(CR^8R^{8'})_n$—OH, wherein each $R^8$ and $R^{8'}$ is independently selected from the group consisting of H and ($C_1$-$C_6$)alkyl, or further wherein $R^8$ and $R^{8'}$ together with the carbon to which each is attached can cyclicize to form ($C_3$-$C_8$)spirocycloalkyl, $R^9$ is $SO_2$($C_1$-$C_6$)alkyl or $SO_2$($C_3$-$C_8$)cycloalkyl, n is 0-10, providing that when n is 0, G is not attached to Y such that O is linked to O, S, N, or $SO_2$, further providing that when n is 0, G is not attached to Y such that N is linked to O, S or N, and still further providing that when n is 0, G is not attached to Y such that S is linked to O, N or $SO_2$, further wherein, any spirocycloalkyl or cycloalkyl in Formula 2, can be unsubstituted or substituted with one or more ($C_1$-$C_6$)alkyl groups, still further wherein, any Hydrogen atom that is substituted on any alkyl, cycloalkyl, heterocycloalkyl or spirocycloalkyl, in Formula 2, can be replaced by a Deuterium atom.

In another embodiment, in Formula 2, $R^1$ is

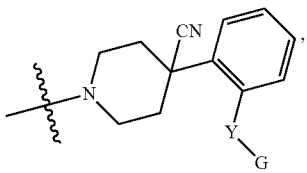

wherein Y is selected from the group consisting of O, S, $NR^8$, $SO_2$ and $CH_2$ and G is selected from the group consisting of:

—$(CH_2)_{1-6}$—C(O)OH,

—$(CH_2)_{0-4}$CH(($C_1$-$C_6$)alkyl)-$(CH_2)_{1-5}$—C(O)OH,

—$(CH_2)_{1-5}$—CH(($C_1$-$C_6$)alkyl)-C(O)OH,

—$(CH_2)_{0-5}$—($C_3$-$C_8$)cycloalkyl-C(O)OH,

—$(CH_2)_{0-5}$—($C_3$-$C_8$)cycloalkyl-$(CH_2)_{1-6}$-C(O)OH,

—$(CH_2)_{1-6}$—C(O)—NH—$SO_2$—($C_3$-$C_8$)cycloalkyl,

—$(CH_2)_{1-6}$—C(O)—N—$SO_2$—($C_1$-$C_6$)alkyl,

—$(CD_2)_{1-6}$—C(O)OH,

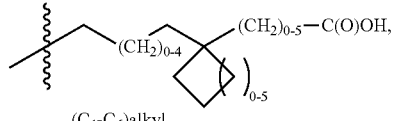

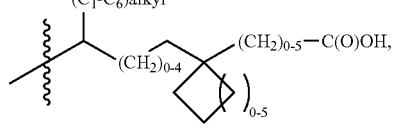

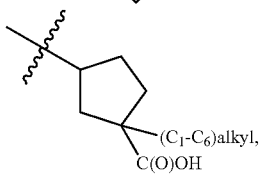

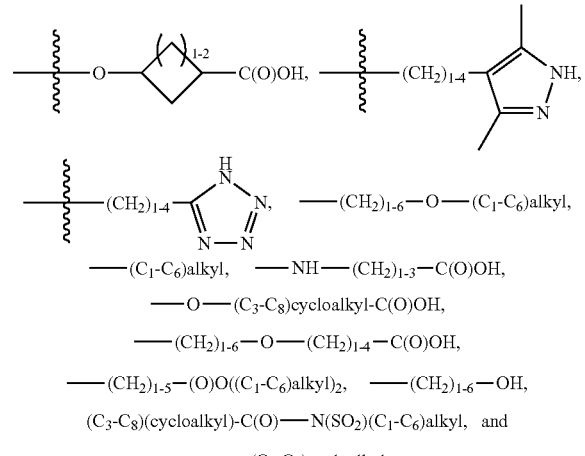

providing that G is not attached to Y such that O is linked to O, S, N, or $SO_2$, further providing that G is not attached to Y such that N is linked to O, S or N, and still further providing that G is not attached to Y such that S is linked to O, N or $SO_2$.

In another embodiment, in Formula 2, $R^1$ is

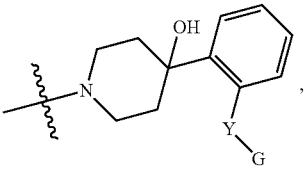

wherein Y is selected from the group consisting of O, S, $NR^8$, $SO_2$ and $CH_2$ and G is selected from the group consisting of:

—$(CH_2)_{1-6}$—C(O)OH,

—$(CH_2)_{0-4}$CH(($C_1$-$C_6$)alkyl)-$(CH_2)_{1-5}$—C(O)OH,

—$(CH_2)_{1-5}$—CH(($C_1$-$C_6$)alkyl)-C(O)OH,

—$(CH_2)_{0-5}$—($C_3$-$C_8$)cycloalkyl-C(O)OH,

—$(CH_2)_{0-5}$—($C_3$-$C_8$)cycloalkyl-$(CH_2)_{1-6}$-C(O)OH,

—$(CH_2)_{1-6}$—C(O)—NH—$SO_2$—($C_3$-$C_8$)cycloalkyl,

—$(CH_2)_{1-6}$—C(O)—N—$SO_2$—($C_1$-$C_6$)alkyl,

—$(CD_2)_{1-6}$—C(O)OH,

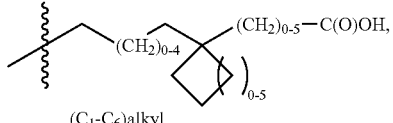

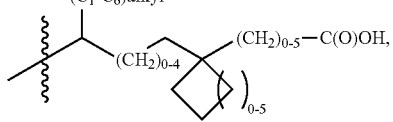

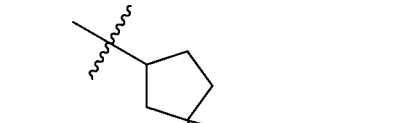

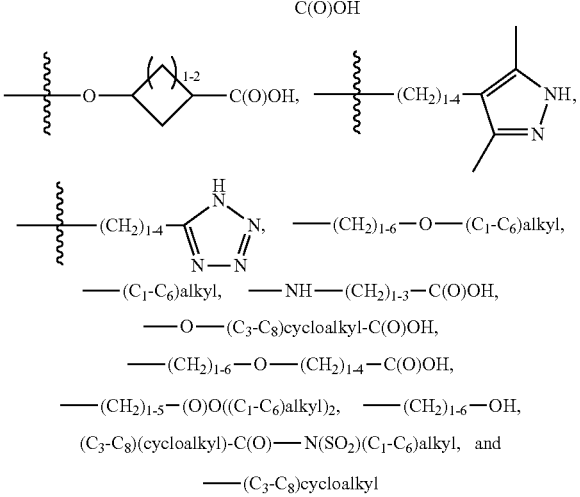

providing that G is not attached to Y such that O is linked to O, S, N, or $SO_2$, further providing that G is not attached to Y such that N is linked to O, S or N, and still further providing that G is not attached to Y such that S is linked to O, N or SO$_2$.

In another embodiment, in Formula 2, R$^1$ is

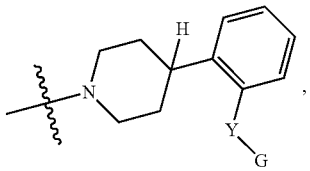, wherein Y is selected from the group consisting of O, S, NR$^8$, SO$_2$ and CH$_2$ and G is selected from the group consisting of:

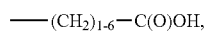

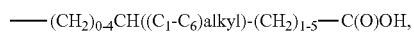

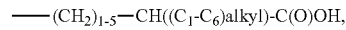

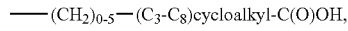

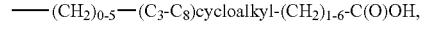

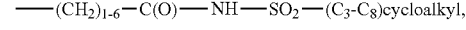

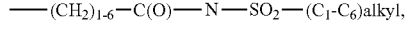

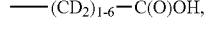

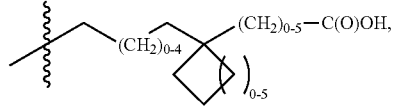

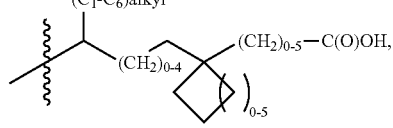

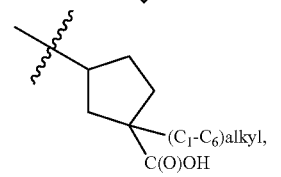

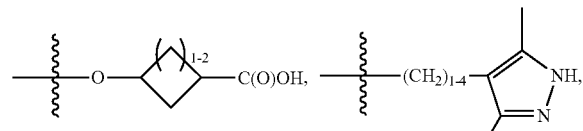

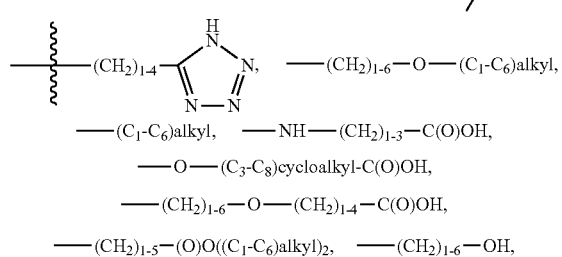

-continued

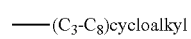, and

—(C$_3$-C$_8$)cycloalkyl providing that G is not attached to Y such that O is linked to O, S, N, or SO$_2$, further providing that G is not attached to Y such that N is linked to O, S or N, and still further providing that G is not attached to Y such that S is linked to O, N or SO$_2$.

In another embodiment, in Formula 2, R$^1$ is G

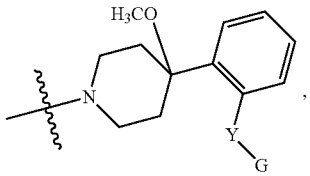, wherein Y is selected from the group consisting of O, S, NR$^8$, SO$_2$ and CH$_2$ and G is selected from the group consisting of:

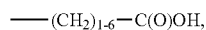

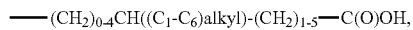

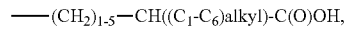

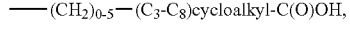

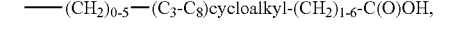

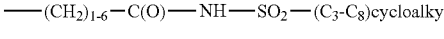

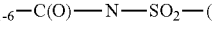

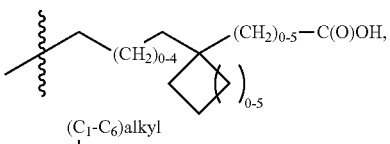

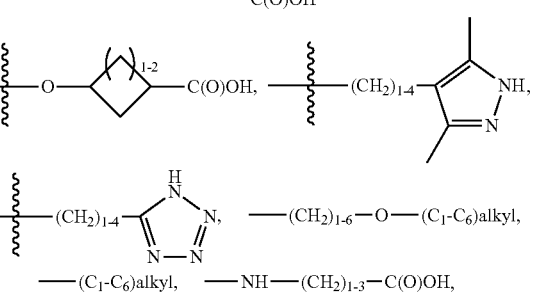

-continued

—O—(C$_3$-C$_8$)cycloalkyl-C(O)OH,

—(CH$_2$)$_{1-6}$—O—(CH$_2$)$_{1-4}$—C(O)OH,

—(CH$_2$)$_{1-5}$—(O)O((C$_1$-C$_6$)alkyl)$_2$, —(CH$_2$)$_{1-6}$—OH, (C$_3$-C$_8$)(cycloalkyl)-C(O)—N(SO$_2$)(C$_1$-C$_6$)alkyl, and —(C$_3$-C$_8$)cycloalkyl providing that G is not attached to Y such that O is linked to O, S, N, or SO$_2$, further providing that G is not attached to Y such that N is linked to O, S or N, and still further providing that G is not attached to Y such that S is linked to O, N or SO$_2$.

In another embodiment, in Formula 2, R$^1$ is

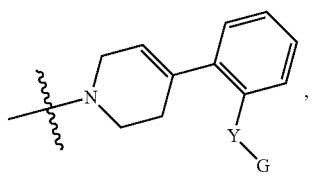

wherein Y is selected from the group consisting of O, S, NR$^8$, SO$_2$ and CH$_2$ and G is selected from the group consisting of:

—(CH$_2$)$_{1-6}$—C(O)OH,

—(CH$_2$)$_{0-4}$CH((C$_1$-C$_6$)alkyl)-(CH$_2$)$_{1-5}$—C(O)OH,

—(CH$_2$)$_{1-5}$—CH((C$_1$-C$_6$)alkyl)-C(O)OH,

—(CH$_2$)$_{0-5}$—(C$_3$-C$_8$)cycloalkyl-C(O)OH,

—(CH$_2$)$_{0-5}$—(C$_3$-C$_8$)cycloalkyl-(CH$_2$)$_{1-6}$-C(O)OH,

—(CH$_2$)$_{1-6}$—C(O)—NH—SO$_2$—(C$_3$-C$_8$)cycloalkyl,

—(CH$_2$)$_{1-6}$—C(O)—N—SO$_2$—(C$_1$-C$_6$)alkyl,

—(CD$_2$)$_{1-6}$—C(O)OH,

-continued

—(CH$_2$)$_{1-4}$—[tetrazole], —(CH$_2$)$_{1-6}$—O—(C$_1$-C$_6$)alkyl,

—(C$_1$-C$_6$)alkyl, —NH—(CH$_2$)$_{1-3}$—C(O)OH,

—O—(C$_3$-C$_8$)cycloalkyl-C(O)OH,

—(CH$_2$)$_{1-6}$—O—(CH$_2$)$_{1-4}$—C(O)OH,

—(CH$_2$)$_{1-5}$—(O)O((C$_1$-C$_6$)alkyl)$_2$, —(CH$_2$)$_{1-6}$—OH, (C$_3$-C$_8$)(cycloalkyl)-C(O)—N(SO$_2$)(C$_1$-C$_6$)alkyl, and —(C$_3$-C$_8$)cycloalkyl providing that G is not attached to Y such that O is linked to O, S, N, or SO$_2$, further providing that G is not attached to Y such that N is linked to O, S or N, and still further providing that G is not attached to Y such that S is linked to O, N or SO$_2$.

In another embodiment, in Formula 2, R$^2$ is

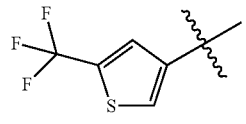

In another embodiment, in Formula 2, R$^2$ is

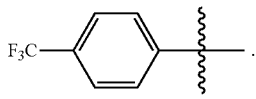 [SMILES: *c1ccc(C(F)(F)F)cc1]

In another embodiment, in Formula 2, X is

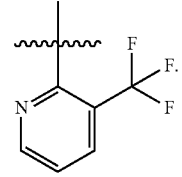 [SMILES: *c1ncccc1C(F)(F)F]

In another embodiment, in Formula 2, X is N.

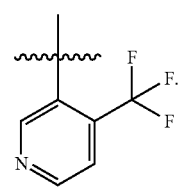 [SMILES: *c1cnccc1C(F)(F)F]

In another embodiment, in Formula 2, Y is O, S, NR$^8$, SO$_2$, or CR$^8$R$^{8'}$.

In another embodiment, the compounds are represented by Formula 2A below:

Formula 2A

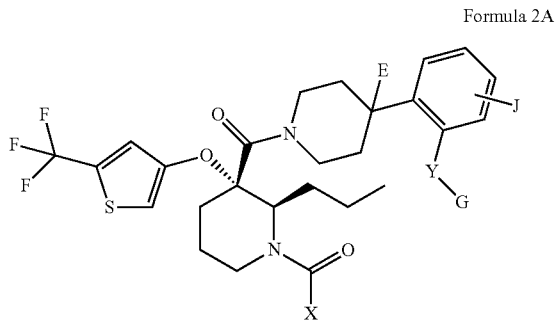

wherein E, Y, G and X, are selected independently of each other and wherein:

E is selected from the group consisting of H, halo, OH, CN, —O—(C$_1$-C$_6$)alkyl, (C$_1$-C$_6$)alkyl, —C(O)OH, —C(O)NR$^8$R$^{8'}$, —(C$_1$-C$_6$)—C(O)OH, —(C$_1$-C$_6$)—C(O)NR$^8$R$^{8'}$, —(C$_2$-C$_6$)alkenyl, —(C$_2$-C$_6$)alkynyl or heterocyclyl;

J, G and Y may or may not be present, wherein when Y is not present, G is not present, when Y is present it is selected from the group consisting of O, S, NR$^8$, SO$_2$, and CR$^8$R$^{8'}$, further wherein, when J is present, it is one or more moieties independently selected from the group consisting of halo;

X is

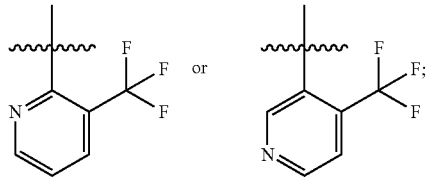 [SMILES: *c1ncccc1C(F)(F)F ; "or" ; *c1cnccc1C(F)(F)F]

G is selected from the group consisting of —(CR$^8$R$^{8'}$)$_n$—C(O)OH, —(CR$^8$R$^{8'}$)$_n$-heteroaryl, —(CR$^8$R$^{8'}$)$_n$—C(O)NR$^8$R$^9$, —(CR$^8$R$^{8'}$)$_n$—(C$_3$-C$_8$)Cycloalkyl-C(O)NR$^8$R$^9$, —(CR$^8$R$^{8'}$)$_n$—(C$_3$-C$_8$)cycloalkyl-(CR$^8$R$^{8'}$)$_n$—C(O)OH, —(CR$^8$R$^{8'}$)$_n$—O—(CR$^8$R$^{8'}$)$_n$—C(O)OH, —(CR$^8$R$^{8'}$)$_n$—S—(CR$^8$R$^{8'}$)$_n$—C(O)OH, —(CR$^8$R$^{8'}$)$_n$—NH—(CR$^8$R$^{8'}$)$_n$—C(O)OH, —(CR$^8$R$^{8'}$)$_n$—O—(CR$^8$R$^{8'}$)$_n$—CH$_3$, —(CR$^8$R$^{8'}$)$_n$—S—(CR$^8$R$^{8'}$)$_n$—CH$_3$, —(CR$^8$R$^{8'}$)$_n$—NH—(CR$^8$R$^{8'}$)$_n$—CH$_3$, —(CR$^8$R$^{8'}$)$_n$—CH$_3$, —(CR$^8$R$^{8'}$)$_n$-heteroaryl, —(CR$^8$R$^{8'}$)$_n$—P(O)OR$^8$OR$^{8'}$, —(CR$^8$R$^{8'}$)$_n$—P(O)O$_2$, —(CR$^8$R$^{8'}$)$_n$—OH, wherein each R$^8$ and R$^{8'}$ is independently selected from the group consisting of H and (C$_1$-C$_6$)alkyl; or further wherein R$^8$ and R$^{8'}$ together with the carbon to which each is attached can cyclicize to form (C$_3$-C$_8$)spirocycloalkyl, R$^9$ is SO$_2$(C$_1$-C$_6$)alkyl or SO$_2$(C$_3$-C$_8$)cycloalkyl, n is 0-10, providing that when n is 0, G is not attached to Y such that O is linked to O, S, N, or SO$_2$, further providing that when n is 0, G is not attached to Y such that N is linked to O, S or N, and still further providing that when n is 0, G is not attached to Y such that S is linked to O, N or SO$_2$, further wherein, any spirocycloalkyl or cycloalkyl in Formula 2A, can be unsubstituted or substituted with one or more (C$_1$-C$_6$)alkyl groups, still further wherein, any Hydrogen atom that is substituted on any alkyl, cycloalkyl, heterocycloalkyl or spirocycloalkyl, in Formula 2A, can be replaced by a Deuterium atom.

In another embodiment, the compounds are represented by Formula 2B below:

Formula 2B

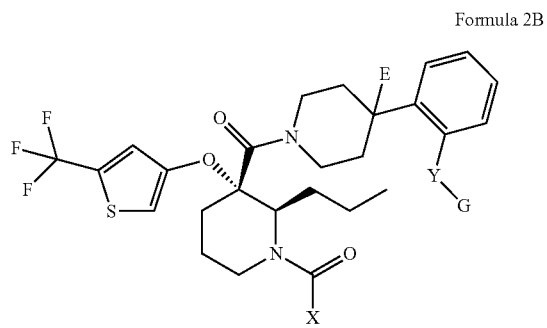

wherein E, Y, G and X, are selected independently of each other and wherein:

E is selected from the group consisting of H, OH, CN, —O—(C$_1$-C$_6$)alkyl, —C(O)OH, —C(O)NR$^8$R$^{8'}$, —(C$_1$-C$_6$)—C(O)OH, and —(C$_1$-C$_6$)—C(O)NR$^8$R$^{8'}$;

G and Y may or may not be present, wherein when Y is not present, G is not present, when Y is present it is selected from the group consisting of O, S, SO$_2$, NR$^8$ and CR$^8$R$^{8'}$;

X is

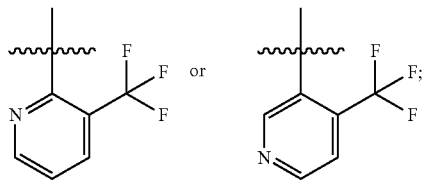 [SMILES: *c1ncccc1C(F)(F)F ; "or" ; *c1cnccc1C(F)(F)F]

G is selected from the group consisting of —(CR$^8$R$^{8'}$)$_n$—C(O)OH, —(CR$^8$R$^{8'}$)$_n$-heteroaryl, —(CR$^8$R$^{8'}$)$_n$—C(O)NR$^8$R$^9$, —(CR$^8$R$^{8'}$)$_n$—(C$_3$-C$_8$)Cycloalkyl-C(O)NR$^8$R$^9$, —(CR$^8$R$^{8'}$)$_n$—(C$_3$-C$_8$)cycloalkyl-(CR$^8$R$^{8'}$)$_n$—C(O)OH, —(CR$^8$R$^{8'}$)$_n$—O—(CR$^8$R$^{8'}$)$_n$—C(O)OH, —(CR$^8$R$^{8'}$)$_n$—S—(CR$^8$R$^{8'}$)$_n$—C(O)OH, C(O)OH, —(CR$^8$R$^{8'}$)$_n$—NH—(CR$^8$R$^{8'}$)$_n$—C(O)OH, —(CR$^8$R$^{8'}$)$_n$—O—(CR$^8$R$^{8'}$)$_n$—CH$_3$, —(CR$^8$R$^{8'}$)$_n$—S—(CR$^8$R$^{8'}$)$_n$—CH$_3$, —(CR$^8$R$^{8'}$)$_n$—NH—(CR$^8$R$^{8'}$)$_n$—CH$_3$, —(CR$^8$R$^{8'}$)$_n$—CH$_3$, —(CR$^8$R$^{8'}$)$_n$-heteroaryl, —(CR$^8$R$^{8'}$)$_n$—P(O)OR$^8$OR$^{8'}$, —(CR$^8$R$^{8'}$)$_n$—P(O)O$_2$, —(CR$^8$R$^{8'}$)$_n$—OH, wherein each R$^8$ and R$^{8'}$ is independently selected from the group consisting of H and (C$_1$-C$_6$)alkyl, or further wherein R$^8$ and R$^{8'}$ together with the carbon to which each is attached can cyclicize to form (C$_3$-C$_8$)spirocycloalkyl, R$^9$ is SO$_2$(C$_1$-C$_6$)alkyl or SO$_2$(C$_3$-C$_8$)cycloalkyl, n is 0-10, providing that when n is 0, G is not attached to Y such that O is linked to O, S, N, or SO$_2$, further providing that when n is 0, G is not attached to Y such that N is linked to O, S or N, and still further providing that when n is 0, G is not attached to Y such that S is linked to O, N or SO$_2$, further wherein, any spirocycloalkyl or cycloalkyl in Formula 2, can be unsubstituted or substituted with one or more (C$_1$-C$_6$)alkyl groups, still further wherein, any Hydrogen atom that is substituted on any alkyl, cycloalkyl, heterocycloalkyl or spirocycloalkyl, in Formula 2, can be replaced by a Deuterium atom.

In another embodiment, the compounds are represented by Formula 2C below:

Formula 2C

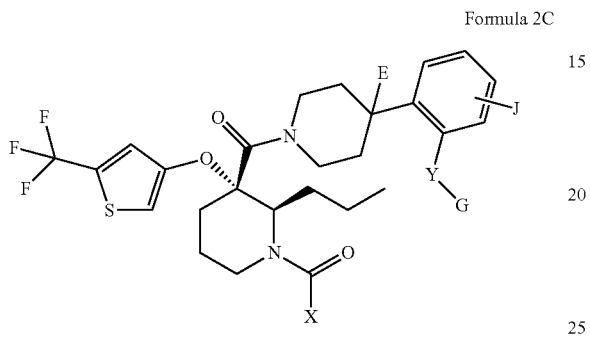

wherein E, Y, G and X, are selected independently of each other and wherein:

E is selected from the group consisting of H, halo, OH, CN, —O—(C$_1$-C$_6$)alkyl, (C$_1$-C$_6$)alkyl, —C(O)OH, —C(O)NR$^8$R$^{8'}$, —(C$_1$-C$_6$)—C(O)OH, —(C$_1$-C$_6$)—C(O)NR$^8$R$^{8'}$, —(C$_2$-C$_6$)alkenyl, —(C$_2$-C$_6$)alkynyl or heterocyclyl;

J, G and Y may or may not be present, wherein when Y is not present, G is not present, when Y is present it is selected from the group consisting of O, S, NR$^8$, SO$_2$, and CR$^8$R$^{8'}$, further wherein, when J is present, it is one or more moieties independently selected from the group consisting of halo;

X is

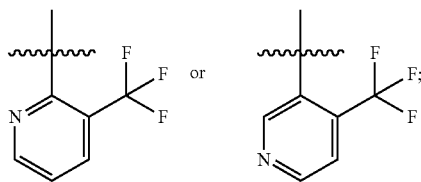 [SMILES: *c1ncccc1C(F)(F)F ; "or" ; *c1cnccc1C(F)(F)F]

G is selected from the group consisting of:

—(CH$_2$)$_{1-6}$—C(O)OH,

—(CH$_2$)$_{0-4}$CH((C$_1$-C$_6$)alkyl)-(CH$_2$)$_{1-5}$—C(O)OH,

—(CH$_2$)$_{1-5}$—CH((C$_1$-C$_6$)alkyl)-C(O)OH,

—(CH$_2$)$_{0-5}$—(C$_3$-C$_8$)cycloalkyl-C(O)OH,

—(CH$_2$)$_{0-5}$—(C$_3$-C$_8$)cycloalkyl-(CH$_2$)$_{1-6}$—C(O)OH,

—(CH$_2$)$_{1-6}$—C(O)—NH—SO$_2$—(C$_3$-C$_8$)cycloalkyl,

—(CH$_2$)$_{1-6}$—C(O)—N—SO$_2$—(C$_1$-C$_6$)alkyl,

—(CD$_2$)$_{1-6}$—C(O)OH,

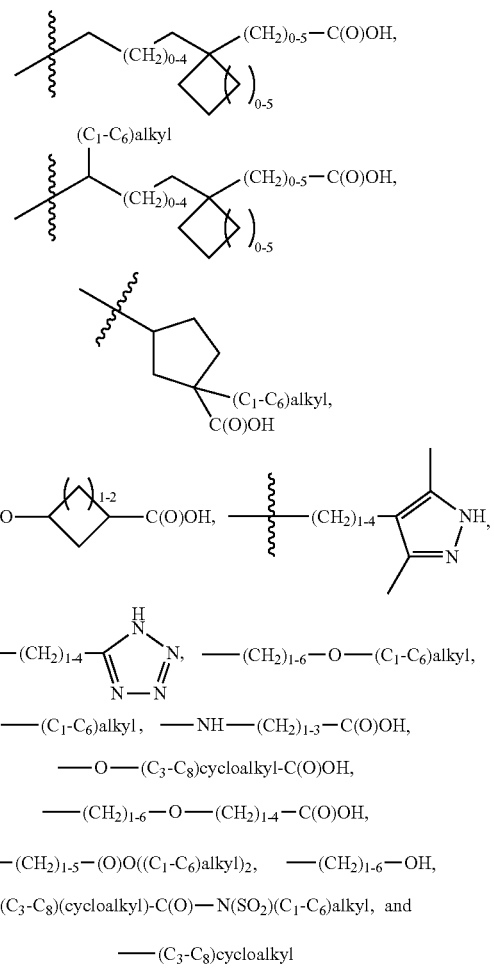

—(C$_1$-C$_6$)alkyl, —NH—(CH$_2$)$_{1-3}$—C(O)OH,

—O—(C$_3$-C$_8$)cycloalkyl-C(O)OH,

—(CH$_2$)$_{1-6}$—O—(CH$_2$)$_{1-4}$—C(O)OH,

—(CH$_2$)$_{1-5}$—(O)O((C$_1$-C$_6$)alkyl)$_2$, —(CH$_2$)$_{1-6}$—OH, (C$_3$-C$_8$)(cycloalkyl)-C(O)—N(SO$_2$)(C$_1$-C$_6$)alkyl, and —(C$_3$-C$_8$)cycloalkyl providing that G is not attached to Y such that O is linked to O, S, N, or SO$_2$, further providing that G is not attached to Y such that N is linked to O, S or N, and still further providing that G is not attached to Y such that S is linked to O, N or SO$_2$.

In another embodiment, the compounds are represented by Formula 2D below:

Formula 2D

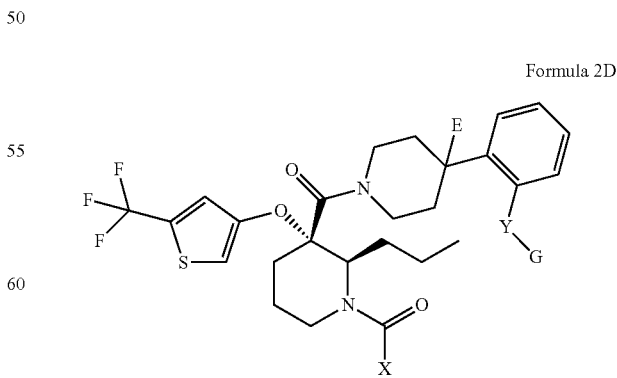

wherein E, Y, G and X, are selected independently of each other and wherein:

E is selected from the group consisting of H, OH, CN, —O—(C$_1$-C$_6$)alkyl, —C(O)OH, —C(O)NR$^8$R$^{8'}$, —(C$_1$-C$_6$)—C(O)OH, and —(C$_1$-C$_6$)—C(O)NR$^8$R$^{8'}$;

G and Y may or may not be present,
wherein when Y is not present, G is not present,
when Y is present it is selected from the group consisting of O, S, SO$_2$, NR$^8$ and CR$^8$R$^{8'}$;

X is

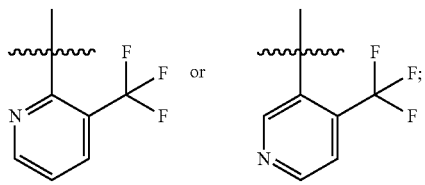 [SMILES: *c1ncccc1C(F)(F)F ; "or" ; *c1cnccc1C(F)(F)F]

G is selected from the group consisting of:

—(CH$_2$)$_{1-6}$—C(O)OH,
—(CH$_2$)$_{0-4}$CH((C$_1$-C$_6$)alkyl)-(CH$_2$)$_{1-5}$—C(O)OH,
—(CH$_2$)$_{1-5}$—CH((C$_1$-C$_6$)alkyl)-C(O)OH,
—(CH$_2$)$_{0-5}$—(C$_3$-C$_8$)cycloalkyl-C(O)OH,
—(CH$_2$)$_{0-5}$—(C$_3$-C$_8$)cycloalkyl-(CH$_2$)$_{1-6}$—C(O)OH,
—(CH$_2$)$_{1-6}$—C(O)—NH—SO$_2$—(C$_3$-C$_8$)cycloalkyl,
—(CH$_2$)$_{1-6}$—C(O)—N—SO$_2$—(C$_1$-C$_6$)alkyl,
—(CD$_2$)$_{1-6}$—C(O)OH,

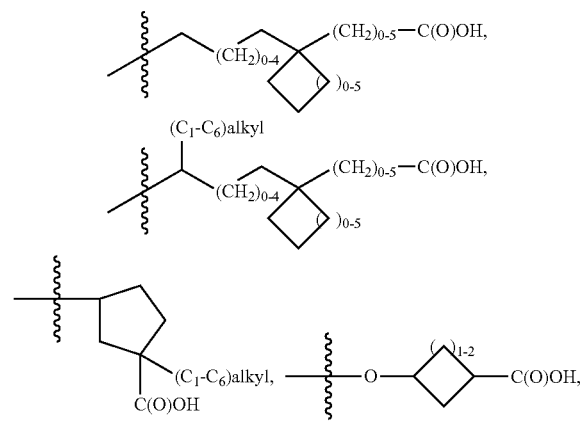

—(CH$_2$)$_{1-6}$—O—(C$_1$-C$_6$)alkyl, —(C$_1$-C$_6$)alkyl,
—NH—(CH$_2$)$_{1-3}$—C(O)OH, —O—(C$_3$-C$_8$)cycloalkyl-C(O)OH,
—(CH$_2$)$_{1-6}$—O—(CH$_2$)$_{1-4}$—C(O)OH,
—(CH$_2$)$_{1-5}$—(O)O((C$_1$-C$_6$)alkyl)$_2$, —(CH$_2$)$_{1-6}$—OH,
(C$_3$-C$_8$)(cycloalkyl)-C(O)—N(SO$_2$)(C$_1$-C$_6$)alkyl, and
—(C$_3$-C$_8$)cycloalkyl providing that G is not attached to Y such that O is linked to O, S, N, or SO$_2$,
further providing that G is not attached to Y such that N is linked to O, S or N, and
still further providing that G is not attached to Y such that S is linked to O, N or SO$_2$.

Non-limiting examples of compounds of the present invention of Formula 2 include:

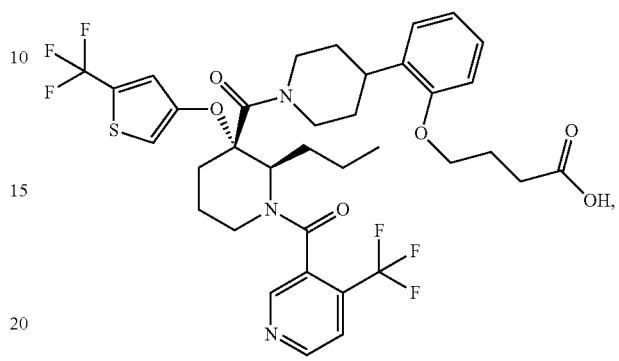

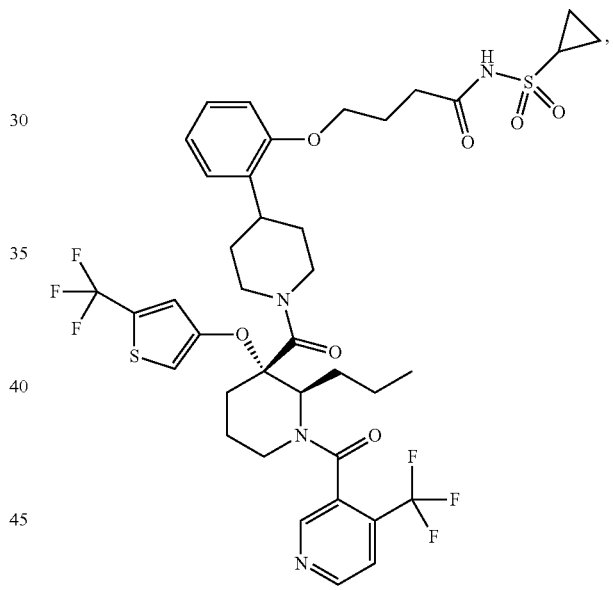

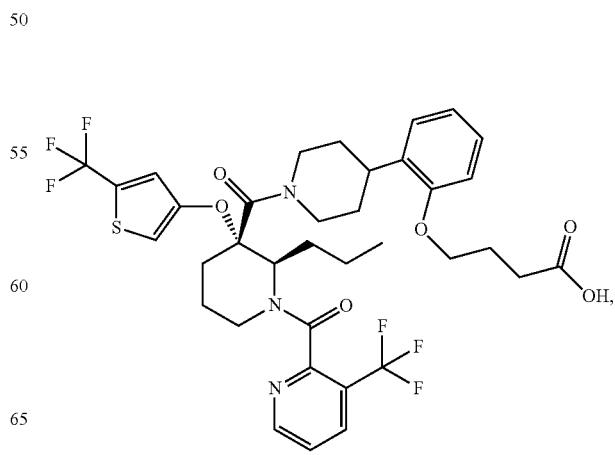

73
-continued
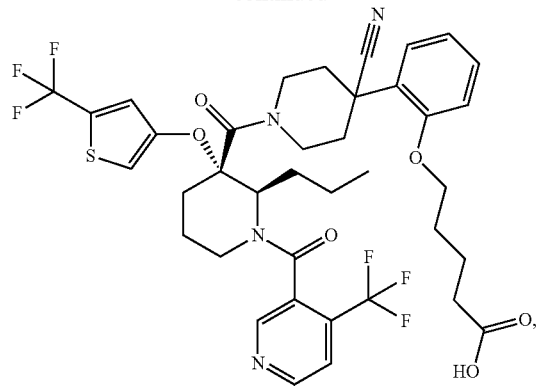
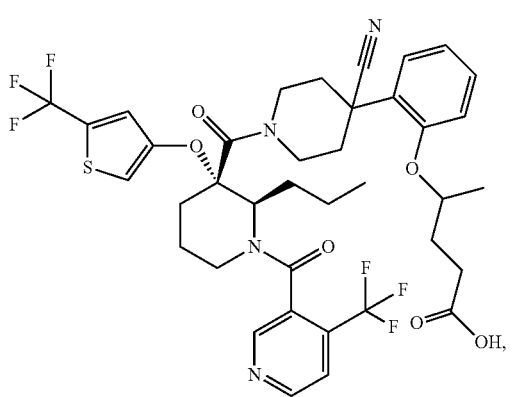
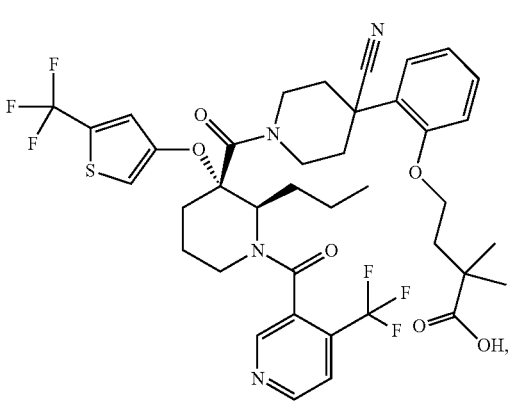
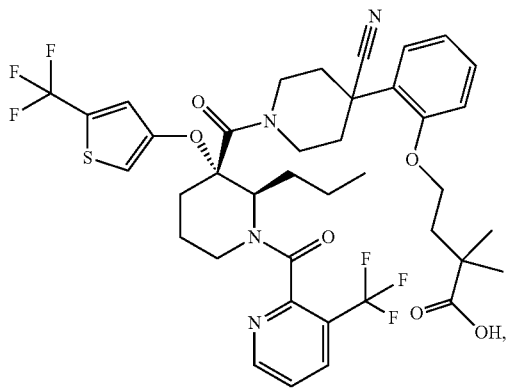
74
-continued
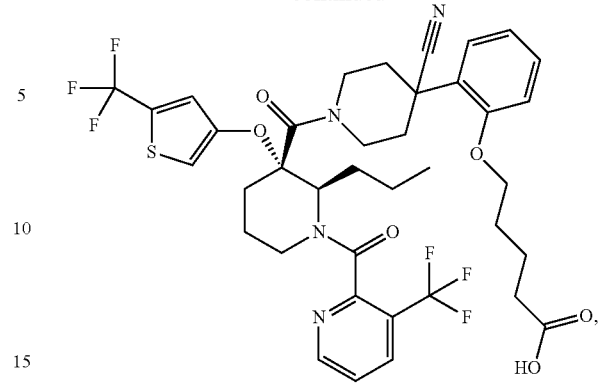
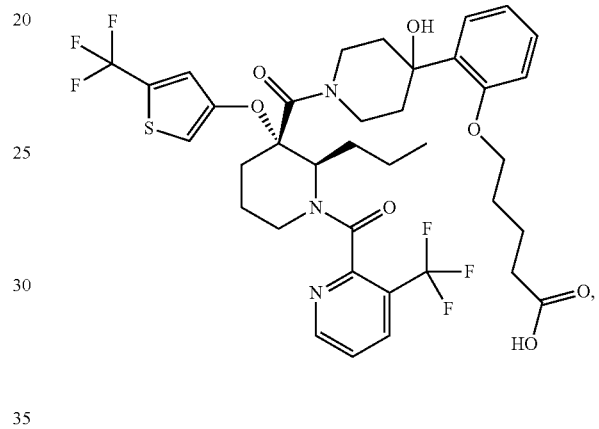
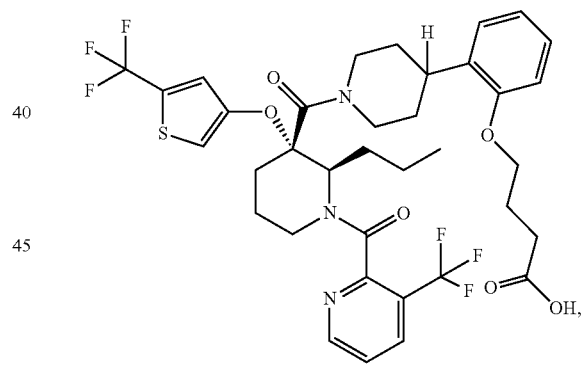
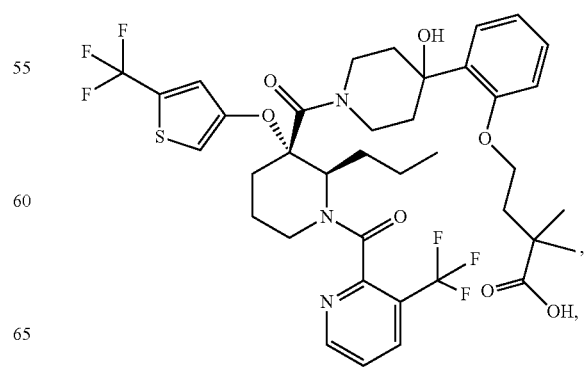

75
-continued
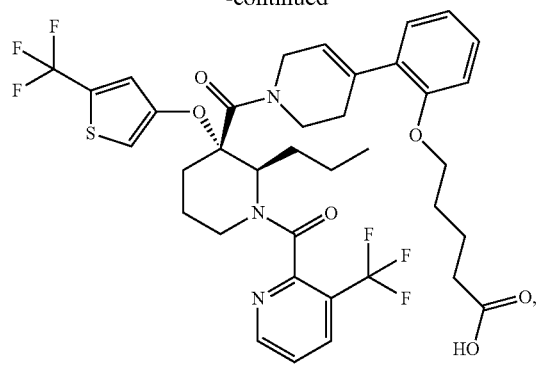
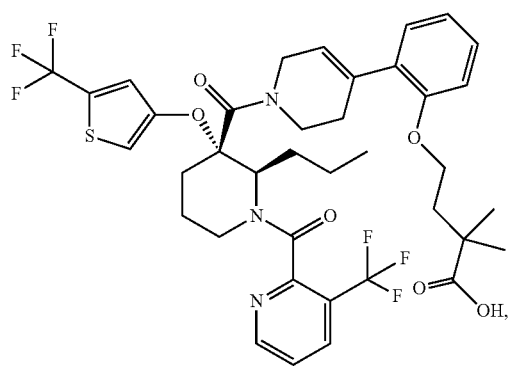
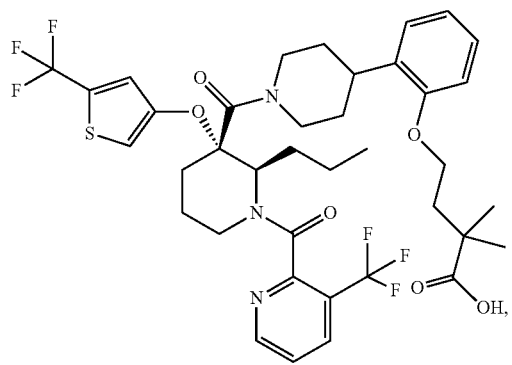
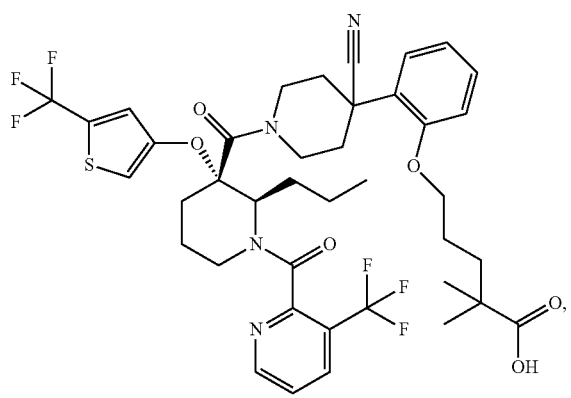
76
-continued
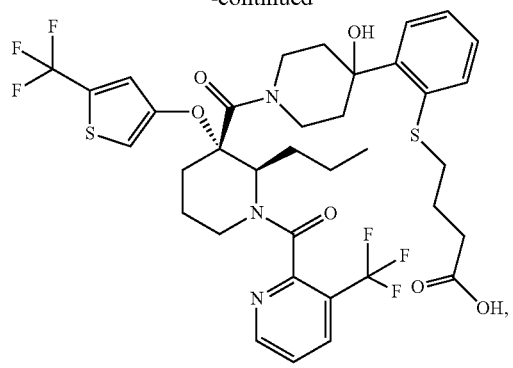
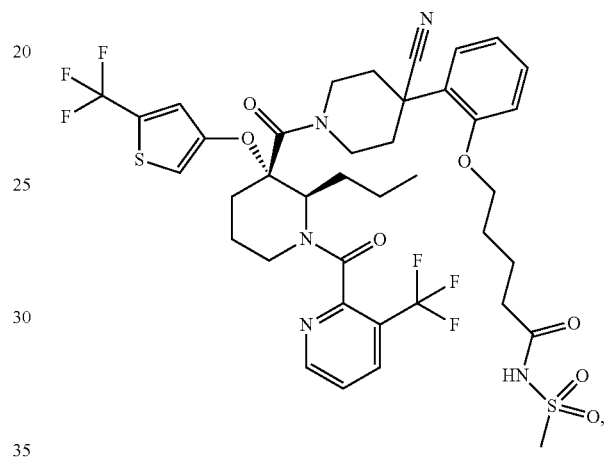
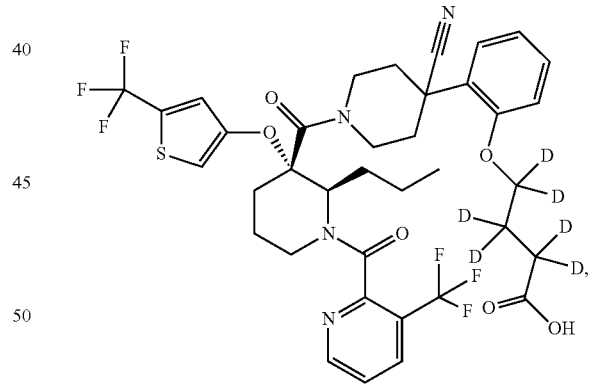
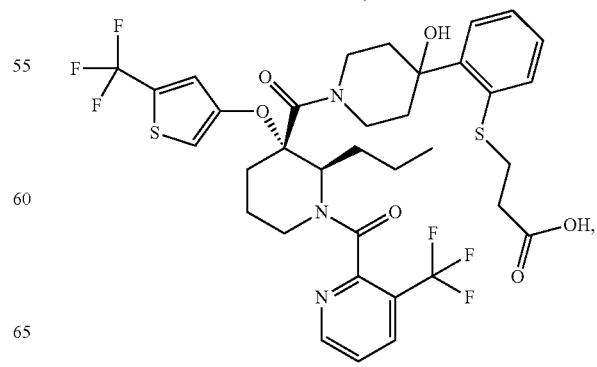

77
-continued
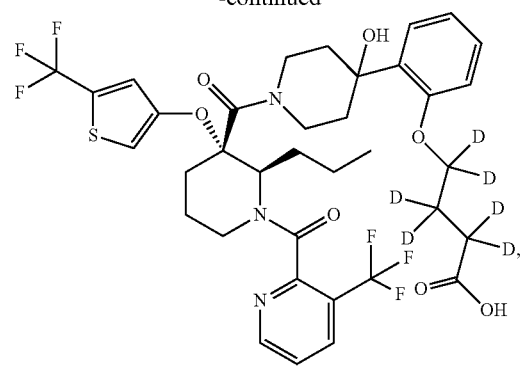
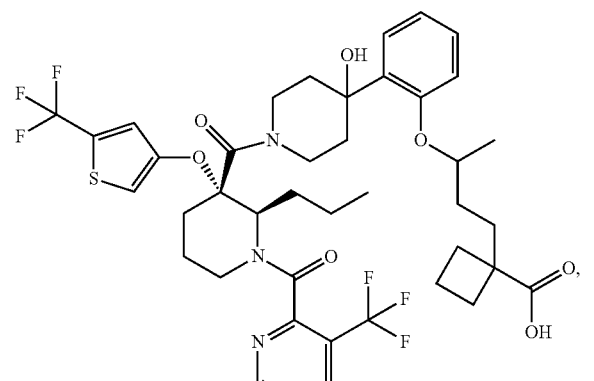
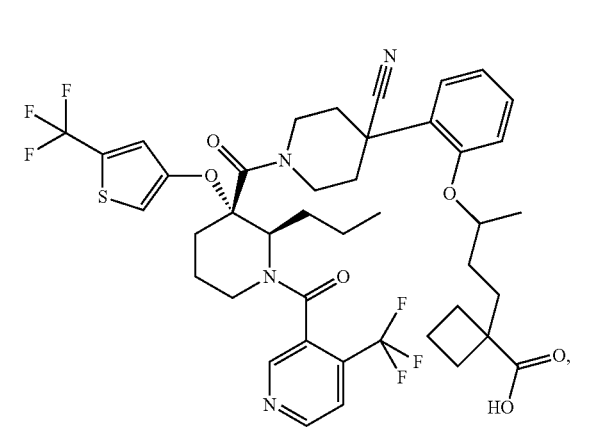
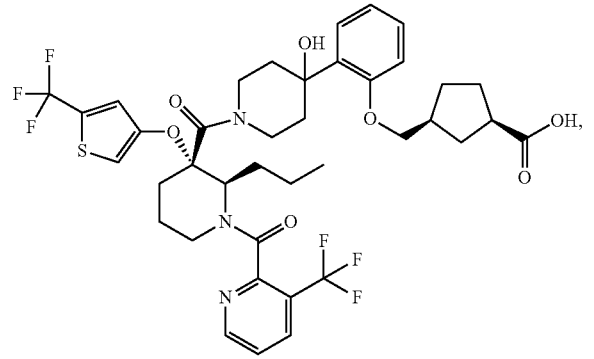
78
-continued
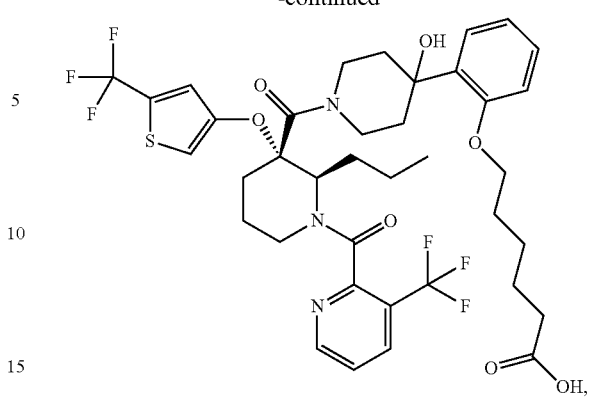
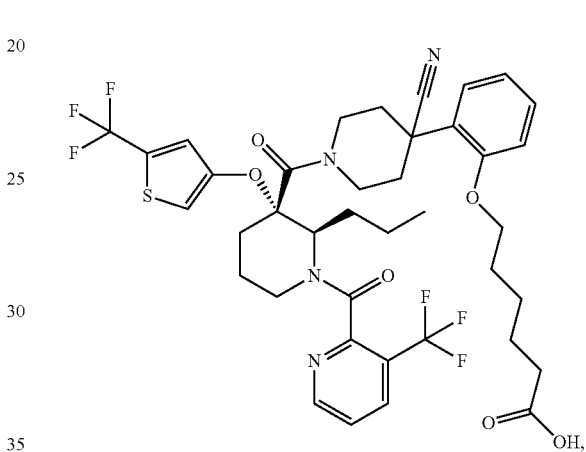
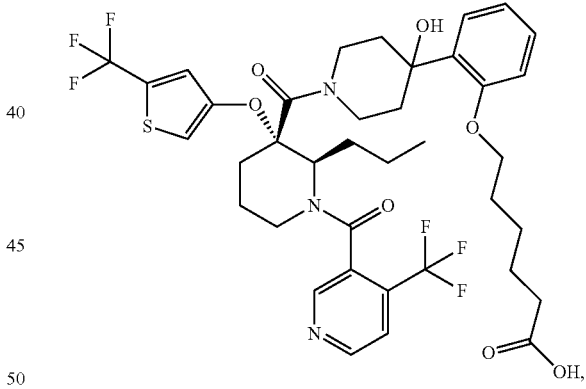
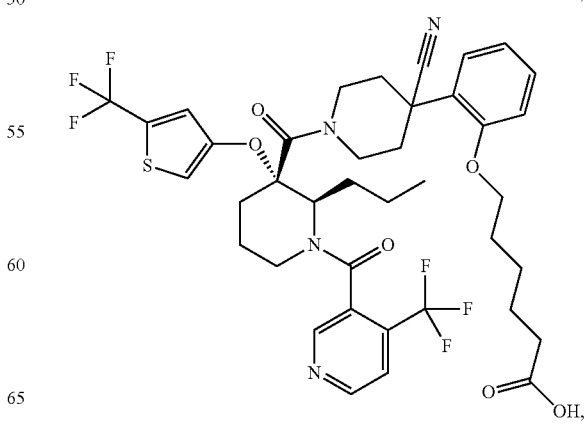

79
-continued
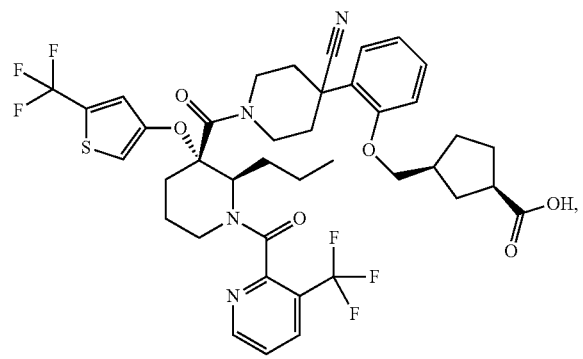
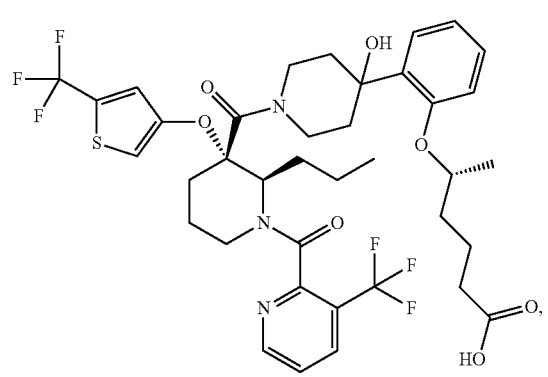
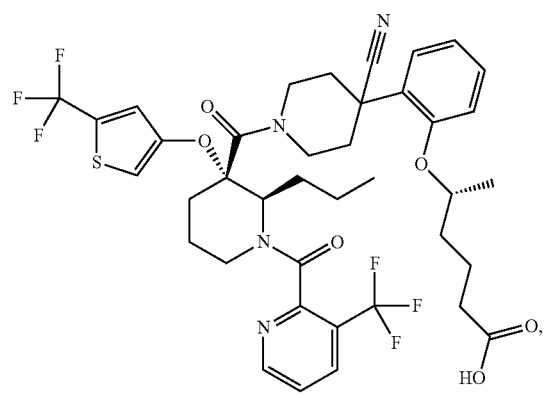
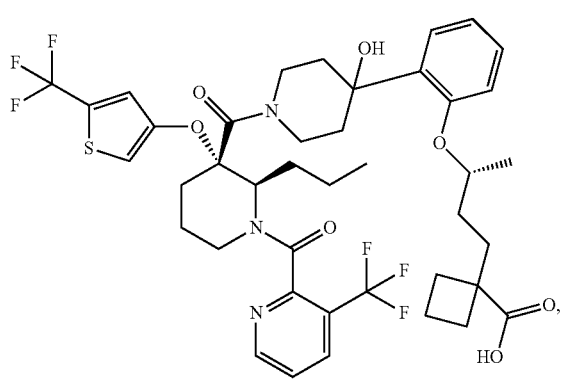
80
-continued
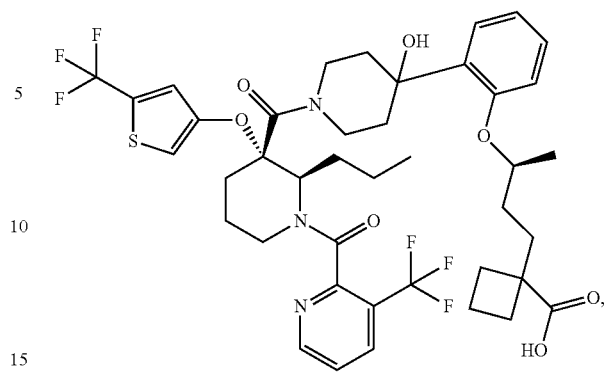
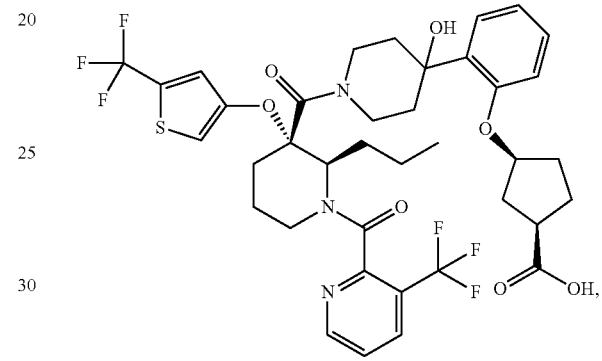
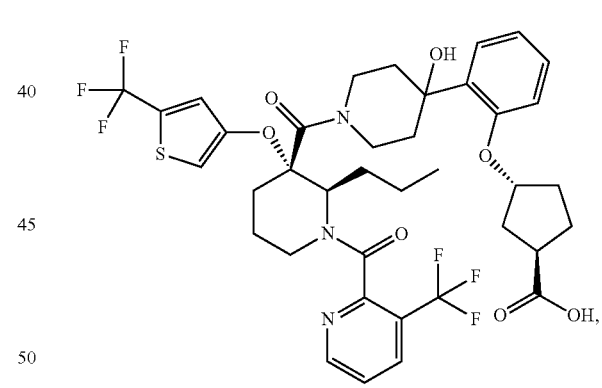
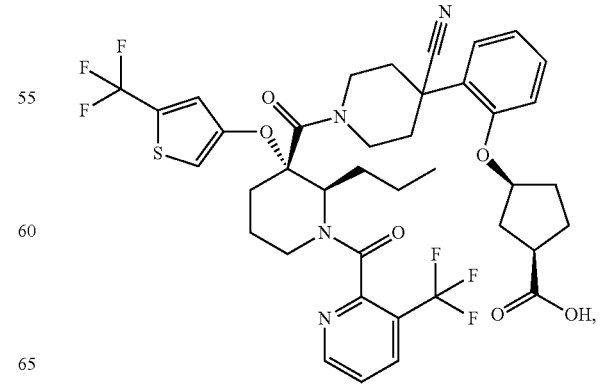

81
-continued
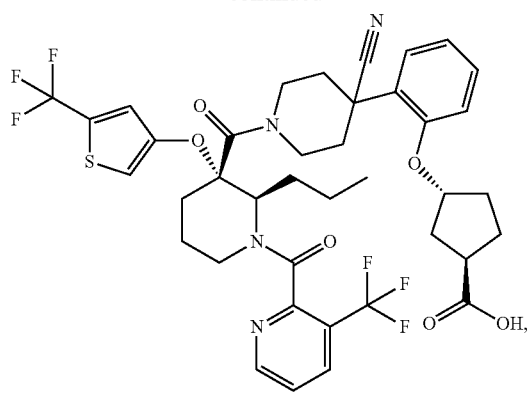
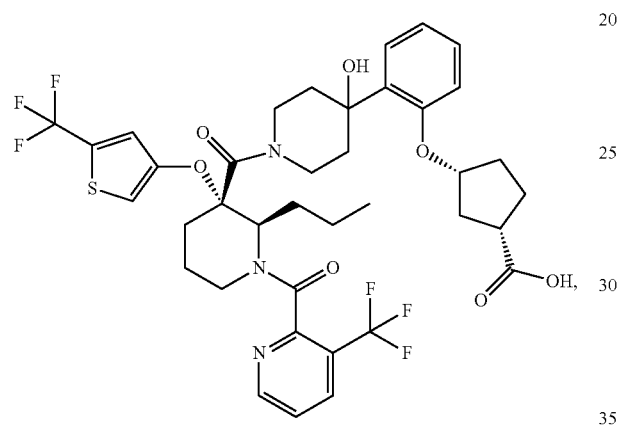
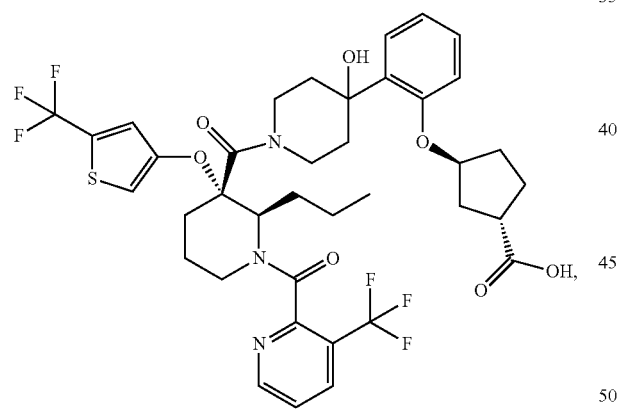
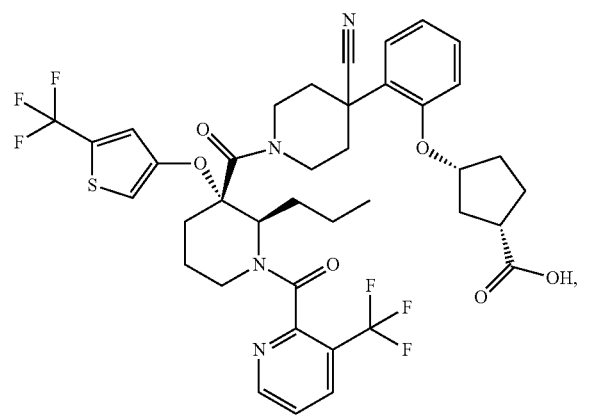
82
-continued
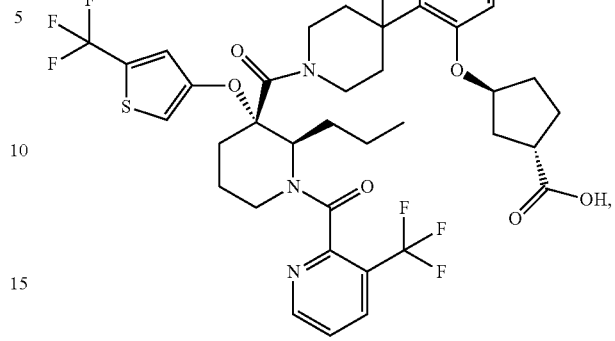
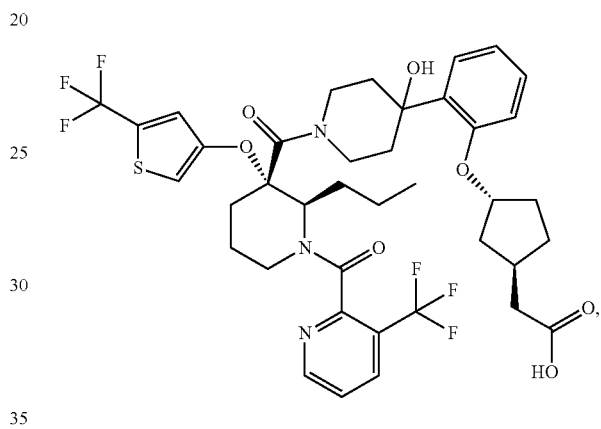
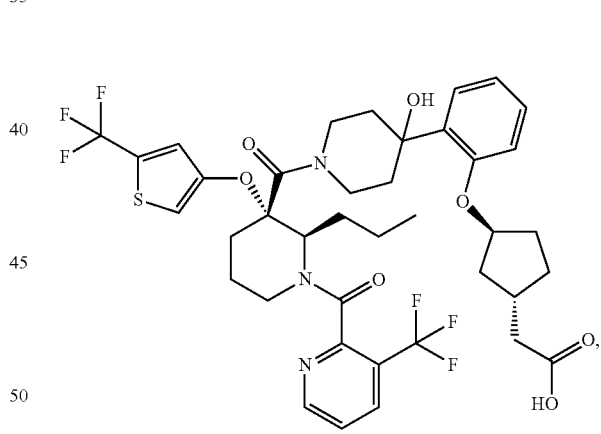
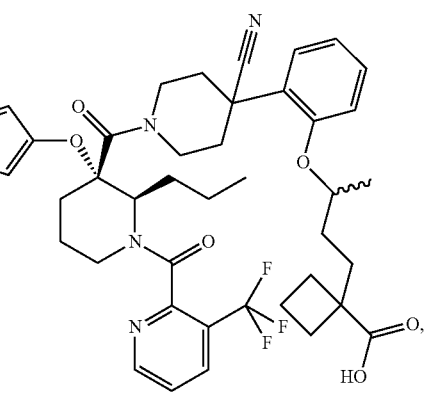

83
-continued
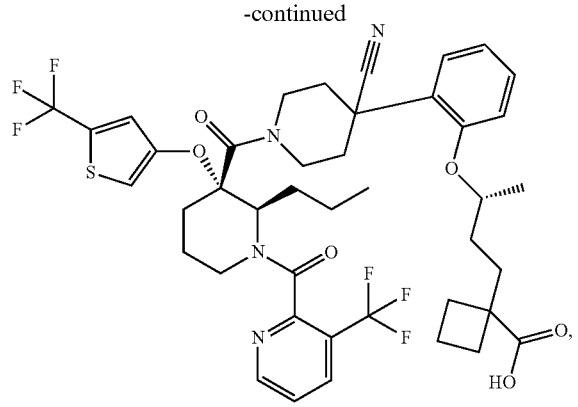
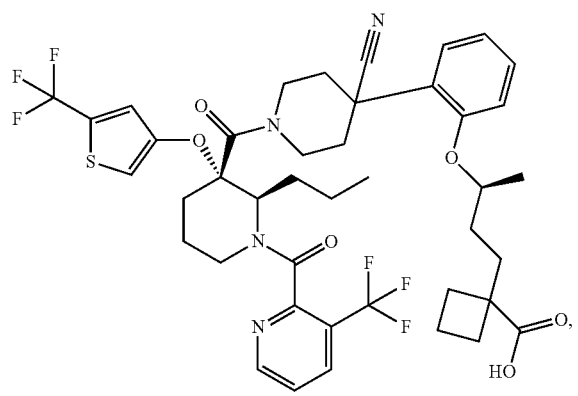
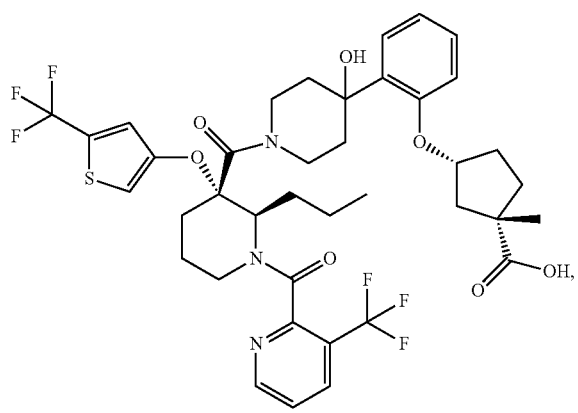
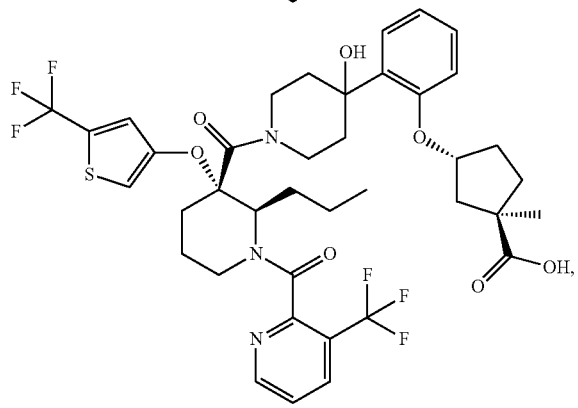
84
-continued
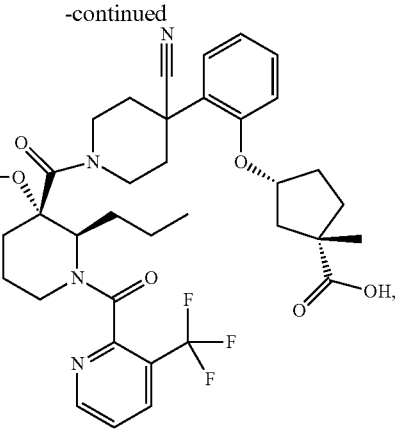
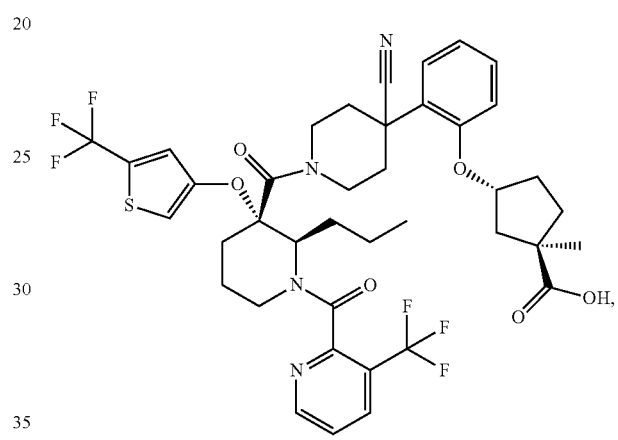
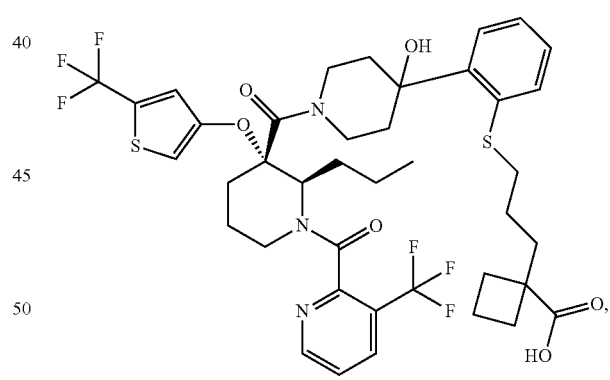
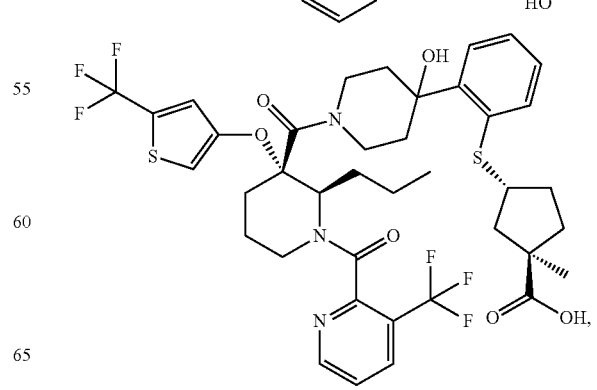

85
-continued
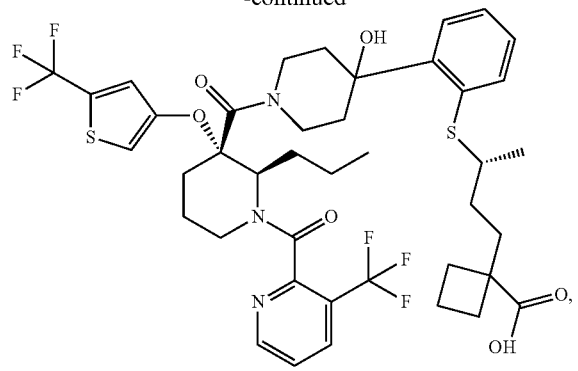
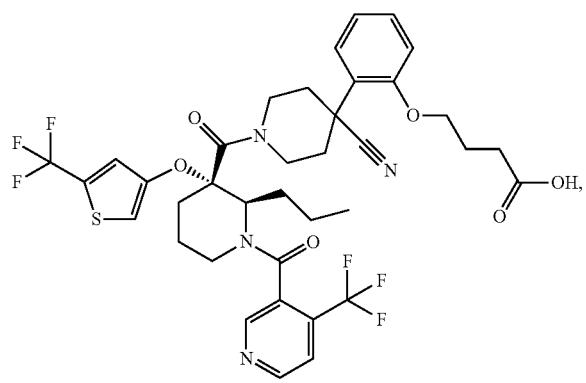
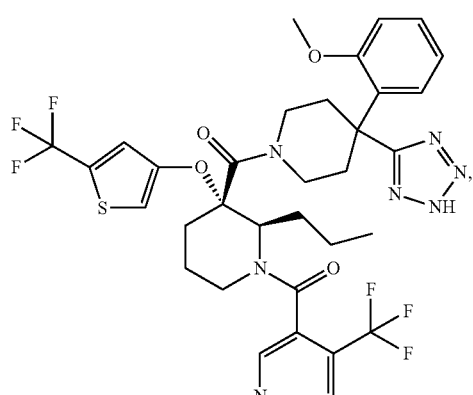
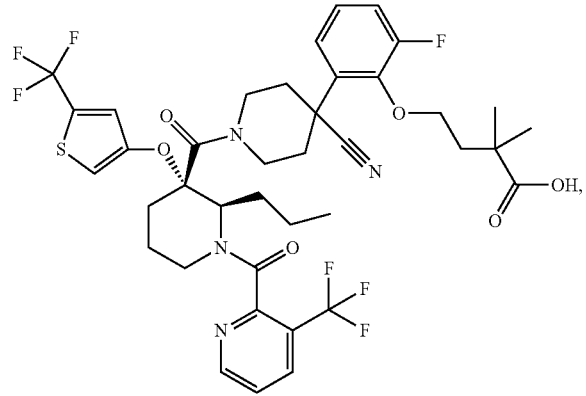
86
-continued
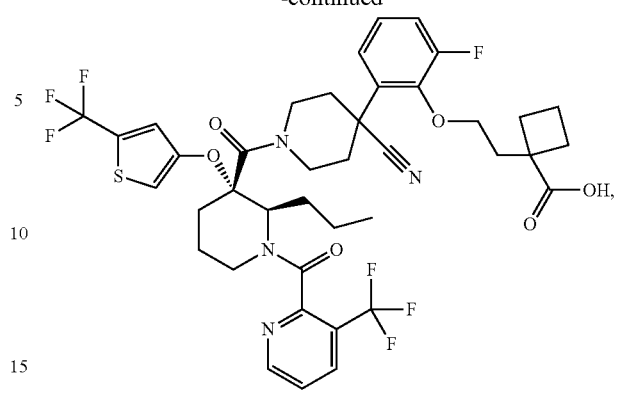
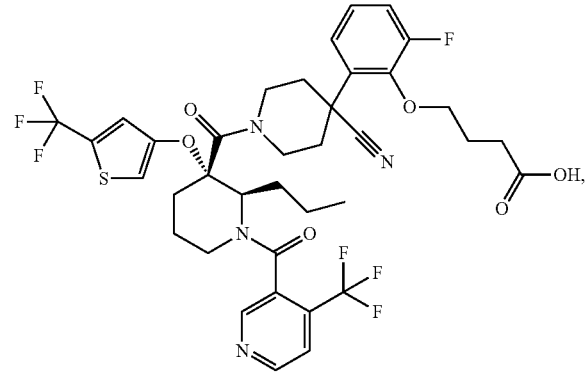
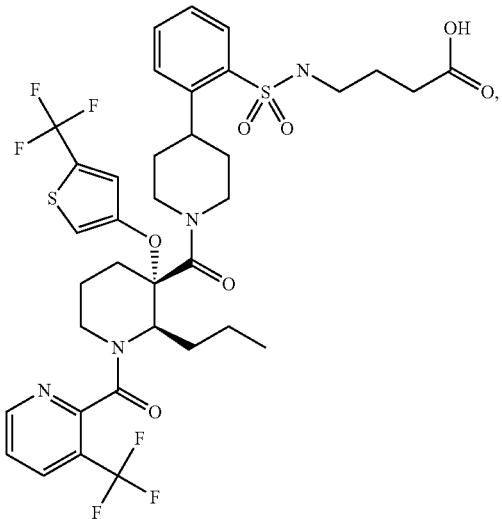

87
-continued
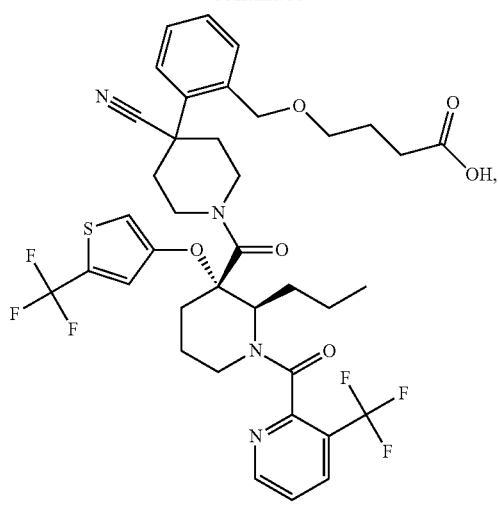
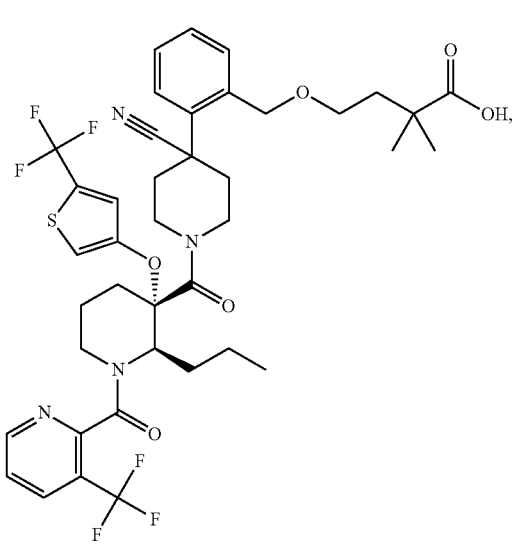
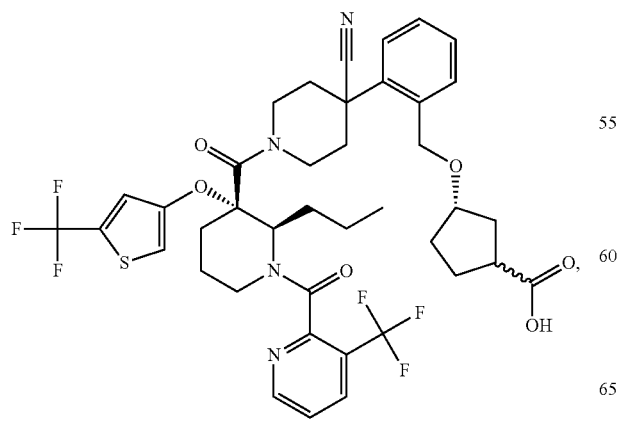
88
-continued
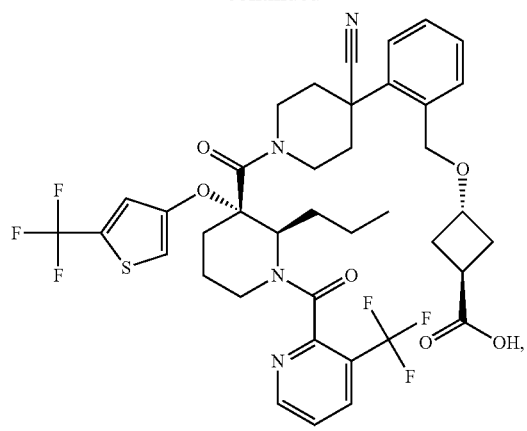
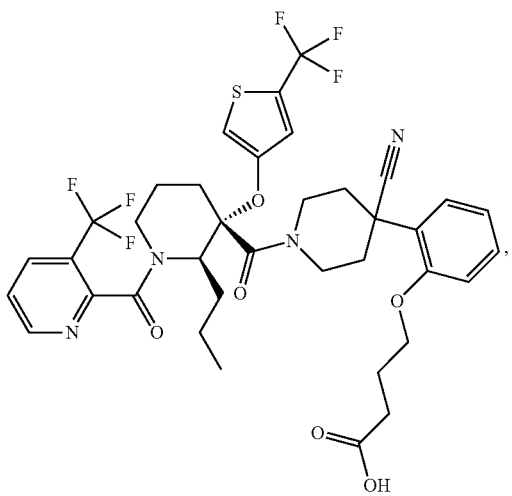

89
-continued
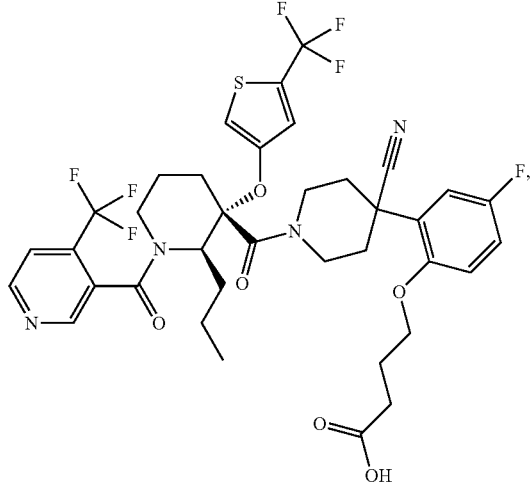
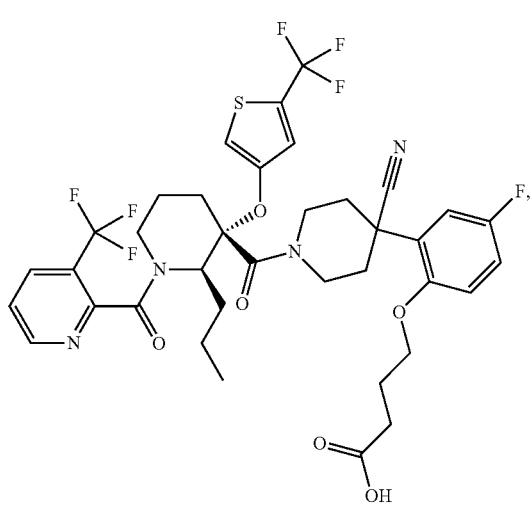
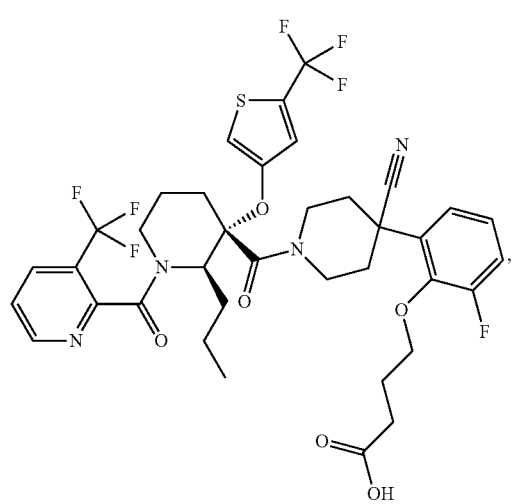
90
-continued
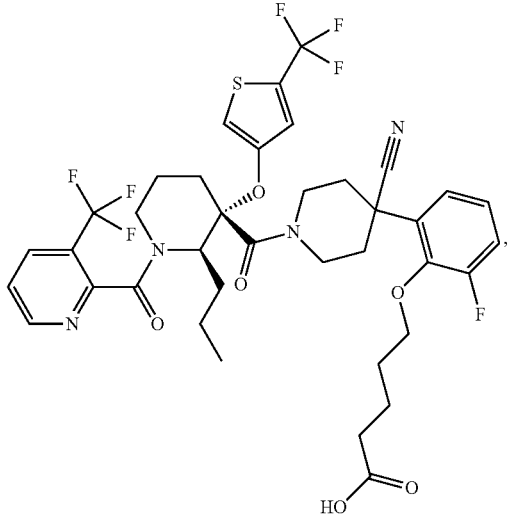
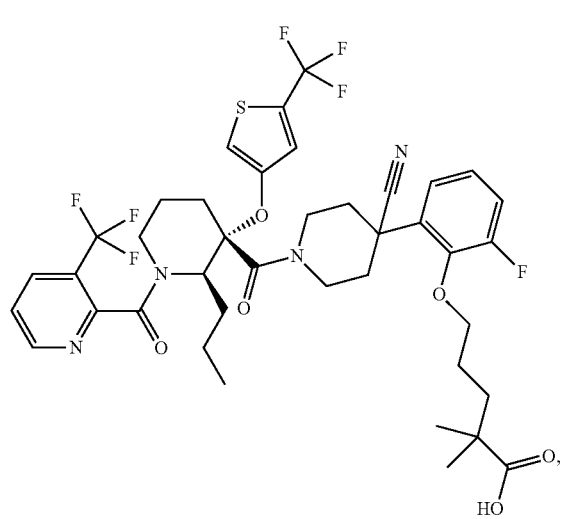
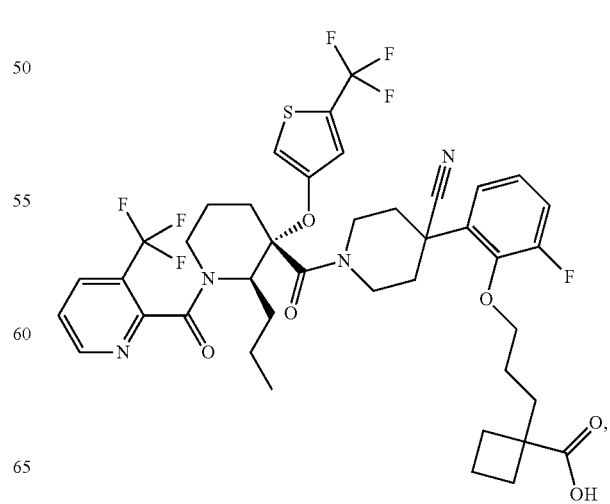

| 91 | 92 |
|---|---|
| -continued | -continued |
| 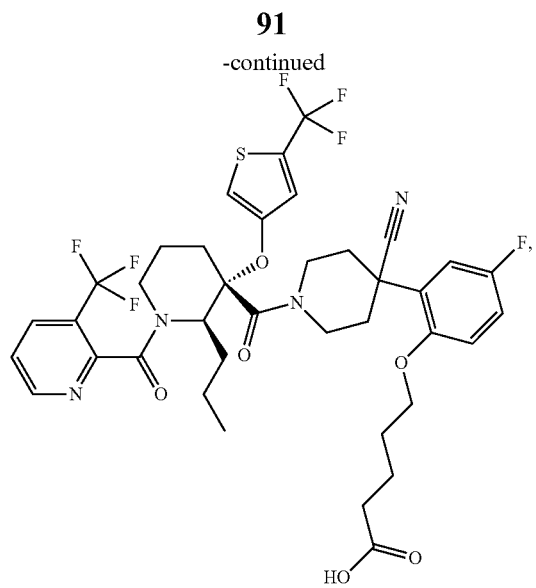 | 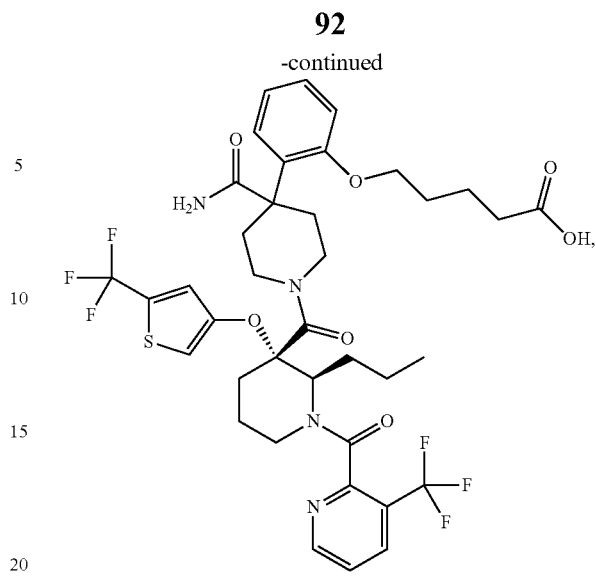 |
| 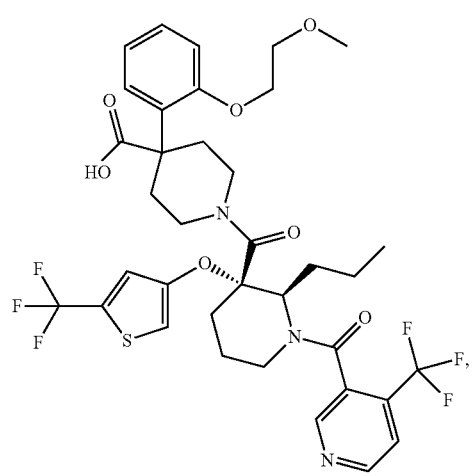 | 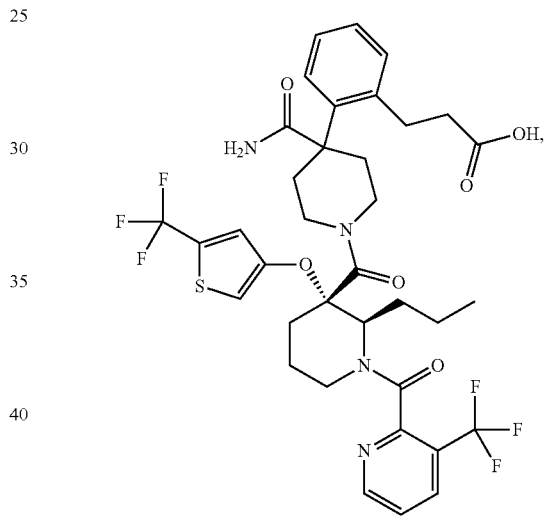 |
| 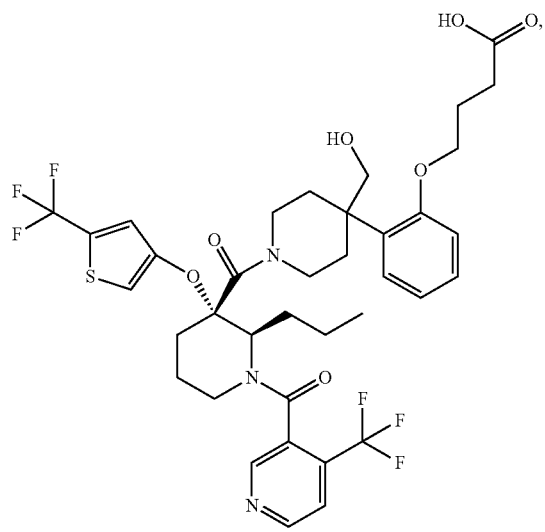 | 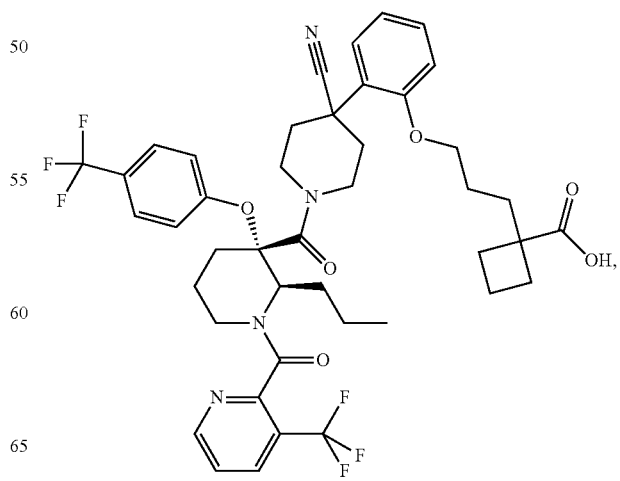 |

93
-continued
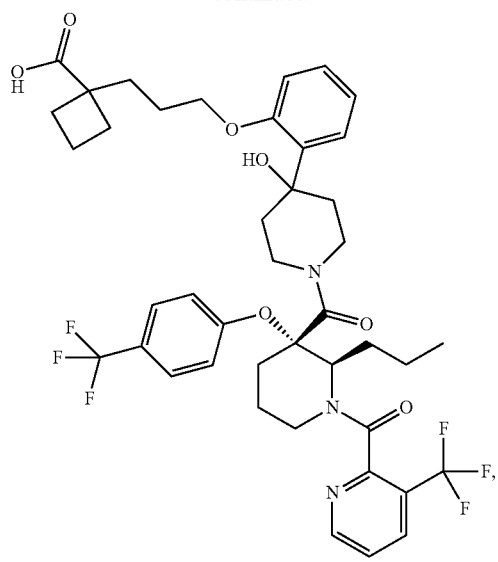
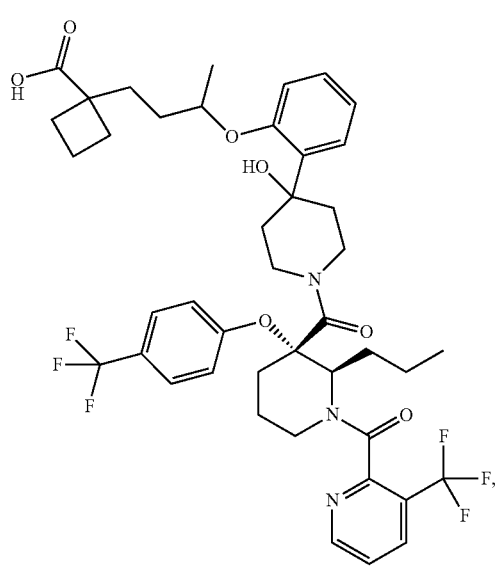
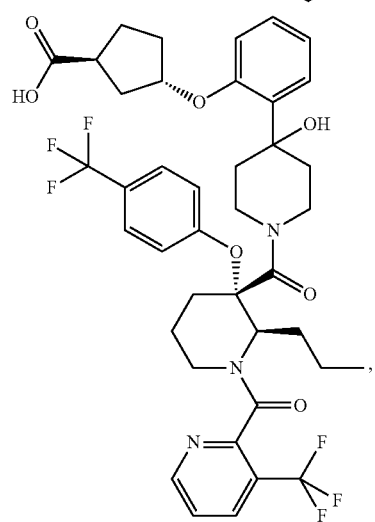
94
-continued
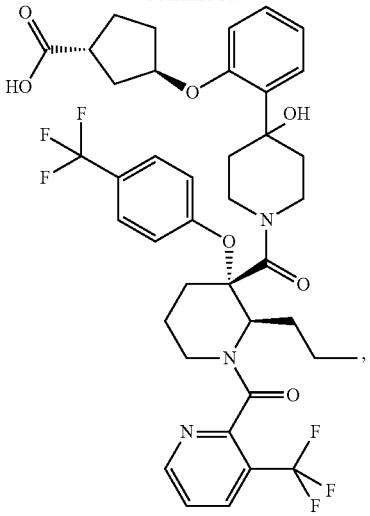
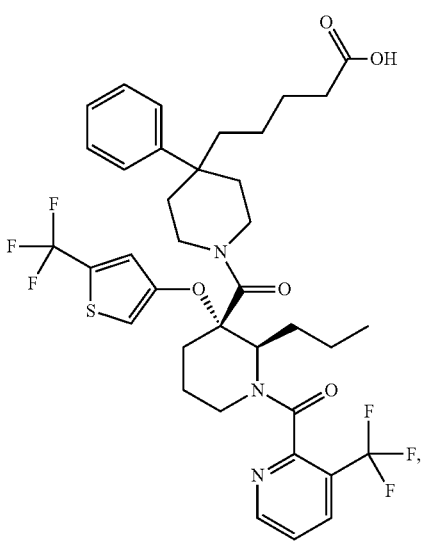
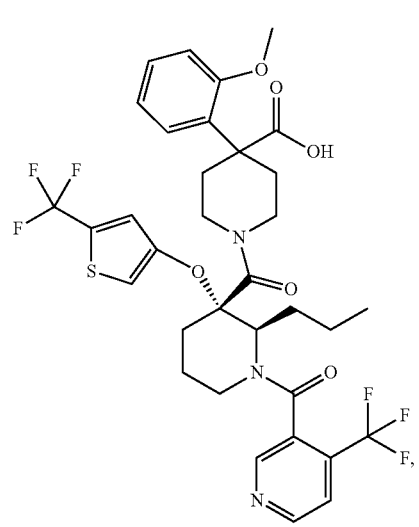

95
-continued
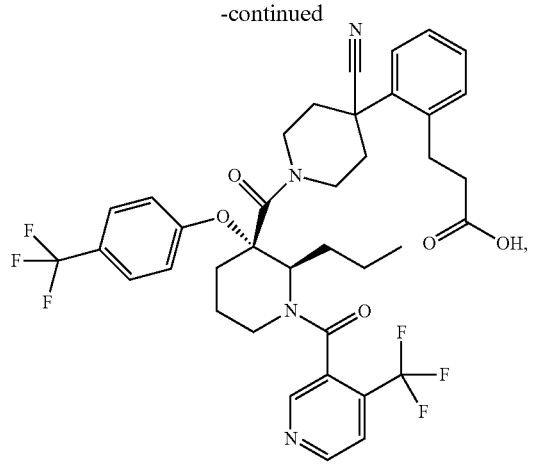
96
-continued
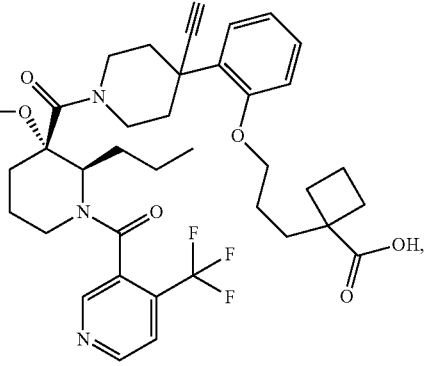
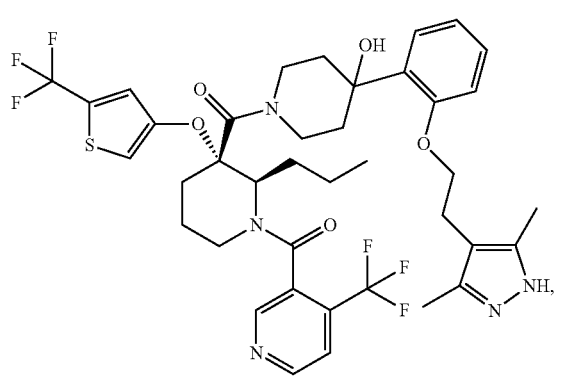
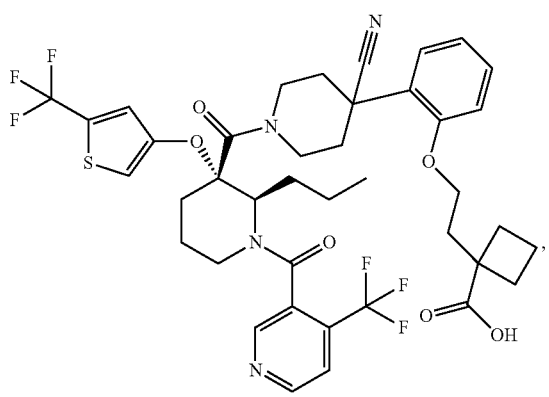
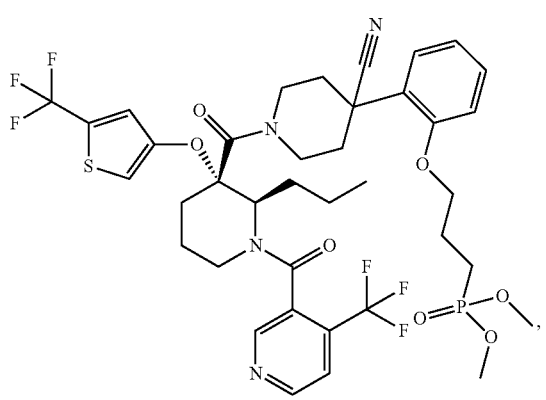
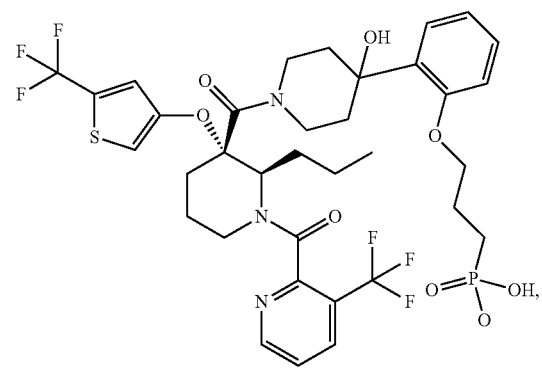
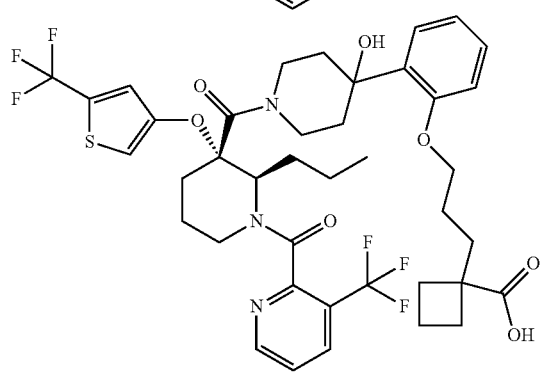

97
-continued
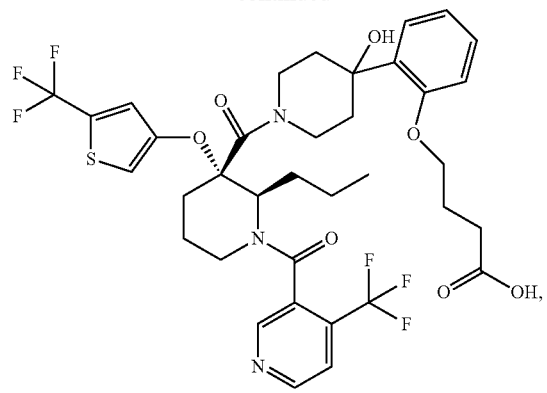
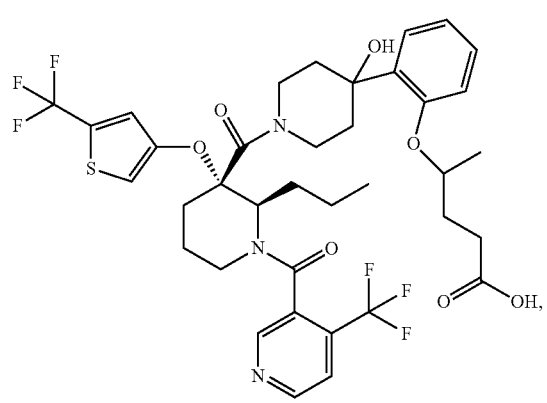
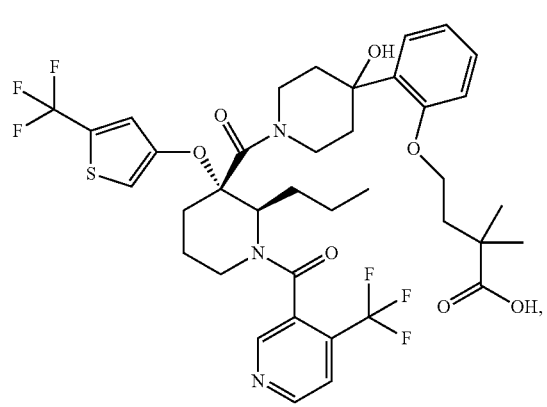
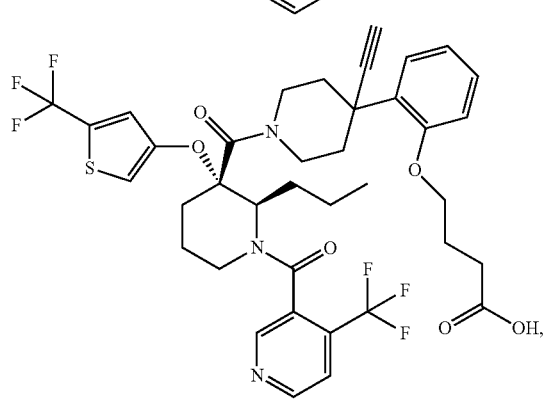
98
-continued
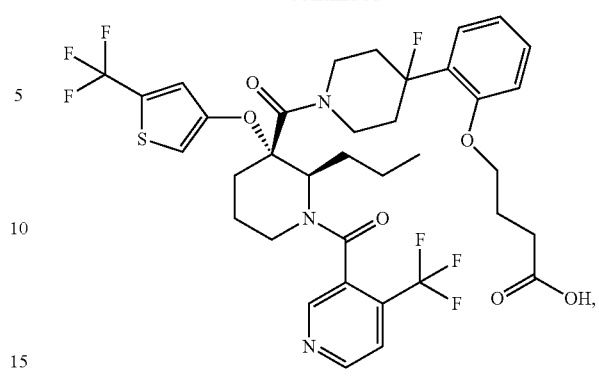
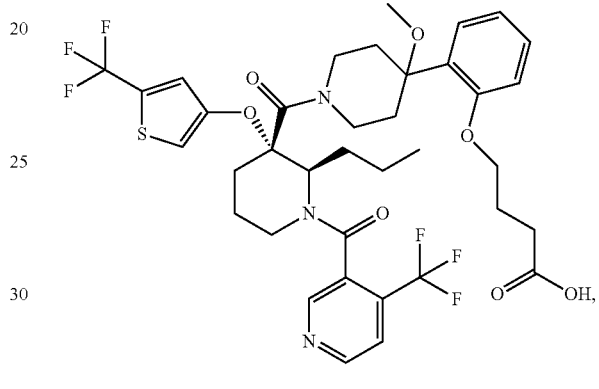
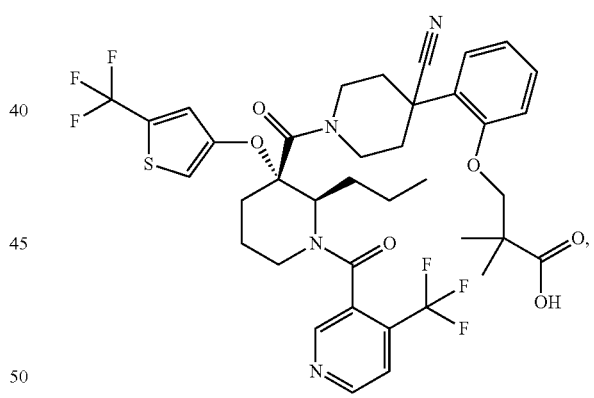
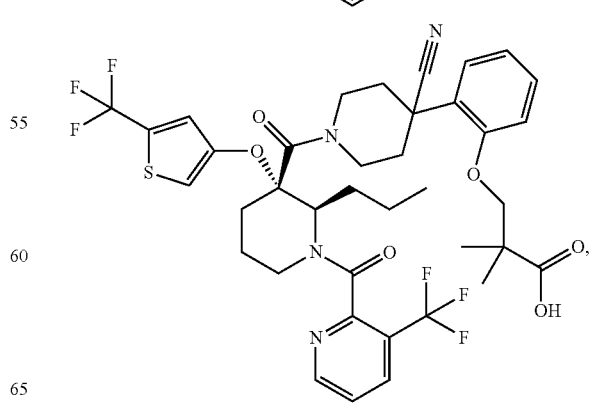

99
-continued
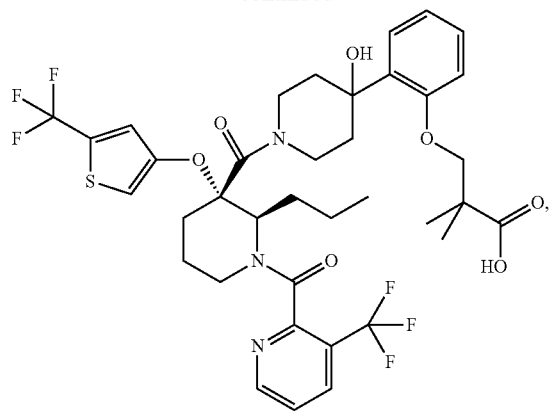
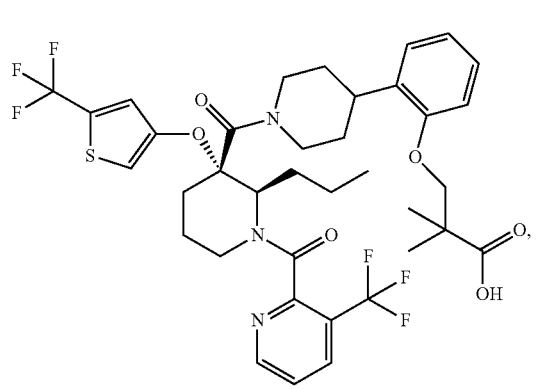
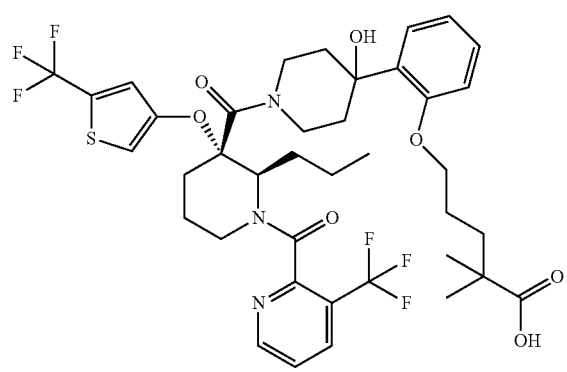
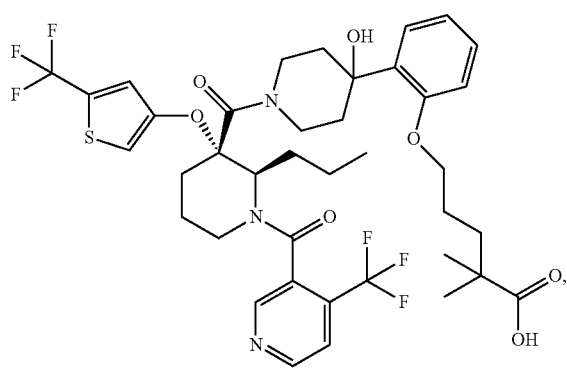
100
-continued
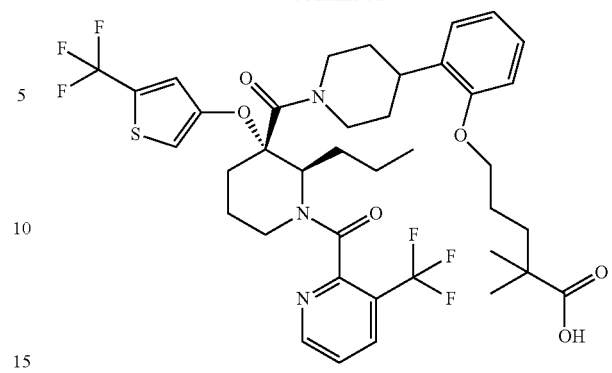
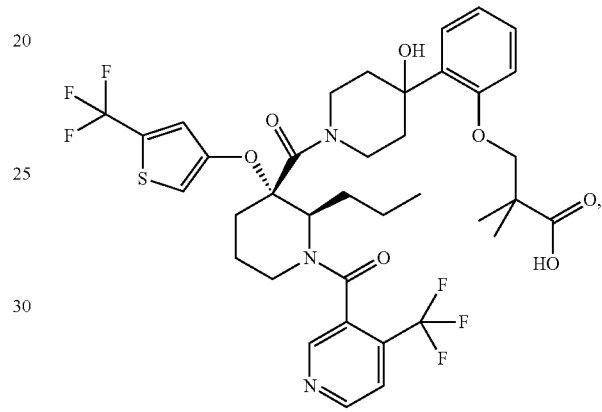
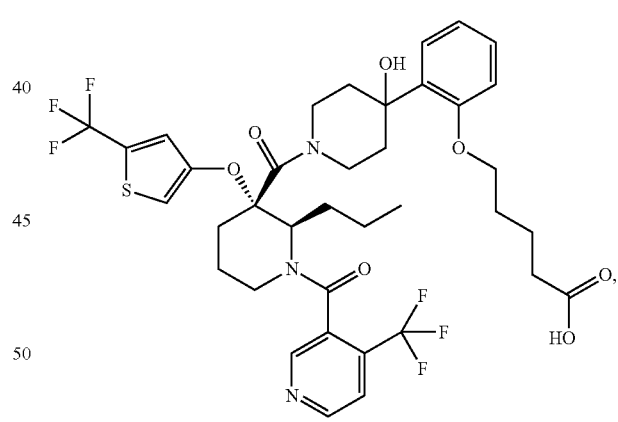
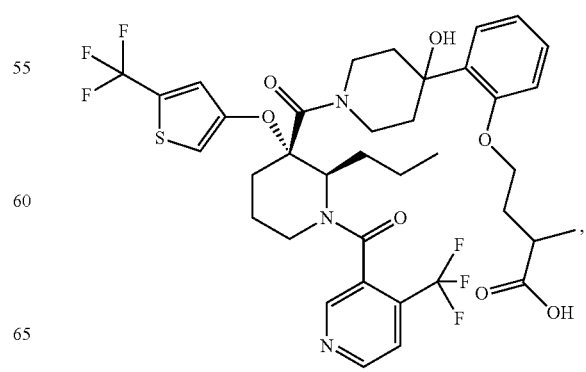

101
-continued
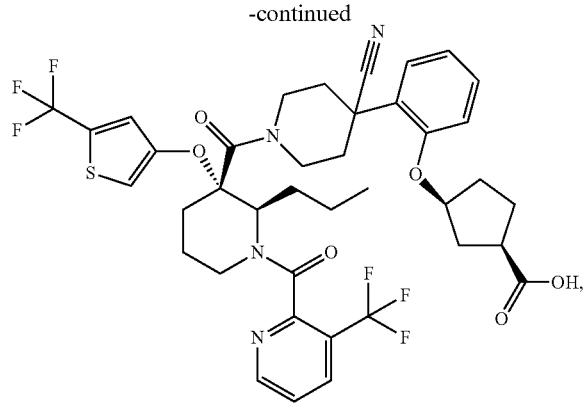
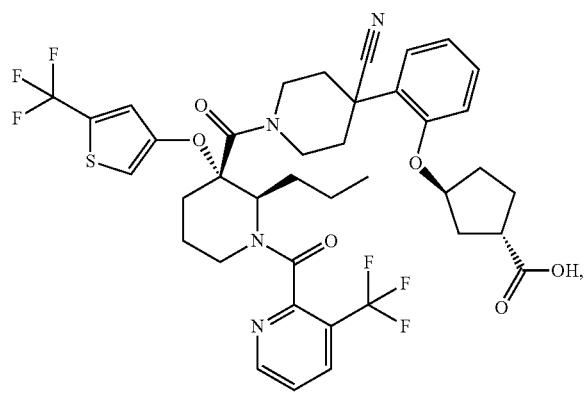
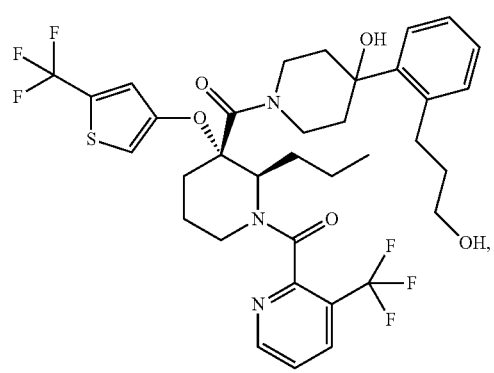
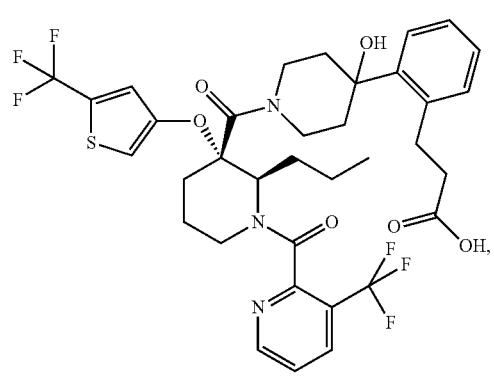
102
-continued
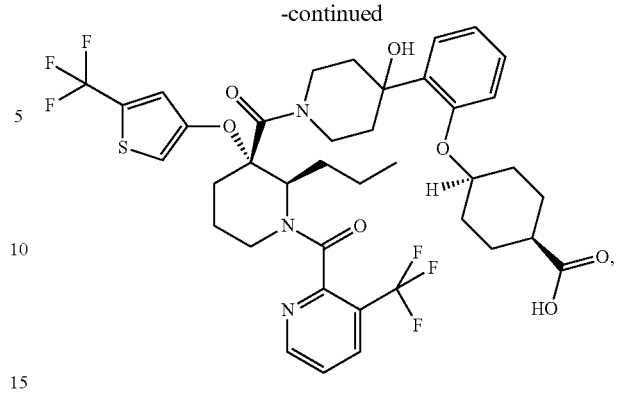
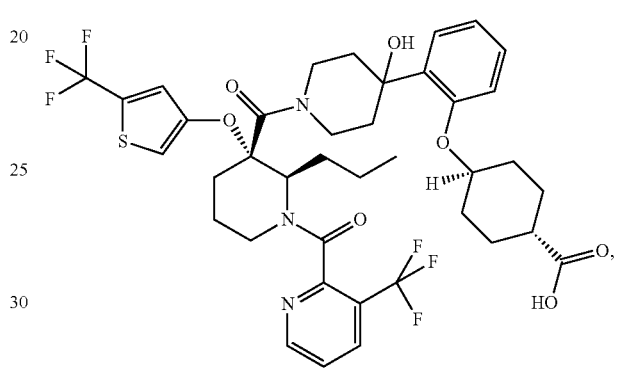
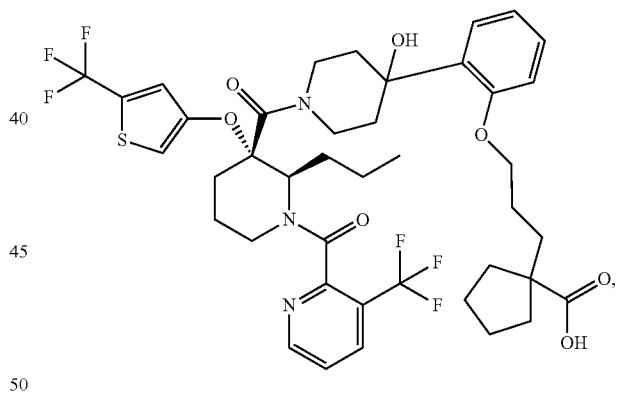
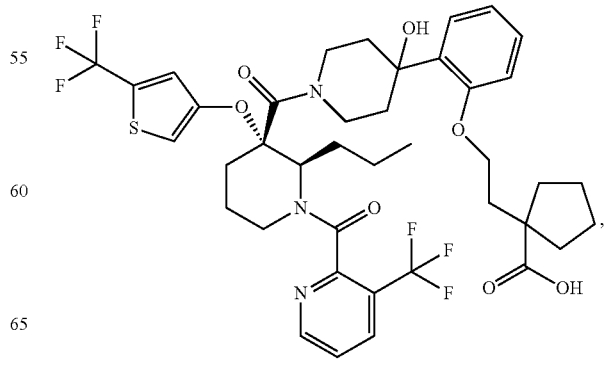

103
-continued
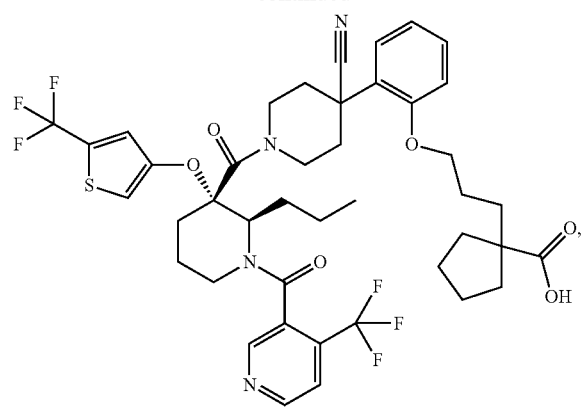
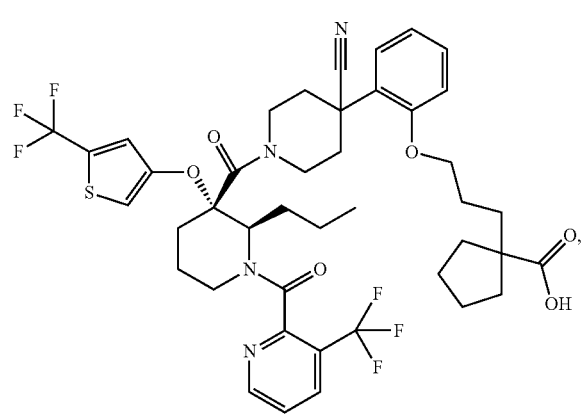
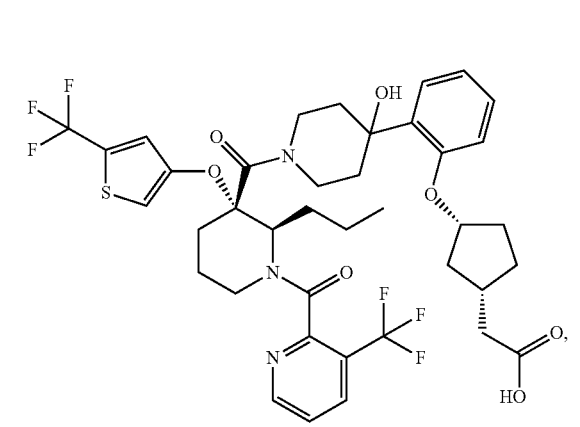
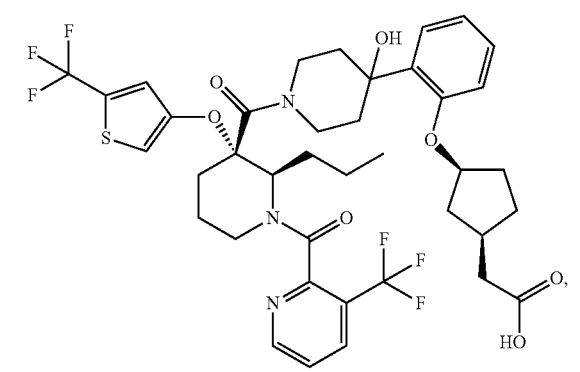
104
-continued
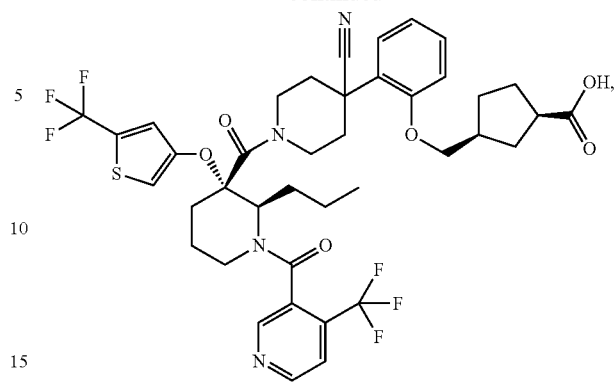
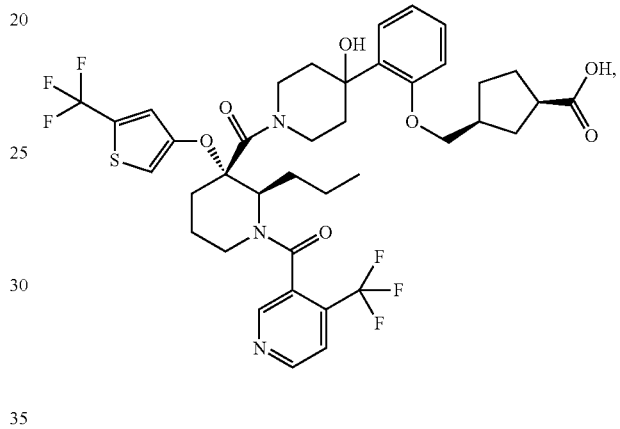
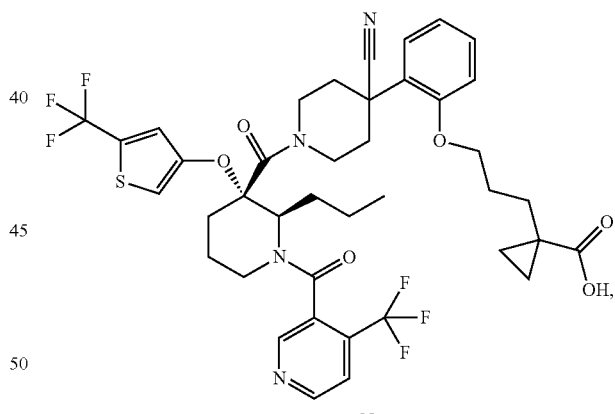
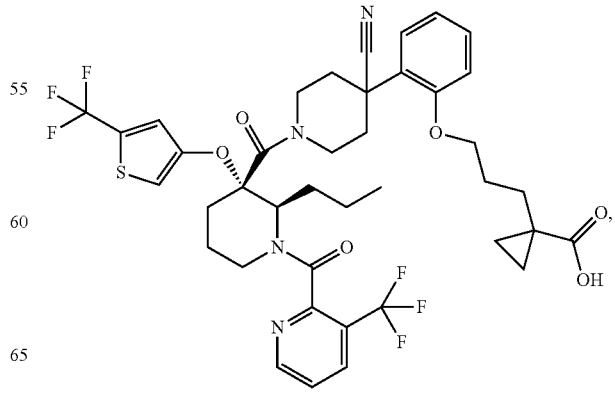

105
-continued
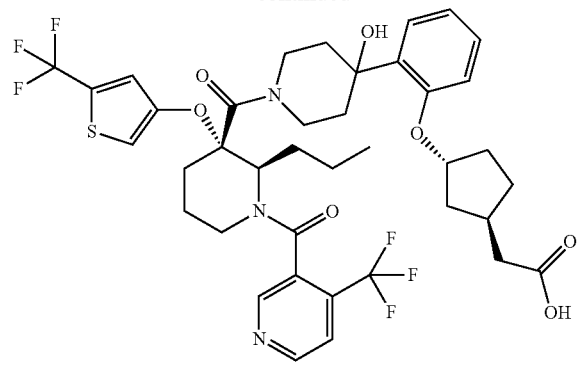
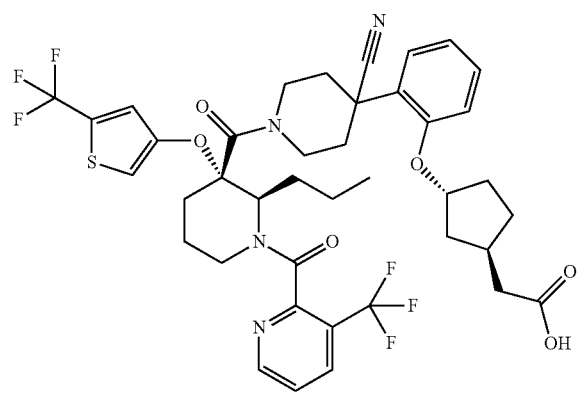
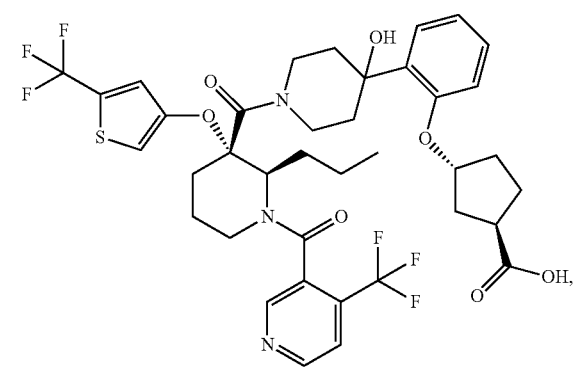
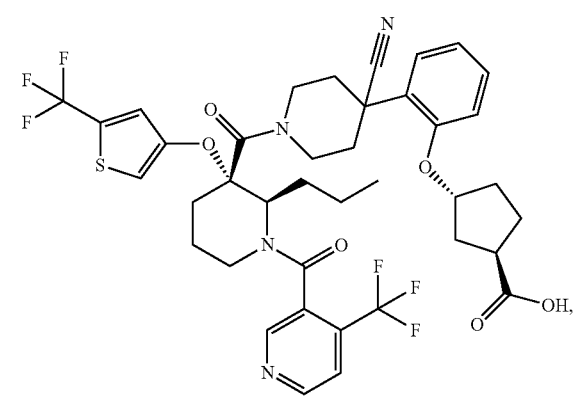
106
-continued
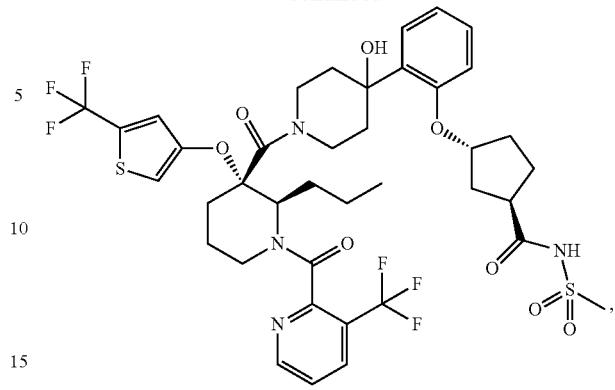
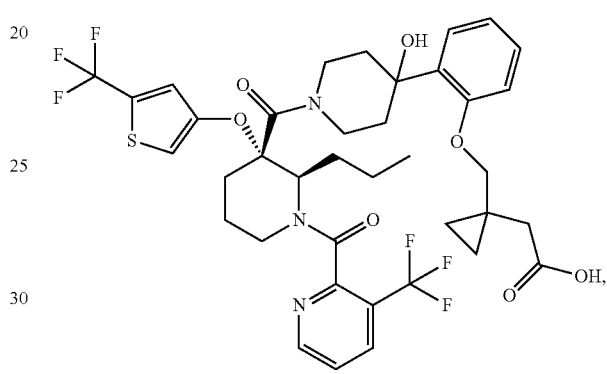
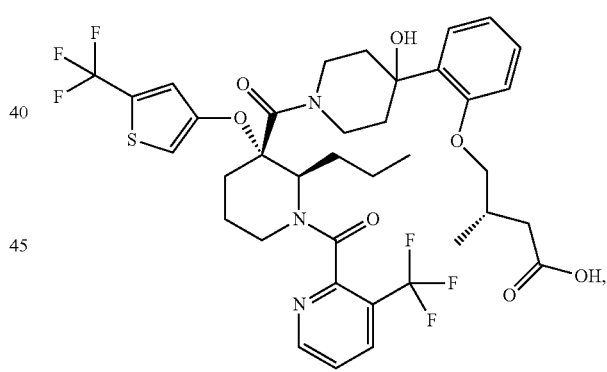
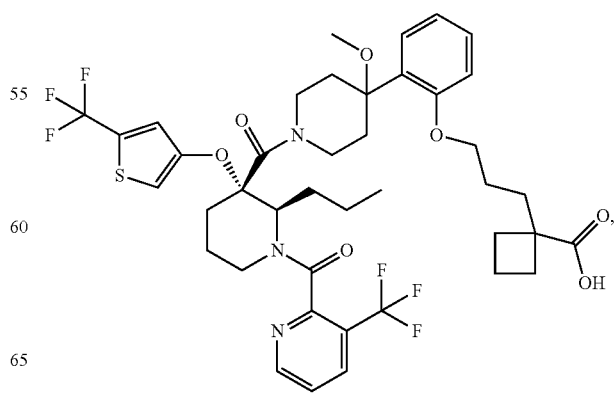

107
-continued
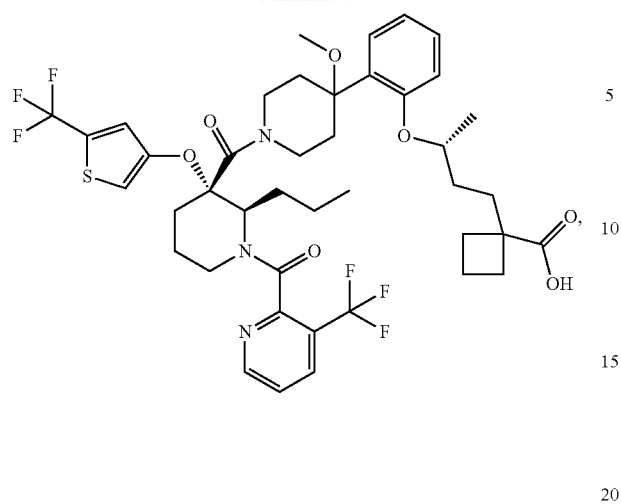
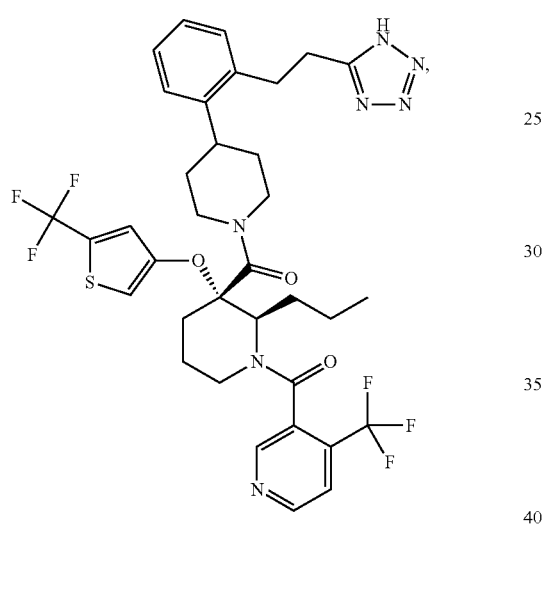
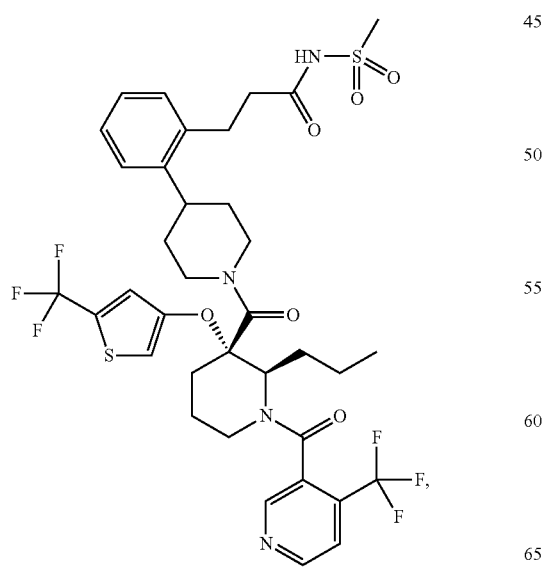
108
-continued
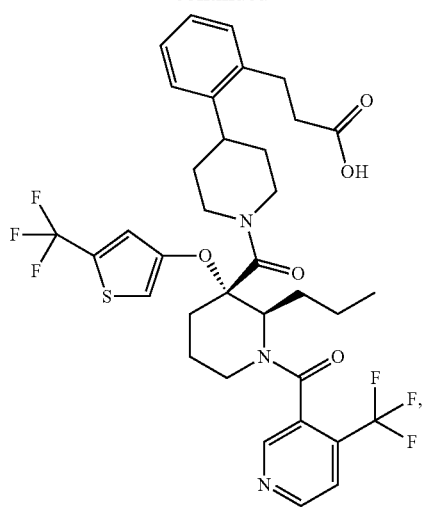
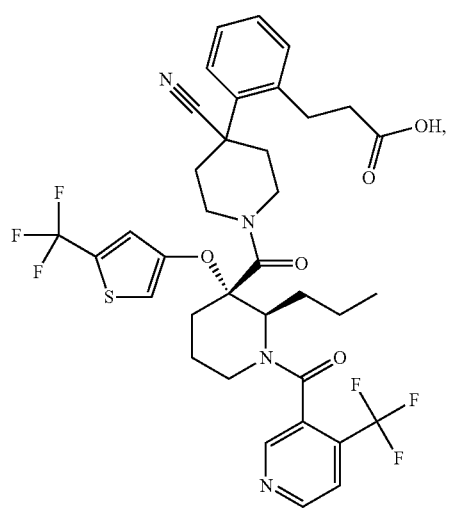
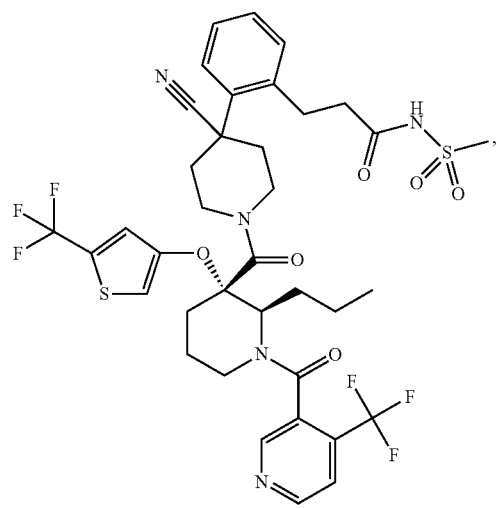

-continued

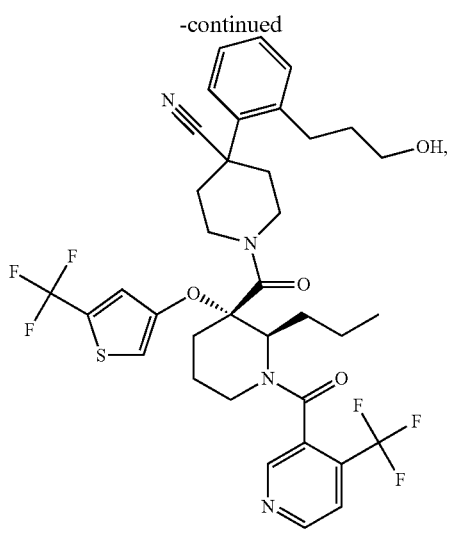

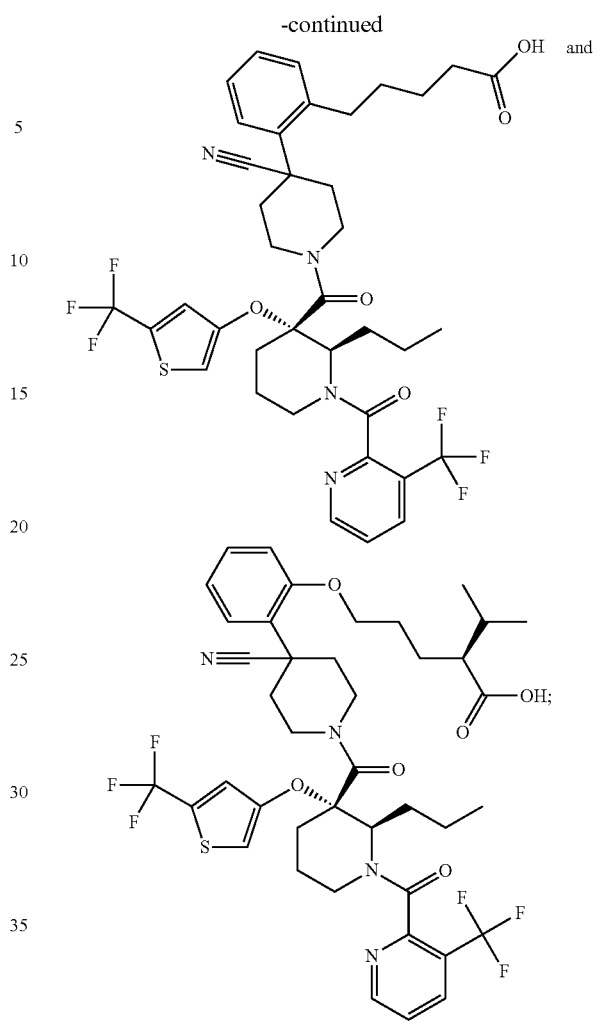

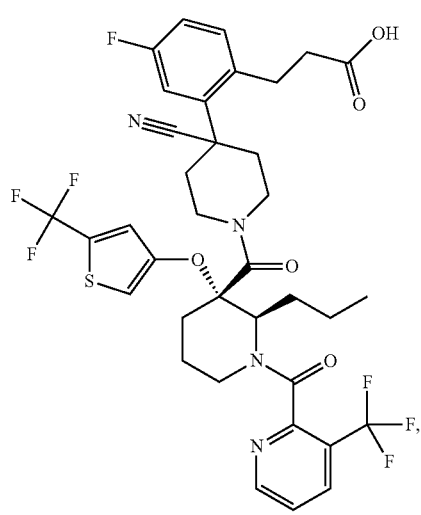

or a pharmaceutically acceptable salt, solvate, ester or prodrug thereof.

As used above, and throughout this disclosure, the following terms, unless otherwise indicated, shall be understood to have the following meanings. Any additional needed definition is understood to be the same as those disclosed in WO2008/005268 (equivalent of US Patent Publication US 2008/0004287 A1).

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkoxyalkoxy, alkylthio, amino, —NH (alkyl), —NH(cycloalkyl), —N(alkyl)$_2$, carboxy and —C(O) O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, carbazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH₃)₂— and the like which form moieties such as, for example:

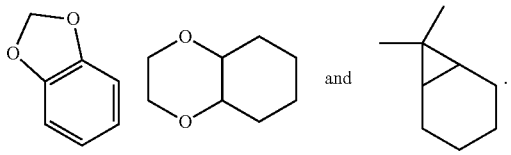

and

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heteroalkyl" is a saturated or unsaturated chain (unsaturated chain may also be interchangeably referred to as heteroalkenyl) containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of suitable bicyclic heterocyclyl rings include decahydro-isoquinoline, decahydro-[2,6]naphthyridine, and the like. "Heterocyclyl" may also mean a single moiety (e.g., carbonyl) which simultaneously replaces two available hydrogens on the same carbon atom on a ring system. Example of such moiety is pyrrolidone:


"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 15 ring atoms, preferably about 5 to about 14 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 13 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 1,2,3,4-tetrahydro-isoquinolinyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:


"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

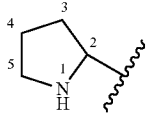

there is no —OH attached directly to carbons marked 2 and 5.

It should also be noted that tautomeric forms such as, for example, the moieties:

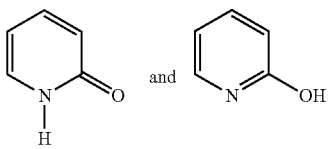 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Spiro ring systems" have two or more rings linked by one common atom. Preferred spiro ring systems include spiroheteroaryl, spiroheterocyclenyl, spiroheterocyclyl, spirocycloalkyl, spirocyclenyl, and spiroaryl. The spiro ring systems can be optionally substituted by one or more ring system substituents, wherein "ring system substituent" is as defined above. Non-limiting examples of suitable spiro ring systems include

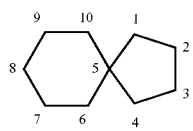

spiro[4.5]decane,

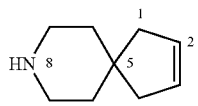

8-azaspiro[4.5]dec-2-ene, and

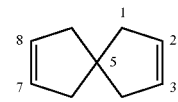

spiro[4.4]nona-2,7-diene.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen. An alkoxy linked directly to another alkoxy is an "alkoxyalkoxy".

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" or "thioalkoxy" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula 1 or 2, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula 1 or 2 or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula 1 or 2 or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$) alkyl, and the like.

Similarly, if a compound of Formula 1 or 2 contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl-α-aminoacyl, where each α-aminoacyl group is independently selected from the naturally occurring L-amino acids, P(O)$(OH)_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula 1 or 2 incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)$OY^1$ wherein $Y^1$ is H, ($C_1$-$C_6$)alkyl or benzyl, —C($OY^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino($C_1$-$C_4$)alkyl or mono-N- or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula 1 or 2 can form salts which are also within the scope of this invention. Reference to a compound of Formula 1 or 2 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 or 2 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula 1 or 2 may be formed, for example, by reacting a compound of Formula 1 or 2 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula 1 or 2, and salts, solvates, esters and prodrugs thereof, may exist in their tautomeric form (for example, as an amide or imino ether). All such tautomeric forms are contemplated herein as part of the present invention.

The compounds of Formula 1 or 2 may contain asymmetric or chiral centers, and, therefore, exist in different stereoisomeric forms. It is intended that all stereoisomeric forms of the compounds of Formula 1 or 2 as well as mixtures thereof, including racemic mixtures, form part of the present invention. In addition, the present invention embraces all geometric and positional isomers. For example, if a compound of Formula 1 or 2 incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula 1 or 2 may be atropisomers (e.g., substituted biaryls) and are considered as part of this invention. Enantiomers can also be separated by use of chiral HPLC column.

It is also possible that the compounds of Formula 1 or 2 may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula 1 or 2 incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula 1 or 2 (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances.

The term "Deuterated" in describing the compounds of this invention means that the deuterium-to-hydrogen ratio in the deuterated areas of the molecule substantially exceeds the naturally occurring deuterium-to-hydrogen ratio. Wikipedia (http://en.wikipedia.org/wiki/Deuterium) suggests that deuterium has a natural abundance in the oceans of Earth of approximately one atom in 6500 of hydrogen (~154 PPM). Deuterium thus accounts for approximately 0.015% (on a weight basis, 0.030%) of all naturally occurring hydrogen in the oceans on Earth. However, other sources suggest a much higher abundance of e.g. $6\cdot10^{-4}$ (6 atoms in 10,000 or 0.06% atom basis).

Deuteration of molecules and preparation of deuterated drugs are known. See, for example, M. Tanabe et al, "The Pharmacologic Effect of Deuterium Substitution on 5-n-Butyl-5-ethyl Barbituric Acid', *Life Sciences* (1969) Vol. 8, part I, pp. 1123-1128; N. J. Haskins, "The Application of Stable Isotopes in Biomedical Research", *Biomedical Mass Spectrometry* (1981), Vol. 9 (7), pp. 2690277; and the announcements from Concert Pharma (http://www.concertpharma.com/ConcertAnnouncesPreclinicalResultsICAAC.htm) regarding preclinical results of their deuterated antibiotic, C-20081, and http://www.concertpharma.com/news/ConcertBeginsCTP347PhaseI.htm regarding Phase I clinical trials of their deuterium-containing serotonin modulator, CTP-347.

Isotopically labelled compounds of Formula 1 or 2 can generally be prepared by following procedures analogous to those disclosed in the Schemes and/or in the Examples hereinbelow, by substituting an appropriate isotopically labelled reagent for a non-isotopically labelled reagent. For example, deuteration is specifically exemplified in representative Examples 63 and 64.

Polymorphic forms of the compounds of Formula 1 or 2, and of the salts, solvates, esters and prodrugs of the compounds of Formula 1 or 2, are intended to be included in the present invention.

HDM2, Hdm2, hDM2, and hdm2 are all equivalent representations of the Human Double Minute 2 protein. Likewise, MDM2, Mdm2, mDM2, and mdm2 are all equivalent representations mouse Double Minute 2 protein.

The compounds of Formula 1 or 2 can be inhibitors or antagonists of the Human or Mouse Double Minute 2 protein interaction with p53 protein and it can be activators of the p53 protein in cells. Furthermore, the pharmacological properties of the compounds of Formula 1 or 2 can be used to treat or prevent cancer, treat or prevent other disease states associated with abnormal cell proliferation, and treat or prevent diseases resulting from inadequate levels of p53 protein in cells.

Those skilled in the art will realize that the term "cancer" to be the name for diseases in which the body's cells become abnormal and divide without control.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecoloqical: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin:

malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, nuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compounds, compositions and methods of the invention include breast and prostate.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-

O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO003/049527, WO003/049679, WO003/049678, WO004/039774, WO03/079973, WO03/099211, WO003/105855, WO003/106417, WO004/037171, WO04/058148, WO004/058700, WO004/126699, WO005/018638, WO005/019206, WO05/019205, WO005/018547, WO005/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example PLX-4032), inhibitors of MEK (for example Arry-162, RO-4987655 and GSK-1120212), inhibitors of mTOR (for example AZD-8055, BEZ-235 and everolimus), and inhibitors of PI3K (for example GDC-0941, BKM-120).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862,5-methoxy-4-[2-methyl-3-(3-methyl-2-butenyl)oxiranyl]-1-oxaspiro[2,5]oct-6-yl(chloroacetyl)carbamate, acetyldinaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha v \beta_3$ integrin, to compounds which selectively antagonize, inhibit or counteract binding of a physiological ligand to the $\alpha v \beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with potassium salts, magnesium salts, beta-blockers (such as atenolol) and endothelin-a (ETa) antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors: olaparib, MK-4827 and veliparib.

A compound of the instant invention may also be useful for treating cancer in combination with the following chemotherapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/1-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), and the Physician's Desk Reference, 57th Edition, 2003 (published by Thompson PDR, Montvale, N.J. 07645-1742); the disclosures of which is incorporated herein by reference thereto.

The compounds of Formula 1 or 2 can be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostrate, larynx, ovaries, stomach, uterus, sarcoma and thyroid cancer;

hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoetic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderma pigmentosum, keratoctanthoma, thyroid follicular cancer and Kaposi's sarcoma.

Due to the key role of p53 in the regulation of cellular apoptosis (cell death), the compounds of Formula 1 or 2 could act as agent to induce cell death which may be useful in the treatment of any disease process which features abnormal cellular proliferation eg, cancers of various origin and tissue types, inflammation, immunological disorders.

Due to the key role of HDM2 and p53 in the regulation of cellular proliferation, the compounds of Formula 1 or 2 could act as reversible cytostatic agents which may be useful in the treatment of any disease process which features abnormal cellular proliferation, inhibitors could act as reversible cytostatic agents which may be useful in the treatment of any disease process which features abnormal cell proliferation, e.g., benign prostrate hyperplasia, familial adenomatosis polyposis, neuro-fibromatosis, atherosclerosis, pulmonary fibrosis, arthritis, psoriasis, glomerulonephritis, restenosis following angioplasty, or vascular surgery, hypertrophic scar formation, inflammatory bowel disease, transplantation rejection, endotoxic shock, and fungal infections.

Compounds of Formula 1 or 2 may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula 1 or 2 may also be useful in inhibiting tumor angiogenesis and metastasis.

Another aspect of this invention is a method of treating a mammal (e.g., human) having a disease or condition associated with HDM2 by administering a therapeutically effective amount of at least one compound of Formula 1 or 2, or a pharmaceutically acceptable salt, solvate, ester or prodrug of said compound to the mammal.

A preferred dosage is about 0.001 to 500 mg/kg of body weight/day of the compound of Formula 1 or 2. An especially preferred dosage is about 0.01 to 25 mg/kg of body weight/day of a compound of Formula 1 or 2, or a pharmaceutically acceptable salt, solvate, ester or prodrug of said compound.

The compounds of this invention may also be useful in combination (administered together or sequentially) with one or more of anti-cancer treatments such as radiation therapy, and/or one or more anti-cancer agents different from compound of Formula 1 or 2. The compounds of the present invention can be present in the same dosage unit as the anti-cancer agent or in separate dosage units.

Another aspect of the present invention is a method of treating one or more diseases associated with HDM2, comprising administering to a mammal in need of such treatment an amount of a first compound, which is a compound of the present invention, or a pharmaceutically acceptable salt, solvate, ester or prodrug thereof; and an amount of at least one second compound, the second compound being an anti-cancer agent different from the compounds of the present invention, wherein the amounts of the first compound and the second compound result in a therapeutic effect.

Non-limiting examples of suitable anti-cancer agents include cytostatic agents, cytotoxic agents, targeted therapeutic agents (small molecules, biologics, siRNA and microRNA) against cancer and neoplastic diseases, 1) anti-metabolites (such as methoxtrexate, 5-fluorouracil, gemcitabine, fludarabine, capecitabine);
2) alkylating agents, such as temozolomide, cyclophosphamide,
3) DNA interactive and DNA damaging agents, such as cisplatin, oxaliplatin, doxorubicin,
4) Ionizing irradiation, such as radiation therapy,
5) topoisomerase II inhibitors, such as etoposide, doxorubicin,
6) topoisomerase I inhibitors, such as irinotecan, topotecan,
7) tubulin interacting agents, such as paclitaxel, docetaxel, Abraxane, epothilones,
8) kinesin spindle protein inhibitors,
9) spindle checkpoint inhibitors,
10) Poly(ADP-ribose) polymerase (PARP) inhibitors, such as olaparib, MK-4827 and veliparib
11) Matrix metalloprotease (MMP) inhibitors
12) Protease inhibitors, such as cathepsin D and cathepsin K inhibitors
13) Proteosome or ubiquitination inhibitors, such as bortezomib,
14) Activator of mutant p53 to restore its wild-type p53 activity
15) Adenoviral-p53
16) Bcl-2 inhibitors, such as ABT-263
17) Heat shock protein (HSP) modulators, such as geldanamycin and 17-AAG
18) Histone deacetylase (HDAC) inhibitors, such as vorinostat (SAHA),
19) sex hormone modulating agents,
   a. anti-estrogens, such as tamoxifen, fulvestrant,
   b. selective estrogen receptor modulators (SERM), such as raloxifene,
   c. anti-androgens, such as bicalutamide, flutamide
   d. LHRH agonists, such as leuprolide,
   e. 5α-reductase inhibitors, such as finasteride,
   f. Cytochrome P450 C17 lyase (CYP450c17, also called 17α-hydroxylase/17,20 lysase) inhibitors, such as Abiraterone acetate, VN/124-1, TAK-700
   g. aromatase inhibitors, such as letrozole, anastrozole, exemestane,
20) EGFR kinase inhibitors, such as geftinib, erlotinib, laptinib
21) dual erbB1 and erbB2 inhibitors, such as Lapatinib
22) multi-targeted kinases (serine/threonine and/or tyrosine kinase) inhibitors,
   a. ABL kinase inhibitors, imatinib and nilotinib, dasatinib
   b. VEGFR-1, VEGFR-2, PDGFR, KDR, FLT, c-Kit, Tie2, Raf, MEK and ERK inhibitors, such as sunitinib, sorafenib, Vandetanib, pazopanib, PLX-4032, Axitinib, PTK787, GSK-1120212
   c. Polo-like kinase inhibitors,
   d. Aurora kinase inhibitors,
   e. JAK inhibitor
   f. c-MET kinase inhibitors
   g. Cyclin-dependent kinase inhibitors, such as CDK1 and CDK2 inhibitor SCH 727965
   h. PI3K and mTOR inhibitors, such as GDC-0941, BEZ-235, BKM-120 and AZD-8055
   i. Rapamycin and its analogs, such as Temsirolimus, everolimus, and deforolimus
23) and other anti-cancer (also know as anti-neoplastic) agents include but are not limited to ara-C, adriamycin, cytoxan, Carboplatin, Uracil mustard, Clormethine, Ifosfsmide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Vinorelbine, Navelbine, Bleomycin, Dactinomycin, Daunorubicin, Doxorubicin, Epirubicin, teniposide, cytarabine, pemetrexed, Idarubicin, Mithramycin, Deoxycoformycin, Mitomycin-C, L-Asparaginase, Teniposide 17-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Flutamide Medroxyprogesteroneacetate, Toremifene, goserelin, Carboplatin, Hydroxyurea, Amsacrine, Procarbazine, Mitotane, Mitoxantrone, Levamisole, Drolloxafine, Hexamethylmelamine, Bexxar, Zevalin, Trisenox, Profimer, Thiotepa, Altretamine, Doxil, Ontak, Depocyt, Aranesp, Neupogen, Neulasta, Kepivance.
24) Farnesyl protein transferase inhibitors, such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-piperidinecarboxamide, tipifarnib
25) interferons, such as Intron A, Peg-Intron,
26) anti-erbB1 antibodies, such as cetuximab, panitumumab,
27) anti-erbB2 antibodies, such as trastuzumab,
28) anti-CD52 antibodies, such as Alemtuzumab,
29) anti-CD20 antibodies, such as Rituximab
30) anti-CD33 antibodies, such as Gemtuzumab ozogamicin
31) anti-VEGF antibodies, such as Avastin,
32) TRIAL ligands, such as Lexatumumab, mapatumumab, and AMG-655
33) Anti-CTLA-4 antibodies, such as ipilimumab
34) antibodies against CTA1, CEA, CD5, CD19, CD22, CD30, CD44, CD44V6, CD55, CD56, EpCAM, FAP, MHCII, HGF, IL-6, MUC1, PSMA, TAL6, TAG-72, TRAILR, VEGFR, IGF-2, FGF,
35) anti-IGF-1R antibodies, such as dalotuzumab (MK-0646) and robatumumab (SCH 717454)

If formulated as a fixed dose such combination products employ the compounds of this invention within the dosage range described herein and the other pharmaceutically active agent or treatment within its dosage range. Compounds of Formula 1 or 2 may also be administered sequentially with known anticancer or cytotoxic agents when a combination formulation is inappropriate. The invention is not limited in the sequence of administration; compounds of Formula 1 or 2 may be administered either concurrent with, prior to or after administration of the known anticancer or cytotoxic agent. Such techniques are within the skills of the persons skilled in the art as well as attending physicians.

Accordingly, in an aspect, this invention includes combinations comprising an amount of at least one compound of Formula 1 or 2, or a pharmaceutically acceptable salt, solvate, ester or prodrug thereof, and an amount of one or more anti-cancer treatments and anti-cancer agents listed above wherein the amounts of the compounds/treatments result in desired therapeutic effect.

Another aspect of the invention is a method of protecting normal, healthy cells of a mammal from cytotoxic induced side-effects comprising administering at least one compound of the invention or a pharmaceutically acceptable salt, solvate, ester or prodrug thereof to a cancer patient, in particular those carrying mutated p53, prior to administration of anti-cancer agents other than the compounds of the invention, such as paclitaxel.

A method of inhibiting one or more HDM2 proteins in a patient in need thereof, comprising administering to the patient a therapeutically effective amount of at least one compound of claim 1 or a pharmaceutically acceptable salt, solvate, ester or prodrug thereof.

Another aspect of the present invention is a method of treating, or slowing the progression of a disease associated with one or more HDM2 proteins in a patient, comprising administering to a patient in need thereof, a therapeutically effective amount of at least one compound of the present invention or a pharmaceutically acceptable salt, solvate, ester or prodrug thereof.

Another aspect of the present invention is a method of treating, or slowing the progression of a disease associated with inadequate p53 levels in a patient, comprising administering to a patient in need thereof, a therapeutically effective amount of at least one compound of the present invention or a pharmaceutically acceptable salt, solvate, ester or prodrug thereof.

Yet another aspect of the present invention is a method of treating one or more diseases associated with HDM2, comprising administering to a mammal in need of such treatment an amount of a first compound, which is a compound of the present invention, or a pharmaceutically acceptable salt, solvate, ester or prodrug thereof; and an amount of at least one second compound, the second compound being an anti-cancer agent, wherein the amounts of the first compound and the second compound result in a therapeutic effect.

Another aspect of the present invention is a method of treating one or more diseases associated with inadequate p53 levels, comprising administering to a mammal in need of such treatment an amount of a first compound, which is a compound of the present invention, or a pharmaceutically acceptable salt, solvate, ester or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with a HDM2 protein comprising administering to a patient in need thereof, a therapeutically effective amount of a pharmaceutical composition comprising in combination at least one pharmaceutically acceptable carrier and at least one compound according to the present invention, or a pharmaceutically acceptable salt, solvate, ester or prodrug thereof.

Another aspect of the present invention is a method of treating, or slowing the progression of, a disease associated with inadequate p53 levels in a patient, comprising administering to a patient in need thereof, a therapeutically effective amount of a pharmaceutical composition comprising in combination at least one pharmaceutically acceptable carrier and at least one compound according to the present invention, or a pharmaceutically acceptable salt, solvate, ester or prodrug thereof.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Another embodiment of the invention discloses a method of making the substituted compounds disclosed above. The compounds may be prepared by several processes well known in the art. In one method, the starting material, 1-benzyl-3-(4-trifluoromethyl-phenoxy)-piperidine-3-carboxylic acid is converted to its diisopropylethyl ammonium salt of the dicarboxylic acid ester. This ester is combined with 1-(2-methoxy-phenyl)-piperazine forming the HCL salt of 4-(2-methoxy-phenyl)-piprazinl-yl]-[3-(4-trifluormethylphenoxy)-piperidin-3-yl]-methanone, which combined with 4-trifluoromethyl-nicotinic acid to form the target compound. Other substituted compounds of this invention can be made.

Isolation of the compound at various stages of the reaction may be achieved by standard techniques such as, for example, filtration, evaporation of solvent and the like. Purification of the product, intermediate and the like, may also be performed by standard techniques such as recrystallization, distillation, sublimation, chromatography, conversion to a suitable derivative, which may be recrystallized and converted back to the starting compound, and the like. Such techniques are well known to those skilled in the art.

The compounds of this invention may be analyzed for their composition and purity as well as characterized by standard analytical techniques such as, for example, elemental analysis, NMR, mass spectroscopy, and IR spectra.

In another embodiment, this invention provides pharmaceutical compositions comprising the above-described inventive substituted compounds as an active ingredient. The pharmaceutical compositions generally additionally comprise a pharmaceutically acceptable carrier diluent, excipient or carrier (collectively referred to herein as carrier materials). Because of their HDM2 or MDM2 antagonist activity, such pharmaceutical compositions possess utility in treating cancer, abnormal cell proliferation, and the like diseases.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Lubricants in these dosage forms include boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. anti-cell proliferation activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. For example, water or water-propylene glycol solutions may be included for parenteral injections or sweeteners and pacifiers may be added for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool to solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Another aspect of this invention is a kit comprising a therapeutically effective amount of at least one compound of Formula 1I or 2, or a pharmaceutically acceptable salt, solvate, ester or prodrug of said compound and a pharmaceutically acceptable carrier, vehicle or diluent.

Yet another aspect of this invention is a kit comprising an amount of at least one compound of Formulas 1 or 2, or a pharmaceutically acceptable salt, solvate, ester or prodrug of said compound and an amount of at least one anticancer therapy and/or anti-cancer agent listed above, wherein the amounts of the two or more ingredients result in desired therapeutic effect.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refer to the active ingredients dispersed or solubilized in a hydrophillic semi-solid matrix.

Powders for constitution refer to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The invention disclosed herein is exemplified by the following preparations and examples which should not be construed to limit the scope of the disclosure. Alternative mechanistic pathways and analogous structures will be apparent to those skilled in the art.

The following abbreviations have the following meanings unless defined otherwise:
ACN Acetonitrile
AcOH Acetic acid
DAST (diethylamino)sulfur trifluoride
DCC Dicyclohexylcarbodiimide
DCU Dicyclohexylurea
DCM Dichloromethane
DI Deionized water
DIAD Diisopropylazodicarboxylate
DIEA Diisopropylethylamine
DMAP 4-Dimethylaminopyridine
DME Dimethoxyethane
DMF Dimethylformamide
DMFDMA N,N-Dimethylformamide dimethylacetal
DMSO Dimethyl sulfoxide
DTT Dithiothreitol
EDCl 1-(3-dimethylamino-propyl)-3-ethylcarbodiimide hydrochloride
EtOAc Ethyl acetate
EtOH Ethanol
HATU N,N,N',N'-Tetramethyl-O-(7-Azabenzotriazol-1-yl) Uronium hexafluorophosphate
Hex hexanes
HOBt 1-Hydroxylbenzotriazole
HPLC High pressure liquid chromatography
LCMS Liquid chromatography mass spectrometry
LDA Lithium diisopropylamide
mCPBA meta-Chloroperoxybenzoic acid
MeOH Methanol
MTT (3-[4,5-dimethyl-thiazol-2-yl]-2,5-diphenyltetrazolium bromide, Thiazolyl blue)
NMR Nuclear magnetic resonance
PFP Pentafluorophenol
PMB p-methoxybenzyl
Pyr Pyridine
Rb Round bottom flask
Rbt Round bottom flask
RT Room temperature
SEMCl 2-(Trimethylsily)ethoxy methyl chloride
TBTU O-(Benzotriazol-1-yl)-N,N,N',N'-tetramethyluronium tetrafluoroborate
TEA Triethylamine
Tr Triphenyl methane
Trt Triphenyl methane
TrCl Triphenyl methane chloride
TFA Trifluoroacetic acid
THF Tetrahydrofuran
TLC Thin layer chromatography
TMS Trimethylsilyl Representative Procedures to Prepare Substituted Piperidines Used in the Synthesis of HDM2 Inhibitors Included in Table 1

Representative Example 1

Preparation of 4-(2-hydroxyphenyl)piperidin-4-ol 3

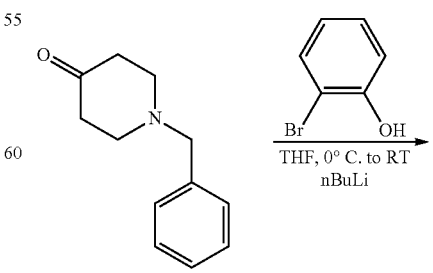

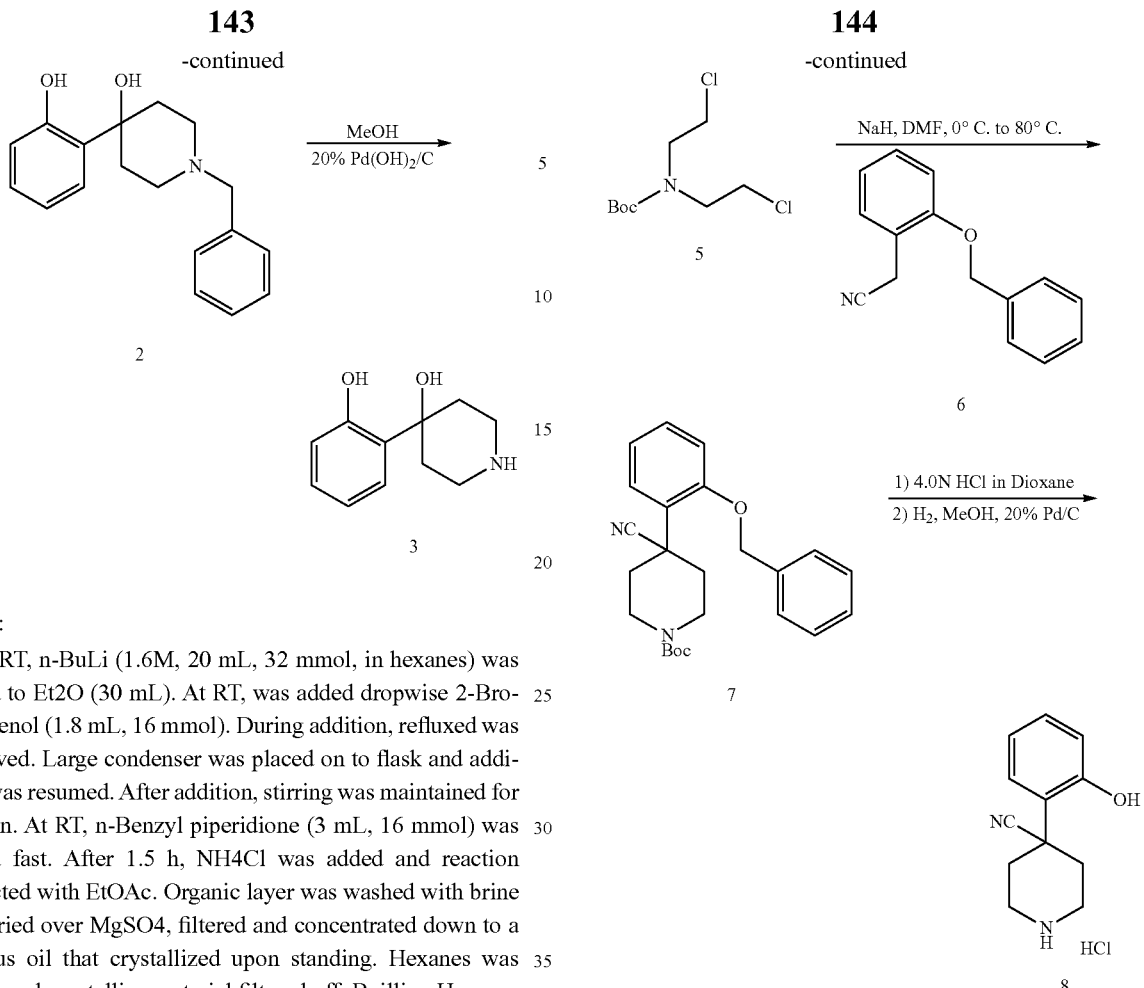

Step 1:

At RT, n-BuLi (1.6M, 20 mL, 32 mmol, in hexanes) was added to Et2O (30 mL). At RT, was added dropwise 2-Bromophenol (1.8 mL, 16 mmol). During addition, refluxed was observed. Large condenser was placed on to flask and addition was resumed. After addition, stirring was maintained for 45 min. At RT, n-Benzyl piperidione (3 mL, 16 mmol) was added fast. After 1.5 h, NH4Cl was added and reaction extracted with EtOAc. Organic layer was washed with brine and dried over MgSO4, filtered and concentrated down to a viscous oil that crystallized upon standing. Hexanes was added and crystalline material filtered off. Boilling Hexanes was added to the first drop of crystalline 2. Slurry was stirred and crystalline material filtered off and dried under Nitrogen. After drying, 2.32 g of crystalline product was obtained with LCMS purity >99.5%.

Step 2:

To 2 (2.04 g, 5.46 mmol) in 25 mL of MeOH was added 20% Pd(OH)$_2$/C (1 g, 50% w/w). The mixture was stirred at RT under H$_2$ overnight. The reaction was filtered through a pad of celite and filtrate was concentrated to dryness to give 1.03 g (100% yield) of solid product 3.

Representative Example 2

Preparation of 4-(2-hydroxyphenyl)piperidine-4-carbonitrile hydrochloride 8

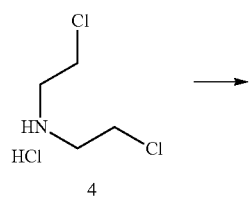

Step 1:

To the amine, 4 (80 g, 45 mmol, 1 equi.) dissolved in acetonitrile/water (800/80 mL) was added sodium hydroxide (2 equi., 291 mmol, 36 g) and to the stirring solution, Boc anhydride (1.02 equi, 46 mmol, 101 g) dissolved in acetonitrile (200 mL) was added drop wise and stirred for 18 hours at room temperature. Volatile was removed to 300 mL and solid residue was filtered out. Washed the solid with dichloromethane and evaporated off the solvent to provide 102 g of intermediate 5.

Step 2:

Nitrile 6 (15 g, 1 equi.) was dissolved in DMF (100 mL) and was cooled to 0° C. NaH (60% in mineral oil, 2.1 equi.) was added and the reaction was warmed to 23° C. and stirred for 10 min. Dichloride. 5 (1 equi) was added and the reaction was heated to 80° C. and stirred overnight. The reaction was cooled to 23° C. and was quenched with aqueous saturated. NH$_4$Cl (20 mL). The mixture was extracted with EtOAc (3×100 mL). The organic layers were washed with brine (1×50 ml), dried over Na$_2$SO$_4$, filtered and concentrated down to dryness. The residue was purified by silica gel chromatography (10% to 80% ethyl acetate/hexanes) to provide 21.4 g of intermediate 7 (74% yield).

Step 3:

Intermediate 7 (15.6 gm, 1 equiv.) dissolved in MeOH (150 mL). The solution was degassed with N$_2$ few times. Pd/C (20%, 3 mg) was added and H$_2$ was bubbled in for a few minutes. The reaction was stirred under a H$_2$ balloon at 23° C. for 4 hrs. The reaction was filtered through a pad of celite and filtrate was concentrated to dryness to give 11.8 g (98% yield) of product to which 4 M HCl/dioxane (120 mL) was added. Slurry was stirred at 23° C. for 1.5 h. The solution was concentrated to yield hydrochloride 8 (9 g, 96% yield over 2 steps).

Representative Example 3

Preparation of 4-(2-methoxyphenyl)-4-methylpiperidine 11 and 4-ethynyl-4-(2-methoxyphenyl)piperidine 13

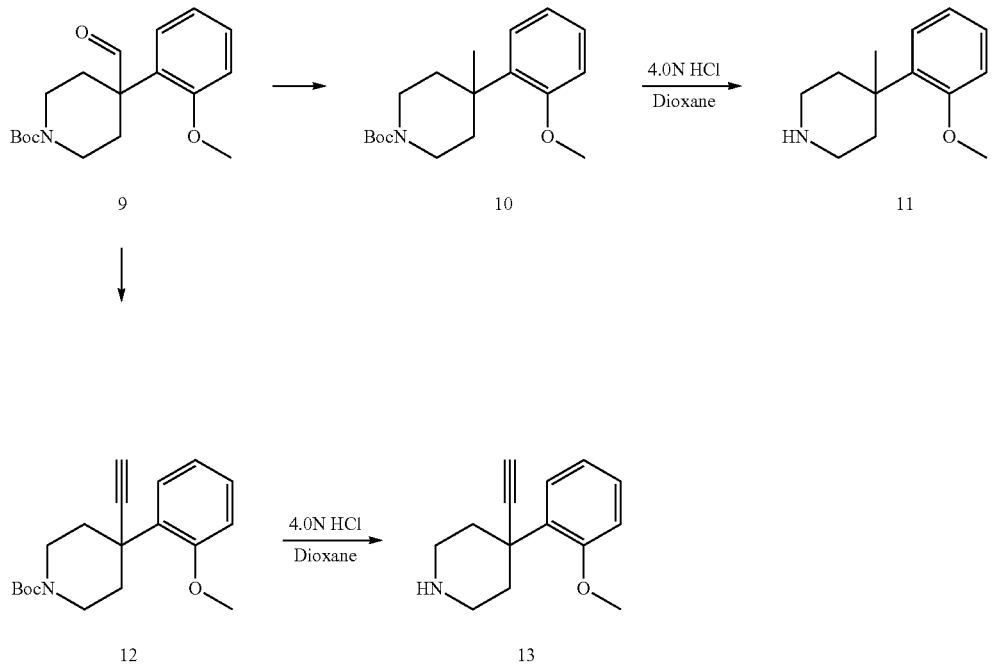

Intermediate 10 was prepared according a published procedure (*J. Org. Chem.*, 2001, 4, 1434) from corresponding aldehyde 9. Piperidine 11 was obtained following same procedure described in example 2, step3. Intermediate 12 was prepared from same aldehyde 9 using Ohira's phosphonate. Piperidine 13 was obtained following same procedure described in example 2, step3.

Representative Example 4

Preparation of 2-methoxyethyl 4-(2-(2-methoxyethoxy)phenyl)piperidine-4-carboxylate hydrochloride 18

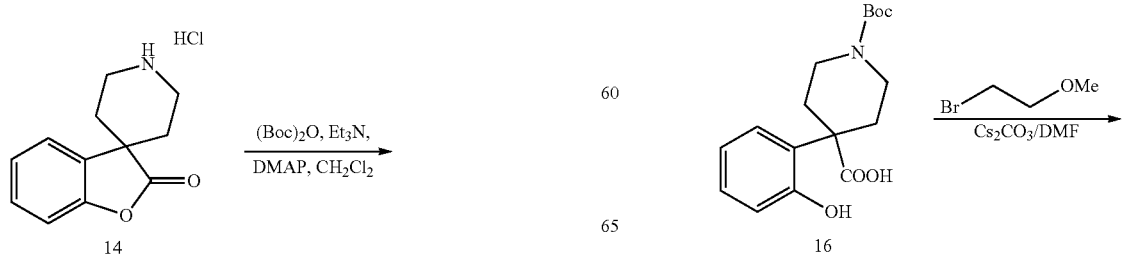

-continued

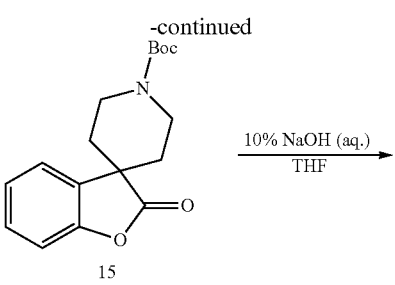

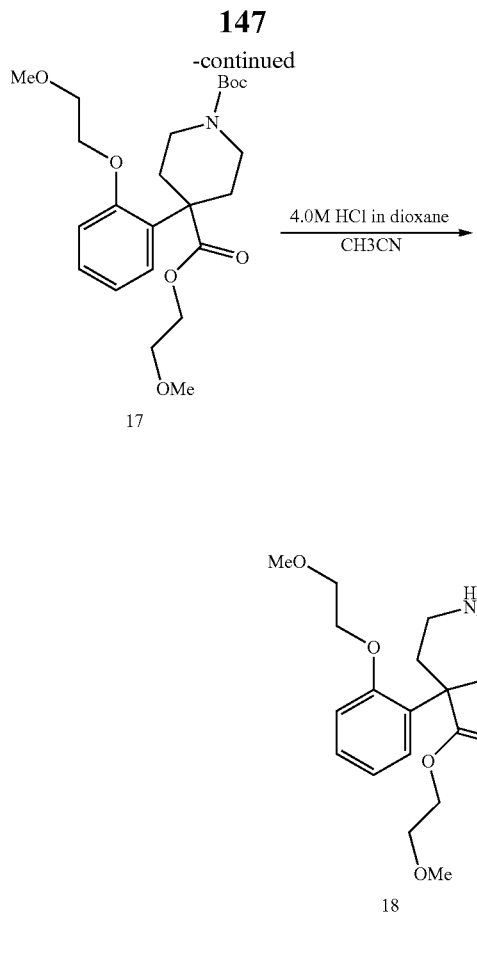

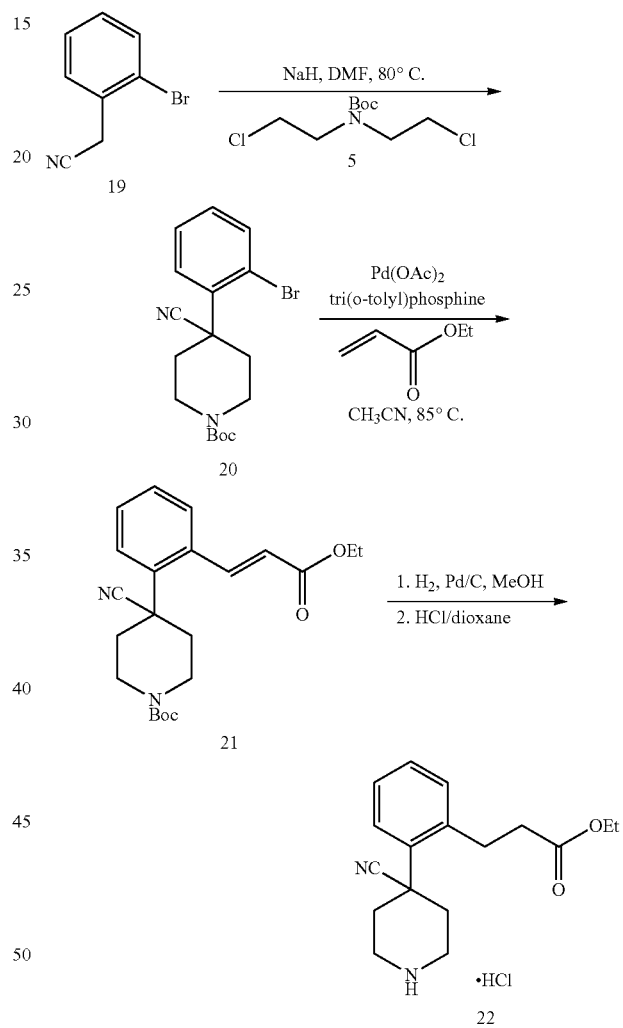

Step 4:

To a solution of 17 in acetonitrile at room temperature was added 4.0 M hydrochloride in 1,4-dioxane. After 10 min, the solvent and volatile were removed by lyophilization, to give 18 as yellowish oil.

Representative Example 5

Preparation of ethyl 3-(2-(4-cyanopiperidin-4-yl)phenyl)propanoate hydrochloride 22

Step 1:

To a stirring suspension of 14 (3.3 mmol, 0.8 g) in dichloromethane and triethylamine (8.25 mmol, 1.15 ml) at room temperature was added di-t-butyl dicarbonate (4.0 mmol, 0.87 g) followed by DMAP (0.33 mmol, 40 mg). The reaction mixture was stirred at room temperature for 6 hours and then diluted with EtOAc (200 ml), washed with water (2×40 ml), brine (40 ml), then dried (Na2SO4). The solvent was removed in vacuo. The crude product 15 (0.97 g) was obtained as colorless oil, which was used in the next step without further purification.

Step 2:

To a stirring solution of 15 (0.33 mmol, 100 mg) in THF (1 ml) was added 10% NaOH (2 ml) and the solution was stirred at room temperature overnight. The reaction mixture was neutralized with 0.5 N HCl to PH ~4, then extracted with EtOAc (2×25 ml). The combined organic layer was dried and concentrated. The crude product 16 (110 mg) was obtained as white solid, which was used in the next step without further purification.

Step 3:

To a stirring solution of 16 (0.44 mmol, 0.140 g) in DMF (5 ml) at room temperature was added cesium carbonate (4.4 mmol, 1.43 g) followed by 2-Bromoethyl methyl ether (4.4 mmol, 0.42 ml). The reaction mixture was stirred at room temperature overnight. The solvent was removed in vacuo. The residue was dissolved in EtOAc (50 ml), washed with water (2×10 ml), brine (10 ml), and dried (Na2SO4). The solvent was removed in vacuo. The crude product was purified by Biotage (EtOAc in hexane: 0-25%) to yield pure 17.

Step 1:

Nitrile 19 (1.0 g, 5.10 mmol) was dissolved in DMF (20 mL) and was cooled to 0° C. NaH (60% in mineral oil, 449 mg, 11.22 mmol) was added and the reaction was warmed to 23° C. and was stirred for 10 min. Dichloride (5, 1.3 g, 5.36 mmol) was added and the reaction was heated at 80° C. overnight. The reaction was cooled to 23° C. and was quenched with aqueous sat'd NH4Cl (5 mL). The mixture was extracted with EtOAc (3×). The organic layers were washed with brine (1×), dried over MgSO4, filtered and concentrated. The crude residue was recrystallized with EtOAc/hexanes to obtain pure tert-butyl 4-(2-bromophenyl)-4-cyanopiperidine-1-carboxylate as an off-white solid (20, 1.1 g, 59% yield). 1H NMR (400 MHz, CDCl$_3$): δ 7.70-7.68 (m, 1H), 7.39-7.37 (m, 2H), 7.25-7.21 (m, 2H), 4.31-4.27 (m, 2H), 3.29 (bt, 2H), 2.58-2.52 (m, 2H), 1.98 (td, 2H), 1.48 (s, 9H).

Step 2:

Tert-butyl 4-(2-bromophenyl)-4-cyanopiperidine-1-carboxylate (20, 100 mg, 0.28 mmol) and Pd(OAc)$_2$ (7.0 mg, 0.030 mmol) were added to a vial, followed by tri(o-tolyl) phosphine (14 mg, 0.047 mmol). The reaction vial was purged with Ar (3×). Dry CH$_3$CN (1.4 mL) and Et$_3$N (103 μL, 0.74 mmol) were added, followed by ethylacrylate (36 μL, 0.33 mmol). The reaction mixture was heated at 85° C. overnight. The reaction was concentrated. Et$_2$O (2 mL) was added to the mixture and was then filtered through Celite. The crude residue was purified by silica gel chromatography (gradient, 10% to 20% EtOAc/hexanes) to yield (E)-tert-butyl 4-cyano-4-(2-(3-ethoxy-3-oxoprop-1-enyl)phenyl)piperidine-1-carboxylate as a pale yellow oil (21, 102 mg, 96% yield). $^1$H NMR (400 MHz, CDCl$_3$): δ 8.51 (d, 1H), 7.58 (dd, 1H), 7.41 (td, 1H), 7.38-7.34 (m, 1H), 6.31 (d, 1H), 4.29 (q, 1H), 3.29 (bt, 2H), 2.35-2.31 (m, 2H), 1.90 (dt, 2H), 1.47 (s, 9H), 1.35 (t, 3H).

Step 3:

(E)-tert-butyl 4-cyano-4-(2-(3-ethoxy-3-oxoprop-1-enyl)phenyl)piperidine-1-carboxylate (21, 278 mg, 0.72 mmol) was dissolved in MeOH (7 mL). The solution was degassed with Ar for 2 min. Pd/C (10%, 30 mg) was added and H$_2$ was bubbled in for a few minutes. The reaction was stirred under a H$_2$ balloon at 23° C. overnight. The solution was filtered through Celite and was concentrated to yield tert-butyl 4-cyano-4-(2-(3-ethoxy-3-oxopropyl)phenyl)piperidine-1-carboxylate. $^1$H NMR (400 MHz, CDCl$_3$): δ 7.32-7.30 (m, 2H), 7.26-7.24 (m, 2H), 4.28 (bd, 2H), 4.17 (q, 2H), 3.29-3.25 (m, 4H), 2.78-2.74 (m, 2H), 2.34-2.30 (m, 2H), 1.91 (td, 2H), 1.48 (s, 9H), 1.26 (t, 3H). LC/MS RT (5 min method)=2.19 min. Mass observed: 287.22 (M-Boc+H).

Step 4:

4 M HCl/dioxane (905 μL, 3.62 mmol) was added to neat tert-butyl 4-cyano-4-(2-(3-ethoxy-3-oxopropyl)phenyl)piperidine-1-carboxylate at 23° C. and was stirred for 2 h. The solution was concentrated to yield ethyl 3-(2-(4-cyanopiperidin-4-yl)phenyl)propanoate hydrochloride (22, 230 mg, 99% yield over 2 steps).

Representative Example 6

Synthesis of ethyl 3-(2-(piperidin-4-yl)phenyl)propanoate hydrochloride 24

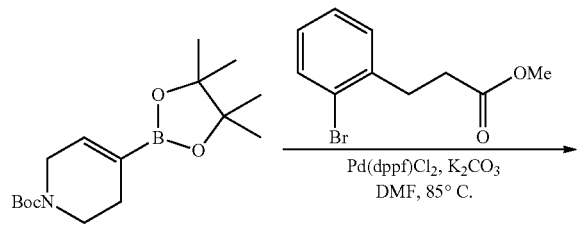

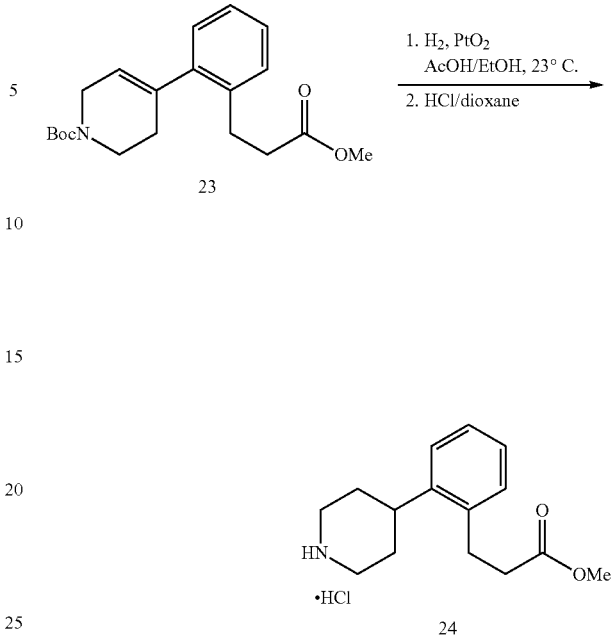

Step 1:

To Methyl 3-(2-bromophenyl)propanoate (715 mg, 2.94 mmol) and 3,6-dihydro-2H-pyridine-1-N-Boc-4-boronic acid pinacol ester (1.0 g, 3.23 mmol) were added to a flask, followed by Pd(dppf)Cl$_2$ (151 mg, 0.21 mmol) and K$_2$CO$_3$ (1.22 g, 8.82 mmol). The reaction flask was purged with Ar (3×). Dry DMF (22 mL) was added and the solution was degassed for 10 min. The reaction mixture was heated to 85° C. overnight. The mixture was filtered through Celite and was concentrated. The crude residue was purified by silica gel chromatography (gradient, 10% to 30% EtOAc/hexanes) to give tert-butyl 4-(2-(3-methoxy-3-oxopropyl)phenyl)-5,6-dihydropyridine-1(2H)-carboxylate (23) as a pale yellow oil (970 mg, 96% yield). $^1$H NMR (400 MHz, CDCl$_3$): δ 7.21-7.16 (m, 3H), 7.09-7.06 (m, 1H), 5.57-5.55 (m, 1H), 4.03 (q, 2H), 3.67 (s, 3H), 3.63 (t, 2H), 2.95-2.91 (m, 2H), 2.59-2.55 (m, 2H), 2.37-2.33 (m, 2H), 1.50 (s, 9H). LC/MS RT (5 min method)=2.10 min. Mass observed: 246.19 (M-Boc+H).

Step 2:

23 (310 mg, 0.90 mmol) was dissolved in EtOH/AcOH (4 mL/4 mL). The solution was degassed with Ar for 2 min. PtO$_2$ (61 mg, 0.27 mmol) was added to the mixture and H$_2$ was bubbled in for 2 min. The reaction was stirred under a H$_2$ balloon overnight. The reaction mixture was filtered through Celite and was concentrated to yield tert-butyl 4-(2-(3-methoxy-3-oxopropyl)phenyl)piperidine-1-carboxylate. LC/MS RT (5 min method)=2.47 min. Mass observed: 248.21 (M-Boc+H).

4 M HCl/dioxane (2.2 mL, 8.97 mmol) was added to neat tert-butyl 4-(2-(3-methoxy-3-oxopropyl)phenyl)piperidine-1-carboxylate at 23° C. and was stirred overnight. The reaction mixture was concentrated to yield methyl 3-(2-(piperidin-4-yl)phenyl)propanoate hydrochloride (24, 250 mg, 98% yield). LC/MS RT (5 min method)=1.14 min. Mass observed: 248.16 (M+H).

Representative Example 7

Preparation of 4-(2-(3-hydroxypropyl)phenyl)piperidin-4-ol 27

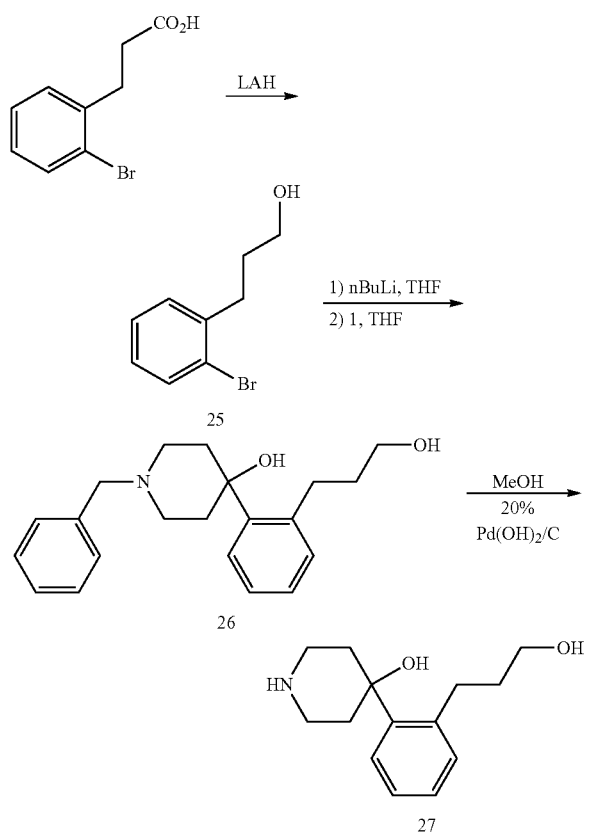

Step 1:
To 3-(2-Br-phenyl)propionic acid (2.0 g, 8.73 mmol) in THF was added LAH (8.73 mL, 8.73 mmol, 1 eq.) at 0° C. The mixture was stirred at 0° C. for 1 hour. Reaction was quenched by addition of $Na_2SO_4.10H_2O$ and stirred for 15 min. The reaction mixture was diluted with EtOAc and washed with 1N HCl and brine. Filtered and concentrated to dryness to give 1.16 g of crude product alcohol 25 (62% yield).

Step 2:
To 25 (0.46 g, 2.14 mmol) in 8 mL of THF was added nBuLi (2.9 mL, 4.28 mmol, 2.0 eq.) slowly at −78° C. The mixture was stirred at −78° C. for 30 min, followed by the addition of 1-Benzy-4-piperidone 1 (405 mg, 2.14 mmol, 1 eq.) in 3 mL of THF. The mixture was stirred at −78° C. and warmed up to −10° C. in 1 hour, then stirred at room temperature for 2 hours. Reaction mixture was quenched with water. Reaction was diluted with EtOAc and washed with water and brine. The organic layer was dried over $MgSO_4$, filtered and concentrated down. The residue was purified by silica gel chromatography (10% to 60% ethyl acetate/hexanes) to provide 0.154 g of product 26 (22% yield).

Step 3:
To 26 (90 mg, 0.28 mmol) in 2 mL of MeOH at room temperature was added 20% $Pd(OH)/C$ (72 mg, 80% w/w). The reaction was stirred under a $H_2$ balloon overnight. The reaction mixture was filtered through Celite and was concentrated to yield 57 mg of product 27 (85% yield).

Representative Example 8

Synthesis of 3-(2-(piperidin-4-yl)phenyl)propanenitrile hydrochloride 28

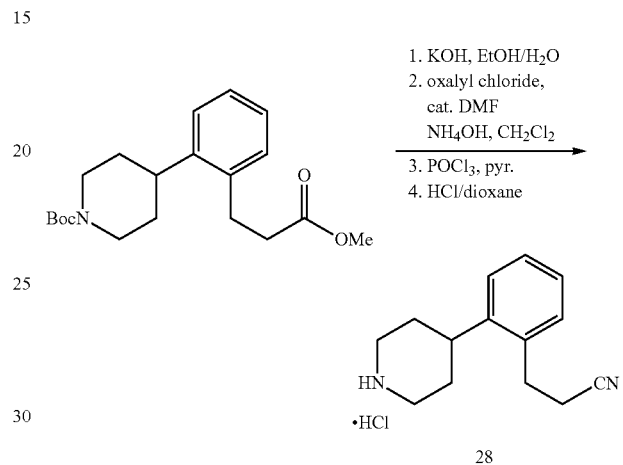

Step 1:
tert-butyl 4-(2-(3-methoxy-3-oxopropyl)phenyl)piperidine-1-carboxylate obtained in step 3 of representative example 6 (300 mg, 0.86 mmol) was dissolved in $EtOH/H_2O$ (6.0 mL/5 drops). KOH (121 mg, 2.16 mmol) was added and the reaction was heated at 70° C. for 3 h. The reaction mixture was cooled and then concentrated. The residue was dissolved in $H_2O$ and acidified to pH~4 with 1 M HCl. The solution was extracted with EtOAc (3×15 mL), dried over $Na_2SO_4$ and concentrated.

Step 2:
The crude acid (100 mg, 0.30 mmol) was dissolved in $CH_2Cl_2$ (3.0 mL) and then DMF (2 drops) was added. Oxalyl chloride (34 μL, 0.36 mmol) was added dropwise and the reaction was stirred at 23° C. under Ar for 1 h. $NH_4OH$ (28%) was added to the reaction mixture and was stirred for 15 min. The mixture was extracted with EtOAc (2×15 mL). The organic layer was washed with water (1×20 mL), and brine (1×20 mL). The solution was dried over $Na_2SO_4$ and concentrated.

Step 3:
The crude amide (96 mg, 0.29 mmol) was dissolved in pyridine (700 μL) under Ar. The mixture was cooled to 0° C. and $POCl_3$ (28 μL, 0.30 mmol) was added dropwise. The mixture was warmed to 23° C. and was further stirred for 3 h. The reaction mixture was quenched with 2 M HCl (~1 mL) and was extracted with EtOAc (2×15 mL). The organic layer was washed with sat'd $CuSO_4$ (2×15 mL) and brine (1×15 mL). The solution was dried over $Na_2SO_4$ and concentrated.

Step 4:
To the crude Boc-piperidine nitrile, 4 M HCl/dioxane (725 μL, 2.90 mmol) was added under Ar at 23° C. and was stirred for 1 h. The reaction mixture was concentrated to obtain 3-(2-(piperidin-4-yl)phenyl)propanenitrile hydrochloride 28. LC/MS RT (5 min method)=0.92 min. Mass observed: 215.15 (M+H).

Representative Example 9

Synthesis of N-(methylsulfonyl)-3-(2-(piperidin-4-yl)phenyl)propanamide hydrochloride 29

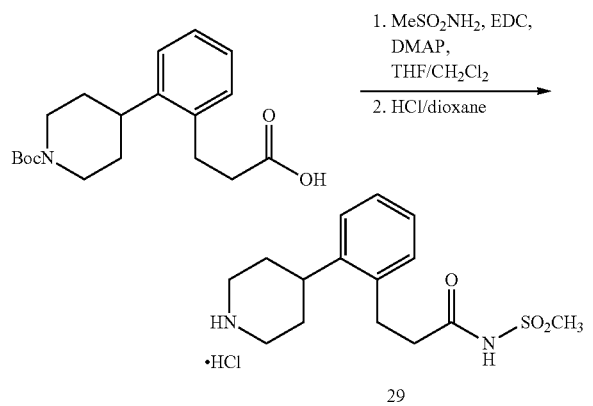

Acid 3-(2-(1-(tert-butoxycarbonyl)piperidin-4-yl)phenyl)propanoic acid obtained in step 1 of representative example 8 (40 mg, 0.12 mmol) and methane sulfonamide (17 mg, 0.18 mmol) were dissolved in THF/CH$_2$Cl$_2$ (0.5 mL/1.0 mL). DMAP (22 mg, 0.18 mmol) and EDC.HCl (35 mg, 0.18 mmol) were added and the reaction was stirred at 23° C. overnight. Water was added to the reaction mixture and was extracted with EtOAc (2×10 mL). The organic layers were dried over Na$_2$SO$_4$ and concentrated.

Representative Example 10

Synthesis of 3-(2-(4-cyanopiperidin-4-yl)phenyl)-N-(methylsulfonyl)propanamide hydrochloride 30

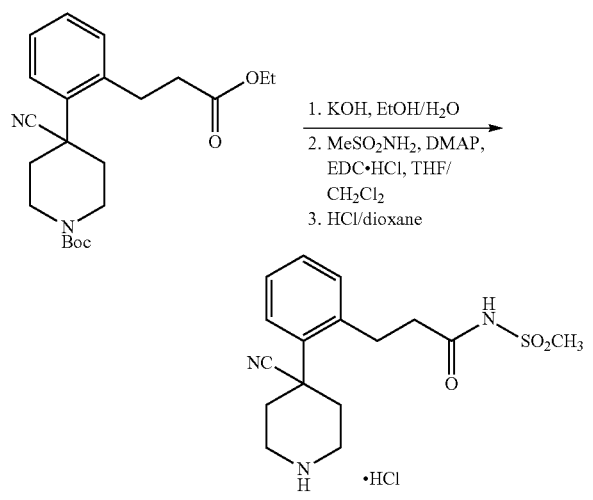

Hydrolysis of the tert-butyl 4-cyano-4-(2-(3-ethoxy-3-oxopropyl)phenyl)piperidine-1-carboxylate obtained from representative example 5, step3, to the carboxylic acid tert-butyl 4-cyano-4-(2-(3-ethoxy-3-oxopropyl)phenyl)piperidine-1-carboxylate was followed similarly to the aforementioned procedures. Acylsulfonamide formation, followed by Boc-deprotection was followed by the synthesis of amine 29 to yield 3-(2-(4-cyanopiperidin-4-yl)phenyl)-N-(methylsulfonyl)propanamide hydrochloride 30.

Representative Example 11

Synthesis of ethyl 3-(2-(4-cyanopiperidin-4-yl)-4-fluorophenyl)propanoate hydrochloride 34

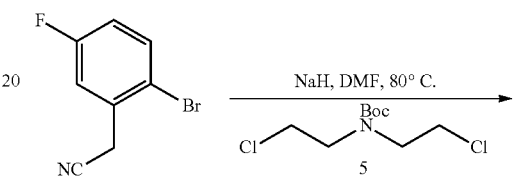

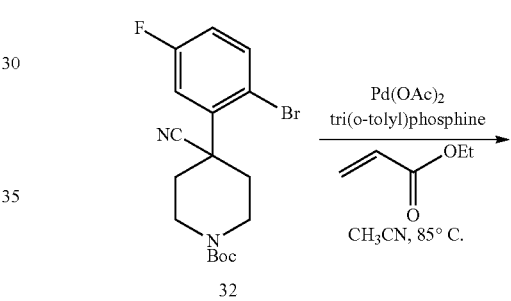

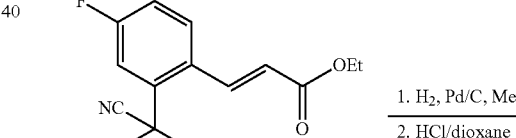

Procedure to prepare ethyl 3-(2-(4-cyanopiperidin-4-yl)-4-fluorophenyl)propanoate hydrochloride 34 (LC/MS RT (5 min method)=1.19 min. Mass observed: 305.16 (M+H). is identical to the procedure used to prepare ethyl 3-(2-(4-cyanopiperidin-4-yl)phenyl)propanoate hydrochloride 22 from Representative example 5 by replacing in step 1, nitrile 19 with nitrile 31.

Representative Example 12

Preparation of ethyl 5-(4-phenylpiperidin-4-yl)pentanoate hydrochloride 41

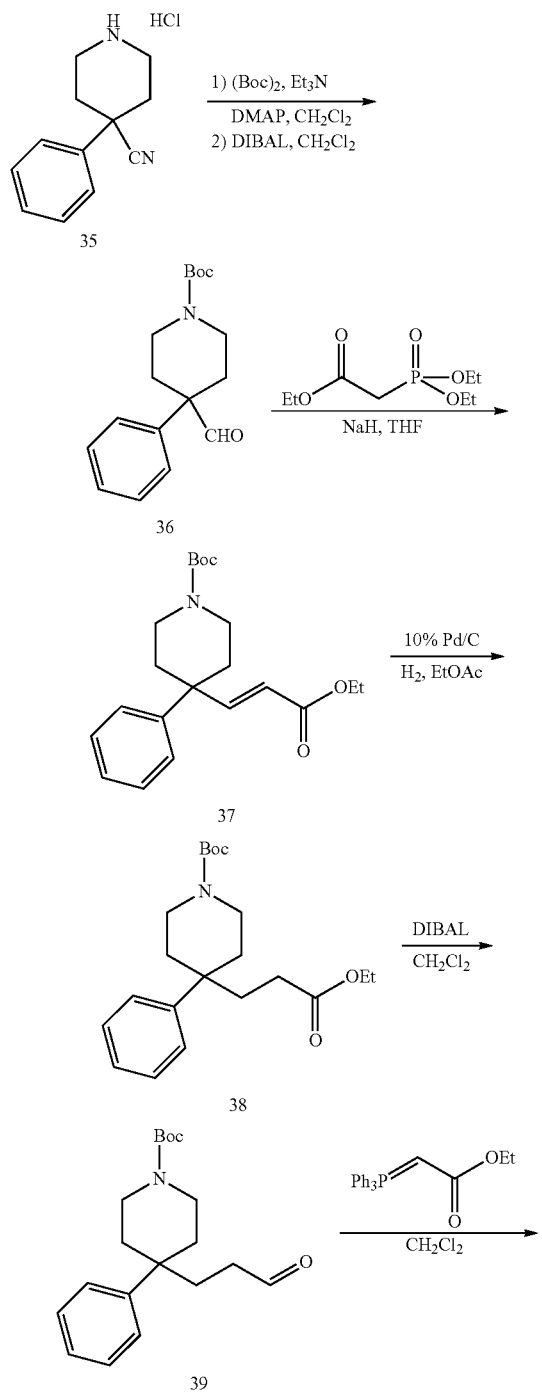

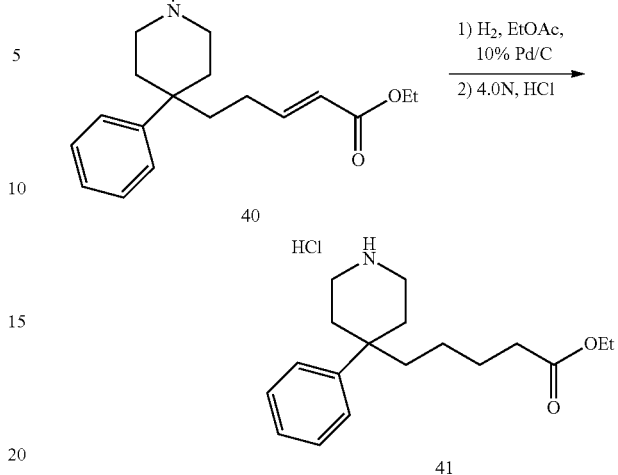

Step 1:

To a stirring suspension of 35 (4.5 mmol, 1.0 g) in dichloromethane and triethylamine (11 mmol, 1.6 ml) at room temperature was added di-t-butyl dicarbonate (5.4 mmol, 1.2 g) followed by DMAP (0.45 mmol, 55 mg). The reaction mixture was stirred at room temperature overnight and then diluted with EtOAc (50 ml), washed with water (2×10 ml), brine (10 ml), then dried (MgSO4). The solvent was removed in vacuo. The crude product (1.3 g) was obtained as brownish oil. To a solution of this crude product (4.5 mmol, 1.2 g) in dichloromethane at 0° C. was added diisobutylaluminum hydride (1.0 M in DCM, 5.0 ml, 5.0 mmol). The reaction mixture was stirred at room temperature for 2 hours Then Rochelle Salt solution was added and the mixture was stirred vigorously for 1 hour, then diluted with EtOAc. The organic phase was separated and the aqueous was extracted with EtOAc. The combined organic layer was washed with brine, dried (MgSO4), concentrated. The crude product 36 was obtained as slightly yellow oil (~1.2 g), which was used in the next step without further purification.

Step 2:

Sodium hydride (60% in mineral oil, 200 mg, 5 mmol) was washed with hexane twice, then added THF, cooled to 0° C. Triethylphosphonoacetate (1 ml, 5.4 mmol) was added and the mixture was stirred for 30 min, then a solution of 36 in THF was added, warmed to room temperature, and stirred at rt overnight. The reaction was quenched with saturated NH4Cl, extracted with EtOAc. The combined organic layer was washed with brine, dried (MgSO4), concentrated, purified on Biotage (EtOAc in hexane: 10-25%) to give 37 as colorless oil (0.6 g).

Step 3:

To a stirring solution of 37 (1.67 mmol, 0.6 g) in EtOAc at room temperature was added catalytical amount of 10% palladium on carbon and the reaction mixture was purged with Hydrogen gas. After stirring at room temperature for 4 h, the mixture was filtered through celite and concentrated in vacuo, to give 38 (0.5 g) as orange oil, which was used in the next step without further purification.

Step 4:

To a solution of 38 in dichloromethane at 0° C. was added diisobutylaluminum. The reaction mixture was stirred at −78° C. for 1 h. Then Rochelle Salt solution was added and the mixture was stirred vigorously for 30 min, then extracted with EtOAc. The organic phase was separated and the aqueous was extracted with EtOAc, dried (MgSO4), concentrated. The crude product 39 was used in the next step without further purification.

Step 5:

To a stirring solution of 39 in DCM at room temperature was added (carbethoxymethylene) triphenylphosphorane and the reaction mixture was stirred at reflux overnight. The solvent was removed in vacuo. The crude product was purified on Biotage (EtOAc in hexane: 10-25%) to give 40 as colorless oil.

Step 6:

To a stirring solution of 40 in EtOAc was added catalytical amount of 10% palladium on carbon and the reaction mixture was purged with Hydrogen gas. After stirring at room temperature overnight, the mixture was filtered through celite and concentrated in vacuo, to give a colorless oil to which was added 4.0 M hydrochloride in 1,4-dioxane. After 1 h, the solvent and volatile were removed by lyophilization, to give 41 as yellowish oil.

Representative Example 13

Synthetic route to fluorinated cyanophenylpiperidines (5-Fluoro regioisomer) tert-butyl 4-cyano-4-(5-fluoro-2-hydroxyphenyl)piperidine-1-carboxylate 48.

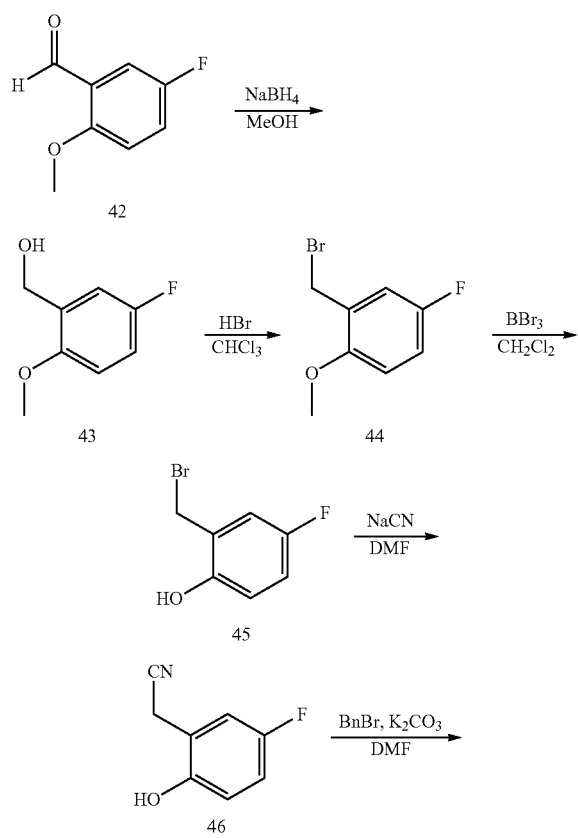

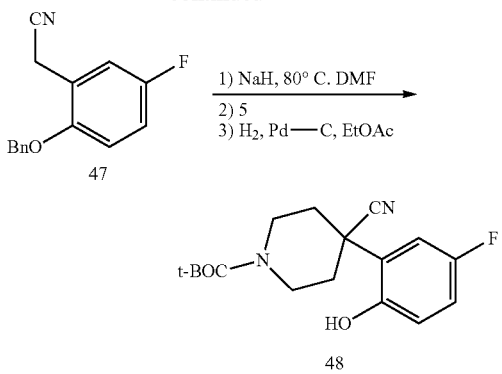

Step 1:

To 42 (1 eq, 17.1 mmol, 2.6 g) in MeOH (68 mL) at room temperature, added $NaBH_4$ (1.2 eq, 20.5 mmol, 775 mg) and the reaction mixture stirred 18 h, then concentrated in vacuo. The crude residue was diluted with ethyl acetate, washed with 1N aqueous HCl then brine, dried over sodium sulfate, and concentrated in vacuo to give 43 (2.8 g) as a pale yellow oil Step 2:

To 43 (1 eq, 17.9 mmol, 2.8 g) in $CHCl_3$ (18 mL) at room temperature, added HBr (22 mL) and the reaction mixture was stirred 2 h, then diluted with dichloromethan, washed with water then brine, dried over sodium sulfate, and concentrated in vacuo to give 44 (3.3 g) as an off-white solid.

Step 3:

To 44 (1 eq, 8.67 mmol, 1.9 g) in $CH_2Cl_2$ (58 mL) at −78° C., added $BBr_3$ solution (1.5 eq, 13 mmol, 13 mL) dropwise over 5 min, stirred at −78° C. 3 h, then warmed to room temperature and stirred 18 h. The reaction was quenched with water (10 mL), extracted with dichloromethane then ethyl acetate, the combined organic layers were washed with brine, dried over sodium sulfate, and concentrated in vacuo to give 45 (~2 g) as a brown oily solid.

Step 4:

To 45 (1 eq, 8.5 mmol, 1.75 g) in DMF (43 mL) at room temperature, added NaCN (1.1 eq, 9.30 mmol, 460 mg) and stirred at room temperature 3 days. The reaction mixture was diluted with water, extracted with ethyl acetate, washed with water (3×) then brine, dried over sodium sulfate, and concentrated in vacuo to give 46 (1.47 g) as a brown oil Step 5:

To NaH (2.2 eq, 2.05 mmol, 82 mg) under argon at room temperature with stirring, added a solution of 46 (1 eq, 0.93 mmol, 225 mg) and amine 5 (1.0 eq, 0.93 mmol, 225 mg) in DMF (9 mL) and stirred at room temperature 0.5 h, then heated at 80° C. for 5 h. The reaction was cooled to room temperature, quenched with water (~10 mL), extracted with ethyl acetate, washed with water (3×) then brine, dried over sodium sulfated, and concentrated in vacuo. Purification by flash silica gel chromatography (10%→20%→50% EtOAc/hexane) gave tert-butyl 4-(2-(benzyloxy)-5-fluorophenyl)-4-cyanopiperidine-1-carboxylate (236 mg) as a sticky brown oil. To tert-butyl 4-(2-(benzyloxy)-5-fluorophenyl)-4-cyanopiperidine-1-carboxylate (1 eq, 0.9 mmol, 370 mg) in ethyl acetate (9 mL), added Pd—C (100 mg), purged the reaction vessel with $H_2$, and stirred at room temperature under an $H_2$ atmosphere (balloon) for 3 h. The reaction mixture was filtered through celite and concentrated in vacuo to give 48 (250 mg) as an orange foam.

Representative Example 14

Synthetic route to fluorinated cyanophenylpiperidines (3-Fluoro regioisomer) tert-butyl 4-cyano-4-(5-fluoro-2-hydroxyphenyl)piperidine-1-carboxylate 54

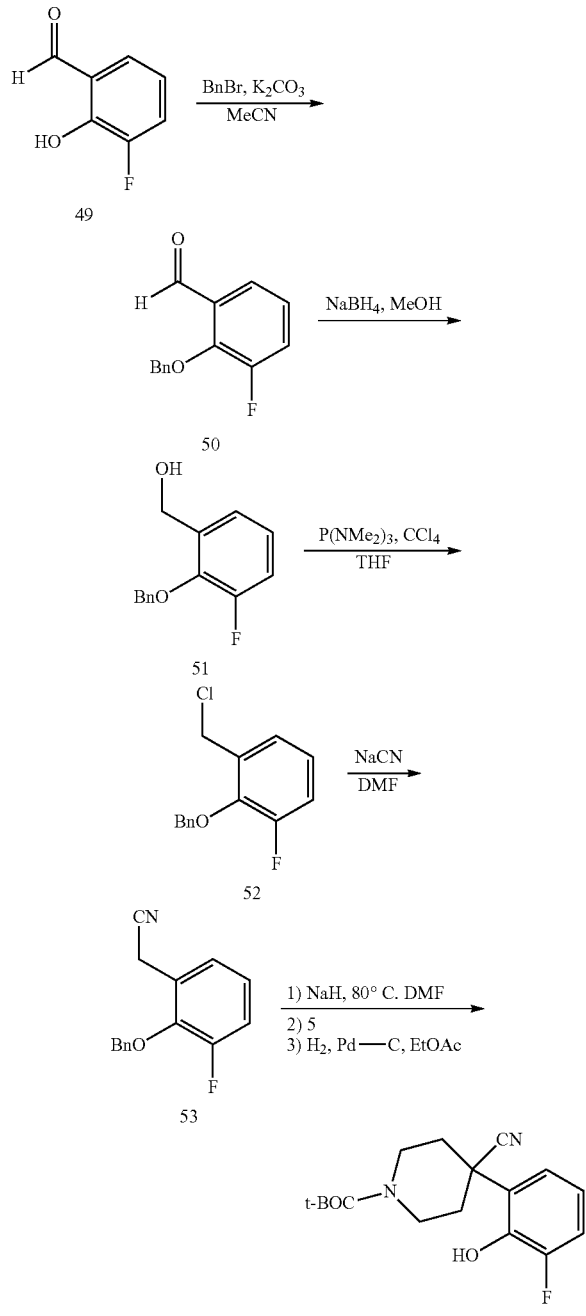

Step 1: To 49 (1 eq, 21 mmol, 3 g) in MeCN (107 mL) at room temperature, added BnBr (1.1 eq, 24 mmol, 2.8 mL) followed by $K_2CO_3$ (1.5 eq, 32 mmol, 4.4 g) and the reaction mixture stirred at room temperature 18 h, filtered through celite, and the solvent removed in vacuo. The crude residue was dissolved in ether, washed with water then brine, dried over sodium sulfate, and concentrated in vacuo to give 50 as a pale yellow oil (5 g).

Step 2: To 50 (1 eq, 22 mmol, 5 g) in MeOH (109 mL) at 0° C., added $NaBH_4$ (1.2 eq, 26 mmol, 0.99 g) and the reaction mixture was warmed to room temperature, stirred 18 h, then concentrated in vacuo. The crude residue was diluted with ethyl acetate, washed with 1N aqueous HCl then brine, dried over sodium sulfate, and concentrated in vacuo to give 51 (4.1 g) as a colorless oil.

Step 3: To 51 (1 eq, 4.15 mmol, 963 mg) and $CCl_4$ (1.1 eq, 4.56 mmol, 441 uL) in THF (28 mL) at 0° C. under argon, added $P(NMe_2)_3$ (1.1 eq, 4.56 mmol, 829 uL) dropwise and the reaction mixture was warmed to room temperature over 2 h, and stirred an additional 2 h. After 51 was consumed as observed by TLC, the solvent was removed in vacuo, the crude residue 52 was dissolved in DMF (15 mL) and NaCN (1.1 eq, 4.56 mmol, 224 mg) was added and the reaction mixture stirred at room temperature 18 h. The mixture was diluted with ethyl acetate, washed with water (3×) then brine, dried over sodium sulfate, and concentrated in vacuo to give 53 (733 mg) as a dark red oil.

Step 4: To NaH (2.2 eq, 2.74 mmol, 109 mg) under argon at room temperature with stirring, added a solution of 53 (1 eq, 1.24 mmol, 300 mg) and 5 (1.1 eq, 1.24 mmol, 300 mg) in DMF (10 mL) and stirred at room temperature 0.5 h, then heated at 80° C. for 5 h. The reaction was cooled to room temperature, quenched with water (~10 mL), extracted with ethyl acetate, washed with water (3×) then brine, dried over sodium sulfated, and concentrated in vacuo. Purification by flash silica gel chromatography (10%→20%→40% EtOAc/hexane) gave tert-butyl 4-(2-(benzyloxy)-3-fluorophenyl)-4-cyanopiperidine-1-carboxylate (189 mg) as an orange oil. To tert-butyl 4-(2-(benzyloxy)-3-fluorophenyl)-4-cyanopiperidine-1-carboxylate (1 eq, 5 mmol, 1.86 g) in ethyl acetate (45 mL), added Pd—C (300 mg), purged the reaction vessel with $H_2$, and stirred at room temperature under an $H_2$ atmosphere (balloon) for 3 h. The reaction mixture was filtered through celite and concentrated in vacuo to give 54 (1.45 g) as a colorless oil.

Representative Example 15

Preparation of ethyl 4-(2-(4-cyanopiperidin-4-yl)-4-fluorophenoxy)butanoate 56

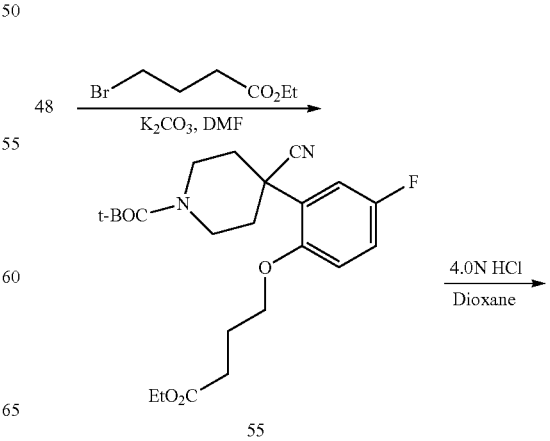

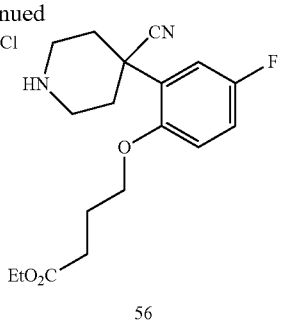

56

Step 1:

To a stirring solution of 48 (1 eq, 0.78 mmol, 250 mg) and ethyl 4-bromobutanoate (1.1 eq, 0.86 mmol, 167 mg) in DMF at room temperature, added K₂CO₃ (2.5 eq, 2.34 mmol, 324 mg) and stirred the reaction mixture 18 h. The mixture was diluted with water, extracted with ethyl acetate, washed with water (3×) then brine, dried over sodium sulfate, and concentrated in vacuo to give 55 (151 mg) as an orange oil.

Step 2:

A solution of 55 (1 eq, 0.348 mmol, 151 mg) was stirred in HCl/dioxane (1 mL) at room temperature 2 h, then concentrated to dryness in vacuo. The crude reside was dissolved in dichloromethane, washed with sodium bicarbonate (aqueous) then brine, dried over sodium sulfate, and concentrated in vacuo to give 56 (80 mg) as a pale brown oil.

Representative Example 16

Preparation of methyl 4-(2-(4-cyanopiperidin-4-yl) benzyloxy)-2,2-dimethylbutanoate 2,2,2-trifluoroacetate 61

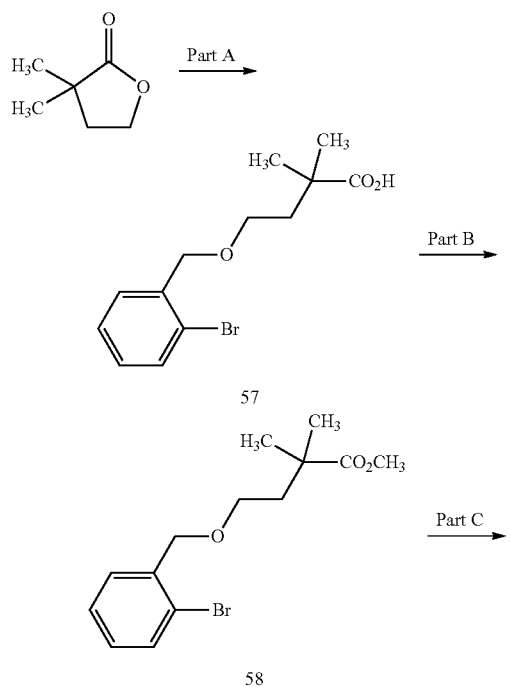

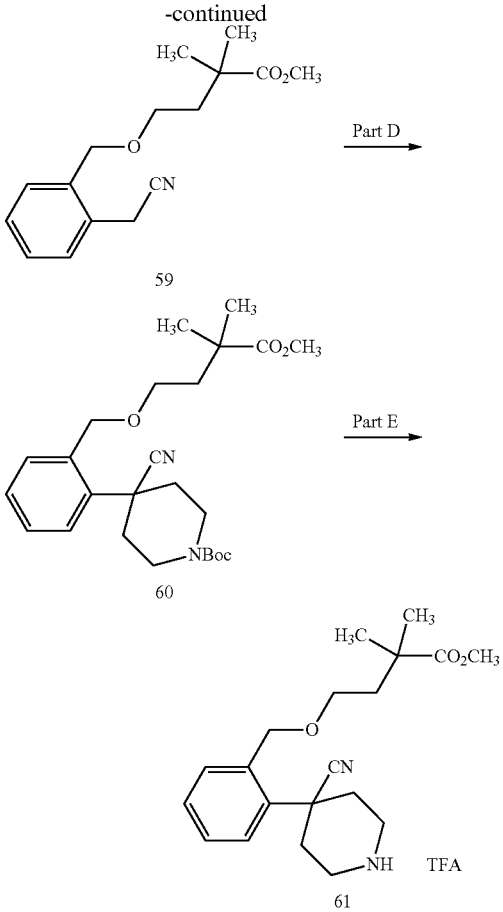

Part A:

Powdered potassium hydroxide (3.99 g, 60.5 mmol) was added in one portion to 3,3-dimethyldihydrofuran-2(3H)-one (2.76 g, 24.2 mmol) and 2-bromobenzylbromide (13.3 g, 53.2 mmol) in anhydrous toluene (100 mL) under nitrogen. The reaction mixture was heated to reflux for 3 h, cooled to room temperature, transferred to a separatory funnel and extracted with 1 N aqueous sodium hydroxide (2×50 mL). The combined aqueous layers were washed with ether (50 mL, discard) then the pH was adjusted to ~1 with 2 N hydrochloric acid and extracted with ether (3×60 mL). The combined organic layers were washed with brine (50 mL), dried over MgSO₄, filtered, and the solvent was removed under reduced pressure. Compound 57 (2.10 g, 29% yield) was isolated as a light brown oil: $^1$H NMR (300 MHz, CDCl₃) 7.51 (d, J=8.1 Hz, 1H), 7.45 (d, J=7.5 Hz, 1H), 7.33-7.26 (m, 1H), 7.12 (td, J=7.7, 1.4 Hz, 1H), 4.53 (s, 2H), 3.64 (t, J=6.6 Hz, 2H), 3.49 (s, 1H), 1.97 (t, J=6.8 Hz, 2H), 1.25 (s, 6H).

Part B:

Thionyl chloride (0.83 g, 6.97 mmol) was added dropwise to 57 (2.10 g, 6.97 mmol) in methanol (75 mL) and stirred at room temperature for 15 h. The solvent was removed by evaporation and the residue taken up in ether (100 mL) then washed with water (25 mL), saturated NaHCO₃ (25 mL), and brine (25 mL). The organic layer was dried over MgSO₄, filtered and evaporated to dryness. The residue was purified by silica gel chromatography (ethyl acetate/hexanes) to provide 58 (1.23 g, 56% yield) as a clear oil: $^1$H NMR (300 MHz, CDCl₃) 7.51 (d, J=7.8 Hz, 1H), 7.45 (d, J=7.8 Hz, 1H), 7.30 (d, J=7.5 Hz, 1H), 7.12 (td, J=7.7, 1.4 Hz, 1H), 4.52 (s, 2H), 3.63-3.56 (m, 5H), 1.94 (t, J=6.8 Hz, 2H), 1.23 (s, 6H).

Part C:

Zinc fluoride (159 mg, 1.53 mmol) was added in one portion to 58 (646 mg, 2.05 mmol), tris(dibenzylideneacetone)dipalladium(0) (75 mg, 0.082 mmol), tri-t-butylphosphonium tetrafluoroborate (48 mg, 0.164 mmol), potassium carbonate (23 mg, 0.164 mmol), and trimethylsilyacetonitrile (348 mg, 3.07 mmol) in anhydrous DMF (2 mL) in a heavy walled test tube with a threaded cap. The tube was sealed and the reaction mixture was heated at 90° C. for 14 h. The reaction mixture was diluted with ether (50 mL) then washed with water (2×10 mL) and brine (10 mL). The organic layer was dried over $MgSO_4$, filtered and evaporated to dryness. The residue was purified by silica gel chromatography (ethyl acetate/hexanes) to provide 59 (300 mg, 53% yield) as a light brown oil: $^1$H NMR (300 MHz, $CDCl_3$) 7.46-7.27 (m, 4H), 4.84 (s, 2H), 3.85 (s, 2H), 3.54 (s, 3H), 3.49 (t, J=6.8 Hz, 2H), 1.88 (t, J=6.8 Hz, 2H), 1.19 (s, 6H).

Part D:

t-Butyl bis(2-chloroethyl)carbamate (572 mg, 2.36 mmol) and 59 (650 mg, 2.36 mmol) in DMF (8 mL) were added dropwise to sodium hydride (60% in mineral oil, 208 mg, 5.19 mmol) suspended in DMF (20 mL) at 0° C. After 30 min at 0° C. the ice bath was removed and the reaction mixture allowed to warm to room temperature for 1.5 h. The reaction was heated to 75° C. for 3 h and cooled back to room temperature. The reaction was quenched by addition of saturated ammonium chloride (50 mL) and extracted with ether (3×50 mL). The combined organic extracts were washed with water (3×20 mL) and brine (40 mL), dried over $MgSO_4$, filtered and evaporated to dryness. The residue was purified by silica gel chromatography (ethyl acetate/hexanes) to provide 60 (683 mg, 65% yield) as a light yellow oil: $^1$H NMR (300 MHz, $CDCl_3$) 7.57-7.52 (m, 1H), 7.39-7.37 (m, 3H), 4.78 (s, 2H), 4.39-4.16 (m, 2H), 3.64-3.52 (m, 5H), 3.36-3.18 (m, 2H), 2.35-2.26 (m, 2H), 1.99-1.85 (m, 4H), 1.48 (s, 9H), 1.22 (s, 6H).

Part E:

Trifluoroacetic acid (2 mL) was added to 60 (222 mg, 0.50 mmol) in methylene chloride (2 mL). The reaction was stirred at ambient temperature for 3 h then concentrated down to yield methyl 4-(2-(4-cyanopiperidin-4-yl)benzyloxy)-2,2-dimethylbutanoate 2,2,2-trifluoroacetate 61.

Representative Example 17

Preparation of ethyl 4-(2-(piperidin-4-yl)phenylsulfonamido)butanoate 2,2,2-trifluoroacetate 66

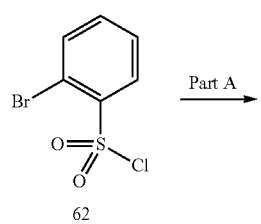

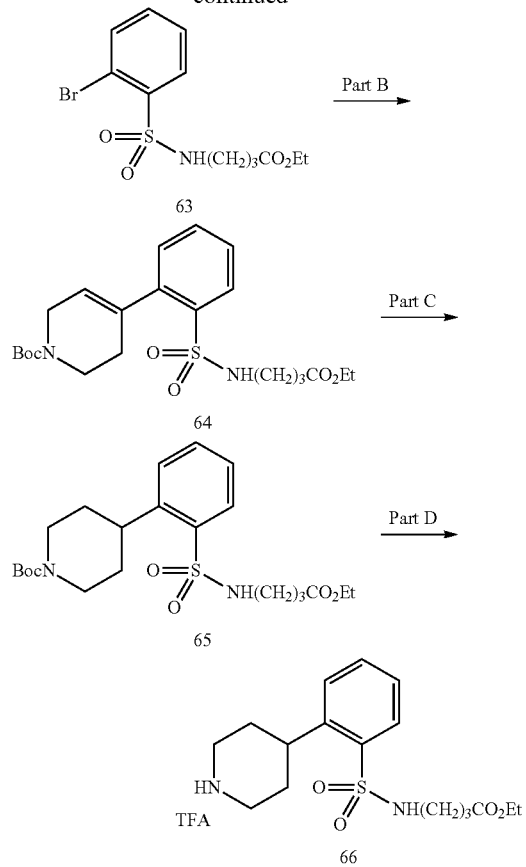

Part A:

A mixture of 2-bromobenzenesulfonyl chloride (62, 1.39 g, 5.43 mmol), ethyl-4-aminobutyrate.HCl (1.27 g, 7.60 mmol), and triethylamine (1.54 g, 15.2 mmol) in methylene chloride (27.1 mL) was stirred at room temperature for 21 h. The mixture was diluted with EtOAc (300 mL), washed with sat'd aq. $NH_4Cl$ (3×100 mL), brine (100 mL), dried over $Na_2SO_4$, filtered and concentrated under reduced pressure to provide sulfonamide 63 (1.67 g, 88%) as a yellow solid which was used in the next step without further purification: $^1$H NMR (300 MHz, $CDCl_3$ 8.13 (dd, J=7.4, 1.7 Hz, 1H), 7.74 (d, J=7.4 Hz, 1H), 7.52-7.37 (m, 2H), 5.30 (s, 1H), 4.11 (q, J=7.1 Hz, 2H), 2.96 (q, J=7.1 Hz, 2H), 2.36 (t, J=7.1 Hz, 2H), 1.81 (pentet, J=7.1 Hz, 2H), 1.30-1.19 (t, J=7.1 Hz, 3H).

Part B:

A mixture of tert-butyl-4-(4,4,5,5-tetramethyl-1,3,2-dioxaborolan-2-yl)-5,6-dihydropyridine-1(2H)-carboxylate (264 mg, 0.854 mmol), compound 63 (272 mg, 0.776 mmol), $Pd(PPh_3)_4$ (44.8 mg, 38.8 umol), 2 M aq. $Na_2CO_3$ (1.17 mL), and DME (5.17 mL) we place in a sealed microwave vial and heated at 80° C. for 3 d.

The mixture was diluted with EtOAc (250 mL), washed with sat'd aq. $NH_4Cl$ (3×100 mL), brine (100 mL), dried over $Na_2SO_4$, filtered and concentrated under reduced pressure. The residue was purified by CombiFlash (40 g, Hex/EtOAc) to provide pure product 64 (325 mg, 93%) as a yellow oil: $^1$H NMR (300 MHz, $CDCl_3$ 7.97 (d, J=7.6 Hz, 1H), 7.52, (t, J=7.6 Hz, 1H), 7.41 (t, J=7.6 Hz, 1H), 7.20 (d, J=7.6 Hz, 1H), 5.62 (s, 1H), 5.30 (s, 1H), 4.62 (d, J=5.9 Hz, 1H), 4.20-4.02 (m, 2H), 3.66 (t, J=5.5 Hz, 2H), 2.91 (q, J=6.6 Hz, 2H), 2.52-2.41 (m, 2H), 2.36 (t, J=7.0 Hz, 2H), 1.79 (pentet, J=6.8 Hz, 2H), 1.63-1.46 (m, 10H), 1.30-1.19 (m, 3H).

Part C:

A solution of compound 64 (320 mg, 0.708 mmol) in ethanol (200 mL) was degassed with nitrogen, added 10% Pd/C (75.3 mg) then hydrogenated at 45 psi overnight. The Pd/C was removed by filtration through Celite, washing with methanol. The filtrate was concentrated under reduced pressure to provide compound 65 (277 mg, 86%) as a yellow oil which was used in the next step without further purification: $^1$H NMR (300 MHz, CDCl$_3$ 7.93 (dd, J=7.9, 1.2 Hz, 1H), 7.58-7.49 (m, 1H), 7.47-7.40 (m, 1H), 7.36-7.27 (m, 1H), 4.85 (t, J=6.2 Hz, 1H), 4.40-4.05 (m, 4H), 3.80-3.53 (m, 1H), 3.06 (q, J=6.7 Hz, 2H), 2.86 (t, J=12.8 Hz, 2H), 2.37 (t, J=6.7 Hz, 2H), 1.90-1.76 (m, 4H), 1.75-1.40 (m, 11H), 1.24 (t, J=7.1 Hz, 3H).

Part D:

Trifluoroacetic acid was added to 65 in methylene chloride (2 mL). The reaction was stirred at ambient temperature for 3 h then concentrated down to yield 4-(2-(piperidin-4-yl)phenylsulfonamido)butanoate 2,2,2-trifluoroacetate 66.

Representative Example 18

Preparation of ethyl (1R,3R)-methyl 3-(2-(4-cyanopiperidin-4-yl)benzyloxy)cyclobutanecarboxylate 2,2,2-trifluoroacetate 71

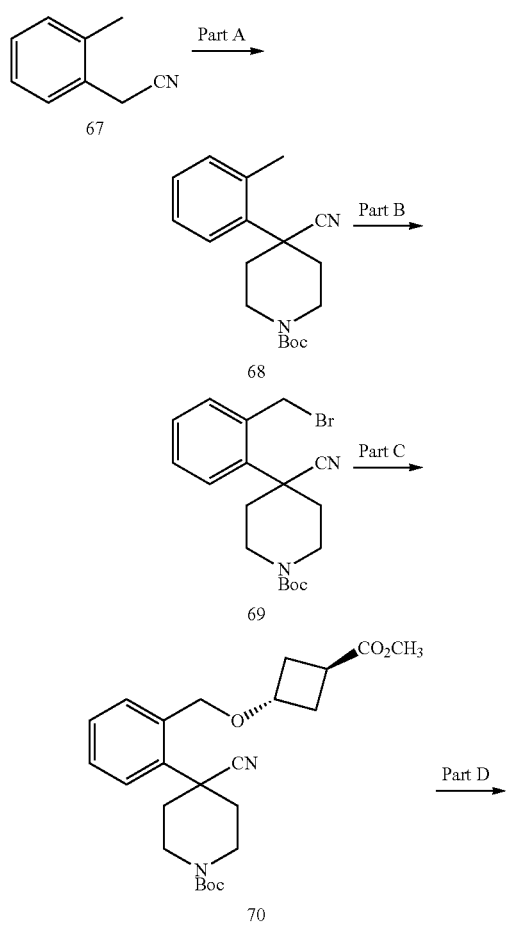

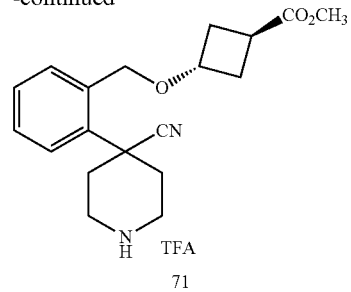

Part A:

Sodium hydride (60% in mineral oil, 8.51 g, 212 mmol) was added in portions to 67 (10.0 g, 76.2 mmol) and t-butyl bis(2-chloroethyl)carbamate (20.3 g, 83.8 mmol) in DMF (150 mL) over a 3 h period under nitrogen. After the addition was complete the reaction was stirred for 1 h at room temperature then 2 h at 70° C. The reaction was cooled to room temperature and the volume was reduced to ~60 mL in vacuo. Saturated ammonium chloride (100 mL) was added with vigorous stirring. The aqueous layer was decanted and the oily solid residue taken up in methylene chloride. The reaction was repeated and combined for purification by chromatography on silica gel (methylene chloride/ethyl acetate) to provide 68 (15.0 g, 33% yield) as a light brown solid: $^1$H NMR (400 MHz, CDCl$_3$) 7.27-7.22 (m, 4H), 4.42-4.18 (m, 2H), 3.37-3.20 (m, 2H), 2.65 (s, 3H), 2.36-2.28 (m, 2H), 1.90 (td, J=9.8, 3.1 Hz, 2H), 1.48 (s, 9H).

Part B:

Bromine (0.72 g, 4.49 mmol) was added to 68 (300 mg, 1.00 mmol) in a mixture of water/chlorobenzene (4:1, 5 mL) at 0° C. in a heavy walled screw cap test tube. Six identical sealed tubes were set up and irradiated with a tungsten lamp for 1 h. The lamp was turned off and stirring was continued for 20 min. The crude reaction mixtures were combined and partitioned between ethyl acetate (100 mL) and saturated sodium thiosulfate (50 mL). The ethyl acetate solution was dried over MgSO$_4$, filtered, evaporated and purified by silica gel chromatography (ethyl acetate/hexanes) to provide compound 69 (0.84 g, 37% yield) as light brown oil contaminated with 68 (~15%): $^1$H NMR (300 MHz, CDCl$_3$) 7.61-7.56 (m, 1H), 7.42-7.33 (m, 3H), 4.91 (s, 2H), 4.48-4.17 (m, 2H), 3.29 (t, J=12.9 Hz, 2H), 2.45-2.33 (m, 2H), 2.03-1.86 (m, 2H), 1.48 (s, 9H).

Part C:

Potassium t-butoxide (1M in THF, 0.4 mL, 0.4 mmol) was added dropwise to methyl trans-3-hydroxycyclobutanecarboxylate (52 mg, 0.399 mmol) and 69 (150 mg, 0.395 mmol) in anhydrous THF (3.6 mL). After 2.5 h the reaction mixture was cooled to 0-5° C. and quenched with 0.5 M hydrochloric acid to a pH of ~2. The reaction mixture was partitioned between water/ethyl acetate (1:1, 20 mL) and extracted further with ethyl acetate (2×10 mL). The combined organic layers were washed with brine (10 mL), dried over MgSO$_4$, filtered and evaporated to dryness. The residue was purified by silica gel chromatography (ethyl acetate/hexane) to provide 70 (36 mg, 21% yield) as a clear oil: $^1$H NMR (300 MHz, CDCl$_3$) 7.58-7.53 (m, 1H), 7.41-7.27 (m, 3H), 4.76 (s, 2H), 4.39-4.14 (m, 2H), 4.07 (quint, J=7.3 Hz, 1H), 3.69 (s, 3H), 3.27 (t, J=12.8 Hz, 2H), 2.75-2.51 (m, 3H), 2.40-2.23 (m, 4H), 2.02-1.86 (m, 2H), 1.48 (s, 9H).

Part D:

Trifluoroacetic acid was added to 70 in methylene chloride (2 mL). The reaction was stirred at ambient temperature for 3 h then concentrated down to yield (1R,3R)-methyl 3-(2-(4-cyanopiperidin-4-yl)benzyloxy)cyclobutanecarboxylate 2,2,2-trifluoroacetate 71.

Representative Example 19

Preparation of ethyl tert-butyl 4-(2-(4-hydroxypiperidin-4-yl)phenethoxy)butanoate 75

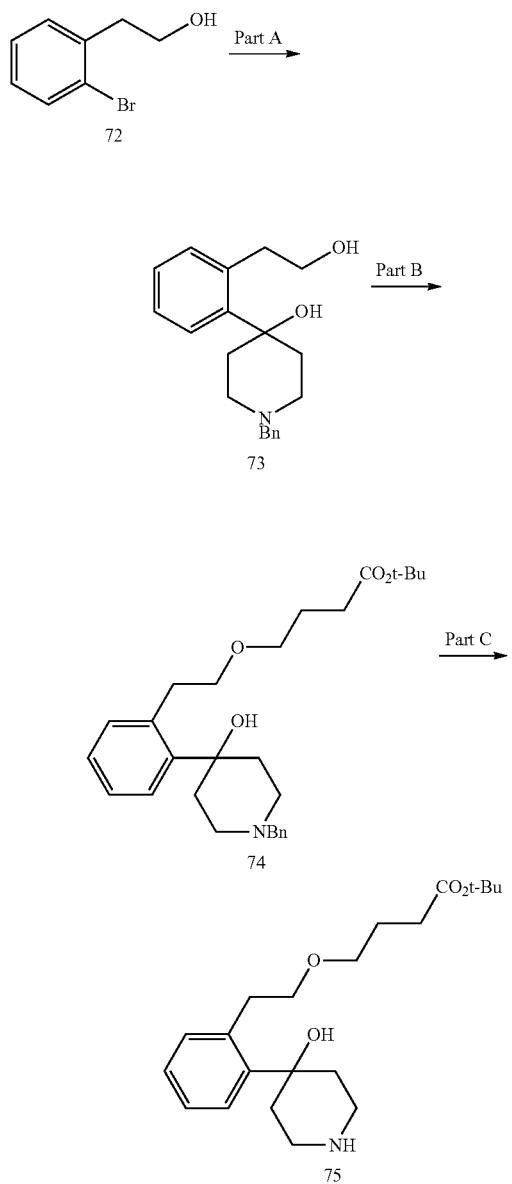

Part A:

n-Butyl lithium (1.6 M in hexanes, 65.2 mL, 104 mmol) was added dropwise to 72 (10 g, 49.7 mmol) in a mixture of ether/THF (1:1, 150 mL) at −78° C. After the addition was complete stirring was continued at −78° C. for 3 h. 1-Benzyl-4-piperidone (10.2 g, 53.6 mmol) in a mixture of ether/THF (1:1, 50 mL) was added dropwise to the reaction mixture and after addition is completed the reaction was allowed to warm to room temperature over 4 h. The reaction was quenched with ice cold water (200 mL) then extracted with ether (3×150 mL). The combined extracts were washed with brine (100 mL) and dried over $Na_2SO_4$ and filtered. The volume of the solvent was reduced by 80% in vacuo at which time a white solid precipitates. The remaining mixture was cooled in an ice water bath and the white solid was filtered to give 73 (7.00 g, 46% yield) as a crystalline solid: $^1$H NMR (400 MHz, $CDCl_3$) 7.40-7.15 (m, 9H), 3.91 (t, J=6.0 Hz, 2H), 3.57 (s, 2H), 3.29 (t, J=6.0 Hz, 2H), 2.81-2.74 (m, 2H), 2.57-2.50 (m, 2H), 2.17 (t, J=12.8, 4.3 Hz, 2H), 1.93-1.87 (m, 2H), 1.74 (br, 2H).

Part B:

18-Crown-6 (896 mg, 3.39 mmol) was added to 73 (480 mg, 1.54 mmol) in anhydrous THF (25 mL) and the resulting mixture was cooled to 0° C. The reaction was allowed to warm to room temperature over 1.5 h then continue stirring for an additional 20 h. The reaction mixture was cooled to 0° C. and quenched with saturated ammonium chloride (10 mL). Extract with ethyl acetate (3×20 mL) and the combined extracts were washed with brine (20 mL), dried over $MgSO_4$, filtered and evaporated to dryness. The residue was purified by silica gel chromatography (methanol/methylene chloride) to provide 74 (50 mg, 7% yield) as a clear oil: $^1$H NMR (300 MHz, $CDCl_3$) 7.40-7.24 (m, 6H), 7.20-7.14 (m, 3H), 3.88 (br, 1H), 3.68 (t, J=5.9 Hz, 2H), 3.41-3.30 (m, 4H), 2.84-2.71 (m, 2H), 2.57 (t, J=10.8 Hz, 2H), 2.23-2.06 (m, 4H), 1.84 (dd, J=13.7, 2.3 Hz, 2H), 1.74 (quint, J=7.0 Hz, 2H), 1.67-1.52 (m, 2H), 1.40 (s, 9H).

Part C:

A solution of palladium hydroxide (25 mg) and 74 (66 mg, 0.145 mmol) in methanol (4 mL) was hydrogenated under a hydrogen balloon for 6 h. The reaction mixture was flushed with nitrogen and the catalyst was removed by filtration. The solvent was removed in vacuo to provide 75 (55 mg, quantitative) as a clear oil: $^1$H NMR (300 MHz, MeOD-$d_3$) 7.45-7.34 (m, 1H), 7.27-7.20 (m, 1H), 7.20-7.11 (m, 2H), 3.67 (t, J=6.9 Hz, 2H), 3.45 (t, J=6.2 Hz, 2H), 3.35-3.18 (m, 4H), 3.05-2.87 (m, 2H), 2.23 (t, J=2.5 Hz, 2H), 2.17-2.01 (m, 2H), 2.00-1.88 (m, 2H), 1.78 (quint, J=6.8 Hz, 2H), 1.43 (s, 9H).

Representative Procedures for Amide Formation, Sidechain Modification, and Ester Formation or Hydrolysis

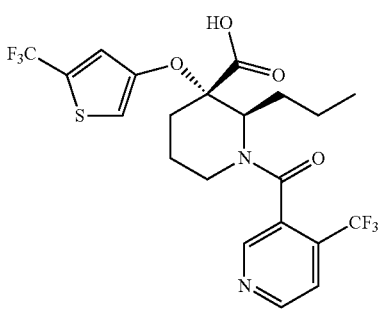

-continued

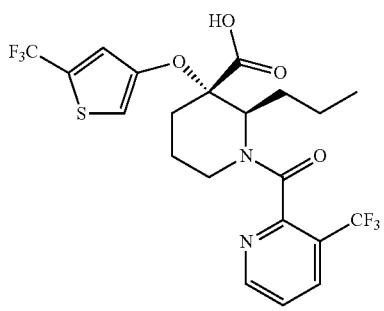

77

Preparation of (2R,3S)-2-propyl-1-(4-(trifluoromethyl)nicotinoyl)-3-(5-(trifluoromethyl)thiophen-3-yloxy)piperidine-3-carboxylic acid 76 has been described in the previous publication (US 2008/0004287 A1). (2R,3S)-2-propyl-1-(3-(trifluoromethyl)picolinoyl)-3-(5-(trifluoromethyl)thiophen-3-yloxy)piperidine-3-carboxylic acid 77 was prepared in a similar manner to 76 by replacing CF3-nicotinic acid with commercially available CF3-picolinic acid.

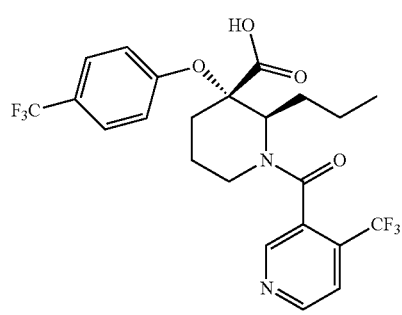

76-A

Preparation of (2R,3S)-2-propyl-1-(4-(trifluoromethyl)nicotinoyl)-3-(4-(trifluoromethyl)phenoxy)piperidine-3-carboxylic acid 76-A has been described in the previous publication (US 2008/0004287 A1). (2R,3S)-2-propyl-3-(4-(trifluoromethyl)phenoxy)-1-(3-(trifluoromethyl)picolinoyl)piperidine-3-carboxylic acid 77-A was prepared in a

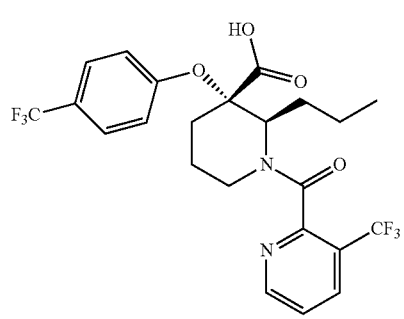

77-A similar manner to acid 76-A by replacing CF3-nicotinic acid with commercially available CF3-picolinic acid.

General Procedure 1

Representative Example 20

Synthesis of (2R,3S)-2-propyl-1-(3-(trifluoromethyl)picolinoyl)-3-(5-(trifluoromethyl)thiophen-3-yloxy)piperidine-3-carbonyl chloride 78 and (2R,3S)-2-propyl-1-(4-(trifluoromethyl)nicotinoyl)-3-(5-(trifluoromethyl)thiophen-3-yloxy)piperidine-3-carbonyl chloride 79

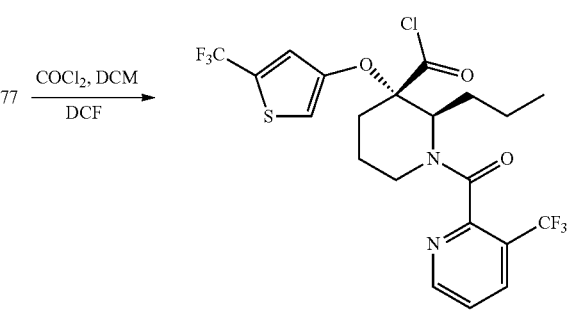

To a 0° C. solution of acid 77 (1.71 mmol, 0.9 g) in DCM (10 mL) was added oxalylchloride (2 equiv, 3.5 mmol, 0.3 mL) followed by DMF (2 drops). Reaction was stirred at 0° C. for 30 min then concentrated to dryness and stored under high vacuum. The resulting (2R,3S)-2-propyl-1-(3-(trifluoromethyl)picolinoyl)-3-(5-(trifluoromethyl)thiophen-3-yloxy)piperidine-3-carbonyl chloride 78 was used without further purification. (2R,3S)-2-propyl-1-(4-(trifluoromethyl)nicotinoyl)-3-(5-(trifluoromethyl)thiophen-3-yloxy)piperidine-3- carbonyl chloride 79 was prepared in similar fashion using acid 76 as starting material instead of acid 77.

General Procedure 2

Representative Example 21

Synthesis of 4-(2-hydroxyphenyl)-1-((2R,3S)-2-propyl-1-(4-(trifluoromethyl)nicotinoyl)-3-(5-(trifluoromethyl)thiophen-3-yloxy)piperidine-3-carbonyl)piperidine-4-carbonitrile 80 and 4-(2-hydroxyphenyl)-1-((2R,3S)-2-propyl-1-(3-(trifluoromethyl)picolinoyl)-3-(5-(trifluoromethyl)thiophen-3-yloxy)piperidine-3-carbonyl)piperidine-4-carbonitrile 81

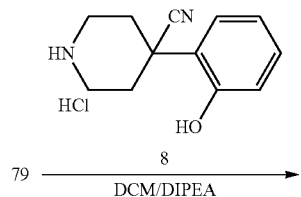

79 $\xrightarrow{\text{8}}$ DCM/DIPEA

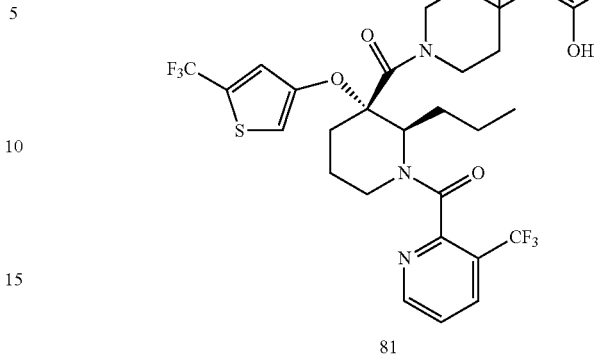
81

To the phenol 8 (1.36 gm, 5.69 mmol, 1.5 equi.) in DCM (100 mL) was added the DIPEA (10 equi., 7 mL) followed by the acid chloride 79 (2 gm, 1 equi., 4.54 mmol) under nitrogen. Reaction was stirred at room temperature for 18 hours and diluted with ethyl acetate, then washed with sat ammonium chloride, sodium bicarbonate and brine. Dried over $Na_2SO_4$, filtered and concentrated to dryness. The residue was purified by silica gel chromatography (10% to 80% ethyl acetate/hexanes) to provide 2.49 g of intermediate 80. Intermediate 81 was prepared in similar fashion using acid chloride 78 as starting material instead of acid chloride 79.

General Procedure 3

Representative Example 22

Synthesis of (4-hydroxy-4-(2-hydroxyphenyl)piperidin-1-yl)((2R,3S)-2-propyl-1-(4-(trifluoromethyl)nicotinoyl)-3-(5-(trifluoromethyl)thiophen-3-yloxy)piperidin-3-yl)methanone 82 and (4-hydroxy-4-(2-hydroxyphenyl)piperidin-1-yl)((2R,3S)-2-propyl-1-(3-(trifluoromethyl)picolinoyl)-3-(5-(trifluoromethyl)thiophen-3-yloxy)piperidin-3-yl)methanone 83

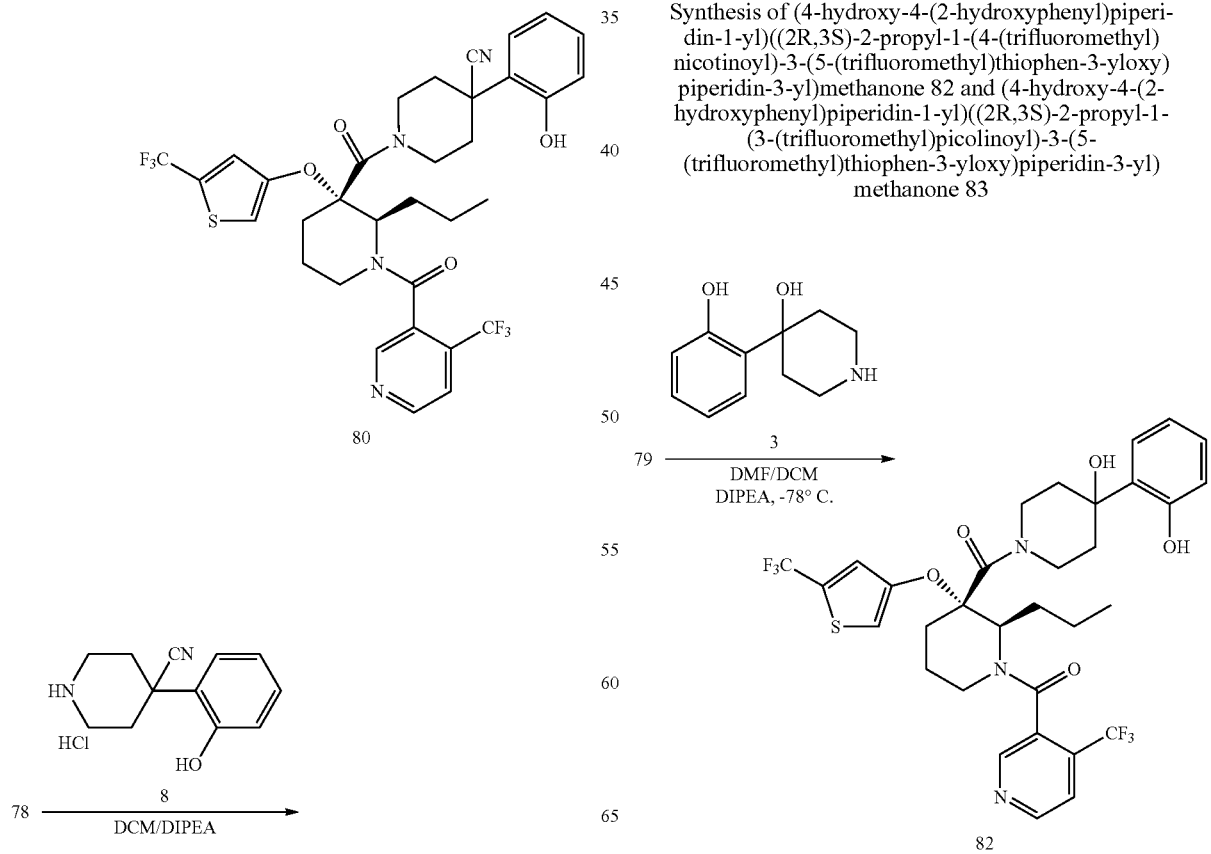

-continued

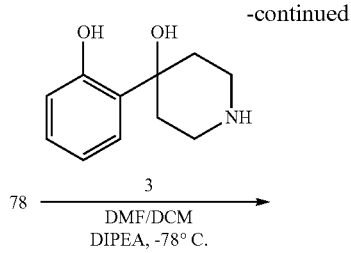

78 →(3, DMF/DCM, DIPEA, −78° C.)

-continued

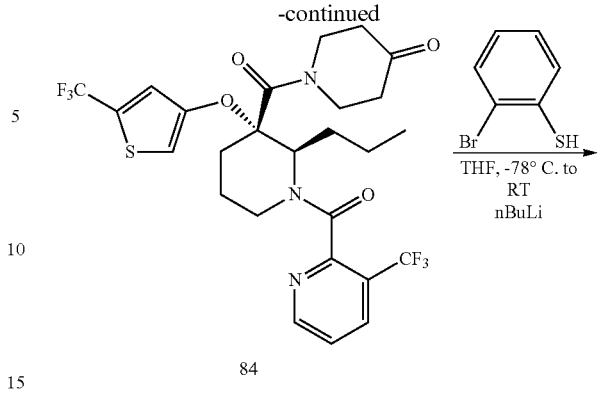

84

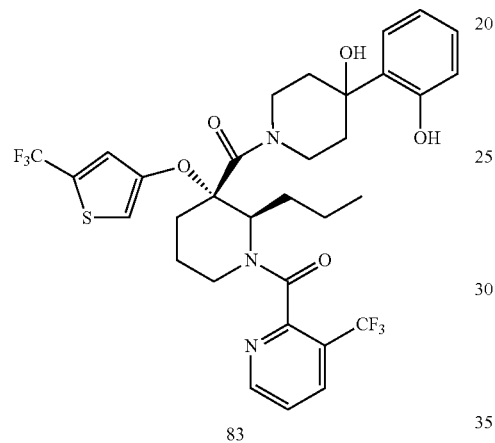

83

To a −50° C. internal temp solution of piperidine 3 (1.5 equiv, 22.5 mmol, 4.4 g) in DMF (100 mL) and DIPEA (5 equiv, 12.4 mL) was added dropwise a DMF solution (100 mL) of acid chloride 78 (15 mmol). Cooling bath was removed and reaction was warmed-up to 23° C. overnight. The reaction mixture was diluted with EtOAc, wash with HCl 1.0N. dried over MgSO4, filtered and concentrated down. The residue was purified by silica gel chromatography (10% to 60% ethyl acetate/hexanes) to provide 7.6 g (74% yield) of intermediate 83 as a white foam.

Intermediate 82 was prepared in similar fashion using acid chloride 79 as starting material instead of acid chloride 78.

Representative Example 23

Synthesis of (4-hydroxy-4-(2-mercaptophenyl)piperidin-1-yl)((2R,3S)-2-propyl-1-(3-(trifluoromethyl)picolinoyl)-3-(5-(trifluoromethyl)thiophen-3-yloxy)piperidin-3-yl)methanone 85

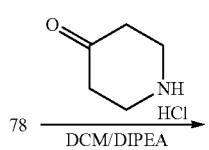

78 →(DCM/DIPEA)

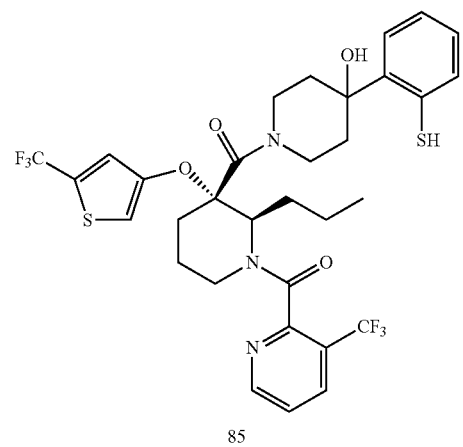

85

Step 1:
Acid chloride 78 (2 mmol) was diluted in DCM (10 mL) and added DIPEA (1 mL) followed by piperidin-4-one hydrochloride (3 mmol, 400 mg). After 15' MS MS analysis showed that all starting material had been consumed. Reaction was diluted with EtOAc, washed with HCl 1.0N and brine. Organic layer was dried over MgSO$_4$, filtered and concentrated down. The residue was purified by C18 column using 60-95% CH3CN in water over 10 minutes. The product was lyophilized to yield 63% of 1-((2R,3S)-2-propyl-1-(3-(trifluoromethyl)picolinoyl)-3-(5-(trifluoromethyl)thiophen-3-yloxy)piperidine-3-carbonyl)piperidin-4-one 84.

Step 2;
To a −78° C. solution of Bromothiophenol (0.6 g, 3 mmol) in THF (5 mL) was added n-BuLi (6 mmol, 2.4 mL). After 30 min, reaction was added to 84 (2 mmol, in THF) at −78° C. After addition, reaction was warmed-up to RT. After 1 hours, NH$_4$Cl was added and reaction was extracted with EtOAc. Organic layer was washed with brine and dried over MgSO$_4$, filtered and concentrated down. The residue was purified by silica gel chromatography 40 g, 20-100% EtOAc in hexanes to provide 390 mg of 85 (30% yield).

General Procedure 4

Representative Example 24

Synthesis of 3-(2-(1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenyl)propanoic acid A135

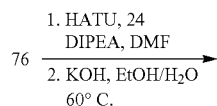

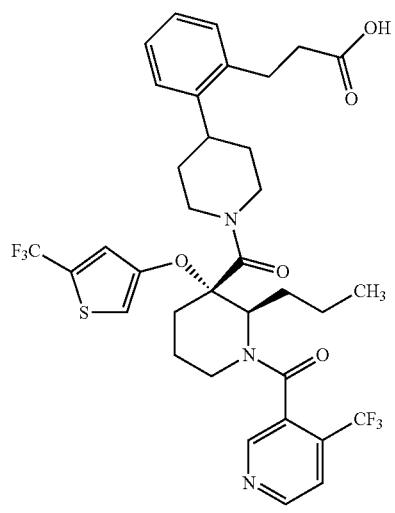

A135

76 (80 mg, 0.16 mmol) and 3-(2-(piperidin-4-yl)phenyl)propanoate hydrochloride 24 (66 mg, 0.20 mmol) were dissolved in DMF (1 mL). HATU (119 mg, 0.31 mmol) and DIPEA (280 µL, 1.57 mmol) were added. The reaction was stirred at 23° C. overnight. The reaction mixture was concentrated. The crude residue was dissolved in EtOH (1 mL). KOH (26 mg, 0.47 mmol) and water (5 drops) were added and the reaction was heated at 65° C. for 2 h. The reaction was concentrated and the residue was dissolved in H₂O (3 mL) and was acidified to pH~4 with aqueous 1 M HCl. The crude residue was purified by reverse phase preparative HPLC to yield 3-(2-(1-((2R,3S)-2-propyl-1-(4-trifluoromethyl)nicotinoyl)-3-(5-(trifluoromethyl)thiophen-3-yloxy)piperidine-3-carbonyl)piperidin-4-yl)phenyl)propanoic acid A135. LC/MS RT (10 min method)=6.31 min. Mass observed: 726.23 (M+H).

Representative Example 25

Synthesis of 3-(2-(4-cyano-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenyl)propanoic acid A136

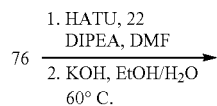

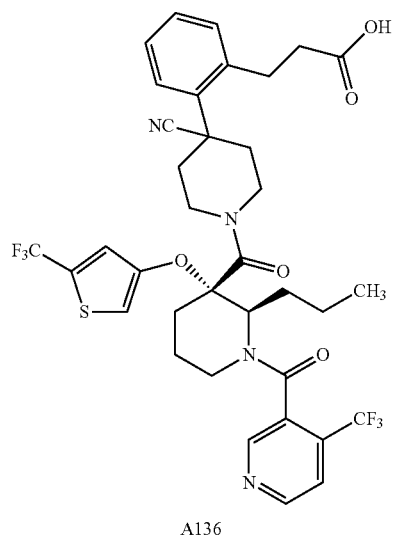

A136

Amide coupling of 76 and 3-(2-(4-cyanopiperidin-4-yl)phenyl)propanoate hydrochloride 22 followed by hydrolysis were performed by following general procedure 4. Reverse phase preparative HPLC purification yielded 3-(2-(4-cyano-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenyl)propanoic acid A136. LC/MS RT (10 min method)=4.55 min. Mass observed: 751.23 (M+H).

Representative Example 26

Synthesis of 4-(2-(3-hydroxypropyl)phenyl)-1-((2R,3S)-2-propyl-1-(4-(trifluoromethyl)nicotinoyl)-3-(5-(trifluoromethyl)thiophen-3-yloxy)piperidine-3-carbonyl)piperidine-4-carbonitrile A138

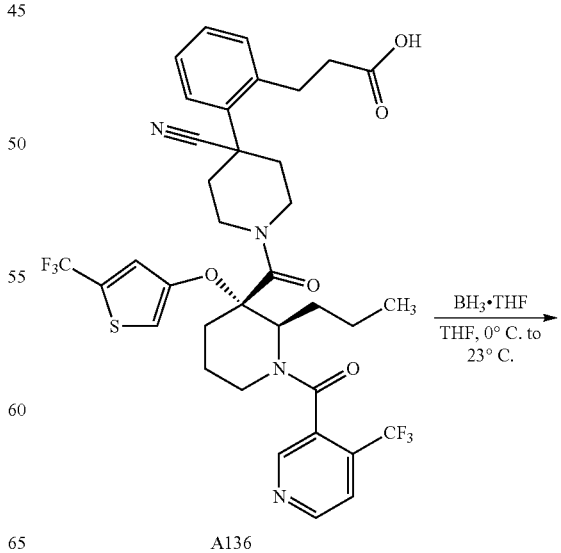

A136

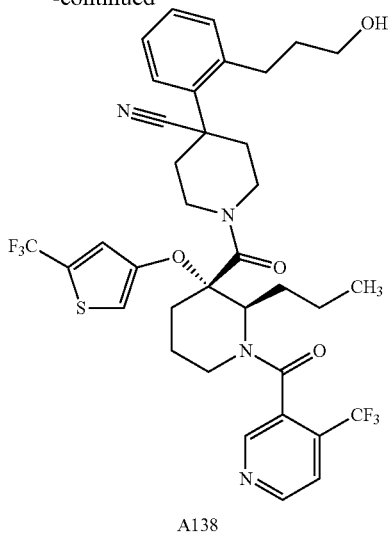

A138

Acid A136 3-(2-(4-cyano-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenyl)propanoic acid (10 mg, 13.3 µmol) was dissolved in THF (0.5 mL). The mixture was cooled to 0° C. and BH₃.THF (30 µL, 27.9 µmol) was added dropwise under Ar. The reaction was warmed to 23° C. and was stirred overnight. The reaction mixture was quenched with 1 M NaOH and was concentrated. The crude residue was purified by reverse phase preparative HPLC to yield 4-(2-(3-hydroxypropyl)phenyl)-1-((2R,3S)-2-propyl-1-(4-(trifluoromethyl)nicotinoyl)-3-(5-(trifluoromethyl)thiophen-3-yloxy)piperidine-3-carbonyl)piperidine-4-carbonitrile A138. LC/MS RT (10 min method)=6.04 min. Mass observed: 737.25 (M+H).

Representative Example 27

Synthesis of 3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenyl)propanoic acid A139

78 →  1) 22, DIPEA, CH₂Cl₂
        2) KOH, EtOH/H₂O, 60° C.

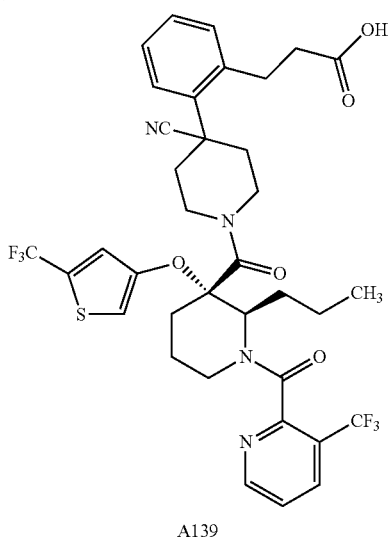

A139

Amide bond formation was followed by general procedure 2. Hydrolysis of the ester to the carboxylic acid was followed as described in general procedure 4. The crude product was purified by reverse phase preparative HPLC to yield 3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenyl)propanoic acid A139. LC/MS RT (10 min method)=4.54 min. Mass observed: 751.23 (M+H).

Representative Example 28

Synthesis of 5-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenyl)pentanoic acid A141

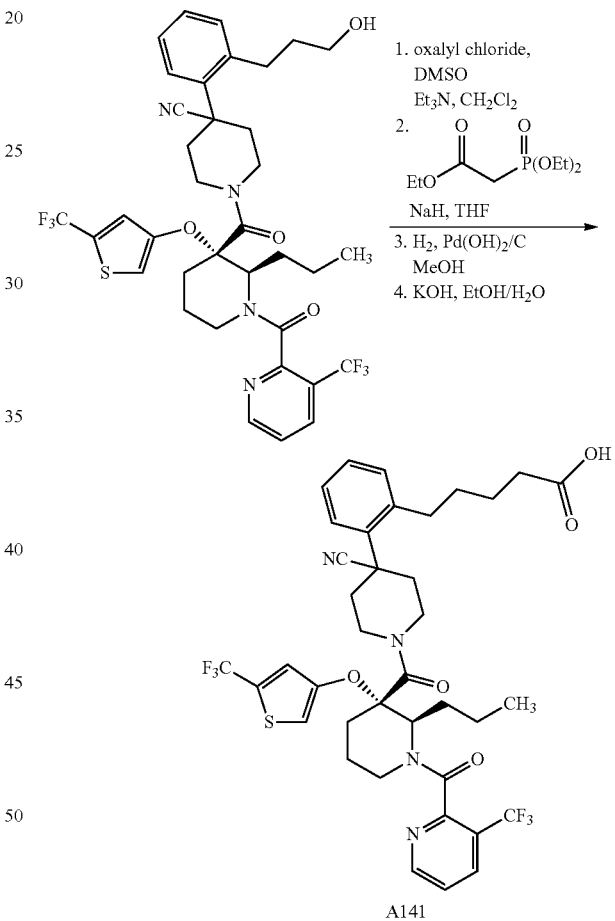

A141

Step 1:

A mixture of DMSO (69 µL, 0.98 mmol) in CH₂Cl₂ (2.0 mL) was cooled to −78° C. Oxalylchloride (46 µL, 0.49 mmol) was added to the mixture and was stirred for 10 min at −78° C. A solution of alcohol A139 4-(2-(3-hydroxypropyl)phenyl)-1-((2R,3S)-2-propyl-1-(3-(trifluoromethyl)picolinoyl)-3-(5-(trifluoromethyl)thiophen-3-yloxy)piperidine-3-carbonyl)piperidine-4-carbonitrile (180 mg, 0.24 mmol) obtained following a similar procedure used to prepare 4-(2-(3-hydroxypropyl)phenyl)-1-((2R,3S)-2-propyl-1-(4-(trifluoromethyl)nicotinoyl)-3-(5-(trifluoromethyl)thiophen-3-yloxy)piperidine-3-carbonyl)piperidine-4-carbonitrile from 3-(2-(4-cyano-1-((2R,3S)-2-propyl-1-(3-(trifluoromethyl) picolinoyl)-3-(5-(trifluoromethyl)thiophen-3-yloxy)piperidine-3-carbonyl)piperidin-4-yl)phenyl)propanoic acid in CH$_2$Cl$_2$ (1.0 mL) was added and was stirred at the same temperature for 1 h. Et$_3$N (204 µL, 1.46 mmol) was added slowly at −78° C. and was warmed to 23° C. The reaction was further stirred at 23° C. for 3 h. The mixture was diluted with CH$_2$Cl$_2$ (10 mL) and was washed with aqueous sat'd NaHCO$_3$ (1×15 mL), and brine (1×15 mL). The organic layer was dried over Na$_2$SO$_4$ and was concentrated to yield the aldehyde.

Step 2:

NaH (60% in mineral oil, 10 mg, 0.26 mmol) was washed with hexanes (2×) and was kept under Ar. THF (2.0 mL) was added and the mixture was cooled to 0° C. Triethyl phosphonoacetate (56 µL, 0.28 mmol) was added and was further stirred at 0° C. for 30 min. A solution of the crude aldehyde (172 mg, 0.23 mmol) in THF (1.0 mL) was added at 0° C. The reaction was warmed to 23° C. and was stirred overnight. The reaction was quenched with aqueous sat'd NH$_4$Cl (2 mL) and the solution was extracted with EtOAc (3×15 mL). The organic layers were washed with brine (1×15 mL), dried over Na$_2$SO$_4$ and was concentrated. The crude residue was purified by silica gel chromatography (gradient, 20% to 50% EtOAc/hexanes) to yield the enone as a pale yellow oil. LC/MS RT (5 min method)=2.78 min. Mass observed: 805.28 (M+H).

Step 3:

Hydrogenation, followed by hydrolysis of the ester to the carboxylic acid was followed similarly as shown above. Reverse phase preparative HPLC purification yielded 5-(2-(4-cyano-1-((2R,3S)-2-propyl-1-(3-(trifluoromethyl)picolinoyl)-3-(5-(trifluoromethyl) thiophen-3-yloxy)piperidine-3-carbonyl)piperidin-4-yl)phenyl)pentanoic acid A141. LC/MS RT (10 min method)=4.51 min. Mass observed: 779.26 (M+H).

Representative Example 29

Synthesis of (4-(2-(2-(1H-tetrazol-5-yl)ethyl)phenyl) piperidin-1-yl)((2R,3S)-2-propyl-1-(4-(trifluoromethyl)nicotinoyl)-3-(5-(trifluoromethyl)thiophen-3-yloxy)piperidin-3-yl)methanone A133

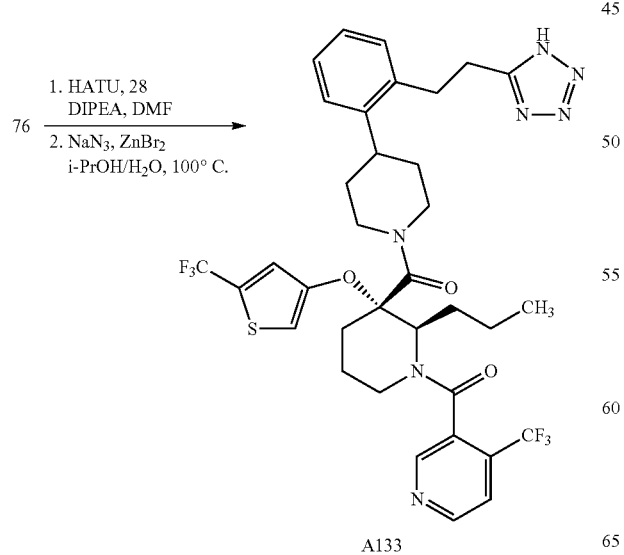

Amine 28 (26 mg, 0.10 mmol) was dissolved in DMF (0.5 mL) and reacted with acid 76 following general procedure 4. The nitrile obtained (10 mg, 14.2 µmol) was dissolved in i-PrOH/H$_2$O (50 µL/150 µL). NaN$_3$ (1.0 mg, 15.6 µmol) and ZnBr$_2$ (3.0 mg, 14.2 µmol) were added. The reaction was heated at 100° C. overnight. The reaction was quenched with 1 M HCl (5 drops) and was then concentrated. The crude residue was purified by preparative HPLC to yield (4-(2-(2-(1H-tetrazol-5-yl)ethyl)phenyl)piperidin-1-yl)((2R,3S)-2-propyl-1-(4-(trifluoromethyl)nicotinoyl)-3-(5-(trifluoromethyl)thiophen-3-yloxy)piperidin-3-yl)methanone. LC/MS RT (10 min method)=5.97 min. Mass observed: 750.26 (M+H) A133.

Representative Example 30

Synthesis of N-(methylsulfonyl)-3-(2-(1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenyl)propanamide A134

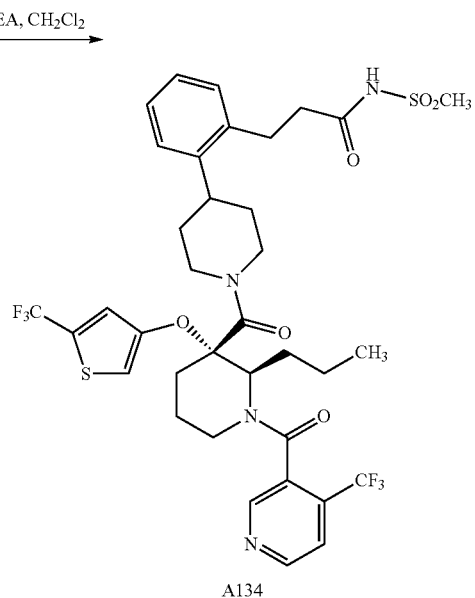

N-(methylsulfonyl)-3-(2-(piperidin-4-yl)phenyl)propanamide hydrochloride 29 (13 mg, 42.5 µmol) was used as described in general procedure 2 using intermediate 79. The reaction was stirred overnight at 23° C. The reaction mixture was concentrated and was purified by reverse phase preparative HPLC to yield N-(methylsulfonyl)-3-(2-(1-((2R,3S)-2-propyl-1-(4-(trifluoromethyl)nicotinoyl)-3-(5-(trifluoromethyl)thiophen-3-yloxy)piperidine-3-carbonyl)piperidin-4- yl)phenyl)propanamide A134. LC/MS RT (10 min method)= 4.56 min. Mass observed: 803.23 (M+H).

Representative Example 31

Synthesis of 3-(2-(4-cyano-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenyl)-N-(methylsulfonyl)propanamide A137

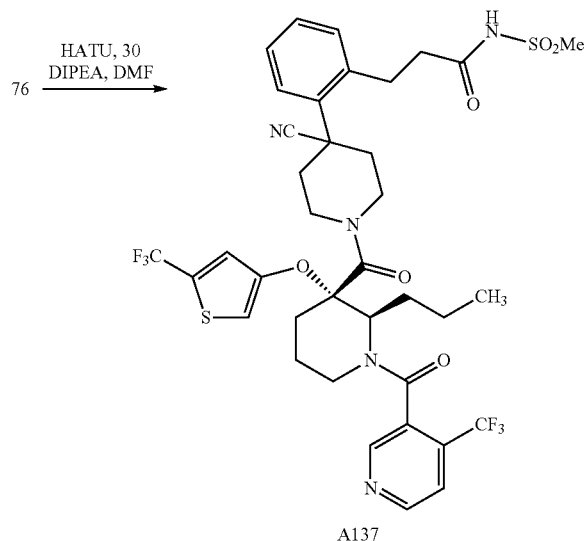

A137

Amide coupling of 76 and 3-(2-(4-cyanopiperidin-4-yl)phenyl)-N-(methylsulfonyl)propanamide hydrochloride 30 was followed by general procedure 4. Reverse phase preparative HPLC purification yielded 3-(2-(4-cyano-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenyl)-N-(methylsulfonyl)propanamide A137. LC/MS RT (10 min method)=5.89 min. Mass observed: 828.22 (M+H).

Representative Example 32

Synthesis of 3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)-4-fluorophenyl)propanoic acid A140

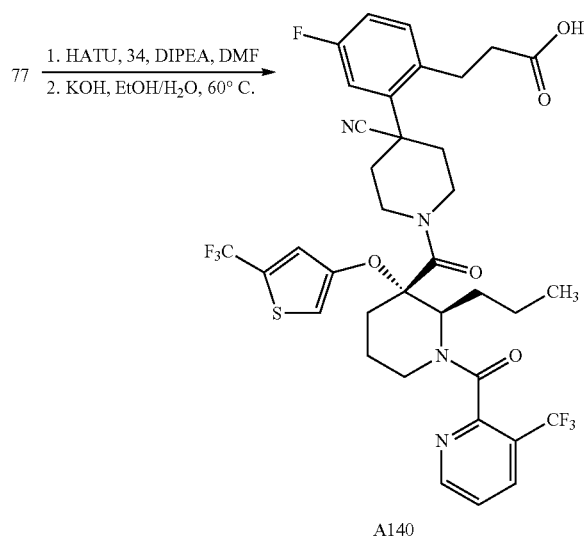

A140

Amide coupling of 77 and 3-(2-(4-cyanopiperidin-4-yl)-4-fluorophenyl)propanoate hydrochloride 34, followed by hydrolysis were performed by following general procedure 4 replacing in step 1, 76 by 77. Reverse phase preparative HPLC purification yielded 3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)-4-fluorophenyl)propanoic acid A140. LC/MS RT (10 min method)=4.34 min. Mass observed: 769.22 (M+H).

Representative Example 33

Synthesis of 5-(4-phenyl-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)pentanoic acid A81

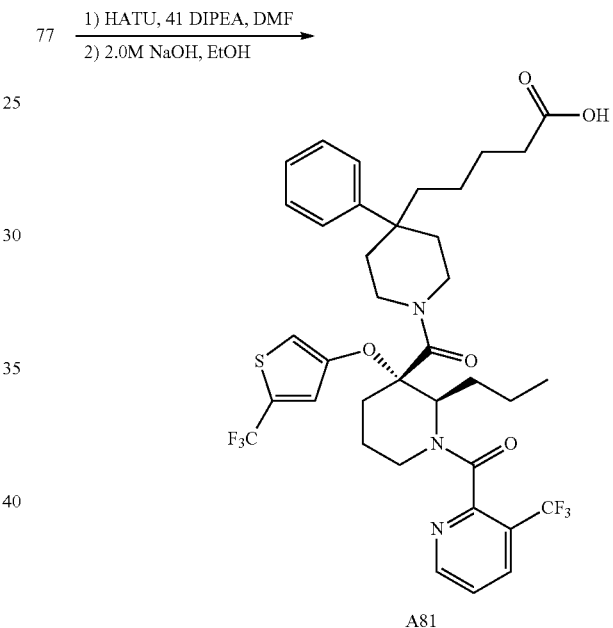

A81

Step 1:

Amide coupling of 77 and 9 (0.2 mmol, 70 mg) was performed by following general procedure 4 replacing in step 1, acid 76 by acid 77. The crude product was purified on Biotage (EtOAc in hexane: 25-50%), to give ethyl 5-(4-phenyl-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)pentanoate as white solid.

Step 2:

To ethyl 5-(4-phenyl-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)pentanoate in ethanol was added 2.0 M NaOH aqueous solution and the mixture was stirred at 70° C. for 1 h. Then the solvent was removed in vacuo. The residue was redissolved in water, acidified with 6N HCl to PH ~4, then extracted with EtOAc (2×30 ml), dried (MgSO4), concentrated, purified on Gilson, treated with 4.0 M HCl in dioxane (2-3 drops), lyophilized, to give 5-(4-phenyl-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)pentanoic acid A81 as white solid.

General Procedure 5

Representative Example 34

Synthesis of 4-(2-(4-hydroxy-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)butanoic acid A91

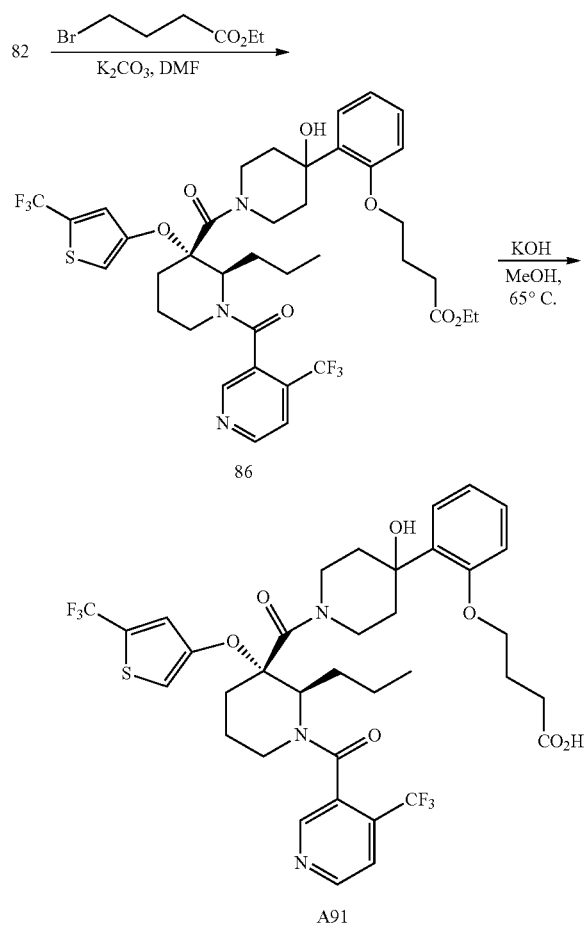

Step 1:

To intermediate 82 (prepared according the aforementioned general procedure 3, 300 mg, 0.44 mmol) in 5 mL of DMF was added K₂CO₃ (608 mg, 4.4 mmol, 10 eq.) followed by ethyl 4-bromobutyrate (94 uL, 0.66 mmol, 1.5 eq.). The mixture was stirred at 60° C. for 18 hours then diluted with EtOAc, washed with water and brine. Organic layer was dried over MgSO4, filtered and concentrated down. Purified by SiO2 column using a gradient 10-40% EtOAc in hexane to give 0.246 g of ethyl 4-(2-(4-hydroxy-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)butanoate 86.

Step 2:

To 86 (40 mg, 0.05 mmol, 1 eq) in MeOH was added KOH (3.5N, 5 equiv). Reaction was brought to 65° C. for 1 hour then cooled down to 23° C. Reaction was diluted with EtOAc, washed with sat. NH₄Cl and brine. The organic layer was dried over MgSO₄, filtered and concentrated down. HPLC purification, C18, CH₃CN/H2O, 70% to 100% CH₃CN provided 37 mg (100% yield) of product A91.

Representative Example 35

Synthesis of dimethyl 3-(2-(4-cyano-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)propylphosphonate A85

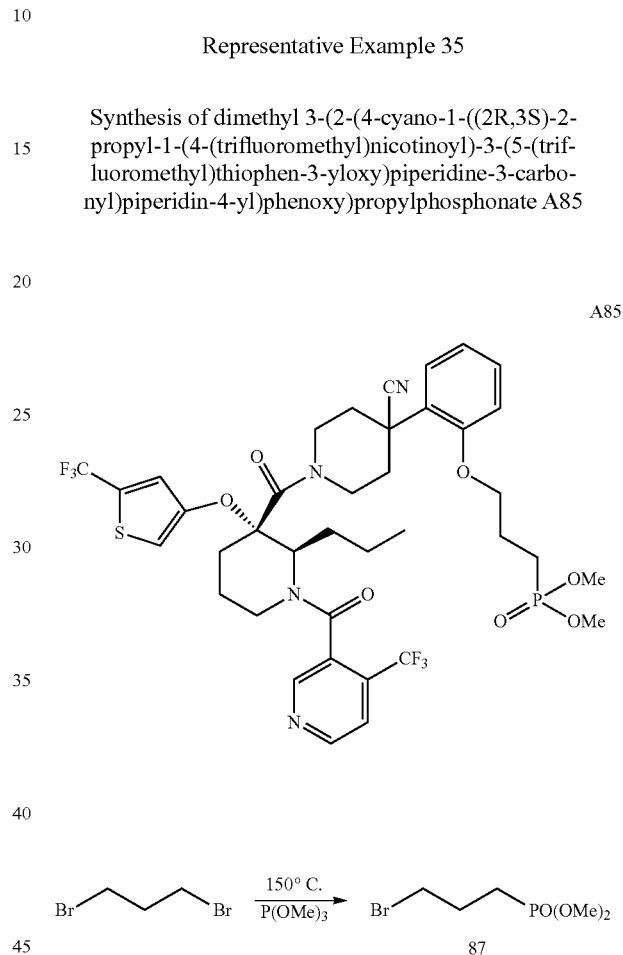

Step 1:

To trimethyl phosphate (2.38 ml, 20.1 mmol) was added dibromopropane (10.2 ml, 5 equi., 0.105 mol). Reaction mixture was brought to 150° C. for 30 min. Volatile were evaporated off excess dibromide was removed by distillation. 4.5 g of dimethyl 3-bromopropylphosphonate 87 was isolated (98% yield).

Step 2:

NaH (2 equiv.) was added to a DMF (2 mL) solution of intermediate 80 (prepared in general procedure 2, 60 mg, 0.086 mmol). Reaction was stirred under nitrogen atmosphere for 10 minutes. To this was added 87 (3 equiv.). Reaction was brought to 60° C. and stirred overnight. Volatiles were removed and the residue was purified by reverse phase HPLC (10% to 100% acetonitrile/water (0.1% TFA) over 40

General Procedure 6

Representative Example 36

Synthesis of 3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)propylphosphonic acid A89

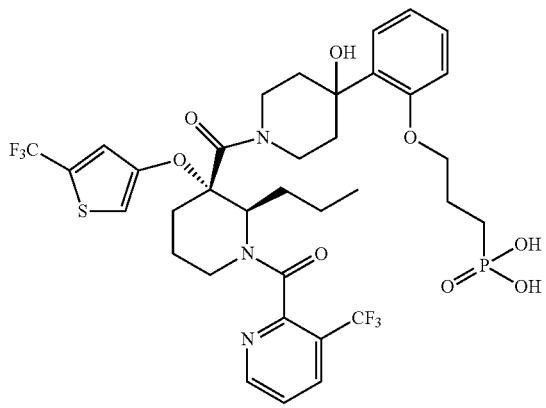

A89

To intermediate 83 (prepared according the aforementioned general procedure 3, 120 mg, 1 equi.) dissolved in DMF (5 mL) was added bromo phosphonate 87 (1.5 equi.) and potassium carbonate (10 equiv.). Reaction mixture was stirred at room temperature overnight. Reaction was diluted with ethyl acetate and washed with water and brine. Volatiles were removed and the residue was purified by reverse phase HPLC (10% to 100% acetonitrile/water (0.1% TFA) over 40 min. Flow rate of 10 mL/min), using a C18, 10 micron (19×250 mm) column. Sample was lyophilized to yield 66 mg of product A89.

Representative Example 37

Synthesis of 4-(2-(4-fluoro-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)butanoic acid A95

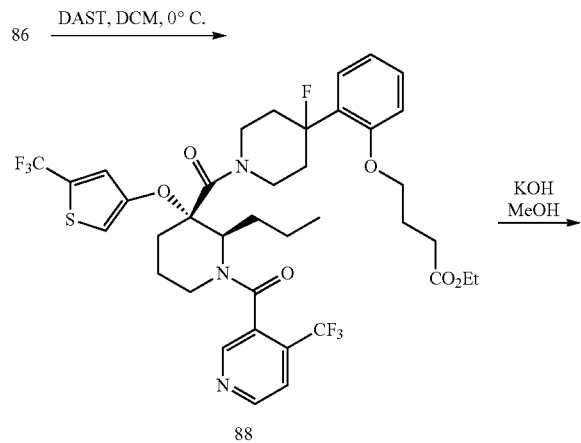

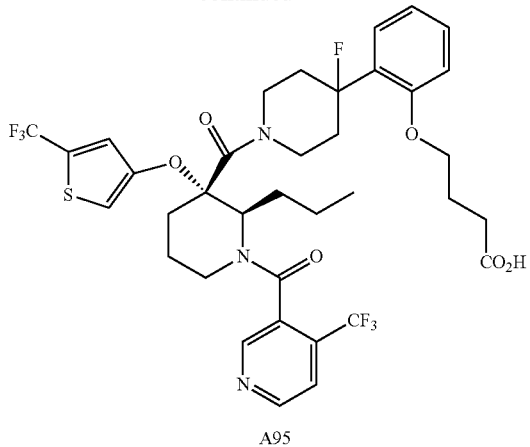

A95

Step 1:
To ethyl 4-(2-(4-hydroxy-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)butanoate 86 (40 mg, 0.05 mmol, 1 eq) in DCM at 0° C. was added DAST (7.4 uL, 0.06 mmol, 1.2 eq.). The reaction was stirred at room temperature for overnight. The reaction mixture was diluted with EtOAc and washed with saturated aqueous NH4Cl and brine. The organic layer was dried over MgSO4, filtered and concentrated down. HPLC purification, C18, CH3CN/H2O, 60% to 90% CH3CN provided 38 mg (99% yield) of ester ethyl 4-(2-(4-fluoro-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)butanoate 88.

Step 2:
To ester 88 (38 mg, 0.047 mmol) in 1.0 mL of MeOH was added aqueous KOH (0.2 mL, 0.71 mmol, 15 equiv). Reaction was stirred at 45° C. for 15 hours. Reaction was concentrated to a lower and 3 mL of EtOAc was added. Water (5 mL) was added and the mixture was acidified with aqueous 1N HCl to PH=3.5. EtOAc layer was separated and washed with brine. The Organic later was dried over MgSO4 filtered and concentrated to dryness to give 36 mg of product A95 (100% yield).

Representative Example 38

Synthesis of 4-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-2,2-dimethylbutanoic acid A11

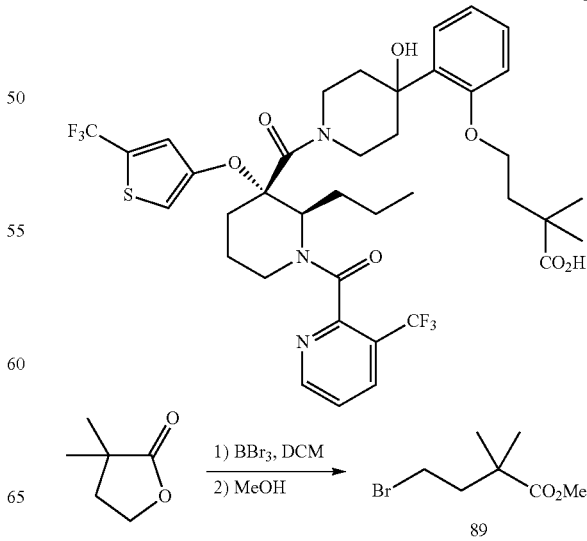

Step 1:

To alpha,alpha-dimethyl-gamma-butyrolactone (1.49 g, 13.05 mmol) in 10 mL of anhydrous DCM was added BBr3 (3.7 mL, 13.7 mmol, 1.05 eq.) slowly at 0° C. The mixture was stirred at room temperature over night. Reaction was quenched by addition of MeOH (1 mL) at 0° C. Reaction was further stirred at room temperature for 20 min then diluted with saturated aqueous NaHCO3 and extracted with DCM. Organic layer was washed with aqueous $Na_2S_2O_4$, brine and dried over $MgSO_4$, filtered and concentrated down. The residue was purified by silica gel chromatography (100% DCM) to provide 1.9 g (68% yield) of methyl 4-bromo-2,2-dimethylbutanoate 89.

Step 2:

89 was reacted as described in general procedure 6 to yield 4-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-2,2-dimethylbutanoic acid. Hydrolysis of 4-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-2,2-dimethylbutanoic acid was performed as described in general procedure 5, step 2 to yield A11.

Representative Example 39

Synthesis of 5-(2-(4-hydroxy-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)-2,2-dimethylpentanoic acid A102

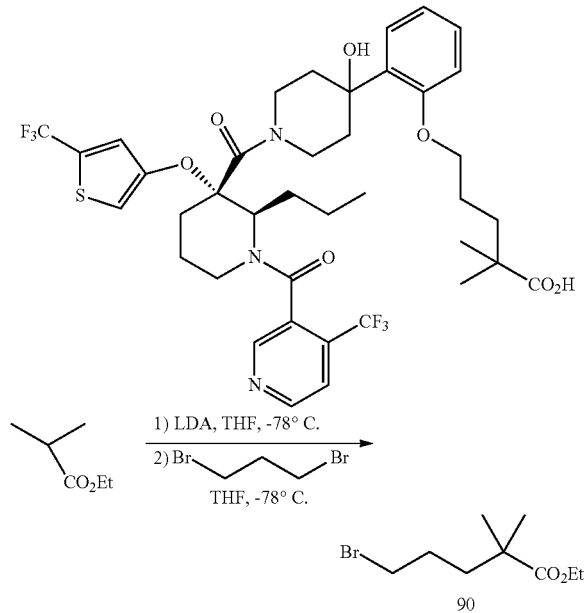

Step 1:

To a 0° C. solution of diisopropylamine (14.35 mL, 0.102 mol) in 70 mL of THF was added n-BuLi (68 mL, 0.102 mol). The mixture was stirred at 0~5° C. for 30 min. After the mixture was cooled to −78° C., ethyl isobutyrate (13.7 mL, 0.102 mol, 1 eq.) was added drop wise and stirring was maintained at −78° C. for 1 h. 1,3-Dibromopropane (1.01 equiv, 10.5 mL) was added drop wise at −78° C. and stirring was maintained at −78° C. for 1 h. Reaction was then warmed up to 23° C. over 2 hrs. Reaction mixture was added to an aqueous NH4Cl solution and extracted with EtOAc. The organic layer was washed with 1N HCl and brine, dried over $MgSO_4$, filtered and concentrated down to give 23 g of crude product. The residue was purified by silica gel chromatography (5% to 30% EtOAc in hexanes) to provide 17.4 g (73% yield) of ethyl 5-bromo-2,2-dimethylpentanoate 90.

Step 2:

90 was reacted as described in general procedure 5 to yield A102.

Representative Example 40

Synthesis of 1-(3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)propyl)cyclobutanecarboxylic acid A86

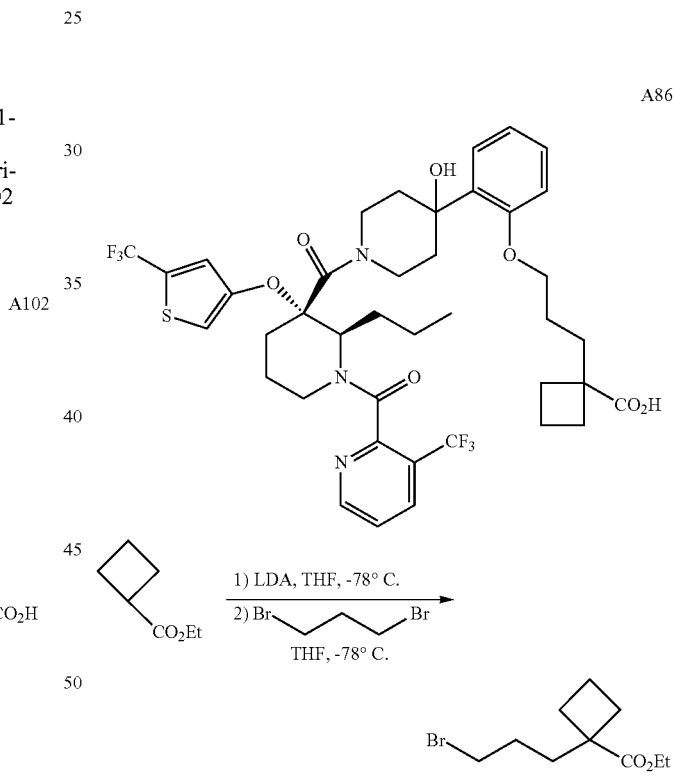

Step 1:

Procedure described in representative example A102 was used by replacing in step1, ethyl isobutyrate with Ethyl cyclobutanecarboxylate to prepare ethyl 1-(3-bromopropyl)cyclobutanecarboxylate 91.

Step 2:

91 was reacted with intermediate 83 as described in general procedure 6 to give ethyl 1-(3-(2-(4-hydroxy-1-((2R,3S)-2- propyl-1-(3-(trifluoromethyl)picolinoyl)-3-(5-(trifluoromethyl)thiophen-3-yloxy)piperidine-3-carbonyl)piperidin-4-yl)phenoxy)propyl)cyclobutanecarboxylate. Hydrolysis of ethyl 1-(3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)propyl)cyclobutanecarboxylate was performed as described in general procedure 5, step 2 to yield A86.

Representative Example 41

Synthesis of 1-(3-(2-(4-methoxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)propyl)cyclobutanecarboxylic acid A131

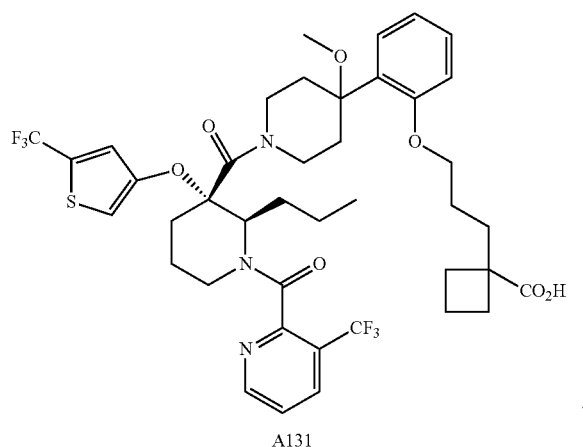

A131

Representative Example 42

Synthesis of 1-(3-(2-(4-cyano-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)butyl)cyclobutanecarboxylic acid A22

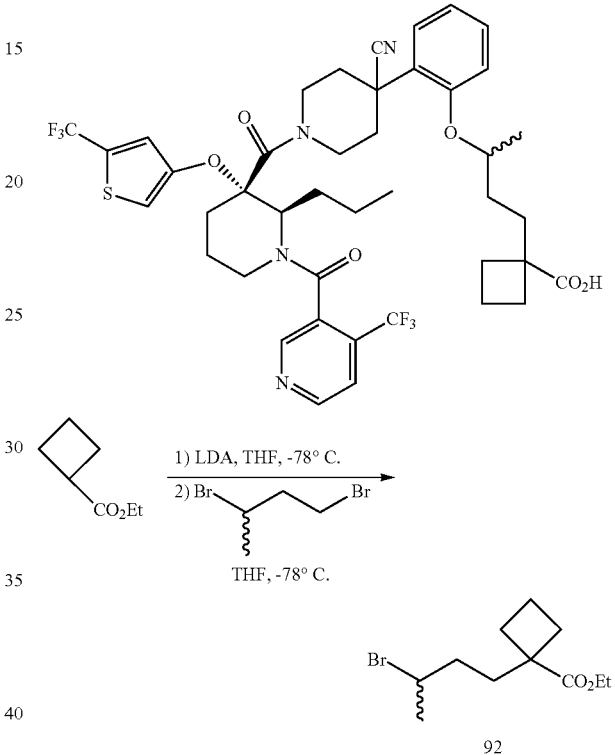

To A86 prepared in representative example 40 (0.15 g, 0.18 mmol) in THF at 0° C. was added NaH (35 mg, 1.5 mmol, 8 eq.). After 5 minutes, MeI (45 uL, 0.72 mmol, 4 eq.) was added slowly. Reaction was stirred for 2 hours then quenched with saturated aqueous NH₄Cl and extracted with EtOAc. The organic layer was washed with brine and dried over MgSO₄, filtered and concentrated down to yield 1-(3-(2-(4-methoxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)propyl)cyclobutanecarboxylic acid. Hydrolysis of 1-(3-(2-(4-methoxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)propyl)cyclobutanecarboxylic acid was performed as described in general procedure 5, step2 to yield, after HPLC purification, C18, CH3CN/H2O, 60% to 90% CH3CN, 39.6 mg (26% yield) of product A131.

Step 1:

To a 0° C. solution of DIPA (14.3 mL, 102 mmol) in THF (100 mL) was added n-BuLi (2.5M, 102 mmol). The Rx was stirred for 30-45 min then cooled to −78° C. Ethyl cyclobutane carboxylate (102 mmol, 1 equiv) was added slowly and the enolate was allowed to form for ~30 min. At ~78° C., above enolate was poured into 1,3-dibromobutane (2 equiv, 200 mmol) and Rx stirred at −78° C. for 1 h then warmed-up to RT. After 3 hours, NH4Cl was added and reaction extracted with EtOAc and washed with brine. The organic layer was dried over MgSO₄, filtered and concentrated down to give 25 g of crude product. The residue was purified by silica gel chromatography (0% to 10% EtOAc in hexanes) to provide 11 g (42% yield) of racemic ethyl 1-(3-bromobutyl)cyclobutanecarboxylate 92.

Step 2:

Ethyl 1-(3-bromobutyl)cyclobutanecarboxylate 92 was used as described in general procedure 5 by replacing in step 1, intermediate 82 by intermediate 80. Ethyl 1-(3-(2-(4-cyano-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)butyl)cyclobutanecarboxylate obtained was hydrolyzed following the conditions of general procedure 5, step 2 to yield A22 as a mixture of 2 diastereomers.

Representative Example 43

Synthesis of 1-(3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)butyl)cyclobutanecarboxylic acid A21

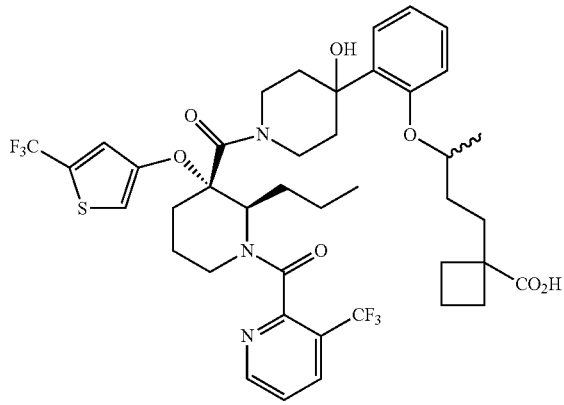

A21

Compound A21 was synthesized in a fashion analogous to compound A22 of representative example 42 starting with intermediate 83 of general procedure 3.

Representative Example 44

Synthesis of 1-((R)-3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)butyl) cyclobutanecarboxylic acid A31

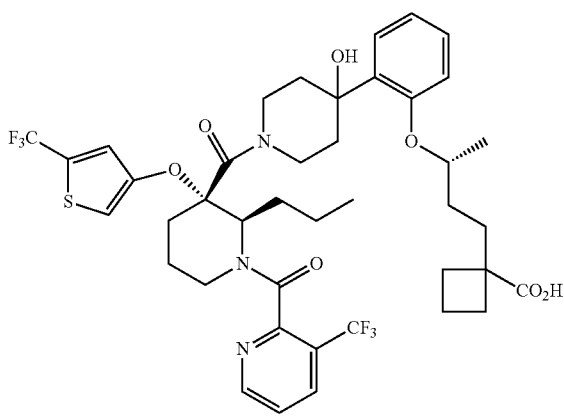

A31

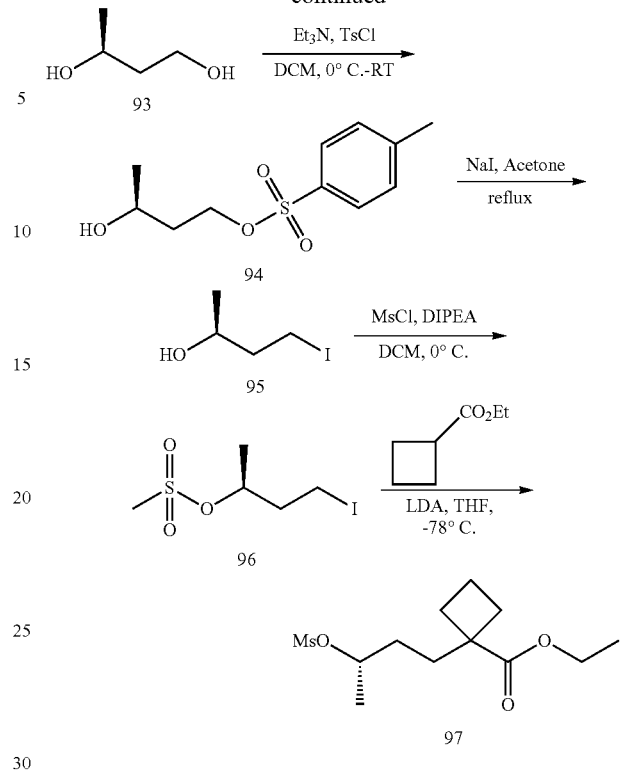

Step 1:

To a 0° C. DCM (100 mL) solution of (S)-(+)-1,3-Butanol (7 g, 77.6 mmol) containing Et$_3$N (14 mL, 1.3 equiv) was added drop wise a DCM solution (60 mL) of TsCl (1.05 equiv, 15 g). Reaction was warmed-up to Rt and stirred overnight. After 18 hours, the DCM layer was washed with HCl 1.0N (×2), then NaHCO$_3$, then brine. Organic layer was dried over MgSO4, filtered and concentrated down to 15 g of crude oil. The residue was purified by silica gel chromatography (10% to 40% EtOAc in hexanes) to provide 13 g (69% yield) of (S)-3-hydroxybutyl 4-methylbenzenesulfonate 94.

Step 2:

To a RT solution of 94 (4 mmol, 1 g) in acetone (10 mL) was added NaI (5 equiv, 20 mmol, 3 g) and the reaction was brought to reflux. After 2 hours, TLC showed that reaction was completed. Insoluble was filtered off trough pad of celite. Filtrate was concentrated down and diluted with EtOAc and water. EtOAc layer was washed with NaHCO$_3$, then Na$_2$S$_2$O$_3$ and brine. Organic layer was dried over MgSO$_4$, filtered and concentrated down to a yellow oil. The residue was purified by silica gel chromatography (10% to 50% EtOAc in hexanes) to provide 0.7 g (88% yield) of (S)-4-iodobutan-2-ol 95.

Step 3:

To a 0° C. solution of alcohol 95 (2.5 mmol, 0.5 g) in DCM (10 mL) was added DIPEA (5 mmol, 0.83 ml) followed by CH$_3$SO$_2$Cl (1.2 equiv, 3 mmol, 0.25 mL). After 10 min, TLC showed that reaction was completed. Reaction was poured into water and EtOAc. Washed with HCl (1.0N) and brine. Organic layer was dried over MgSO$_4$, filtered and concentrated down to a yellow oil. The residue was purified by silica gel chromatography (10% to 50% EtOAc in hexanes) to provide 0.64 g (92% yield) of (S)-4-iodobutan-2-yl methanesulfonate 96.

Step 4:

To a solution of diisopropylamine (9.1 mL, 65 mmol) in 43 mL of THF was added n-BuLi (26 mL, 65 mmol) at 0° C. slowly (5 min). The mixture was stirred at 0~5° C. for 30 min. After the mixture was cooled to −78° C. (10 min), Ethylcyclobutanecarboxylate (8 mL, 59.6 mmol, 1.1 eq.) was added dropwise and stirred at −78° C. for 30 min. The enolate was added into the solution of (S)-4-iodobutan-2-yl methanesulfonate 96 (15 g, 54 mmol) in 100 mL of THF at −78° C. Cooling bath was removed to allow the reaction to warm up to RT. After 30 min at RT, reaction was quenched by addition of water and extracted with EtOAc. The organic layer was washed with brine then dried over MgSO4, filtered and concentrated down. The residue was purified by silica gel chromatography first with (5% to 30% EtOAc in hexanes) then 100% DCM to (98% DCM/2% EtOAc) to provide 5.3 g (36% isolated yield) of (S)-ethyl 1-(3-(methylsulfonyloxy)butyl)cyclobutanecarboxylate 97.

Step 5:

97 was reacted as described in general procedure 6 to yield ethyl 1-((R)-3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)butyl)cyclobutanecarboxylate Hydrolysis of ethyl 1-((R)-3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)butyl)cyclobutanecarboxylate was performed as described in general procedure 5, step2 to yield A31.

Representative Example 45

Synthesis of 1-((S)-3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)butyl)cyclobutanecarboxylic acid A32

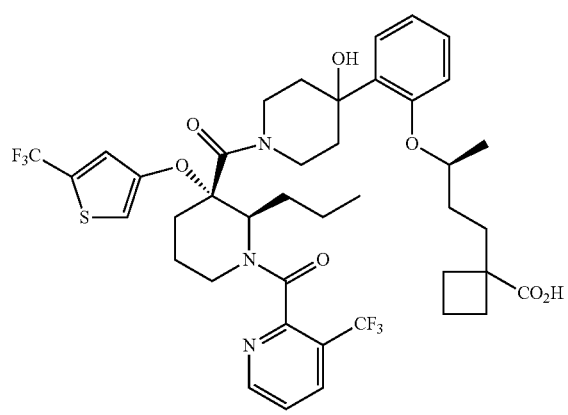

Compound A32 can be prepared in a sequence analogous to the preparation of example A31 from (R)-(−)-1,3-Butanol instead of (S)-(+)-1,3-Butanol 93 in representative example 44, step 1.

Representative Example 46

Synthesis of 1-(2-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)ethyl)cyclobutanecarboxylic acid A88

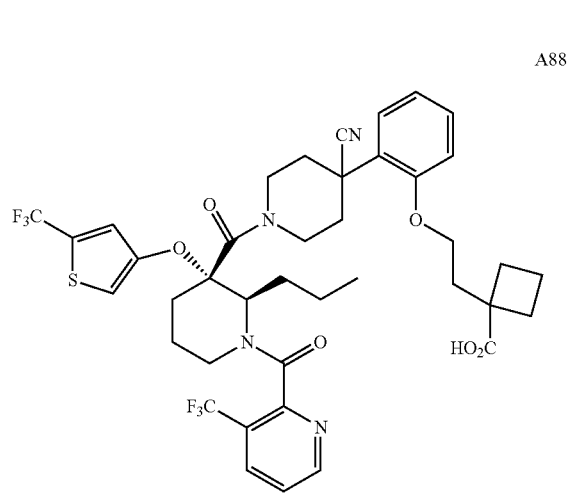

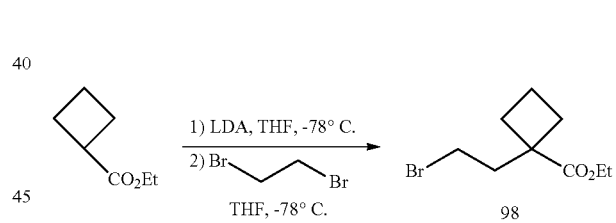

Step 1:

Procedure described in representative example 40, step 1, was used by replacing 1,3-Dibromopropane by 1,3-Dibromoethane to prepare ethyl 1-(2-bromoethyl)cyclobutanecarboxylate 98.

Step 2:

98 was reacted according the general procedure 6 by replacing intermediate 83 with intermediate 81 to give ethyl 1-(2-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)ethyl)cyclobutanecarboxylate. Hydrolysis of ethyl 1-(2-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)

piperidin-4-yl)phenoxy)ethyl)cyclobutanecarboxylate was performed as described in general procedure 5, step 2 to yield A88.

Representative Example 47

Synthesis of (4-(2-(3-(3,5-dimethyl-1H-pyrazol-4-yl)propoxy)phenyl)-4-hydroxypiperidin-1-yl)((2R,3S)-2-propyl-1-(4-(trifluoromethyl)nicotinoyl)-3-(5-(trifluoromethyl)thiophen-3-yloxy)piperidin-3-yl)methanone A84

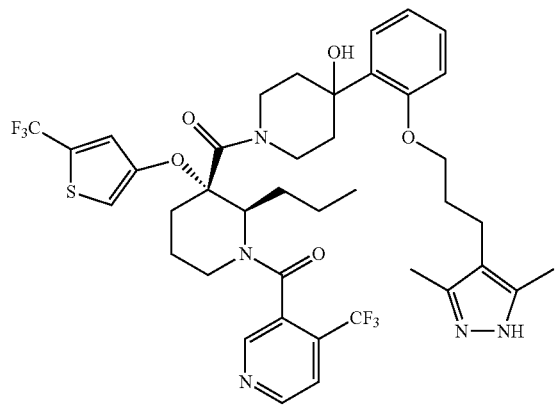

A84

Intermediate 82 was reacted with commercially available 4-(2-bromoethyl)-3,5-dimethyl-1H-pyrazole according the general procedure 5, step 1, to yield A84.

Representative Example 48

Synthesis of (1R,3S)-3-((2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)methyl)cyclopentanecarboxylic acid A23

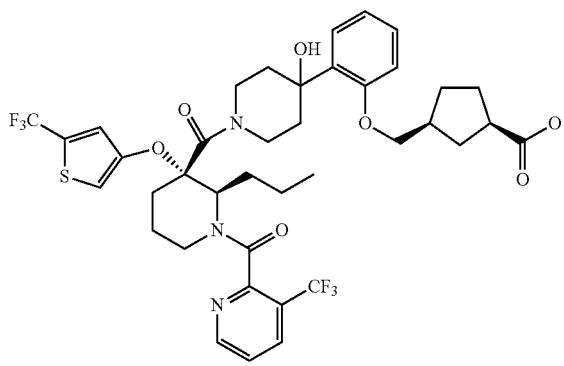

A23

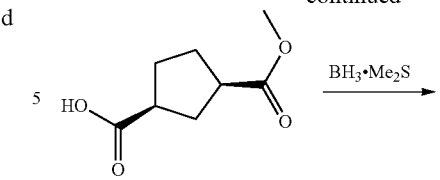

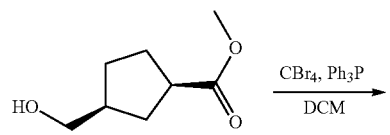

99

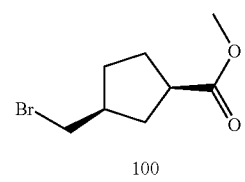

100

Step 1:

(1S,3R)-3-(methoxycarbonyl)cyclopentanecarboxylic acid (15.9 gm, 92.3 mmol, 1 equi.) was dissolved in anhydrous THF (250 mL) and cooled down to −78° C. under nitrogen atmosphere. To this was added borane dimethyl sulfide complex (2M solution in THF, 1.66 equi., 147.7 mmol, 74 mL) and stirring was maintained for one hour allowing the temperature to raise to 0° C. temperature and stirred at room temperature for another three hours. The mixture was cooled down to −20° C. and quenched with a slow addition of 1M KH$_2$PO$_4$. Reaction was warmed up to room temperature and stirred for further 20 min and extracted with ether. Organic layer was washed with brine and dried over MgSO$_4$, filtered and concentrated to dryness. The residue was purified by silica gel chromatography with (10% to 80% EtOAc in hexanes) to provide 13 g of (1R,3S)-methyl 3-(hydroxymethyl)cyclopentanecarboxylate 99.

Step 2:

To a 0° C. solution of 99 (6.6 gm, 50 mmol, 1 equi.) in 60 mL of DCM was added triphenyl phosphine (60 mmol, 1.2 equi, 15.72 gm) followed by carbon tetrabromide (60 mmol, 1.2 equi. 19.86 gm). The reaction mixture was stirred overnight allowing the temperature to rise to room temperature. Reaction was concentrated to dryness and the residue was diluted with ether/DCM (1:1, 20 ml) and filtered through a pad of celite. The filtrate was concentrated to dryness and the residue was purified by silica gel chromatography with (5% to 20% EtOAc in hexanes) to provide 3.5 g of (1R,3S)-methyl 3-(bromomethyl)cyclopentanecarboxylate 100.

Step 3:

100 was reacted as described in general procedure 5 to yield A23.

Representative Example 49

Synthesis of 2-((1S,3R)-3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)cyclopentyl)acetic acid A117

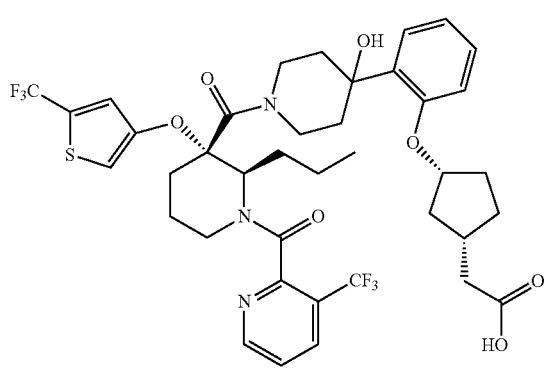

A117

Representative Example 50

Synthesis of (1S,4r)-4-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)cyclohexanecarboxylic acid A112

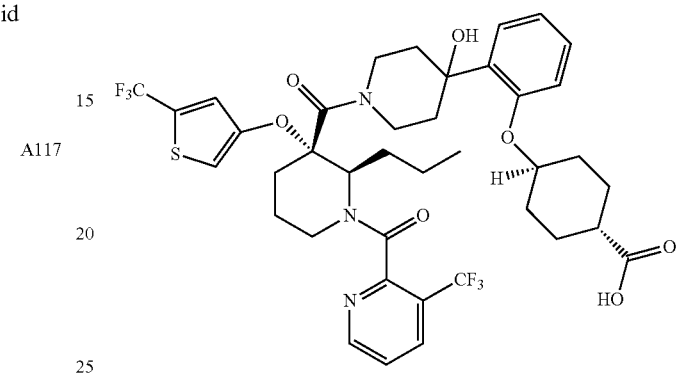

A112

Compound A112 was prepared according the procedure described in representative example 49 by replacing in step 1, (1S,3R)-(3-hydroxy-cyclopentyl)acetic acid methyl ester with trans-ethyl 4-hydroxy-cyclohexanecarboxylate.

Representative Example 51

Synthesis of (1S,3S)-3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)cyclopentanecarboxylic acid A40

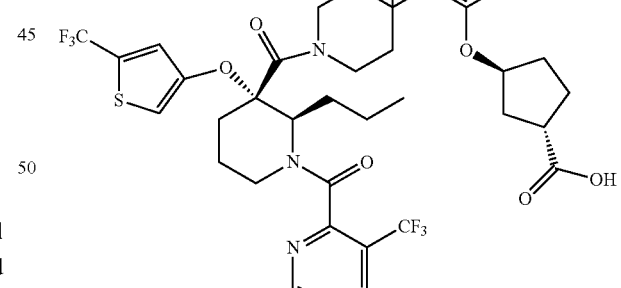

A40

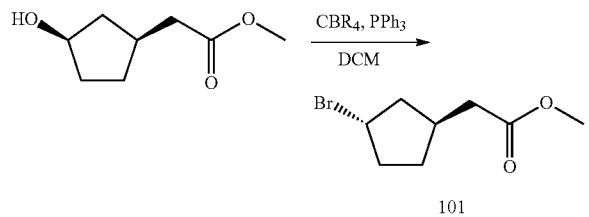

101

Step 1:

To (1S,3R)-(3-hydroxy-cyclopentyl)acetic acid methyl ester (2.0 g, 12.6 mmol) in 10 mL of DCM at 0° C. was added PPh₃ (3.49 g, 13.3 mmol, 1.05 eq.), followed by CBr₄ (4.41 g, 13.3 mmol, 1.05 eq.) slowly. The mixture was stirred at room temperature overnight. The reaction mixture was filtered through a thin layer silica gel and the filtrate was concentrated down. The residue was purified by silica gel chromatography with (15% EtOAc in hexanes) to provide 1.96 g of methyl 2-((1R,3S)-3-bromocyclopentyl)acetate 101.

Step 2:

101 was reacted as described in general procedure 5 to yield A117.

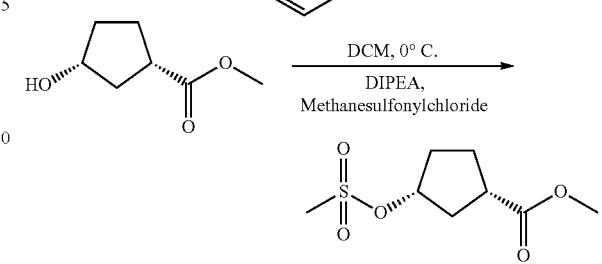

102

Step 1:
To a 0° C. solution of (1S,3R)-methyl 3-hydroxycyclopentanecarboxylate (10 mmol, 1.45 g) in DCM (10 mL) was added DIPEA (15 mmol,) followed by $CH_3SO_2Cl$ (1.2 equiv, 12 mmol, 0.93 mL) and cat DMAP. After 3 h. reaction was washed with $NH_4Cl$, then HCl (0.5N) then brine. Organic layer dried over $MgSO_4$, filtered and concentrated down to provide 102 as a yellowish oil that was used as it is for step 2.
Step 2:
102 was reacted according to the general procedure 6 by replacing intermediate 83 with intermediate 81. Hydrolysis was performed as described in general procedure 5, step 2 to yield A40.

Representative Example 52

Synthesis of (1R,3R)-3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)cyclopentanecarboxylic acid A36

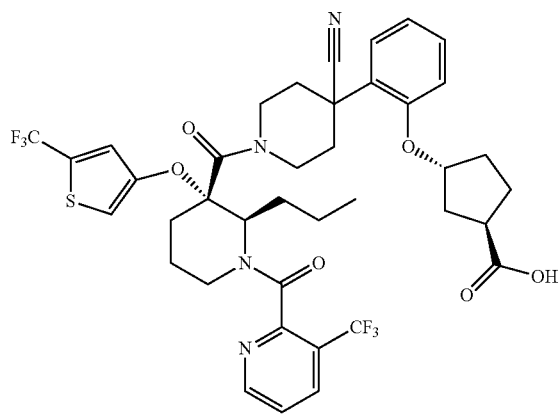

A36

Compound A36 was prepared according the procedure described in representative example 51 by replacing in step1, (1S,3R)-methyl 3-hydroxycyclopentanecarboxylate with (1R,3S)-methyl 3-hydroxycyclopentanecarboxylate.

Representative Example 53

Synthesis of (1R,3R)-3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)cyclopentanecarboxylic acid A34

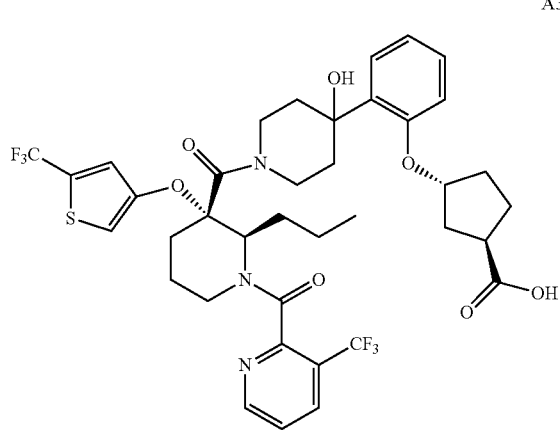

A34

Compound A34 was prepared according the procedure described in representative example 52 by replacing intermediate 81 with intermediate 83.

Representative Example 54

Synthesis of acid (1R,3R)-3-(2-(4-hydroxy-1-((2R,3S)-2-propyl-3-(4-(trifluoromethyl)phenoxy)-1-(3-(trifluoromethyl)picolinoyl)piperidine-3-carbonyl)piperidin-4-yl)phenoxy)cyclopentanecarboxylic acid A80

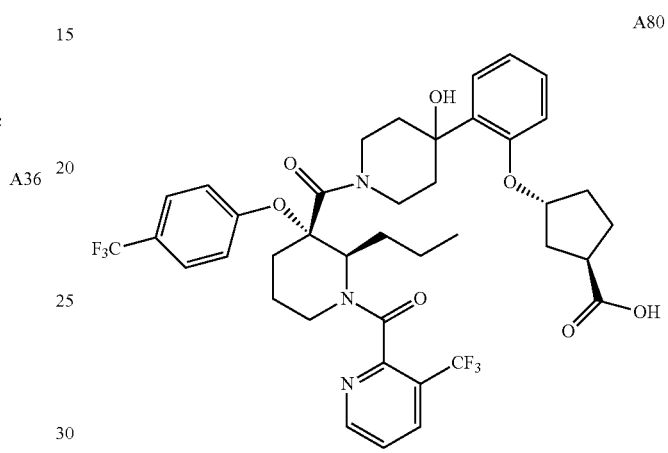

A80

Compound A80 was prepared according the procedure described in representative example 53 by replacing acid 77, used in the preparation of intermediate 83 with acid 77-A.

Representative Example 55

Synthesis of (1R,3R)-3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-N-(methylsulfonyl)cyclopentanecarboxamide A127

A34 →  HATU / DIPEA, $MeSO_2NH_2$

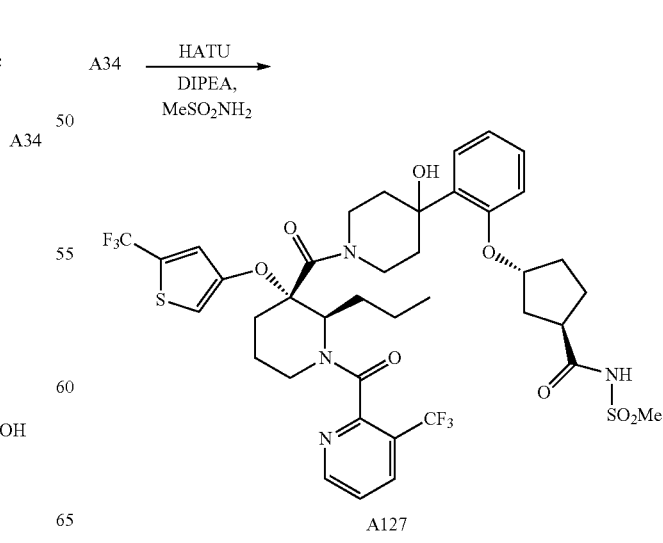

A127

To A34 (40 mg, 0.050 mmol) in DCM/DMF was added methanesulfonamide (33 mg, 0.35 mmol, 7 eq.), HATU (23 mg, 0.060 mmol, 1.2 eq.) and DIPEA (0.050 mL, 0.30 mmol, 6 eq.) at room temperature. The mixture was stirred at room temperature overnight. The reaction mixture was diluted with EtOAc and washed with saturated aqueous NH₄Cl, saturated aqueous NaHCO3 and brine. The organic layer was dried over MgSO₄ and filtered and concentrated down. The residue was purified by reverse phase HPLC (60-90-40% acetonitrile/water with 0.1% TFA in 35 min, with a flow rate of 15 ml/min using a sunfire prep C18 Column, 10 micron (19×250 mm). The residue was lyophilized to provide 19 mg of product A127 (43% yield).

Representative Example 56

Synthesis of (1S,3R)-3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-1-methylcyclopentanecarboxylic acid A46 and (1R, 3R)-3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-1-methylcyclopentanecarboxylic acid A47

A46

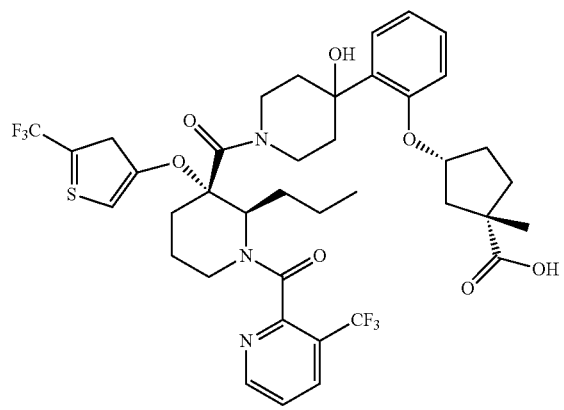

A47

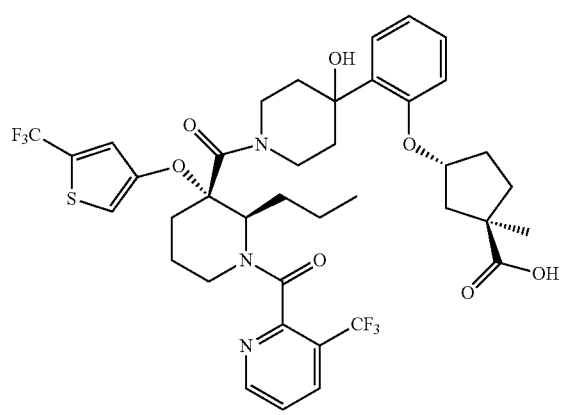

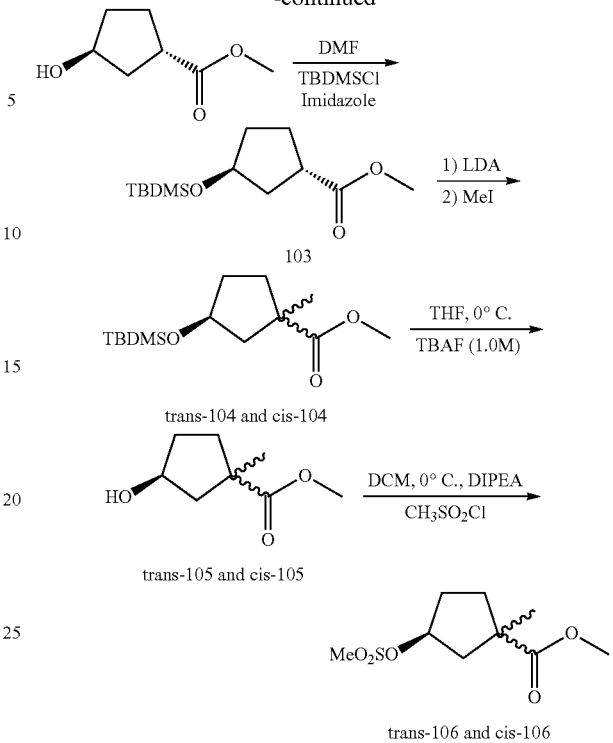

Step 1:
To a RT solution of (1S,3S)-methyl 3-hydroxycyclopentanecarboxylate (23.7 mmol, 3.45 g) in DMF (10 mL) was added imidazole (2.5 equiv, 60 mmol, 4 g) followed by TBDMSCl (1.2 equiv, 4.3 g). After 24 h, reaction was diluted with EtOAc and washed with HCl (1.0N), twice, then NaHCO₃ and brine. Organic layer was dried over MgSO₄, filtered and concentrated down. The residue was purified by silica gel chromatography (5% EtOAc in hexanes) to provide 6 g of 103 (100% yield).

Step 2:
To a −78° C. solution of ester (3.23 g, 12.5 mmol) was added 15 mmol of freshly prepared LDA (23 mL). After 30 minutes, MeI (5 equiv) was added dropwise. After addition, reaction was let under stirring for 1 hour and warmed—up to RT. Reaction was diluted with EtOAc and washed with NH₄Cl and brine. Organic layer was dried over MgSO₄, filtered and concentrated down to an oil. The residue was purified by silica gel chromatography (0% to 5% EtOAc in hexanes) to provide 2.67 g (71% yield) of trans-104 and cis-104 as an inseparable mixture of 2 diastereomers (3.4 (trans-104)/1 (cis-104) ratio).

Step 3:
To a 0° C. solution of the diastereomeric mixture trans-104 and cis-104 (10 mmol, 2.65 g) in THF (30 ml) was added TBAF (1.2 equiv, 12 mmol, 12 mL). After 1 h, reaction was warmed-up to RT and stir overnight. After 18 hours, reaction was diluted with EtOAc and washed with water, HCl (1.0N) and brine. Organic layer dried over MgSO₄, filtered and concentrated down. The residue was purified by silica gel chromatography (0% to 5% EtOAc in hexanes) to provide 1.3 g (83%) trans-105 and cis-105 as an inseparable mixture of 2 diastereomers.

Step 4:
Compounds trans-106 and cis-106 were prepared according the procedure described in representative example 51 by replacing in step1, (1S,3R)-methyl 3-hydroxycyclopentanecarboxylate with trans-105 and cis-105. Compounds trans-106 and cis-106 were used as a mixture of 2 diastereomer in a ~3.4/1 ratio for step 5.

Step 5:

The mixture trans-106 and cis-106 was reacted as described in general procedure 5 to yield A46 and A47 as a mixture of 2 diastereomers that can be separated by reverse phase HPLC using C18 sunfire prep 10 micron (18×250) column, 70% –100% CH3CN in water over 30 min at a flow rate of 15 mL·min. First pic (minor) is A47 Second pic (major) is A46.

Representative Example 57

Synthesis of 1-(3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)propyl)cyclopropanecarboxylic acid A122

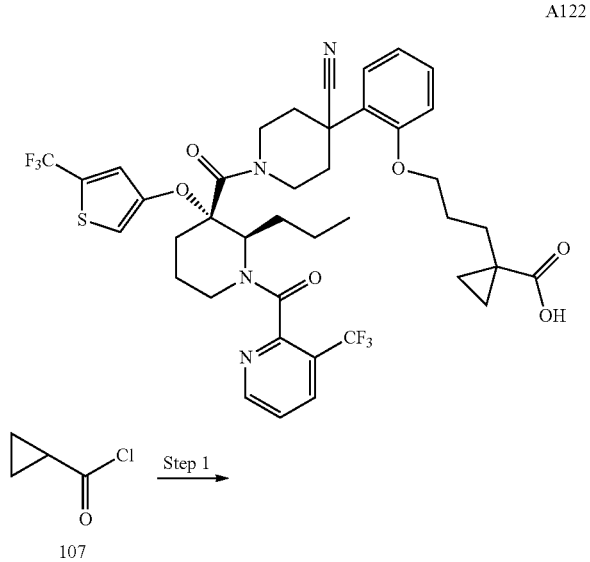

Step 1:

To a solution of tert-butanol (1.16 g, 15.6 mmol) in THF at 0° C. was added n-BuLi (10.4 mL, 15.6 mmol). After 15 min, cyclopropanecarbonyl chloride 107 (1.5 mL, 16.4 mmol, 1.05 eq.) was added slowly. The mixture was stirred at room temperature for 24 hours. The reaction was quenched by the addition of aqueous NH4Cl. The mixture was diluted with EtOAc and washed with brine. Organic layer was dried over MgSO4. Filtered and concentrated down to give 1.91 g (86% yield) of crude product 107.

Step 2:

To a solution of diisopropylamine (2.06 mL, 14.7 mmol) in 20 mL of THF was added n-BuLi (9.4 mL, 14.07 mmol) at 0° C. The mixture was stirred at 0~5° C. for 30 min. Then a solution of 107 (1.91 g, 13.4 mmol) in 5 mL of THF at –78° C. was added slowly, then followed by 1,3-dibromopropane (2.7 mL, 26.8 mmol, 2 eq.). The mixture was stirred at –78° C. and warmed-up to room temperature over 4 hours. The reaction mixture was added to an aqueous solution NH4Cl and extracted with ether. The organic layer was washed with brine. Organic layer was dried over MgSO4, filtered and concentrated down. The residue was purified by silica gel chromatography (10% EtOAc in hexanes) to provide 1.08 g of 109.

Step 4:

109 was reacted according the general procedure 6 by replacing intermediate 83 with intermediate 81 to give tert-butyl 1-(3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)propyl)cyclopropanecarboxylate. To this intermediate (12 mg, 0.014 mmol) in DCM was added TFA. The mixture was stirred at room temperature for 2 hours. The reaction mixture was diluted with EtOAc and washed with saturated aqueous NaHCO3 and brine. The organic layer was dried over MgSO4. Filtered and concentrated down. The residue was purified by reverse phase HPLC (40-90-40% acetonitrile/water with 0.1% TFA in 35 min, with a flow rate of 15 ml/min using sunfire prep C18, 10 micron (19×250 mm)). The residue was lyophilized to provide 7 mg of product A122. (61% yield).

Representative Example 58

Synthesis of 2-(1-((2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)methyl)cyclopropyl)acetic acid A128

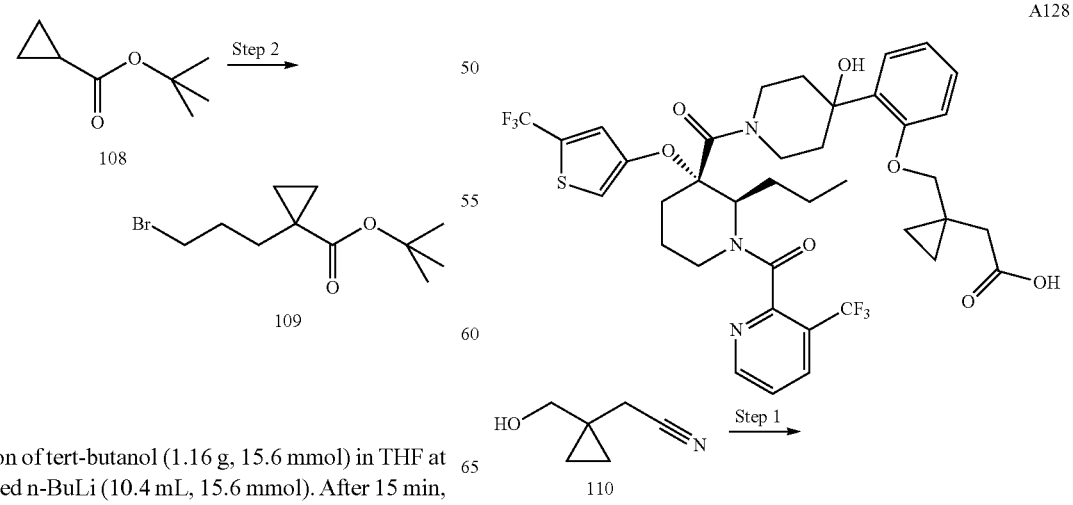

205

-continued

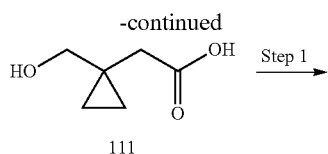

111

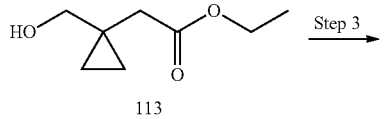

113

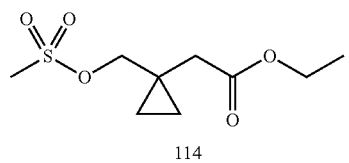

114

Step 1:

To 1-(hydroxymethyl)cyclopropaneacetonitrile 110 (5.0 g, 44.9 mmol) in EtOH was added aqueous KOH (56 mL, 56 mmol, 10 eq.). The mixture was heated at reflux for overnight. The reaction mixture was cooled to room temperature and concentrated to remove solvent. The remaining aqueous solution was cooled to 0° C. and acidified to PH-1 with concentrated aqueous HCl dropwise, then extracted with EtOAc. The combined organic layer was dried over MgSO$_4$, filtered and concentrated to dryness to give 5.35 g of product 111 (92% yield).

Step 2:

To 2-(1-(hydroxymethyl)cyclopropyl)acetic acid 111 (5.35 g, 41.1 mmol) in EtOH was added concentrated sulfuric acid (1.3 mL). The mixture was heated at reflux for 2 hrs. 35 mL of saturated aqueous NaHCO$_3$ was added to the cooled mixture and the mixture was extracted with CH$_2$Cl$_2$. Organic layer was dried over Na$_2$SO$_4$, filtered and concentrated to dryness to give 6.17 g of product 113 (95% yield).

Step 3:

To ethyl 2-(1-(hydroxymethyl)cyclopropyl)acetate 113 (1.0 g, 6.3 mmol) in 5 mL of DCM at 0° C. was added DIPEA (1.8 mL, 10.7 mmol, 1.7 eq.), followed by MsCl (0.73 mL, 9.48 mmol, 1.5 eq.) slowly. The mixture was stirred at 0° C. for 1 hour. TLC indicated the reaction completed. The reaction mixture was diluted with EtOAc and washed with 1N HCl and brine. The organic layer was dried over MgSO$_4$, filtered and concentrated to dryness to give 1.33 g of 114 (89% yield).

Step 4:

Ethyl 2-(1-((methylsulfonyloxy)methyl)cyclopropyl)acetate 114 was reacted as described in general procedure 5 to yield A128.

206

Representative Example 59

Synthesis of (S)-4-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-3-methylbutanoic acid A130

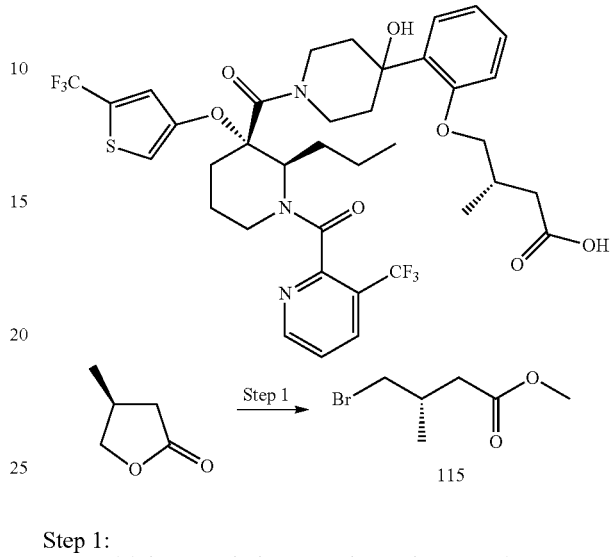

A130

Step 1:

To (S)-beta-methyl-gamma-butyrolactone (1 g, 9.99 mmol) in 10 mL of anhydrous DCM was added BBr$_3$ (10.5 mL, 10.5 mmol, 1.05 eq.) slowly at 0° C. The mixture was stirred at room temperature overnight then quenched by addition of MeOH (2 mL) at 0° C. After the addition, the mixture was stirred at room temperature for 20 min then diluted with saturated aqueous. Organic layer was separated and washed with aqueous Na$_2$S2O$_4$ then brine. The organic layer was dried over MgSO$_4$, filtered and concentrated to dryness to give 1.0 g of crude product 115 (51% yield).

Step 2:

(S)-methyl 4-bromo-3-methylbutanoate 115 was reacted as described in general procedure 5 to yield A130.

Representative Example 60

Synthesis of 4-(2-(4-hydroxy-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)pentanoic acid A92

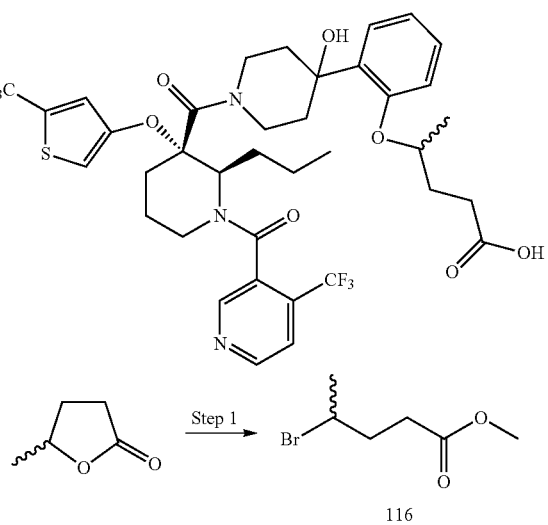

A92

Step 1:

Preparation of intermediate 116 was done according representative example 59, step 1, by replacing (S)-beta-methyl-gamma-butyrolactone with gamma-valerolactone.

Step 2:

Intermediate 82 was reacted with methyl 4-bromopentanoate 116 according the general procedure 5 to yield A92.

Representative Example 61

Synthesis of 4-(2-(4-hydroxy-1-((2R,3S)-2-propyl-1-(4-(trifluoromethyl)nicotinoyl)-3-(5-(trifluoromethyl)thiophen-3-yloxy)piperidine-3-carbonyl)piperidin-4-yl)phenoxy)pentanoic acid A106

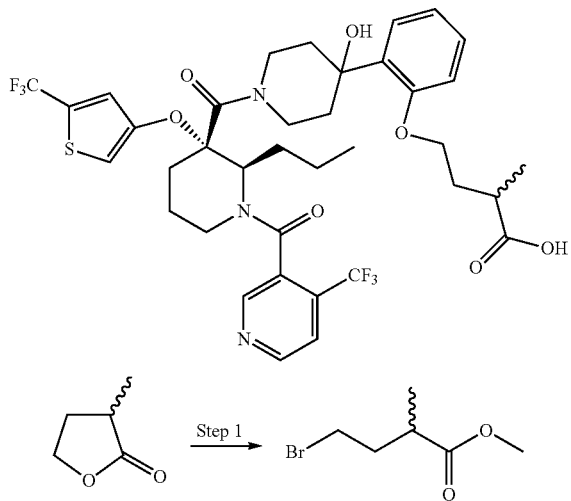

A106

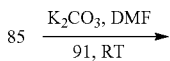

117

Step 1:

Preparation of intermediate 117 was done according representative example 59, step 1, by replacing (S)-beta-methyl-gamma-butyrolactone with alpha-methyl-gamma-butyrolactone.

Step 2:

Intermediate 82 was reacted with methyl 4-bromo-2-methylbutanoate 117 according the general procedure 5 to yield A106.

Representative Example 62

Synthesis of 1-(3-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenylthio)propyl)cyclobutanecarboxylic acid A50

$$85 \xrightarrow{K_2CO_3, DMF} 91, RT$$

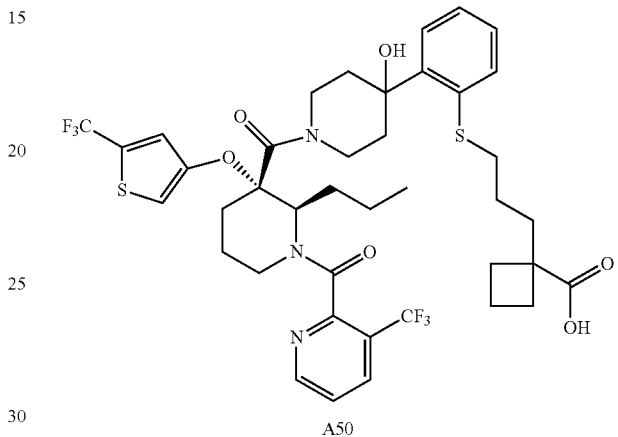

A50

Compound A50 was prepared according the procedure described in representative example 40 by replacing in step 2, intermediate 83 with intermediate 85 of representative example 23.

Representative Example 63

Synthesis of 4-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-2,2,3,3,4,4-hexadeuterobutanoic acid A18

A18

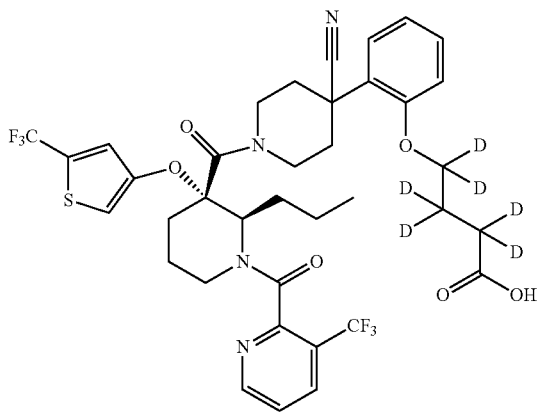

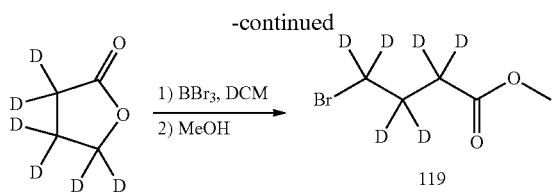

Step 1:

Preparation of intermediate 119 was done according representative example 59, step 1, by replacing (S)-beta-methyl-gamma-butyrolactone with gama-butyrolactone-d6.

Step 2:

Methyl 4-bromo-2,2,3,3,4,4-hexadeuterobutanoate 119 was reacted according the general procedure 6 by replacing intermediate 83 with intermediate 81 to give methyl 4-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-2,2,3,3,4,4-hexadeuterobutanoate. Hydrolysis of methyl 4-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)-2,2,3,3,4,4-hexadeuterobutanoate was performed as described in general procedure 5, step 2 to yield A18.

Representative Example 64

Synthesis of 2,2,3,3,4,4-hexadeutero-4-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenoxy)butanoic acid A20

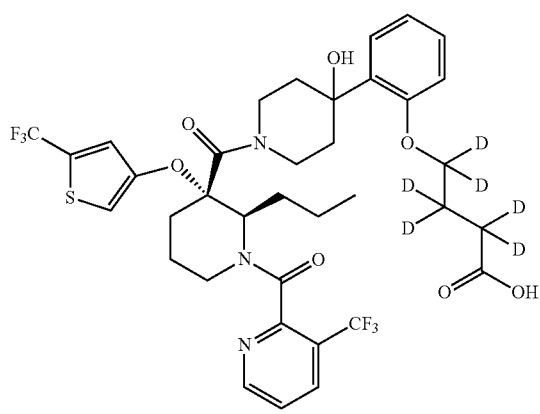

A20

(Methyl 4-bromo-2,2,3,3,4,4-hexadeuterobutanoate 119 of representative example 63 was reacted as described in general procedure 5 with intermediate 83 to yield A20.

Representative Example 65

Synthesis of 4-(2-(4-Cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)benzyloxy)-2,2-dimethylbutanoic acid A60

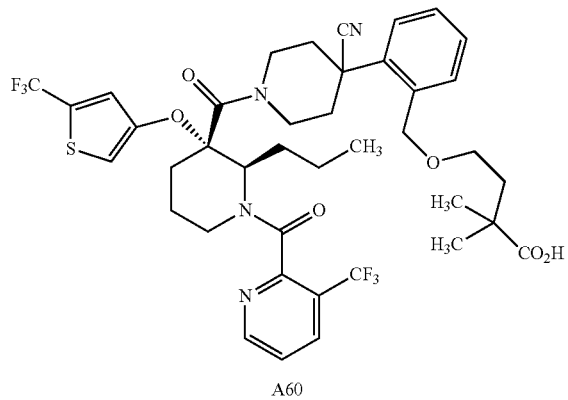

A60

Step 1:
The intermediate TFA salt methyl 4-(2-(4-cyanopiperidin-4-yl)benzyloxy)-2,2-dimethylbutanoate 2,2,2-trifluoroacetate 61 (170 mg, 0.50 mmol), 77 (255 mg, 0.50 mmol) and HATU (228 mg, 0.60 mmol) were taken up in DMF (5 mL) followed by the addition of N-methyl morpholine (505 mg, 5.0 mmol). The reaction mixture was stirred at room temperature for 16 h, then diluted with ethyl acetate (50 mL). The organic phase washed with sat NH$_4$Cl (30 mL), sat NaHCO$_3$ (30 mL), brine (50 mL), and dried over Na$_2$SO$_4$. The reaction mixture was filtered, evaporated to dryness, then purified by silica gel chromatography (ethyl acetate/hexanes) to afford methyl 4-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)benzyloxy)-2,2-dimethylbutanoate (312 mg, 77% yield) as a white solid: $^1$H NMR (CDCl$_3$, 300 MHz) δ 8.80-8.81 (d, J=4.5 Hz, 1H), 8.05-8.07 (d, J=7.8 Hz, 1H), 7.22-7.52 (m, 5H), 7.06-7.08 (m, 1H), 6.52-6.55 (m, 1H), 4.52-5.16 (m, 6H), 3.49-3.67 (m, 3H), 3.10-3.24 (m, 3H), 1.19 (s, 6H), 0.85-2.38 (m, 17H).
Step 2:
2 N Aqueous sodium hydroxide (5.5 mL) was added to methyl 4-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)benzyloxy)-2,2-dimethylbutanoate (312 mg, 0.37 mmol) in THF/methanol (1:3, 12 mL). The reaction was stirred for 8 h at room temperature then concentrated. The residue was diluted ethyl acetate (30 mL) and the pH adjusted to 1 with 1 N hydrochloric acid. The organic layer was washed with brine, dried over Na$_2$SO$_4$, filtered and evaporated to dryness. The residue was purified by C18 semi-prep HPLC to obtain A60 (300 mg, 99% yield) as a white powder after lyophilization from water/acetonitrile: $^1$H NMR (CDCl$_3$, 300 MHz) δ 8.81-8.82 (d, J=3.9 Hz, 1H), 8.06-8.08 (d, J=8.1 Hz, 1H), 7.24-7.50 (m, 5H), 6.84-

6.87 (d, J=8.1 Hz, 1H), 6.53-6.56 (m, 1H), 4.65-5.57 (m, 5H), 3.48-3.75 (m, 6H), 3.08-3.20 (m, 3H), 1.22 (s, 6H), 0.93-2.47 (m, 17H).

Representative Example 66

Synthesis of 4-(2-(4-Cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)benzyloxy)butanoic acid A59

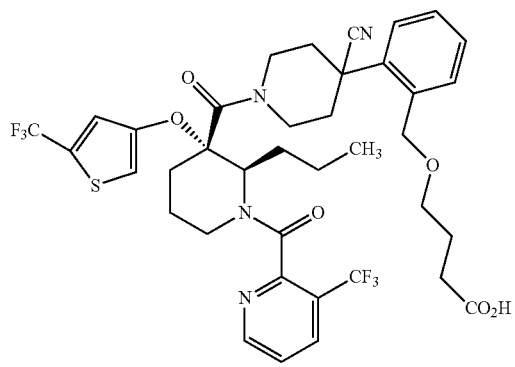

Compound A59 was synthesized in a fashion analogous to compound A60 starting with dihydrofuran-2(3H)-one as starting material instead of 3,3-dimethyldihydrofuran-2(3H)-one and isolated as a white solid after lyophilization from water/acetonitrile. $^1$H NMR (300 MHz, CDCl$_3$ 9.75 (br, s, 1H), 8.79 (d, J=4.4 Hz, 1H), 8.04 (d, J=7.8 Hz, 1H), 7.57-7.00 (m, 6H), 6.53 (s, 1H), 5.55-5.25 (m, 1H), 5.20-4.89 (m, 3H), 4.52-4.38 (m, 1H), 3.72-2.70 (m, 6H), 2.58-0.78 (m, 19H).

Representative Example 67

Synthesis of 4-(2-(1-((2R,3S)-2-Propyl-1-(3-(trifluoromethyl)picolinoyl)-3-(5-(trifluoromethyl)thiophen-3-yloxy)piperidine-3-carbonyl)piperidin-4-yl)phenylsulfonamido)butanoic acid A58

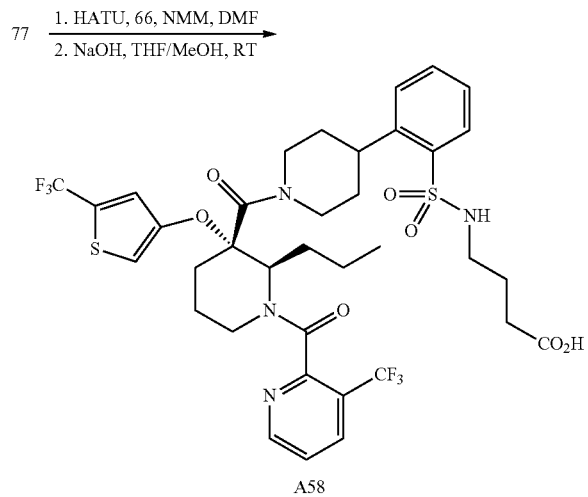

Step 1:
In an analogous procedure to representative example 65 step 1, 66 was coupled to 77 to provide ethyl 4-(2-(1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenylsulfonamido)butanoate: $^1$H NMR (300 MHz, CDCl$_3$ 8.81 (d, J=3.2 Hz, 1H), 8.07 (d, J=7.8 Hz, 1H), 7.98-7.84 (m, 1H), 7.60-7.18 (m, 4H), 6.92 (d, J=7.8 Hz, 1H), 6.73-6.49 (m, 1H), 5.60-5.40 (m, 1H), 5.23-5.01 (m, 2H), 4.90 (d, J=12.8 Hz, 1H), 4.20-4.00 (m, 2H), 3.87-3.60 (m, 1H), 3.51-1.02 (m, 28H).

Step 2:
In an analogous procedure to representative example 65 step 2, ethyl 4-(2-(1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenylsulfonamido)butanoate was saponified to provide A58 as a white solid after lyophilization from water/acetonitrile: $^1$H NMR (300 MHz, CDCl$_3$ 8.80 (d, J=4.4 Hz, 1H), 8.07 (d, J=7.8 Hz, 1H), 7.98-7.84 (m, 1H), 7.60-7.30 (m, 4H), 6.99 (d, J=7.8 Hz, 1H), 6.72-6.50 (m, 1H), 5.61-5.30 (m, 4H), 3.90-3.67 (m, 1H), 3.43-0.70 (m, 25H).

Representative Example 68

Synthesis of (1R,3R)-3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)benzyloxy)cyclobutanecarboxylic acid A62

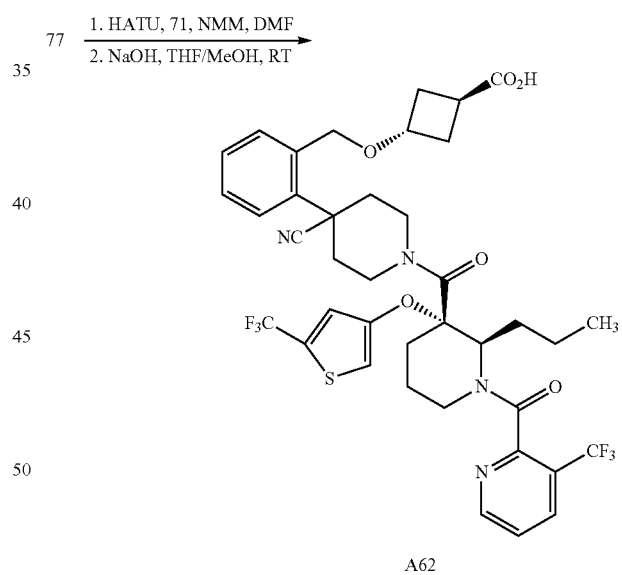

Step 1:
In an analogous procedure to representative example 65 step 1, 71 was coupled to 77 to provide (1S,3R)-methyl 3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)benzyloxy)cyclobutanecarboxylate (41 mg, 59% yield) as a white solid: $^1$H NMR (300 MHz, CDCl$_3$) 8.82 (d, J=4.5 Hz, 1H), 8.07 (d, J=8.1 Hz, 1H), 7.61-7.55 (m, 0.3H), 7.50-7.46 (m, 2H), 7.43-7.27 (m, 2H), 6.87 (d, J=7.8 Hz, 0.7H), 6.56-6.51 (m, 1H), 5.58-5.48 (m, 0.7H), 5.42-5.34 (m, 0.3H), 5.26-5.10 (m, 1H), 4.98-4.87 (m, 1H), 4.83 (dd, J=11.9, 7.4 Hz, 1H), 4.65 (t, J=12.3 Hz, 1H), 4.06 (quint, J=7.3 Hz, 1H), 3.73-3.64 (m, 3H), 3.38-3.02 (m, 3H), 2.73-1.20 (19H), 1.04 (t, J=7.2 Hz, 2H), 0.95 (d, J=7.4 Hz, 1H).

Step 2:

In an analogous procedure to representative example 65 step 2, (1S,3R)-methyl 3-(2-(4-cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)benzyloxy)cyclobutanecarboxylate was saponified to provide A62 (36 mg, 90% yield) as a white solid after lyophilization from water/acetonitrile: $^1$H NMR (400 MHz, CDCl$_3$) 8.81 (d, J=3.0 Hz, 1H), 8.06 (d, J=6.0 Hz, 1H), 7.53-7.46 (m, 1.3H), 7.44-7.18 (3H), 7.07-7.02 (m, 0.7H), 6.59-6.50 (m, 1H), 5.57-5.46 (m, 0.7H), 5.40-5.31 (m, 0.3H), 5.22-4.91 (m, 3H), 4.49 (d, J=8.7 Hz, 0.3H), 4.33 (d, J=8.1 Hz, 0.7H), 4.23-4.12 (m, 1H), 3.69 (t, J=9.3 Hz, 0.7H), 3.52 (d, J=9.9 Hz, 1H), 3.33-3.04 (m, 3H), 2.95-2.05 (m, 10H), 1.99-1.82 (m, 2H), 1.72-1.44 (m, 3H), 1.43-1.28 (m, 3H), 1.08-0.83 (m, 3H).

Representative Example 69

Synthesis of (S)-3-(2-(4-Cyano-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)benzyloxy)cyclopentanecarboxylic acid A61

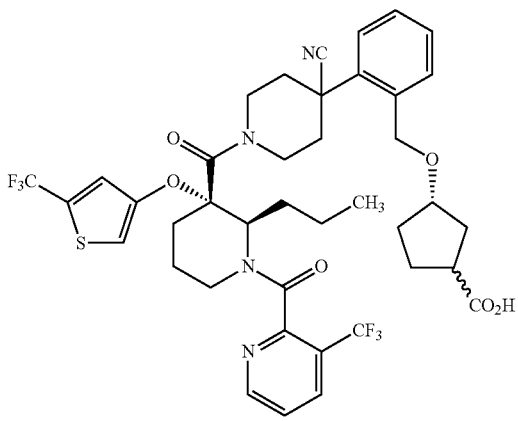

Compound A61 was prepared from intermediate 69 of representative example 18 and (S)-methyl 3-hydroxycyclopentanecarboxylate in a sequence analogous to the preparation of representative example 68 and was isolated as a white powder after lyophilization from water/acetonitrile: $^1$H NMR (300 MHz, CDCl$_3$) 8.86-8.76 (m, 1H), 8.13-8.04 (m, 1H), 7.59-6.85 (m, 5H), 6.60-6.51 (m, 1H), 5.58-5.33 (m, 1H), 5.25-4.38 (m, 7H), 4.26-4.12 (m, 1H), 3.80-3.43 (m, 1H), 3.32-1.15 (m, 20H), 1.18-0.81 (m, 3H).

Representative Example 70

Synthesis of 4-(2-(4-Hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenethoxy)butanoic acid A63

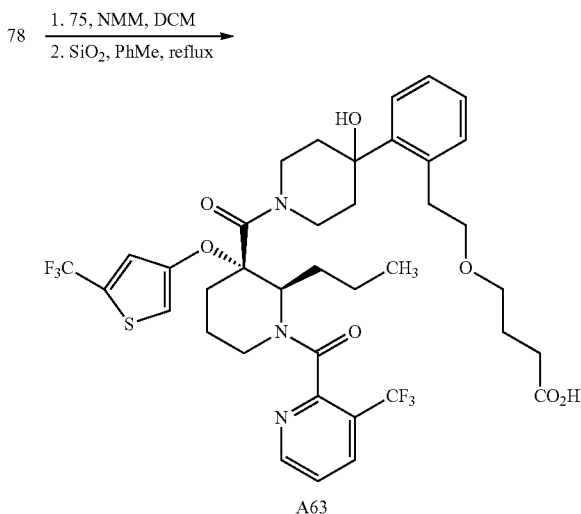

Step 1:

In an analogous procedure to general procedure 2, amine 75 was coupled to 78 to provide tert-butyl 4-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenethoxy)butanoate (54 mg, 60% yield) as a white solid: $^1$H NMR (300 MHz, CDCl$_3$) 8.81 (d, J=4.5 Hz, 1H), 8.06 (d, J=7.8 Hz, 1H), 7.48 (dd, J=7.8, 5.0 Hz, 1H), 7.42-7.27 (m, 0.6H), 7.25-7.04 (m, 2.8H), 6.77 (d, J=7.8 Hz, 0.6H), 6.64 (d, J=1.8 Hz, 0.6H), 6.54 (d, J=1.8 Hz, 0.4H), 5.57 (d, J=10.8 Hz, 0.6H), 5.45 (d, J=10.8 Hz, 0.4H), 4.87 (t, J=13.4 Hz, 1H), 4.66 (d, J=11.4 Hz, 1H), 4.59-4.53 (m, 1H), 3.60-3.49 (m, 3H), 3.43-3.01 (m, 6H), 2.59-1.20 (m, 27H), 1.02 (t, J=7.2 Hz, 3H).

Step 2:

Silica gel (230-400 mesh, 88 mg) was added to tert-butyl 4-(2-(4-hydroxy-1-((2R,3S)-2-propyl-1-(3-(trifluoromethyl)picolinoyl)-3-(5-(trifluoromethyl)thiophen-3-yloxy)piperidine-3-carbonyl)piperidin-4-yl)phenethoxy)butanoate (15 mg, 0.018 mmol) in toluene (0.5 mL) and heated to reflux with vigorous stirring for 6 h. Additional silica gel (44 mg) and toluene (0.5 mL) were added and reflux was continued for 18 h. The reaction mixture was cooled to room temperature and the silica gel was removed by filtration through Celite washing with methylene chloride/methanol (1:1, 10 mL) and methanol (10 mL). The solvent was removed under reduced pressure and the residue purified by silica gel chromatography (methanol/methylene chloride) to provide A63 (9.8 mg, 70% yield) as a white solid after lyophilization from water/acetonitrile: $^1$H NMR (300 MHz, CDCl$_3$) 8.81 (d, J=4.8 Hz, 1H), 8.06 (d, J=8.1 Hz, 1H), 7.49 (dd, J=8.0, 5.0 Hz, 1H), 7.23-7.05 (m, 3H), 6.71 (d, J=7.5 Hz, 0.7H), 6.68 (d, J=1.8 Hz, 0.7H), 6.54 (d, J=1.8 Hz, 0.3H), 5.57-5.40 (m, 1H), 4.93-4.73

(m, 1H), 4.70-4.45 (m, 2H), 3.95-3.01 (m, 9H), 2.81 (dt, J=14.1, 3.67 Hz, 1H), 2.59-1.24 (m, 18H), 1.08-0.96 (m, 3H).

Representative Example 71

Synthesis of ethyl 3-(4-(2-methoxyphenyl)piperidin-2-yl)propanoate hydrochloride (A143)

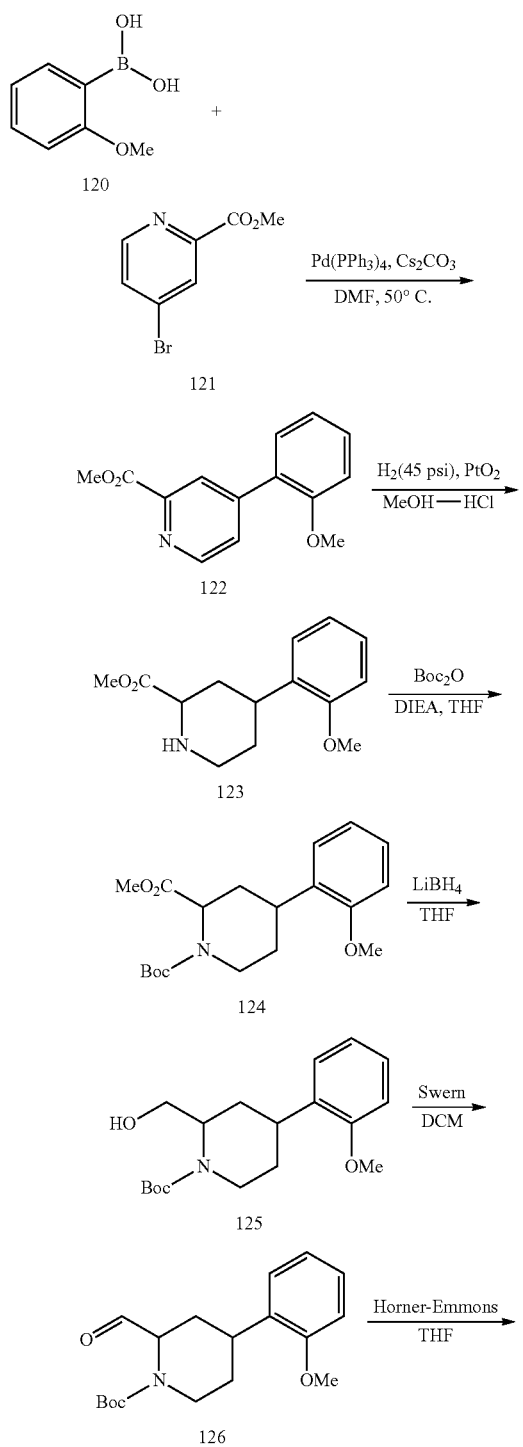

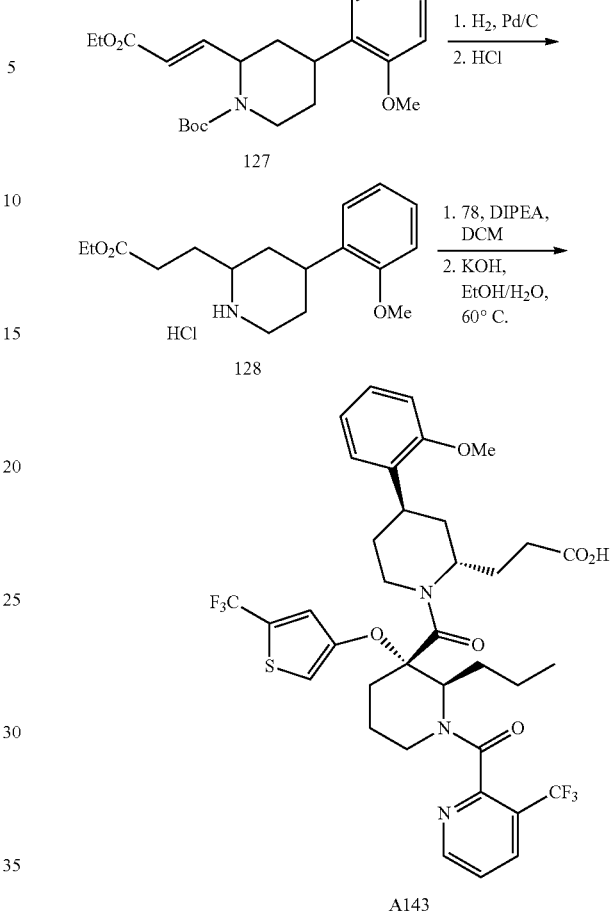

Step 1:

A reaction mixture of 2-methoxyphenylboronic acid 120 (600 mg, 4 mmol), Cs₂CO₃ (2.6 g, 8 mmol), Pd(PPh₃)₄ (200 mg, 0.2 mmol) and methyl 4-bromopicolinate 121 (864 mg, 4 mmol) in DMF (4 mL), was degassed and heated to 50° C. under Argon for 5 hr. The mixture was filtered through Celite and was concentrated. The crude residue was purified by silica gel chromatography (gradient, 10% to 50% EtOAc/hexanes) to give methyl 4-(2-methoxyphenyl)picolinate 122. LC/MS RT (5 min method)=1.703 min. Mass observed: 244.1 (M+H).

Step 2:

To a solution of methyl 4-(2-methoxyphenyl)picolinate 122 (240 mg, 1 mmol) in MeOH (10 mL) and 1M HCl in ether (2 mL), PtO₂ (10 mg) was added. The reaction mixture was stirred under H₂ at 60 psi overnight. The mixture was filtered through Celite and was concentrated to give the crude product methyl 4-(2-methoxyphenyl)piperidine-2-carboxylate 123. LC/MS RT (5 min method)=1.114 min. Mass observed: 250.2 (M+H).

Step 3:

To a solution of methyl 4-(2-methoxyphenyl)piperidine-2-carboxylate 123 (1.1 g, 4.1 mmol) in THF (10 mL), Boc₂O (900 mg, 4.1 mmol) and ⁱPr₂NEt (1.4 mL, 8.2 mmol) was added. The reaction mixture was stirred at r.t overnight. After removal of solvent, the crude residue was purified by silica gel chromatography (gradient, 10% to 50% EtOAc/hexanes) to give a mixture of diasteremers of 1-tert-butyl 2-methyl 4-(2-methoxyphenyl)piperidine-1,2-dicarboxylate 124. LC/MS RT (5 min method)=2.271 min. Mass observed: 250.1 (M-Boc+H).

Step 4:

At 0° C., to a solution of 1-tert-butyl 2-methyl 4-(2-methoxyphenyl)piperidine-1,2-dicarboxylate 124 (640 mg, 1.83 mmol) in THF (10 mL) and MeOH (0.5 mL), LiBH$_4$ (60 mg, 2.74 mmol) was added. The reaction solution was stirred at r.t overnight, The reaction was quenched with water and the mixture was extracted with ethyl acetate. After removal of solvent, the crude product of tert-butyl 2-(hydroxymethyl)-4-(2-methoxyphenyl)piperidine-1-carboxylate 125 was obtained without further purification. LC/MS RT (5 min method)=2.027 min. Mass observed: 222.2 (M-Boc+H).

Step 5:

At −78° C., to a solution of Oxalyl Chloride (0.24 mL, 2.75 mmol) in DCM (4 mL), DMSO (0.43 mL, 6.04 mmol) was added. The reaction solution was stirred at the same temperature for 30 min and then a solution of tert-butyl 2-(hydroxymethyl)-4-(2-methoxyphenyl)piperidine-1-carboxylate 125 (580 mg, 1.8 mmol) in DCM (2 mL) was added. The reaction mixture was stirred at −78° C. for 30 min, followed by the addition of Et$_3$N (1.1 mL, 7.32 mmol). The reaction mixture was warmed up to r.t overnight. The reaction was quenched with water and the mixture was extracted with ethyl acetate. After removal of solvent, the crude product of tert-butyl 2-formyl-4-(2-methoxyphenyl)piperidine-1-carboxylate 126 was obtained without further purification. LC/MS RT (5 min method)=2.406 min. Mass observed: 264.1 (M-Buthyl+H).

Step 6:

At 0° C., to a suspension of 60% NaH (100 mg, 2.5 mmol) in THF (3 mL), triethyl phosphono acetate (0.5 mL, 2.5 mmol) was added. After stirring at 0° C. for 30 min, a solution of tert-butyl 2-formyl-4-(2-methoxyphenyl)piperidine-1-carboxylate 126 (540 mg, 1.69 mmol)) in THF (2 mL) was added. The reaction mixture was warmed up to r.t for 3 hr. The reaction was quenched with water and the mixture was extracted with ethyl acetate. After removal of solvent, the crude residue was purified by silica gel chromatography (gradient, 10% to 25% EtOAc/hexanes) to give a mixture of diasteremers of tert-butyl 2-(3-ethoxy-3-oxoprop-1-enyl)-4-(2-methoxyphenyl)piperidine-1-carboxylate 127. LC/MS RT (5 min method)=2.655 min. Mass observed: 290.2 (M-Boc+H).

Step 7:

To a solution of tert-butyl 2-(3-ethoxy-3-oxoprop-1-enyl)-4-(2-methoxyphenyl)piperidine-1-carboxylate 127 (540 mg, 1.4 mmol) in MeOH (5 mL) and EtOAc (5 mL), 10% Pd/C (50 mg) was added. The reaction mixture was stirred under H$_2$ overnight. LC/MS showed the completion of hydrogenation LC/MS RT (5 min method)=2.514 min. Mass observed: 292.3 (M-Boc+H). After the filtration through Celite and removal of solvent, the residue was treated with 4N HCl in dioxane (3 mL). The reaction mixture was stirred at r.t for 1 hr. After removal of solvent, the crude product of ethyl 3-(4-(2-methoxyphenyl)piperidin-2-yl)propanoate hydrochloride 128 was obtained without further purification. LC/MS RT (5 min method)=1.239 min. Mass observed: 292.3 (M+H).

Step 8:

Amide bond formation was done from intermediate 78 following the general procedure 2. Hydrolysis of the ester to the carboxylic acid was followed as described in general procedure 4. The crude product was purified by reverse phase preparative HPLC to yield ethyl 3-(4-(2-methoxyphenyl)piperidin-2-yl)propanoate hydrochloride (A143). LC/MS RT (7 min method)=4.21 min. Mass observed: 756.2 (M+H).

Representative Example 72

Synthesis of 3-(4-hydroxy-4-(2-methoxyphenyl)-1-((2R,3S)-2-propyl-1-(3-(trifluoromethyl)picolinoyl)-3-(5-(trifluoromethyl)thiophen-3-yloxy)piperidine-3-carbonyl)piperidin-2-yl)propanoic acid (A144)

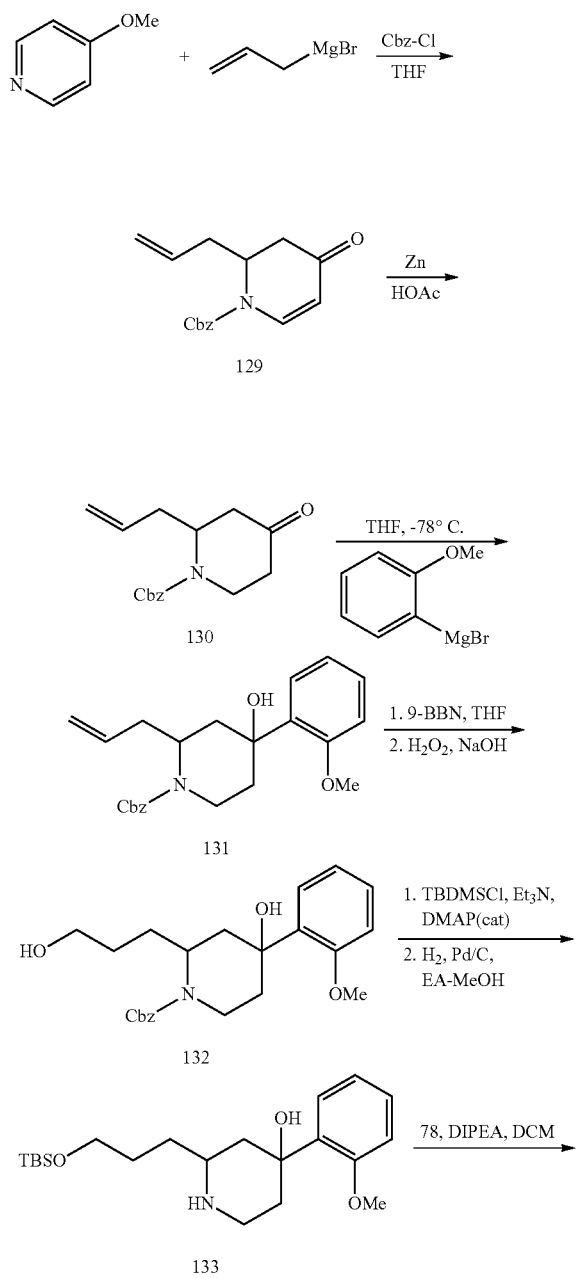

-continued

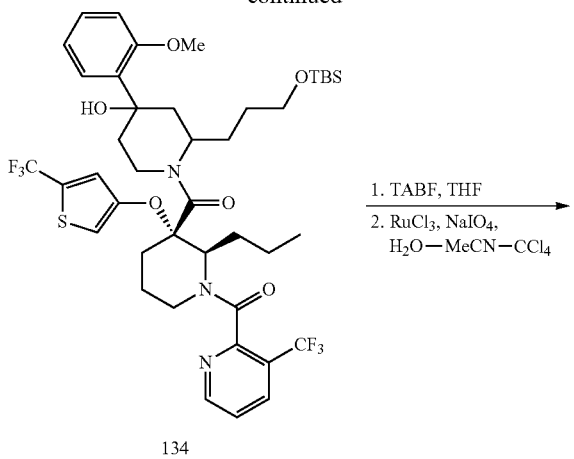

134

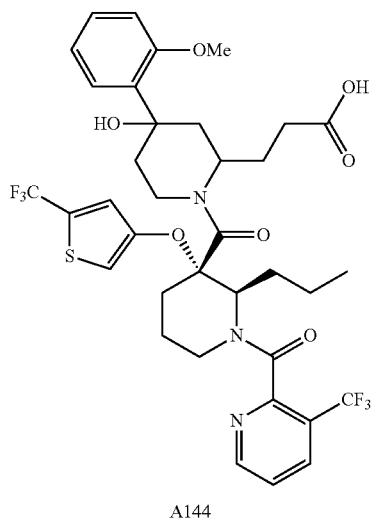

A144

Step 1:

At −23° C., to a solution of 4-methoxypyridine (5.45 g, 50 mmol) in THF (50 mL), 1.0 N Allyl-MgBr (50 mL, 50 mmol) in ether was added to form a yellow suspension. 95% Cbz-Cl (7.4 mL, 50 mmol) was then added dropwise. The yellow mixture was stirred at −23° C. for 30 mins and then poured into 10% HCl (100 mL). The reaction mixture was extracted with ethyl acetate. After removal of solvent, the crude product was purified by silica gel chromatography (gradient, 10% to 25% EtOAc/hexanes) to give benzyl 2-allyl-4-oxo-3,4-dihydropyridine-1(2H)-carboxylate 129. LC/MS RT (2.25 min method)=1.090 min. Mass observed: 272.1 (M+H).

Step 2:

To a solution of benzyl 2-allyl-4-oxo-3,4-dihydropyridine-1(2H)-carboxylate 129 (160 mg, 0.6 mmol) HOAc (2 mL), Zn powder (113 mg, 1.8 mmol) was added. The reaction mixture was heated to 50° C. for 16 hr. After removal of solvent, ethyl acetate and water was added. The reaction mixture was extracted with ethyl acetate. After removal of solvent, the crude product was purified by silica gel chromatography (gradient, 10% to 25% EtOAc/hexanes) to give benzyl 2-allyl-4-oxopiperidine-1-carboxylate 130. LC/MS RT (2.25 min method)=1.080 min. Mass observed: 274.0 (M+H).

Step 3

At −78° C., to a solution of benzyl 2-allyl-4-oxopiperidine-1-carboxylate 130 (895 mg, 3.3 mmol) in THF (5 mL), 1.0 N of 2-methoxyphenyl Grignard reagent in ether (3.6 mL, 3.6 mmol) was added dropwise. The reaction mixture was stirred at −78° C. for 2 hr, and then quenched with water. The reaction mixture was extracted with ethyl acetate. After removal of solvent, the crude product was purified by silica gel chromatography (gradient, 10% to 25% EtOAc/hexanes) to give benzyl 2-allyl-4-hydroxy-4-(2-methoxyphenyl)piperidine-1-carboxylate 131. LC/MS RT (2.25 min method)=1.330 min. Mass observed: 404.1 (M+Na).

Step 4:

To a solution of benzyl 2-allyl-4-hydroxy-4-(2-methoxyphenyl)piperidine-1-carboxylate 131 (220 mg, 0.58 mmol) in THF (2 mL), 0.5 M of 9-BBN in THF (3.5 mL) was added. The reaction solution was stirred at r.t for 16 hr and then 10% NaOH (3 mL) and $H_2O_2$ (3 mL) were added. After stirring for 30 mins, the reaction mixture was extracted with ethyl acetate. After removal of solvent, the crude product was purified by silica gel chromatography (gradient, 30% to 75% EtOAc/hexanes) to give benzyl 4-hydroxy-2-(3-hydroxypropyl)-4-(2-methoxyphenyl)piperidine-1-carboxylate 132. LC/MS RT (2.25 min method)=1.228 min. Mass observed: 400.2 (M+H).

Step 5:

At 0° C., to a solution of benzyl 4-hydroxy-2-(3-hydroxypropyl)-4-(2-methoxyphenyl)piperidine-1-carboxylate 132 (200 mg, 0.5 mmol) in DCM (2 mL), catalytic amount of DMAP and $Et_3N$ (80 µL, 0.57 mmol) was added followed by TBDMSCl (80 mg, 0.53 mmol). After addition, the reaction solution was warmed up to r.t for 16 hr and then quenched with water. The reaction mixture was extracted with ethyl acetate. After removal of solvent, the crude product was purified by silica gel chromatography (gradient, 10% to 25% EtOAc/hexanes) to give the silyl ether: benzyl 2-(3-(tert-butyldimethylsilyloxy)propyl)-4-hydroxy-4-(2-methoxyphenyl)piperidine-1-carboxylate. LC/MS RT (2.25 min method)=1.653 min. Mass observed: 514.1 (M+H).

To a solution of the above product in ethyl acetate (10 mL), 10% Pd/C (10 mg) was added. The reaction mixture was stirred under $H_2$ atmosphere for 2 hr. After filtration off the Pd/C and removal of solvent, the crude product of 2-(3-(tert-butyldimethylsilyloxy)propyl)-4-(2-methoxyphenyl)piperidin-4-ol 133 was obtained without further purification. LC/MS RT (2.25 min method)=0.960 min. Mass observed: 380.4 (M+H).

Step 6:

To a solution of acid chloride 78 (160 mg, 0.32 mmol) in DCM (1 mL) was a solution of 2-(3-(tert-butyldimethylsilyloxy)propyl)-4-(2-methoxyphenyl)piperidin-4-ol 133 (120 mg, 0.32 mmol) and iPr₂NEt (0.17 mL, 1.0 mmol) in DCM (1 mL). The dark yellow reaction solution was stirred at r.t. for 16 hr. After removal of solvent, the residue was purified by silica gel chromatography (gradient, 30% to 50% EtOAc/hexanes) to give (2-(3-(tert-butyldimethylsilyloxy)propyl)-4-hydroxy-4-(2-methoxyphenyl)piperidin-1-yl)((2R,3S)-2-propyl-1-(3-(trifluoromethyl)picolinoyl)-3-(5-(trifluoromethyl)thiophen-3-yloxy)piperidin-3-yl)

methanone 134. LC/MS RT (2.25 min method)=1.883 min. Mass observed: 872.2 (M+H).

Step 7:

To a solution of (2-(3-(tert-butyldimethylsilyloxy)propyl)-4-hydroxy-4-(2-methoxyphenyl)piperidin-1-yl)((2R,3S)-2-propyl-1-(3-(trifluoromethyl)picolinoyl)-3-(5-(trifluoromethyl)thiophen-3-yloxy)piperidin-3-yl)methanone 134 (140 mg, 0.16 mmol) in THF (1 mL), 1.0 M of TBAF in THF (0.2 mL, 0.19 mmol) was added. The yellow reaction solution was stirred at r.t. for 2 hr. After removal of solvent, the residue was purified by silica gel chromatography (gradient, 30% to 50% EtOAc/hexanes) to give de-silyl product (4-hydroxy-2-(3-hydroxypropyl)-4-(2-methoxyphenyl)piperidin-1-yl)((2R,3S)-2-propyl-1-(3-(trifluoromethyl)picolinoyl)-3-(5-(trifluoromethyl)thiophen-3-yloxy)piperidin-3-yl)methanone. LC/MS RT (7 min method)=4.352 min. Mass observed: 758.2 (M+H).

To a solution of the above alcohol (25 mg, 0.03 mmol) in MeCN (0.5 mL), CCl$_4$ (0.5 mL) and H$_2$O (0.75 mL), RuCl$_3$ (1.4 mg, 0.007 mmol) and NaIO$_4$ (14 mg, 0.07 mmol) was added. The bi-layer reaction mixture was stirred at r.t. for 16 hr. The reaction mixture was extracted with ethyl acetate. The residue was purified by reverse phase HPLC to give 3-(4-hydroxy-4-(2-methoxyphenyl)-1-((2R,3S)-2-propyl-1-(3-(trifluoromethyl)picolinoyl)-3-(5-(trifluoromethyl)thiophen-3-yloxy)piperidine-3-carbonyl)piperidin-2-yl)propanoic acid A144. LC/MS RT (7 min method)=4.286 min. Mass observed: 772.1 (M+H).

Representative Example 73

Synthesis of (A145)

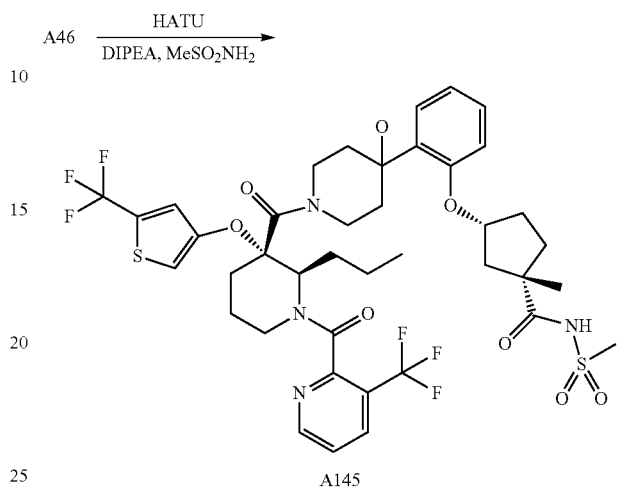

A145

Compound A145 was prepared according the procedure described in representative example 55 by replacing intermediate A34 with intermediate A46. LC/MS RT (4 min method)= 2.44 min. Mass observed: 889.1 (M+H).

The above compounds as well as other compounds prepared by essentially the same procedures given in the preparative examples above are shown below in Table 1.

| Compound number | Mol structure | Observed M + H or M + Na⁺ | HPLC retention time (min) |
|---|---|---|---|
| A1 | | 756.4 | 5.05 |

-continued
| Compound number | Mol structure | Observed M + H or M + Na+ | HPLC retention time (min) |
|---|---|---|---|
| A2 | 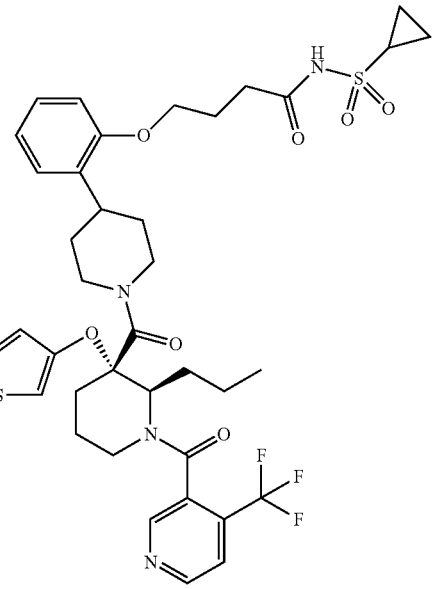 | 859.5 | 5.19 |
| A3 | 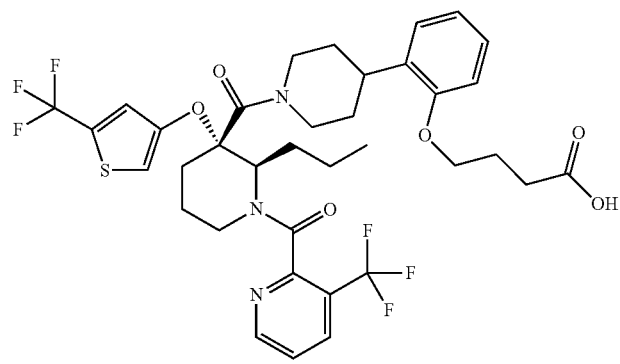 [SMILES: CCC[C@H]1N(C(=O)c2ncccc2C(F)(F)F)CCC[C@@]1(Oc1csc(C(F)(F)F)c1)C(=O)N1CCC(c2ccccc2OCCCC(=O)O)CC1] | 756.7 | 15.58 |
| A4 | 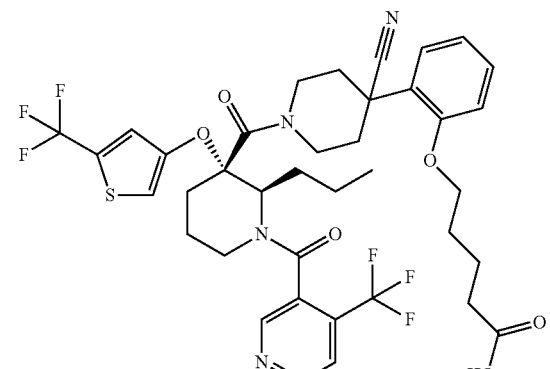 | 795.2 | 2.35 |

-continued

| Compound number | Mol structure | Observed M + H or M + Na⁺ | HPLC retention time (min) |
|---|---|---|---|
| A5 | | 795.2 | 2.34 |
| A6 | | 810.2 | 2.39 |
| A7 | | 809.2 | 2.43 |
| A8 | | 795 | 2.37 |

-continued

| Compound number | Mol structure | Observed M + H or M + Na⁺ | HPLC retention time (min) |
|---|---|---|---|
| A9 | | 808.2 (Na) | 2.33 |
| A10 | | 794 (Na) | 2.3 |
| A11 | | 822.1 (Na) | 2.39 |
| A12 | | 790 (Na) | 2.43 |

-continued

| Compound number | Mol structure | Observed M + H or M + Na+ | HPLC retention time (min) |
|---|---|---|---|
| A13 | | 804 (Na) | 2.48 |
| A14 | | 800 (Na) | 2.49 |
| A15 | | 845 (Na) | 2.59 |
| A16 | | 810 (Na) | 2.37 |

-continued

| Compound number | Mol structure | Observed M + H or M + Na+ | HPLC retention time (min) |
|---|---|---|---|
| A17 | | 872 | 2.44 |
| A18 | | 809 (Na) | 2.41 |
| A19 | | 796 (Na) | 2.35 |
| A20 | | 796 (Na) | 2.73 |

| Compound number | Mol structure | Observed M + H or M + Na+ | HPLC retention time (min) |
|---|---|---|---|
| A21 | | 862 (Na) | 1.27 |
| A22 | | 849 | 1.27 |
| A23 | | 834 (Na) | 1.22 |

-continued

| Compound number | Mol structure | Observed M + H or M + Na+ | HPLC retention time (min) |
| --- | --- | --- | --- |
| A24 | | 822 (Na) | 1.21 |
| A25 | | 831 (Na) | 1.24 |
| A26 | | 822 (Na) | 1.19 |

-continued

| Compound number | Mol structure | Observed M + H or M + Na⁺ | HPLC retention time (min) |
| --- | --- | --- | --- |
| A27 | | 809 | 1.21 |
| A28 | | 843 (Na) | 1.24 |
| A29 | | 822 (Na) | 5.02 |
| A30 | | 809 | 5.06 |

-continued

| Compound number | Mol structure | Observed M + H or M + Na+ | HPLC retention time (min) |
|---|---|---|---|
| A31 | | 862 (Na) | 5.34 |
| A32 | | 862 (Na) | 5.37 |
| A33 | | 821 (Na) | 5 |
| A34 | | 821 (Na) | 4.89 |

-continued

| Compound number | Mol structure | Observed M + H or M + Na$^+$ | HPLC retention time (min) |
|---|---|---|---|
| A35 | | 807 | 5.1 |
| A36 | | 807 | 4.9 |
| A37 | | 821 (Na) | 4.99 |

-continued

| Compound number | Mol structure | Observed M + H or M + Na+ | HPLC retention time (min) |
| --- | --- | --- | --- |
| A38 | | 821 (Na) | 4.89 |
| A39 | | 807 | 5.06 |
| A40 | | 807 | 5.01 |

-continued

| Compound number | Mol structure | Observed M + H or M + Na+ | HPLC retention time (min) |
|---|---|---|---|
| A41 | | 834 (Na) | 4.97 |
| A42 | | 834 (Na) | 2.33 |
| A43 | | 871 (Na) | 5.37 and 5.40 |
| A44 | | 871 (Na) | 5.37 |

-continued

| Compound number | Mol structure | Observed M + H or M + Na$^+$ | HPLC retention time (min) |
| --- | --- | --- | --- |
| A45 | | 871 (Na) | 5.4 |
| A46 | | 834 (Na) | 4.54 |
| A47 | | 834 (Na) | 4.43 |

-continued

| Compound number | Mol structure | Observed M + H or M + Na+ | HPLC retention time (min) |
| --- | --- | --- | --- |
| A48 | | 821 | 2.45 |
| A49 | | 821 | 2.51 |
| A50 | | 864 (Na) | 2.47 |

-continued

| Compound number | Mol structure | Observed M + H or M + Na+ | HPLC retention time (min) |
| --- | --- | --- | --- |
| A51 | | 850 (Na) | 2.43 |
| A52 | | 878 (Na) | 5.27 |
| A53 | | 781.24 | 5.81 |
| A54 | | 752.24 | 5.50 |

| Compound number | Mol structure | Observed M + H or M + Na+ | HPLC retention time (min) |
|---|---|---|---|
| A55 | 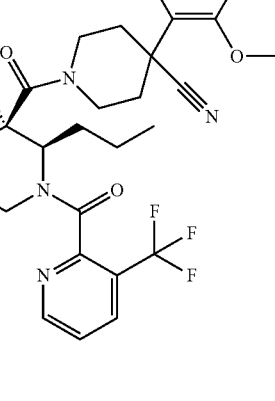 | 827.20 | 4.71 |
| A56 | 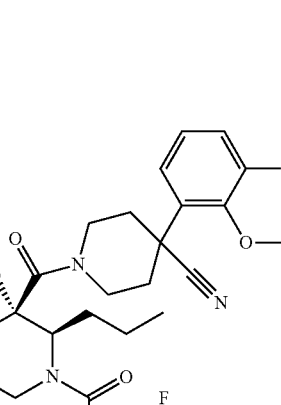 | 839.00 | 6.61 |
| A57 | 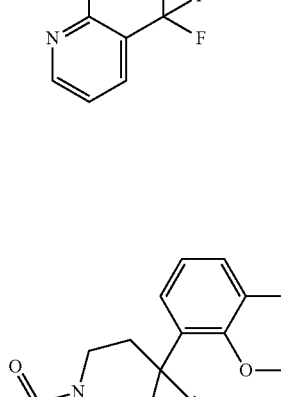 | 799.00 | 5.94 |

-continued

| Compound number | Mol structure | Observed M + H or M + Na+ | HPLC retention time (min) |
|---|---|---|---|
| A58 | | ESI, m/z [M − H]− = 817 | 7.5 |
| A59 | | ESI, m/z [M + H]+ = 795 | 9.72 |
| A60 | | ESI, m/z [M + H]+ = 823 | 9.44 |

-continued

| Compound number | Mol structure | Observed M + H or M + Na+ | HPLC retention time (min) |
|---|---|---|---|
| A61 | | ESI, m/z [M + H]+ = 821 | 9.68 |
| A62 | | ESI, m/z [M + H]+ = 807 | 10.69 |
| A63 | | ESI, m/z [M − H]− = 798 | 9.64 |

-continued
| Compound number | Mol structure | Observed M + H or M + Na+ | HPLC retention time (min) |
|---|---|---|---|
| A64 | 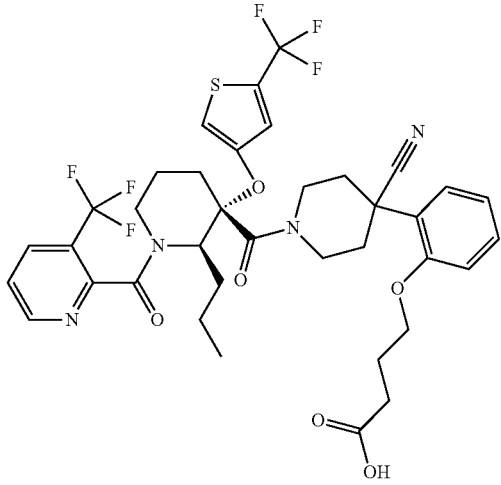 [SMILES: CCC[C@H]1N(C(=O)c2ncccc2C(F)(F)F)CCC[C@@]1(Oc1csc(C(F)(F)F)c1)C(=O)N1CCC(C#N)(c2ccccc2OCCCC(=O)O)CC1] | 781.2 | 6.19 |
| A65 | 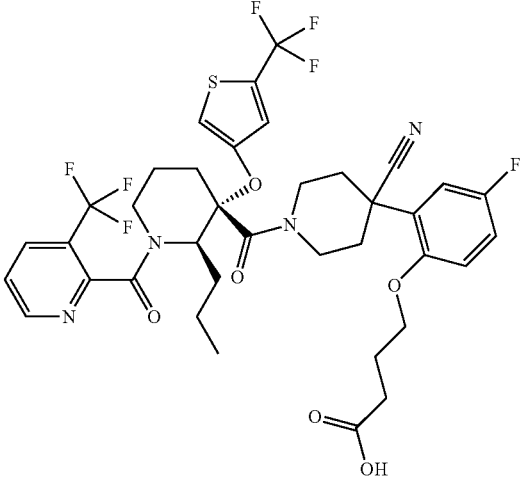 [SMILES: CCC[C@H]1N(C(=O)c2ncccc2C(F)(F)F)CCC[C@@]1(Oc1csc(C(F)(F)F)c1)C(=O)N1CCC(C#N)(c2cc(F)ccc2OCCCC(=O)O)CC1] | 799.2 | 4.55 |
| A66 | 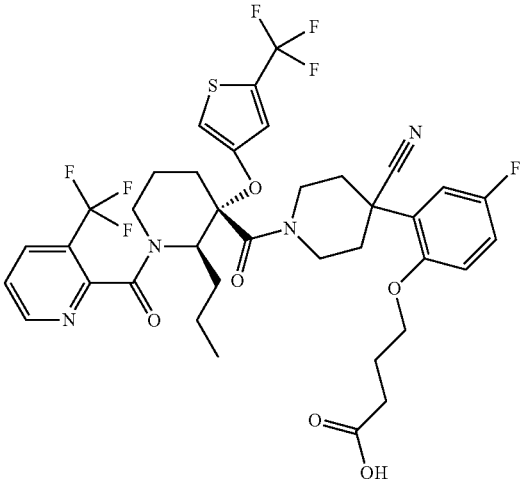 [SMILES: CCC[C@H]1N(C(=O)c2ncccc2C(F)(F)F)CCC[C@@]1(Oc1csc(C(F)(F)F)c1)C(=O)N1CCC(C#N)(c2cc(F)ccc2OCCCC(=O)O)CC1] | 799.2 | 4.66 |

-continued

| Compound number | Mol structure | Observed M + H or M + Na+ | HPLC retention time (min) |
|---|---|---|---|
| A67 | | 799.37 | 5.91 |
| A68 | | 813.40 | 5.80 |
| A69 | | 841.20 | 6.70 |

-continued

| Compound number | Mol structure | Observed M + H or M + Na⁺ | HPLC retention time (min) |
| --- | --- | --- | --- |
| A70 | | 853.20 | 6.74 |
| A71 | | 813.20 | 4.46 |
| A72 | | 772.24 | 4.62 |

| Compound number | Mol structure | Observed M + H or M + Na⁺ | HPLC retention time (min) |
|---|---|---|---|
| A73 | | 786.26 | 5.62 |
| A74 | | 813.27 | 5.67 |
| A75 | | 769.24 | 5.46 |

| Compound number | Mol structure | Observed M + H or M + Na+ | HPLC retention time (min) |
|---|---|---|---|
| A76 | | 829.33 | 6.60 |
| A77 | | 820.33 | 6.41 |
| A78 | | 834.34 | 4.65 |

| Compound number | Mol structure | Observed M + H or M + Na+ | HPLC retention time (min) |
|---|---|---|---|
| A79 | 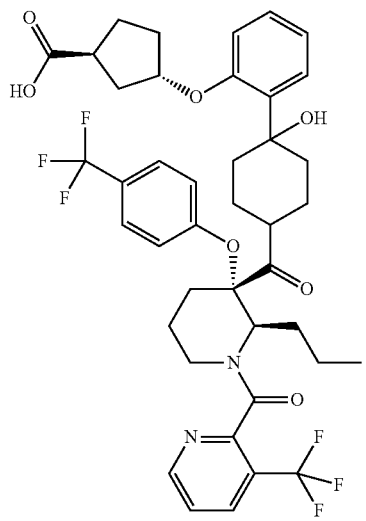 [SMILES: CCC[C@H]1N(C(=O)c2ncccc2C(F)(F)F)CCC[C@@]1(Oc1ccc(C(F)(F)F)cc1)C(=O)C1CCC(O)(c2ccccc2O[C@H]2CC[C@H](C(=O)O)C2)CC1] | 792.30 | 4.27 |
| A80 | 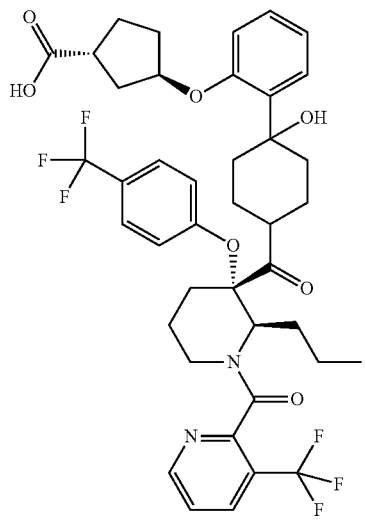 [SMILES: CCC[C@H]1N(C(=O)c2ncccc2C(F)(F)F)CCC[C@@]1(Oc1ccc(C(F)(F)F)cc1)C(=O)C1CCC(O)(c2ccccc2O[C@@H]2CC[C@@H](C(=O)O)C2)CC1] | 792.30 | 4.26 |

-continued

| Compound number | Mol structure | Observed M + H or M + Na$^+$ | HPLC retention time (min) |
|---|---|---|---|
| A81 | | 754.27 | 6.12 |
| A82 | | 728.20 | 6.11 |
| A83 | | 745.30 | 5.46 |

-continued
| Compound number | Mol structure | Observed M + H or M + Na+ | HPLC retention time (min) |
|---|---|---|---|
| A84 | 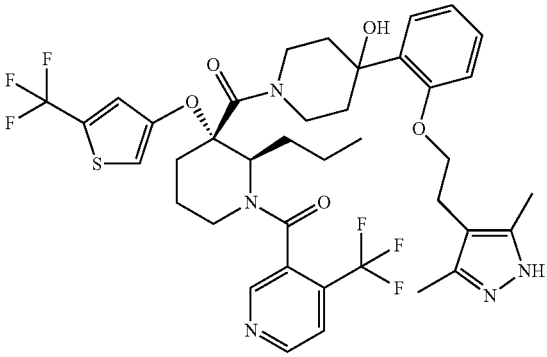 [SMILES: CCC[C@H]1N(C(=O)c2cnccc2C(F)(F)F)CCC[C@@]1(Oc1csc(C(F)(F)F)c1)C(=O)N1CCC(O)(c2ccccc2OCCc2c(C)n[nH]c2C)CC1] | 808.4 (M + H) | 5.02 |
| A85 | 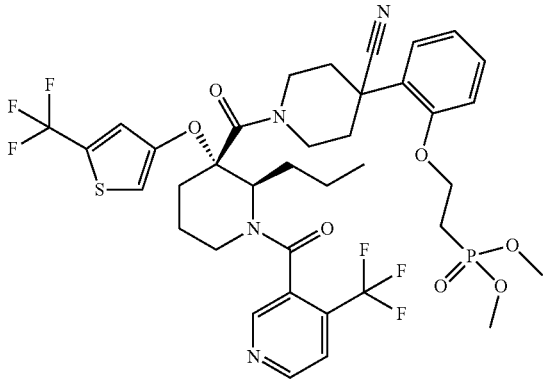 | 845.5 (M + H) | 6.24 |
| A86 | 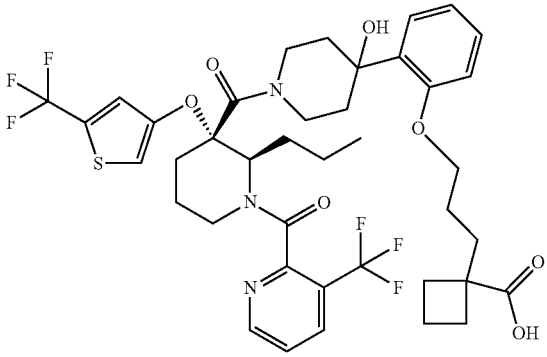 [SMILES: CCC[C@H]1N(C(=O)c2ncccc2C(F)(F)F)CCC[C@@]1(Oc1csc(C(F)(F)F)c1)C(=O)N1CCC(O)(c2ccccc2OCCCC2(C(=O)O)CCC2)CC1] | 826.4 (M + H) | 6.41 |
| A87 | 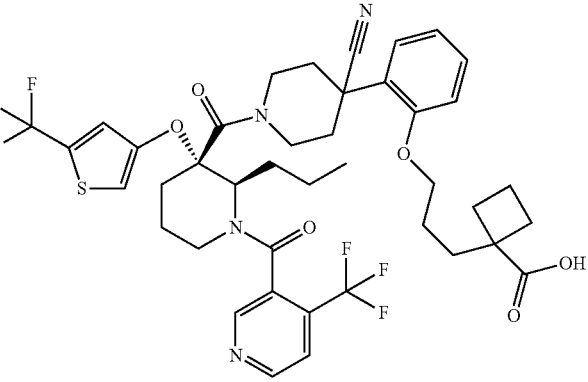 | 835.5 (M + H) | 6.58 |

-continued

| Compound number | Mol structure | Observed M + H or M + Na⁺ | HPLC retention time (min) |
|---|---|---|---|
| A88 | | 821.5 (M + H) | 6.42 |
| A89 | | 830.0 (M + Na) | 1.27 |
| A90 | | 770.4 | 5.32 |
| A91 | | 772 | 2.34 |

-continued

| Compound number | Mol structure | Observed M + H or M + Na+ | HPLC retention time (min) |
|---|---|---|---|
| A92 | | 786.2 | 2.38 |
| A93 | | 754.4 | 4.87 |
| A94 | | 800.4 | 4.6 |
| A95 | | 774.4 | 5.21 |

| Compound number | Mol structure | Observed M + H or M + Na+ | HPLC retention time (min) |
| --- | --- | --- | --- |
| A96 | | 786.4 | 5.13 |
| A97 | | 795.4 | 5.21 |
| A98 | | 795.2 | 2.51 |
| A99 | | 808.2 (Na) | 2.51 |

-continued

| Compound number | Mol structure | Observed M + H or M + Na⁺ | HPLC retention time (min) |
|---|---|---|---|
| A100 | | 770.6 | 13.08 |
| A101 | | 836.4 (Na) | 2.44 |
| A102 | | 836.2 (Na) | 2.4 |
| A103 | | 797.8 | 2.74 |

-continued

| Compound number | Mol structure | Observed M + H or M + Na+ | HPLC retention time (min) |
|---|---|---|---|
| A104 | | 807.8 (Na) | 2.46 |
| A105 | | 807.8 (Na) | 2.39 |
| A106 | | 808.0 (Na) | 2.4 |
| A107 | | 807.4 | 10.34 |

-continued

| Compound number | Mol structure | Observed M + H or M + Na+ | HPLC retention time (min) |
|---|---|---|---|
| A108 | | 807.4 | 11.06 |
| A109 | | 750.2 (Na) | 2.59 |
| A110 | | 764.1 (Na) | 2.35 |
| A111 | | 834.2 (Na) | 2.44 |

-continued

| Compound number | Mol structure | Observed M + H or M + Na+ | HPLC retention time (min) |
|---|---|---|---|
| A112 | | 834.2 (Na) | 2.49 |
| A113 | | 862.0 (Na) | 2.51 |
| A114 | | 848.1 (Na) | 2.46 |
| A115 | | 849.2 | 2.49 |

-continued

| Compound number | Mol structure | Observed M + H or M + Na+ | HPLC retention time (min) |
| --- | --- | --- | --- |
| A116 | | 871.2 (Na) | 1.28 |
| A117 | | 835.2 (Na) | 4.98 |
| A118 | | 835.2 (Na) | 4.98 |
| A119 | | 821.2 | 1.19 |

-continued

| Compound number | Mol structure | Observed M + H or M + Na+ | HPLC retention time (min) |
| --- | --- | --- | --- |
| A120 | | 834.2 (Na) | 1.17 |
| A121 | | 843.2 (Na) | 1.2 |
| A122 | | 821.5 | 11.13 |

-continued

| Compound number | Mol structure | Observed M + H or M + Na⁺ | HPLC retention time (min) |
|---|---|---|---|
| A123 | | 834.2 (Na) | 1.18 |
| A124 | | 821.2 | 1.22 |
| A125 | | 798.2 | 2.34 |
| A126 | | 807.2 | 2.37 |

| Compound number | Mol structure | Observed M + H or M + Na+ | HPLC retention time (min) |
| --- | --- | --- | --- |
| A127 | | 875.2 | 2.23 |
| A128 | | 821.1 (Na) | 2.39 |
| A130 | | 806.2 (Na) | 2.4 |
| A131 | | 862.2 (Na) | 2.62 |

| Compound number | Mol structure | Observed M + H or M + Na+ | HPLC retention time (min) |
|---|---|---|---|
| A132 | | 876.1 (Na) | 2.62 |
| A133 | | 750.26 | 5.97 |
| A134 | | 803.23 | 4.56 |

US 8,859,776 B2

-continued

| Compound number | Mol structure | Observed M + H or M + Na⁺ | HPLC retention time (min) |
|---|---|---|---|
| A135 | | 726.23 | 6.31 |
| A136 | | 751.23 | 4.56 |
| A137 | | 828.22 | 5.89 |

-continued

| Compound number | Mol structure | Observed M + H or M + Na+ | HPLC retention time (min) |
|---|---|---|---|
| A138 | | 737.25 | 6.04 |
| A139 | | 751.23 | 4.54 |
| A140 | | 769.22 | 4.34 |

-continued
| Compound number | Mol structure | Observed M + H or M + Na+ | HPLC retention time (min) |
|---|---|---|---|
| A141 | 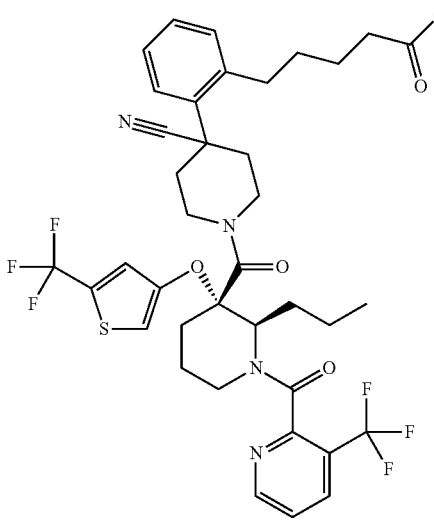 | 779.26 | 4.51 |
| A142 | 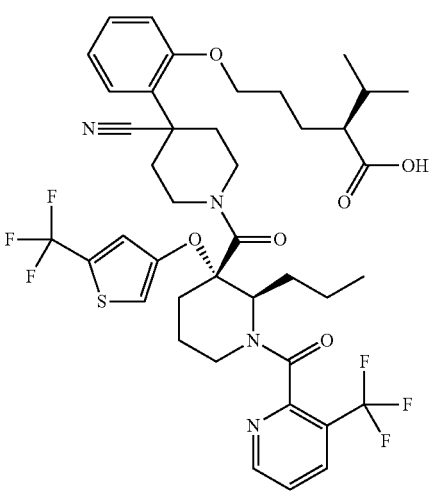 [SMILES: CCC[C@H]1N(C(=O)c2ncccc2C(F)(F)F)CCC[C@@]1(Oc1csc(C(F)(F)F)c1)C(=O)N1CCC(C#N)(c2ccccc2OCCC[C@H](C(=O)O)C(C)C)CC1] | 837.10 | 6.74 |
| A143 | 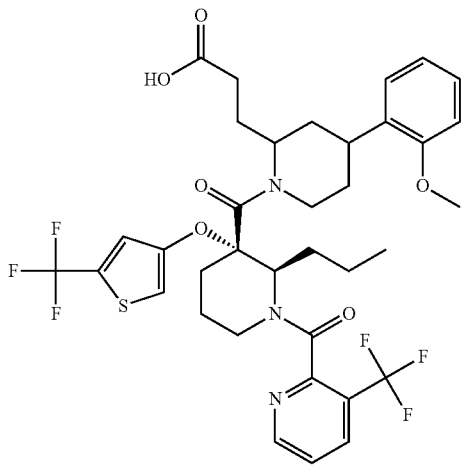 [SMILES: CCC[C@H]1N(C(=O)c2ncccc2C(F)(F)F)CCC[C@@]1(Oc1csc(C(F)(F)F)c1)C(=O)N1CCC(c2ccccc2OC)CC1CCC(=O)O] | 756.2 | 4.21 |

| Compound number | Mol structure | Observed M + H or M + Na⁺ | HPLC retention time (min) |
|---|---|---|---|
| A144 | | 772.1 | 4.28 |
| A145 | | 881 | 2.44 |

The inventive compounds can readily be evaluated to determine activity at the HDM2 protein by known methods such as the fluorescence polarization screening assay that measures the inhibitory concentration that achieves 50% of maximal activity (FP $IC_{50}$) and the dissociation constant for inhibitor binding (FP Ki). [Zhang et al., J. Analytical Biochemistry 331: 138-146 (2004)].

Additionally, compounds are tested for activity at the HDM2 protein using the Cell Viability Assay, which measures the number of viable cells in culture after treatment with the inventive compound for a certain period of time e.g. 72 hours based on quantitation of the ATP present (Cell Viability. $IC_{50}$). [CellTiter-Glo® Luminescent Cell Viability Assay from Promega].

The compounds in one embodiment of the present invention have unexpectedly superior potency over the compounds disclosed in WO2008/005268 (equivalent to U.S. Patent Publication US 2008/0004287). They exhibit FP $IC_{50}$ values of less than 0.5 µM. In one embodiment, the compounds of the present invention exhibit FP $IC_{50}$ values of less than 0.1 µM. Representative FP $IC_{50}$ values for some of the compounds from Table 1 are shown in Table 2:

TABLE 2

| Compound number | FP (IC 50 uM) |
|---|---|
| A2 | 0.009 |
| A4 | 0.014 |
| A54 | 0.019 |
| A83 | 0.013 |
| A89 | 0.011 |
| A109 | 0.018 |
| A133 | 0.011 |
| A145 | 0.008 |

In order to assess the potential for inhibition of Cytochrome P450s (CYPs) and therefore possible drug interactions, human liver microsomes were incubated with several concentrations (0.2, 2, and 20 uM) of compound of the present invention, 1 mM reduced nicotinamide adenine dinucleotide phosphate (NADPH) and substrates for various CYPs at 37° C. for 13 mins. The substrate concentration was kept near the Km value for each CYP reaction. They were 100 M testosterone (6β-hydroxylase reaction) for CYP3A4. The concentrations of the metabolites formed from each substrate after incubation were determined by LC/MS/MS using a standard curve. The concentrations at which 50% of the initial enzyme activity was inhibited ($IC_{50}$) were determined from the graph of the concentrations versus percent of inhibition.

The cytochrome P450 3A4 enzyme inhibition studies of the compounds of the present invention also have an improved CYP3A4 profile relating to $IC_{50}$ CYP3A4 (pre and co incubation), which is unexpectedly superior to the compounds disclosed in WO2008/005268 (U.S. Patent Publication US 2008/0004287).

From these test results, it would be apparent to the skilled artisan that the compounds of the invention have utility in treating cancer, diseases involving abnormal cell proliferation and diseases caused by inadequate functioning p53.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

Each and every reference, whether a published patent application, a granted/issued patent or a nonpatent scientific publication, mentioned herein is incorporated by reference for all purposes.

What is claimed is:
1. A compound of Formula 1:

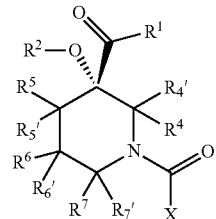

Formula 1 or a pharmaceutically acceptable salt thereof, wherein:
$R^1$ is:

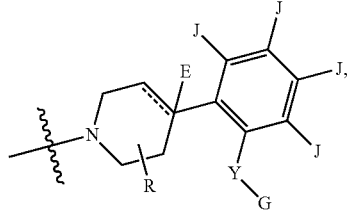

wherein:
E is either present or absent, and when present is selected from the group consisting of H, halo, OH, CN, —O($C_1$-$C_6$)alkyl, —($C_1$-$C_6$)alkyl, —C(O)OH, —C(O)$NR^8R^{8'}$, —($C_1$-$C_6$)alkyl-C(O)OH, —($C_1$-$C_6$)alkyl-OH, —($C_1$-$C_6$)alkyl-C(O)$NR^8R^{8'}$, —($C_2$-$C_6$)alkenyl, —($C_2$-$C_6$)alkynyl, heterocyclyl, and heteroaryl;
each J independently is selected from the group consisting of H and halogen;
Y and R may or may not be present, when Y is present, it is selected from the group consisting of O, S, $NR^8$, $SO_2$, and $CR^8R^{8'}$;
R when present is one or more moieties independently selected from the group consisting of —($C_1$-$C_6$)alkyl, and —($CR^8R^{8'}$)$_n$—C(O)OH;
G is present and is selected from the group consisting of —($CR^8R^{8'}$)$_n$—C(O)OH, —($CR^8R^{8'}$)$_n$—C(O)$NR^8R^9$, —($CR^8R^{8'}$)$_n$—($C_3$-$C_8$)cycloalkyl-C(O)$NR^8R^9$, —($CR^8R^{8'}$)$_n$—($C_3$-$C_8$)cycloalkyl-($CR^8R^{8'}$)$_n$—C(O)OH, —($CR^8R^{8'}$)$_n$—O—($CR^8R^{8'}$)$_n$—($C_3$-$C_8$)cycloalkyl-($CR^8R^{8'}$)$_n$—C(O)OH, —($CR^8R^{8'}$)$_n$—O—($CR^8R^{8'}$)$_n$—C(O)OH, —($CR^8R^{8'}$)$_n$—S—($CR^8R^{8'}$)$_n$—C(O)OH, C(O)OH, —($CR^8R^{8'}$)$_n$—NH—($CR^8R^{8'}$)$_n$—C(O)OH, —($CR^8R^{8'}$)$_n$—O—($CR^8R^{8'}$)$_n$—$CH_3$, —($CR^8R^{8'}$)$_n$—S—($CR^8R^{8'}$)$_n$—$CH_3$, —($CR^8R^{8'}$)$_n$—NH—($CR^8R^{8'}$)$_n$—$CH_3$, —($CR^8R^{8'}$)$_n$—$CH_3$, —($CR^8R^{8'}$)$_n$-heteroaryl, —($CR^8R^{8'}$)$_n$—P(O)$OR^8OR^{8'}$, and —($CR^8R^{8'}$)$_n$—OH;
each $R^8$ and $R^{8'}$ is independently selected from the group consisting of H, D, and ($C_1$-$C_6$)alkyl; or wherein $R^8$ and $R^{8'}$ together with the carbon to which each is attached form ($C_3$-$C_8$)cycloalkyl;
each $R^9$ independently is $SO_2$($C_1$-$C_6$)alkyl or $SO_2$($C_3$-$C_8$)cycloalkyl;
each n independently is 0-10; provided that when n is 0, any oxygen, nitrogen or sulfur atom of Y is not directly linked to any oxygen, nitrogen, sulfur or phosphorus atom of G;
----- represents a single or a double bond, provided that when E is present, ----- represents a single bond;
$R^2$ is

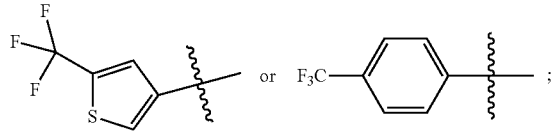 [SMILES: *c1csc(C(F)(F)F)c1 ; *c1ccc(C(F)(F)F)cc1]

$R^4$, $R^{4'}$, $R^5$, $R^{5'}$, $R^6$, $R^{6'}$, $R^7$, and $R^{7'}$ independently are selected from the group consisting of hydrogen and ($C_1$-$C_6$)alkyl; and
X is

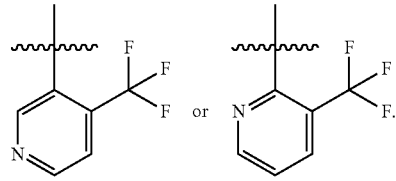 [SMILES: *c1cnccc1C(F)(F)F ; *c1ncccc1C(F)(F)F]

2. The compound of claim 1, wherein E is present and is selected from the group consisting of H, halo, OH, CN, —O($C_1$-$C_6$)alkyl, ($C_1$-$C_6$)alkyl, —C(O)OH, —C(O)$NR^8R^{8'}$, —($C_1$-$C_6$)alkyl-C(O)OH, —($C_1$-$C_6$)alkyl-OH, —($C_1$-$C_6$)alkyl-C(O)$NR^8R^{8'}$, and heteroaryl.

3. The compound of claim 2, wherein said —($C_1$-$C_6$)alkyl-OH is hydroxymethyl; said —($C_1$-$C_6$)alkyl-C(O)$NR^8R^{8'}$ is —C(O)$NH_2$; said —($C_1$-$C_6$)alkyl-C(O)OH is —($CH_2$)$_4$COOH; said halo is —F; said —O($C_1$-$C_6$)alkyl is methoxy; said —($C_1$-$C_6$)alkyl is methyl; and said heteroaryl is tetrazolyl.

4. The compound of claim 1, wherein each J independently is H or Fluoro.

5. The compound of claim 1, wherein Y is present and is selected from the group consisting of O, S, $SO_2$, and $CR^8R^{8'}$.

6. The compound of claim 1, wherein G is present, and is selected from the group consisting of —($CR^8R^{8'}$)$_n$—C(O)OH, —($CR^8R^{8'}$)$_n$—C(O)$NR^8R^9$, —($CR^8R^{8'}$)$_n$—($C_3$-$C_8$)cycloalkyl-C(O)$NR^8R^9$, —($CR^8R^{8'}$)$_n$—($C_3$-$C_8$)cycloalkyl-($CR^8R^{8'}$)$_n$—C(O)OH, —($CR^8R^{8'}$)$_n$—O—($CR^8R^{8'}$)$_n$—($C_3$-

$C_8$)cycloalkyl-$(CR^8R^{8'})_n$—C(O)OH, —$(CR^8R^{8'})_n$—O—$(CR^8R^{8'})_n$—C(O)OH, —$(CR^8R^{8'})_n$—NH—$(CR^8R^{8'})_n$—C(O)OH, —$(CR^8R^{8'})_n$—O—$(CR^8R^{8'})_n$—CH$_3$, —$(CR^8R^{8'})_n$—CH$_3$, —$(CR^8R^{8'})_n$-heteroaryl, —$(CR^8R^{8'})_n$—P(O)OR$^8$OR$^{8'}$, and —$(CR^8R^{8'})_n$—OH.

7. The compound of claim 6, wherein said —$(CR^8R^{8'})_n$—C(O)OH is selected from the group consisting of —$(CH_2)_{1-5}$C(O)OH, —CH(CH$_3$)—$(CH_2)_{2-3}$—C(O)OH, —$(CH_2)_{1-3}$C(CH$_3$)$_2$C(O)OH, —$(CH_2)_3$CH(CH(CH(CH$_3$)$_2$)—C(O)OH, —$(CD_2)_3$C(O)OH, —$(CH_2)_{1-2}$—CH(CH$_3$)—$(CH_2)_{1-2}$—C(O)OH, CH(CH$_3$)—$(CH_2)_{2-3}$—C(O)OH,

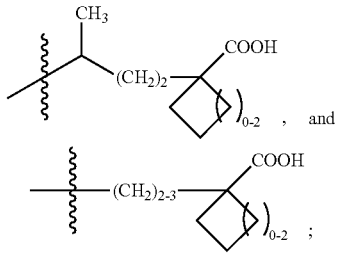

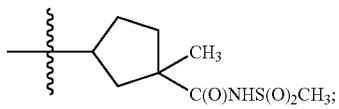

wherein said —$(CR^8R^{8'})_n$—C(O)NR$^8$R$^9$ is —$(CH_2)_{1-4}$—C(O)NH—S(O)$_2$CH$_3$ or —$(CH_2)_{3-4}$—C(O)NH—S(O)$_2$-cyclopropyl; said —$(CR^8R^{8'})_n$—(C$_3$-C$_8$)cycloalkyl-C(O)NR$^8$R$^9$ is -cyclopentyl-C(O)NH—S(O)$_2$—CH$_3$ or

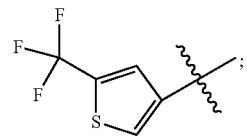

said —$(CR^8R^{8'})$—(C$_3$-C$_8$)cycloalkyl-$(CR^8R^{8'})_n$—C(O)OH is selected from the group consisting of —CH$_2$-cyclopentyl-C(O)OH, -cyclobutyl-C(O)OH, -cyclopentyl-C(O)OH, -cyclohexyl-C(O)OH, and -cyclopentyl-CH$_2$—C(O)OH; said —$(CR^8R^{8'})_n$—O—$(CR^8R^{8'})_n$—(C$_3$-C$_8$)cycloalkyl-$(CR^8R^{8'})_n$—C(O)OH is —O-cyclopentyl-C(O)OH or —O-cyclobutyl-C(O)OH; said —$(CR^8R^{8'})_n$—O—$(CR^8R^{8'})_n$—C(O)OH is selected from the group consisting of —CH$_2$—O—(CH$_2$)$_3$—C(O)OH, —O—(CH$_2$)$_2$—C(CH$_2$)$_2$—C(O)OH, and —O—(CH$_2$)$_3$—C(O)OH; said —$(CR^8R^{8'})_n$—NH—$(CR^8R^{8'})_n$—C(O)OH is —NH(CH$_2$)$_3$C(O)OH; said —$(CR^8R^{8'})_n$—O—$(CR^8R^{8'})_n$—CH$_3$ is —(CH$_2$)$_2$—O—CH$_3$; said —$(CR^8R^{8'})_n$—CH$_3$ is —CH$_3$; said —$(CR^8R^{8'})_n$-heteroaryl is —(CH$_2$)$_2$-(alkyl substituted pyrazolyl); said —$(CR^8R^{8'})_n$—P(O)OR$^8$OR$^{8'}$ is —(CH$_2$)$_3$P(O)(OH)(OH) or —(CH$_2$)$_3$P(O)(OCH$_3$)(OCH$_3$); and said —$(CR^8R^{8'})_n$—OH is —(CH$_2$)$_2$—OH.

8. The compound of claim 1, wherein Y is O and G is selected from the group consisting of —$(CR^8R^{8'})_n$—C(O)OH, —$(CR^8R^{8'})_n$—C(O)NR$^8$R$^9$, —$(CR^8R^{8'})_n$—(C$_3$-C$_8$)cycloalkyl-C(O)NR$^8$R$^9$, —$(CR^8R^{8'})_n$—(C$_3$-C$_8$)cycloalkyl-$(CR^8R^{8'})_n$—C(O)OH, —$(CR^8R^{8'})_n$—O—$(CR^8R^{8'})_n$—CH$_3$, —$(CR^8R^{8'})_n$—CH$_3$, —$(CR^8R^{8'})_n$-heteroaryl, and —$(CR^8R^{8'})_n$—P(O)OR$^8$OR$^{8'}$.

9. The compound of claim 1, wherein Y is S and G is —$(CR^8R^{8'})_n$—C(O)OH or —$(CR^8R^{8'})_n$—(C$_3$-C$_8$)cycloalkyl-$(CR^8R^{8'})_n$—C(O)OH.

10. The compound of claim 1, wherein Y is SO$_2$ and G is —$(CR^8R^{8'})_n$—NH—$(CR^8R^{8'})_n$—C(O)OH.

11. The compound of claim 1, wherein Y is CR$^8$R$^{8'}$ and G is selected from the group consisting of —$(CR^8R^{8'})_n$—O—$(CR^8R^{8'})_n$—C(O)OH, —$(CR^8R^{8'})_n$—O—$(CR^8R^{8'})_n$—(C$_3$-C$_8$)cycloalkyl-$(CR^8R^{8'})_n$—C(O)OH, —$(CR^8R^{8'})_n$—C(O)OH, —$(CR^8R^{8'})_n$—OH, —$(CR^8R^{8'})_n$-heteroaryl, and —$(CR^8R^{8'})_n$—C(O)NR$^8$R$^9$.

12. The compound of claim 1, wherein R$^4$ is hydrogen and R$^4$ is 1-propyl, such that Formula 1 is represented by Formula 1A:

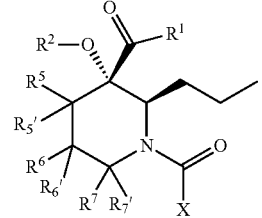

Formula 1A wherein R$^1$, R$^2$, R$^5$, R$^{5'}$, R$^6$, R$^{6'}$, R$^7$, R$^{7'}$, and X are as set forth in Formula 1.

13. The compound of claim 12, wherein R$^5$, R$^{5'}$, R$^6$, R$^{6'}$, R$^7$, and R$^{7'}$ are all hydrogen.

14. The compound of claim 13, wherein:
R$^1$ is

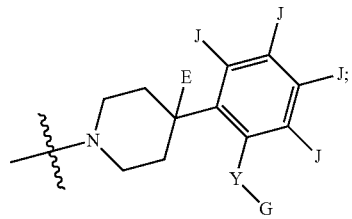

R$^2$ is

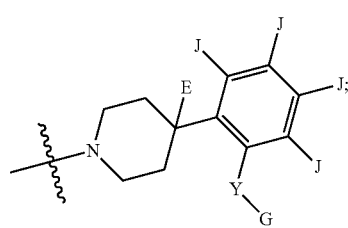

and either (i) each J in R is H, or (ii) one J in R$^1$ is halo, and the remaining three Js are H.

15. The compound of claim 1, wherein:
R$^1$ is $R^2$ is
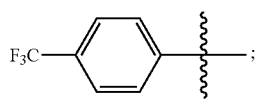
and
each J in $R^1$ is H.
16. A compound selected from the group consisting of:
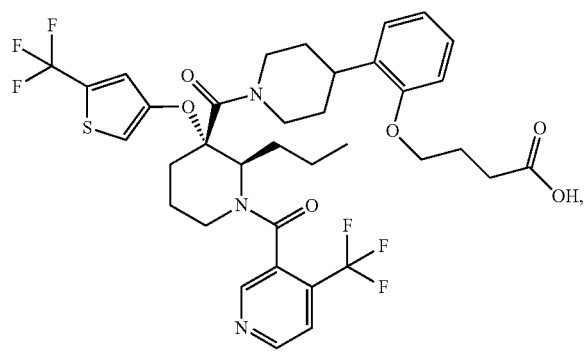
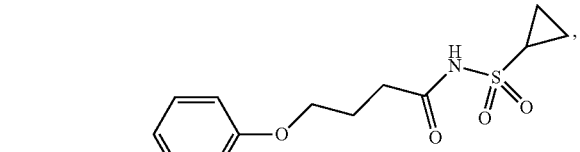
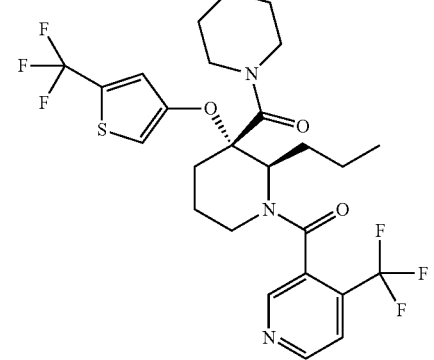
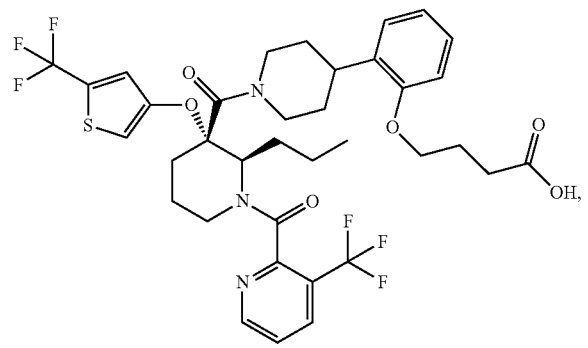
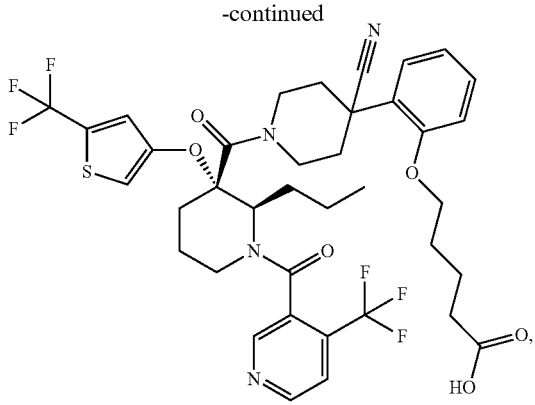
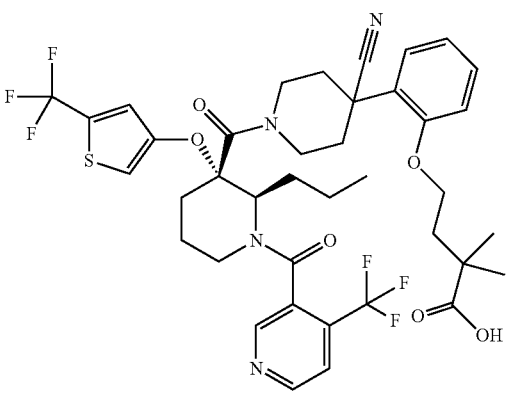
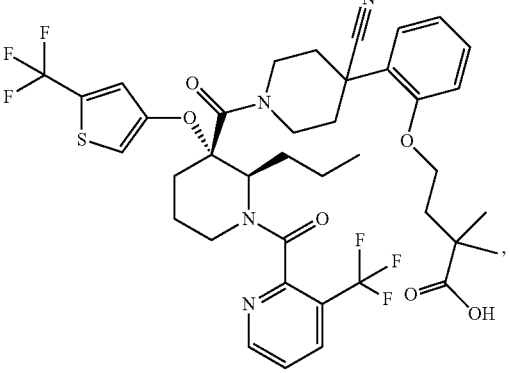

313
-continued
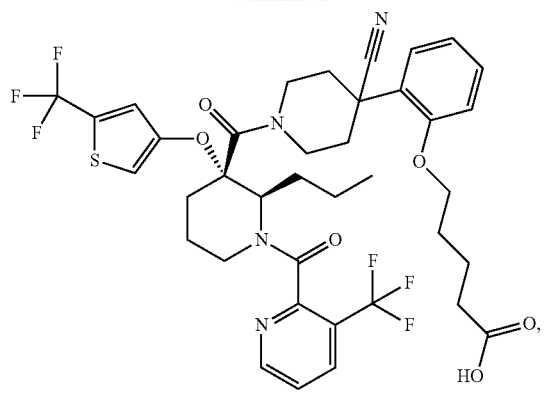
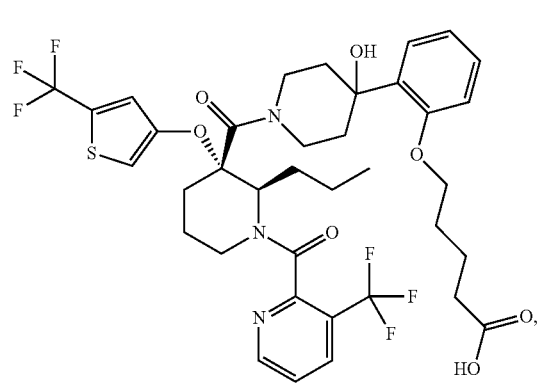
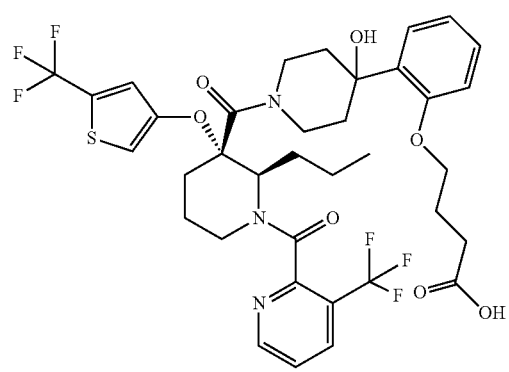
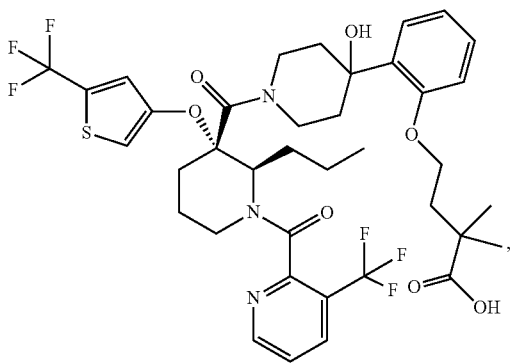
314
-continued
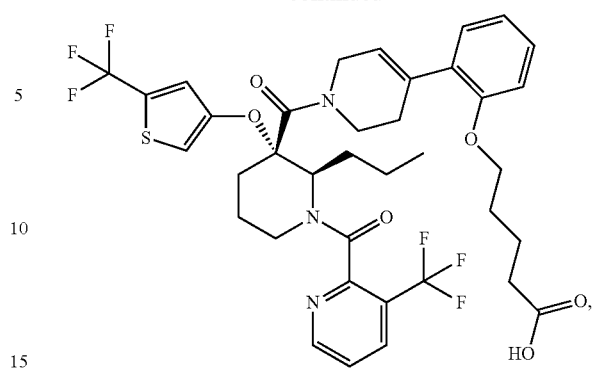
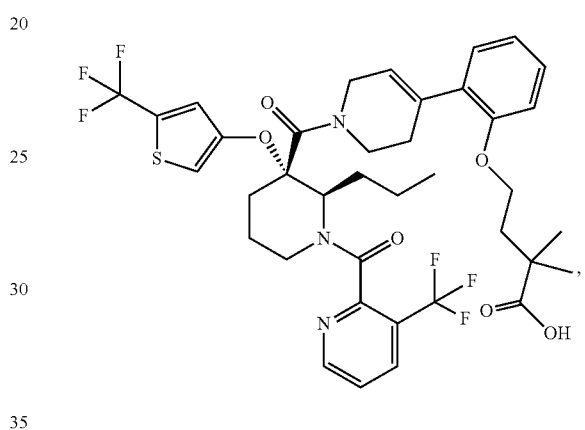
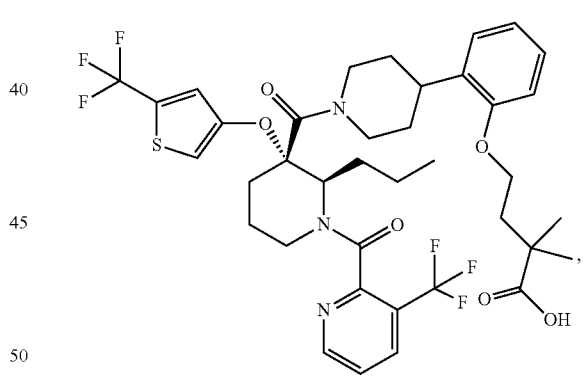
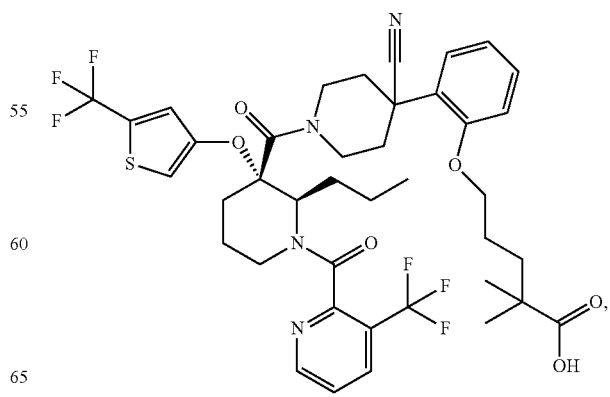

315
-continued
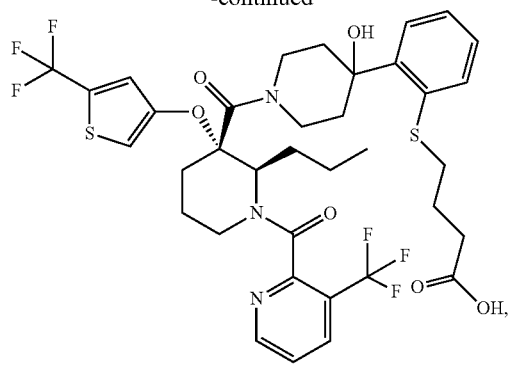
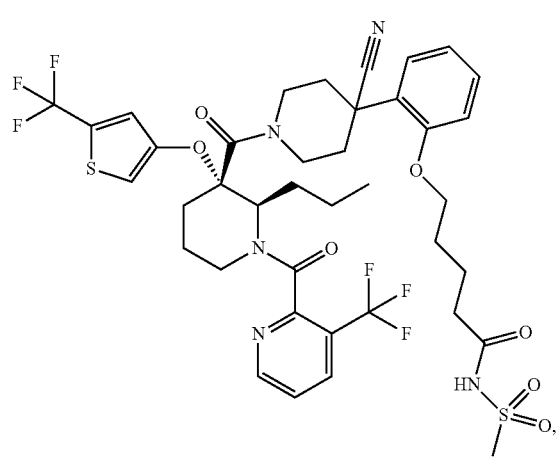
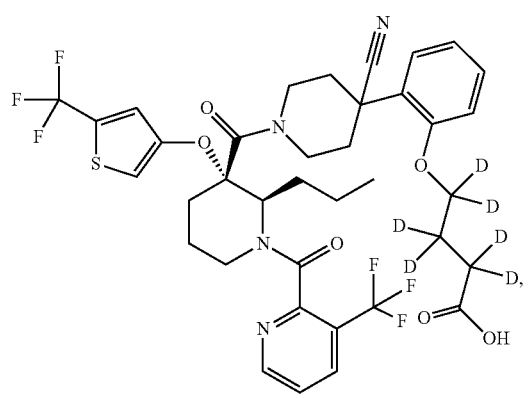
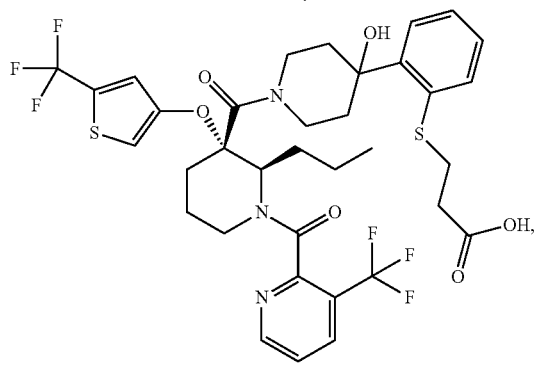
316
-continued
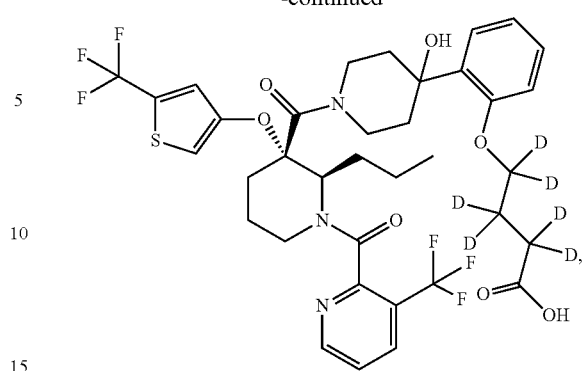
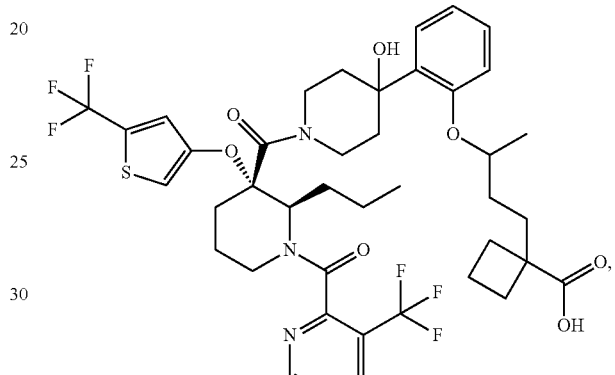
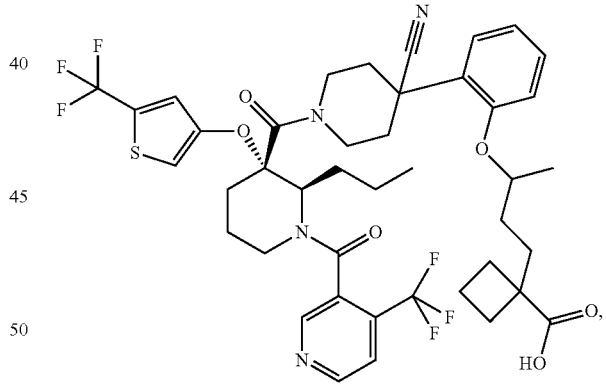
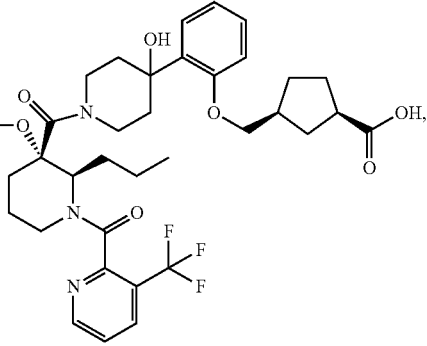

317
-continued
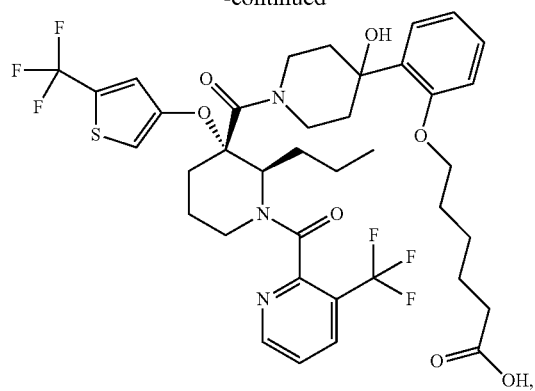
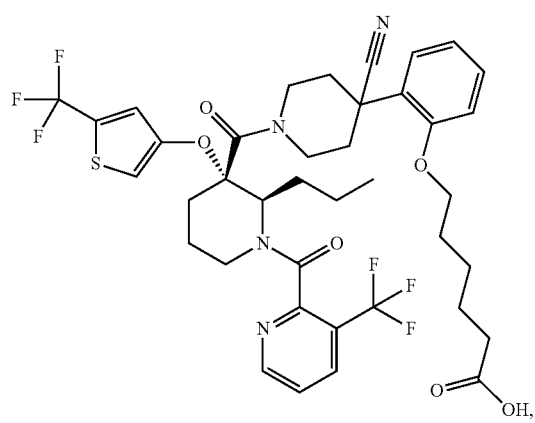
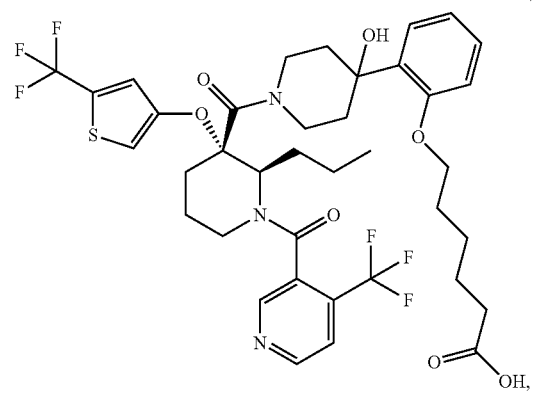
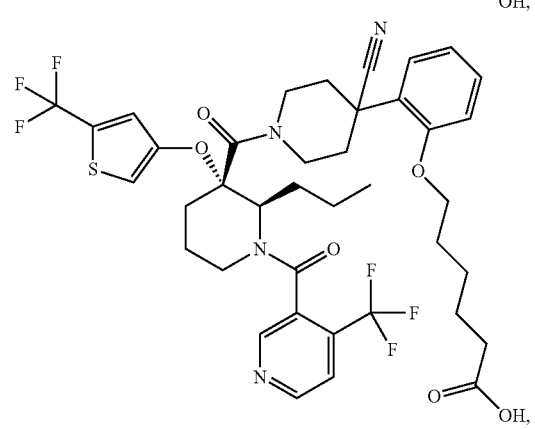
318
-continued
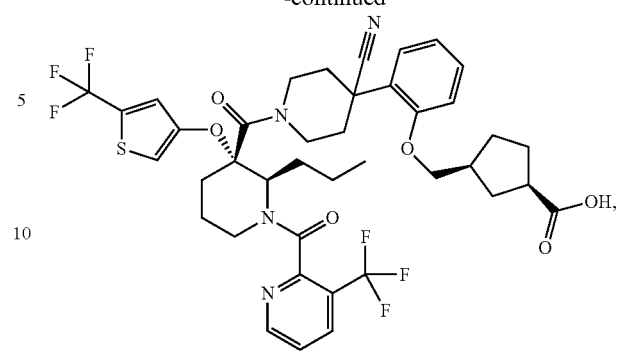
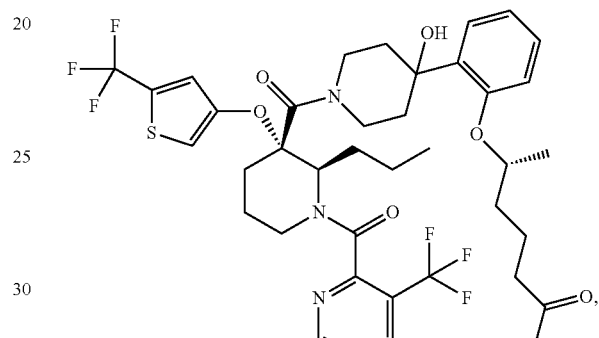
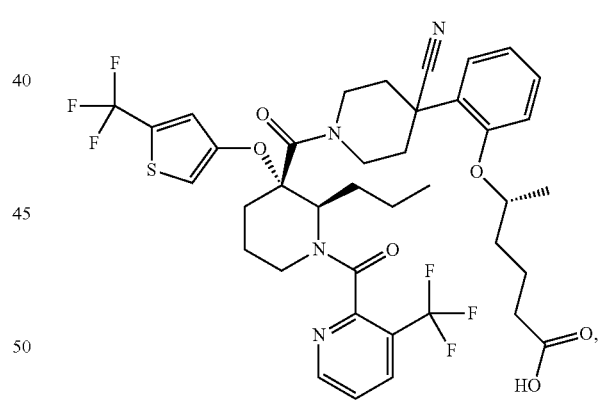
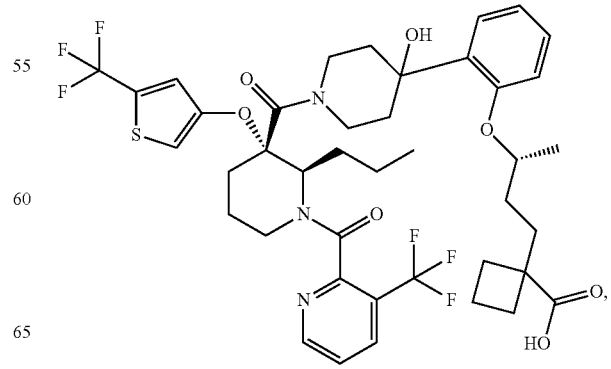

319
-continued
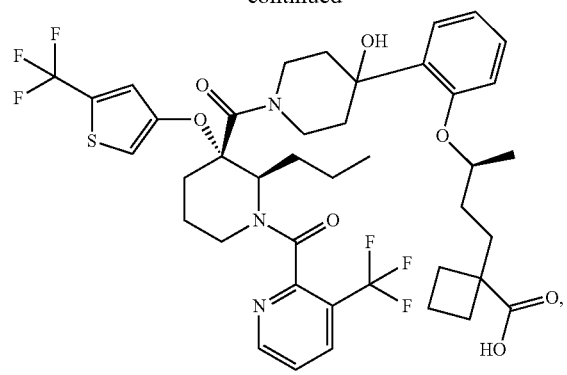
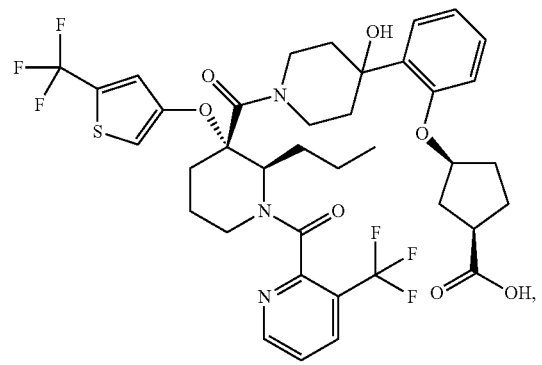
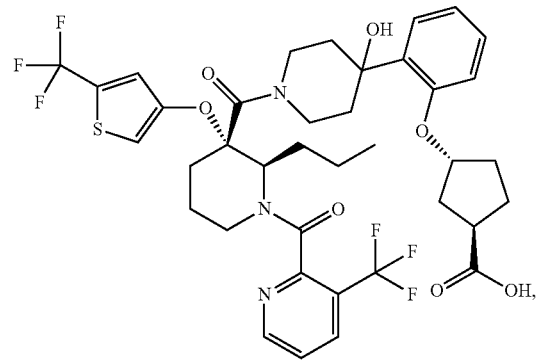
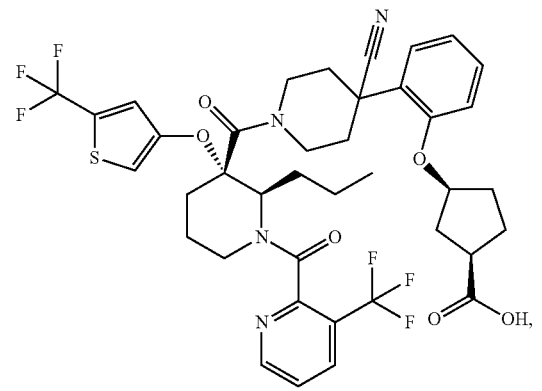
320
-continued
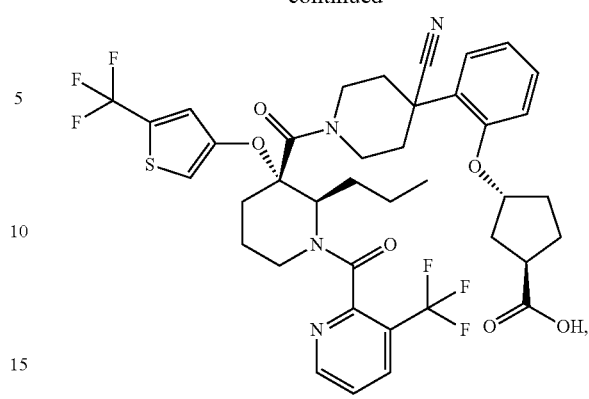
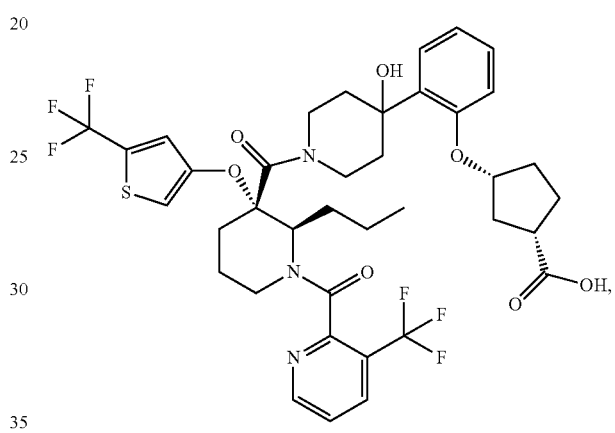
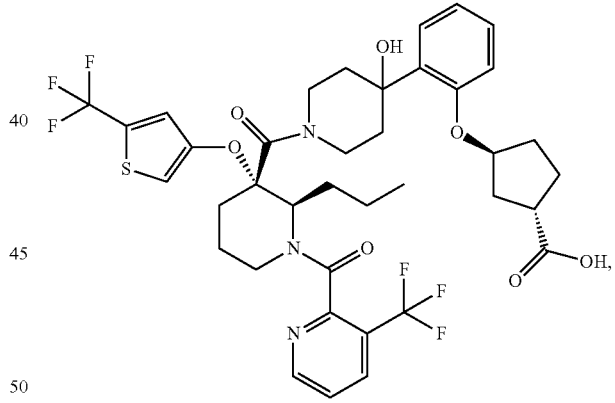
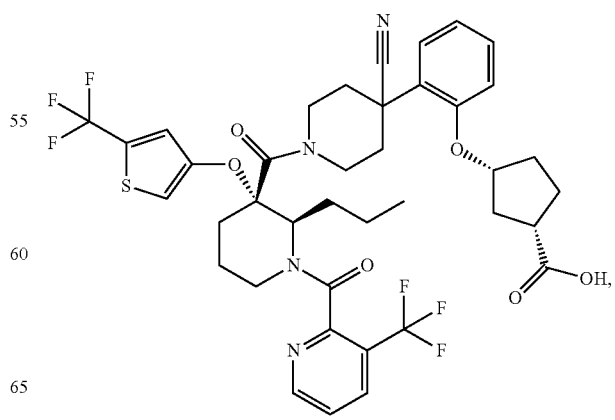

321
-continued
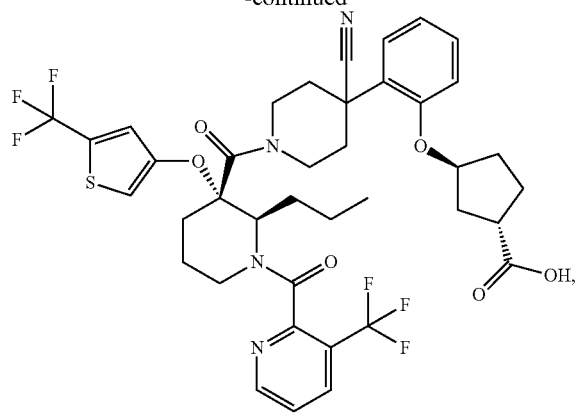
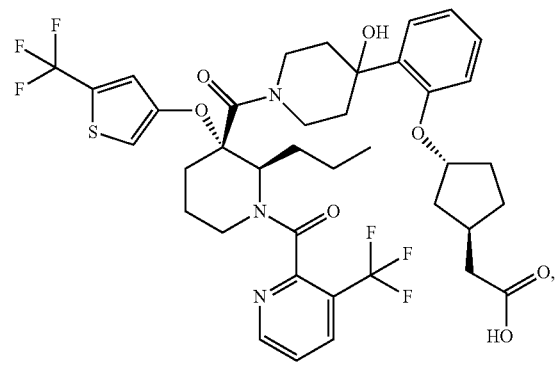
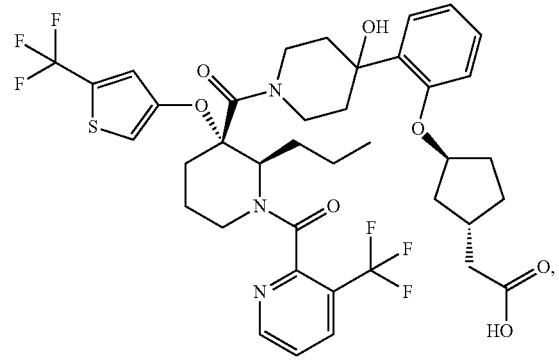
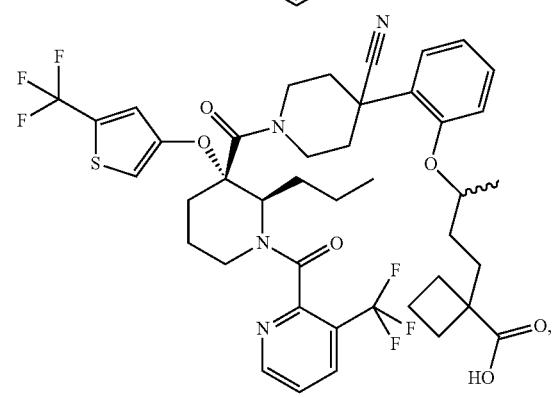
322
-continued
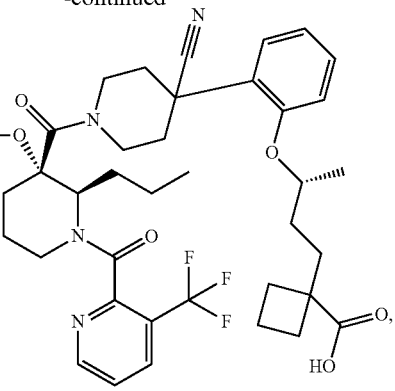
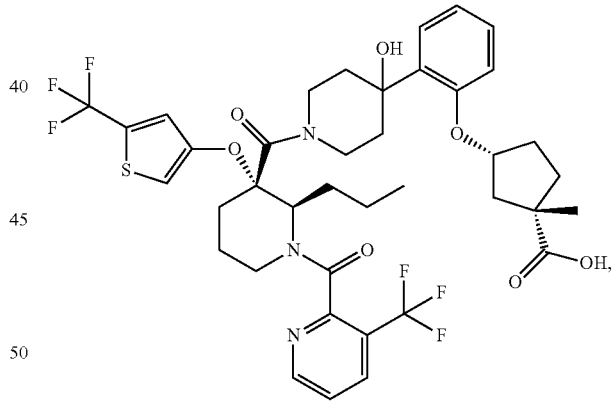
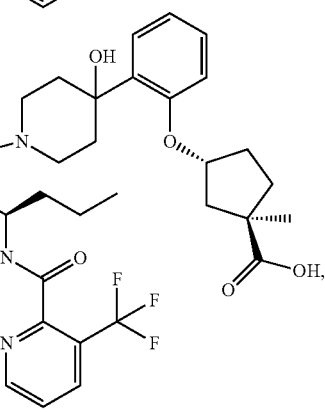

323
-continued
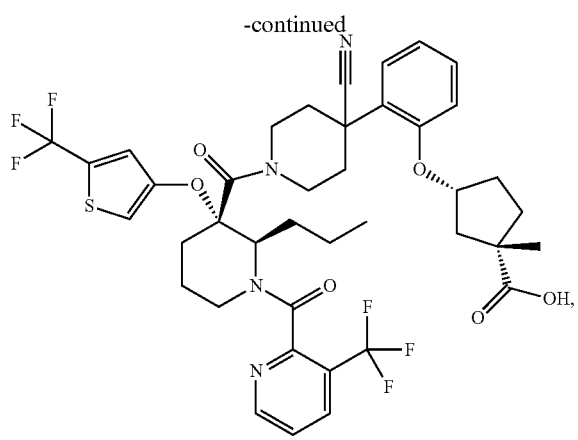
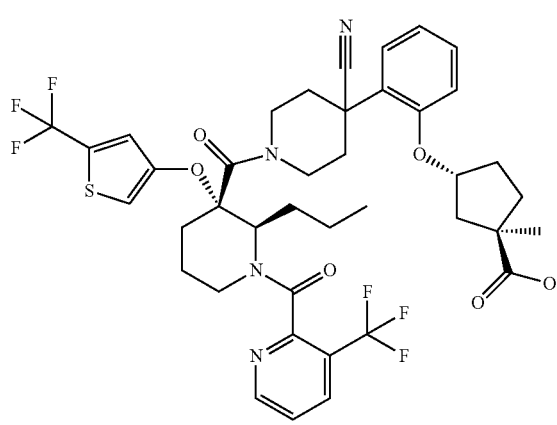
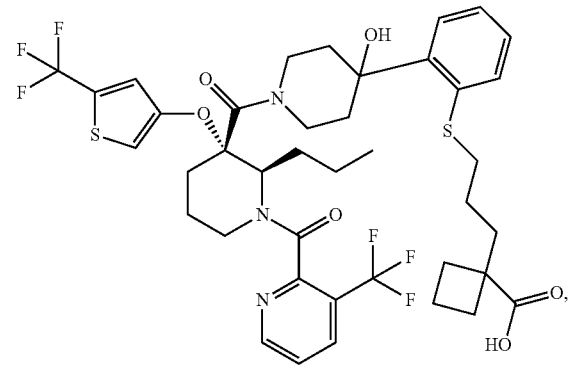
324
-continued
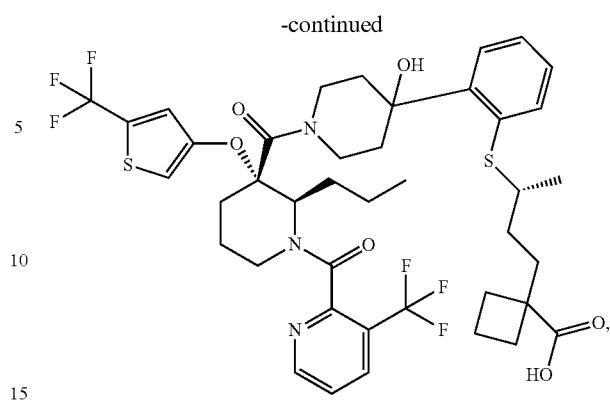
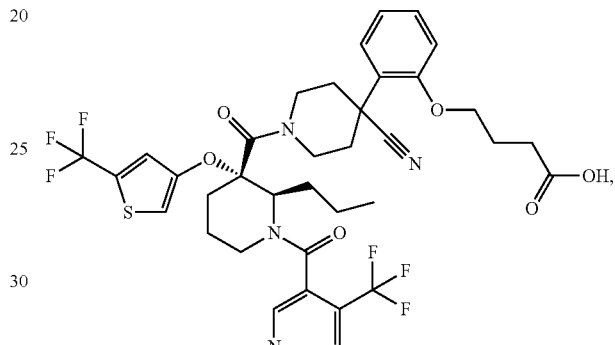
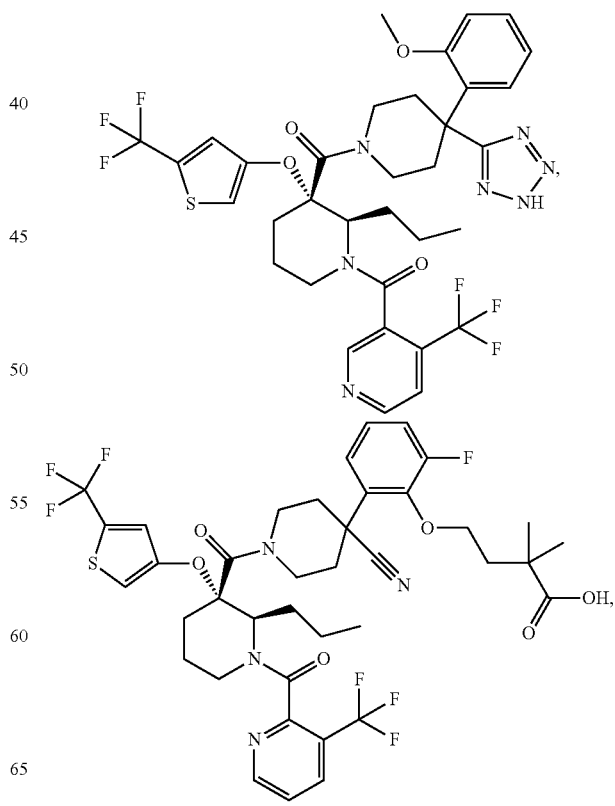

325
-continued
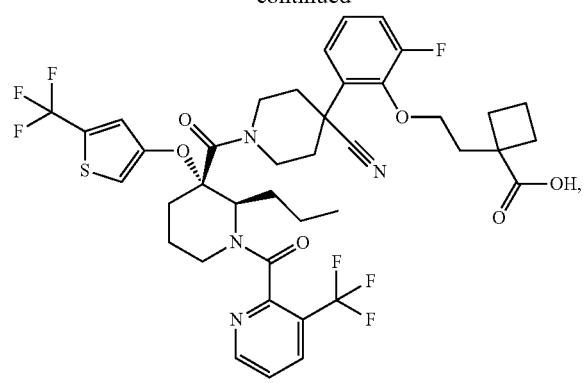
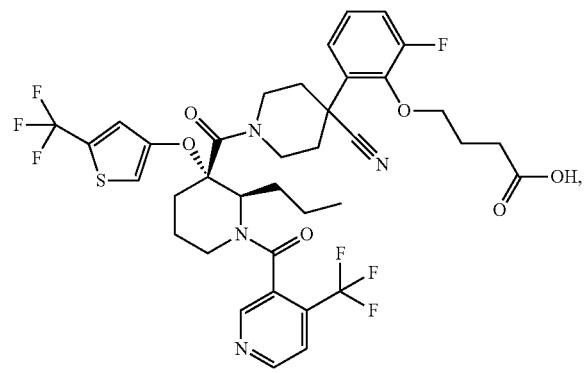
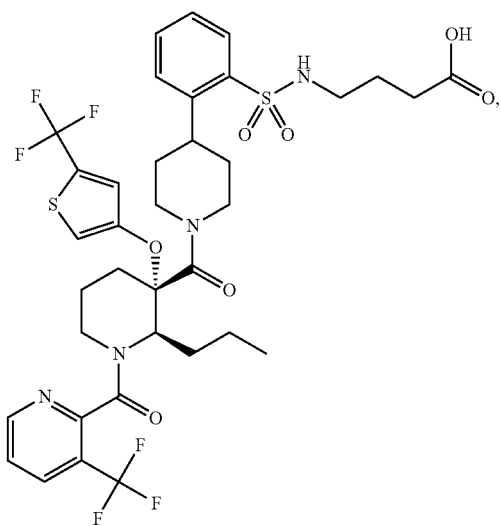
326
-continued
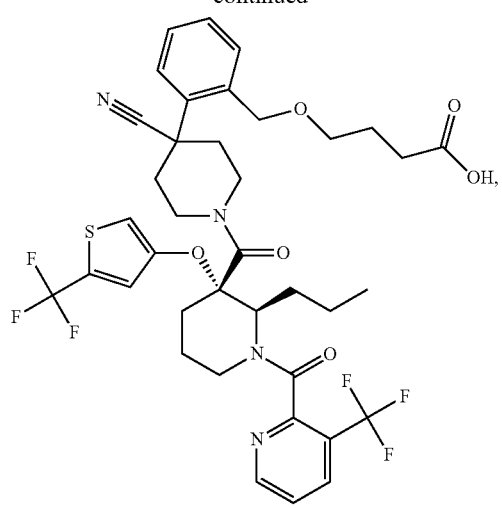
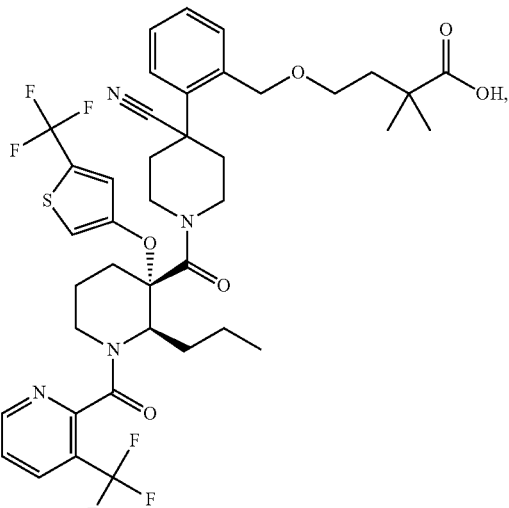
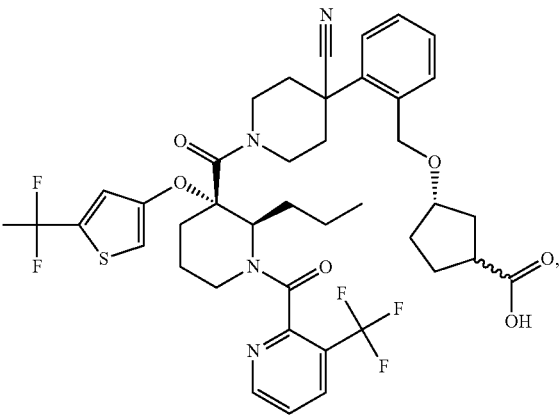

327
-continued
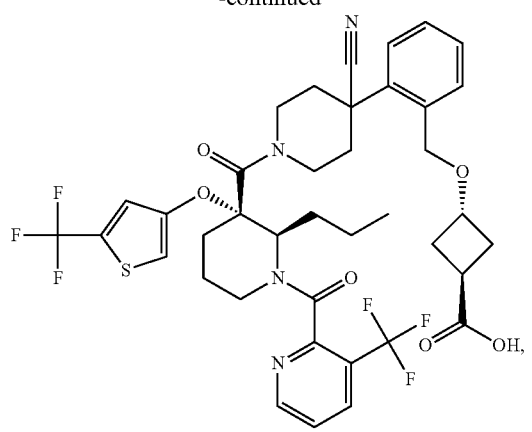
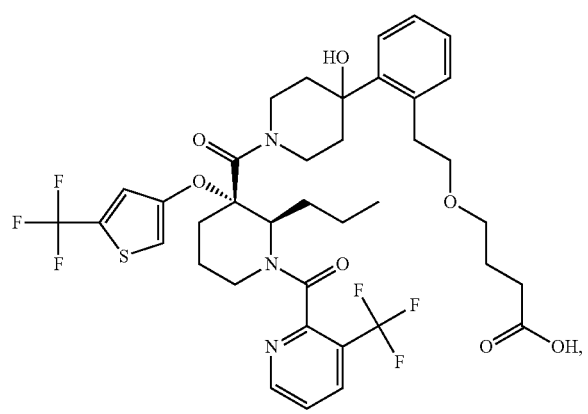
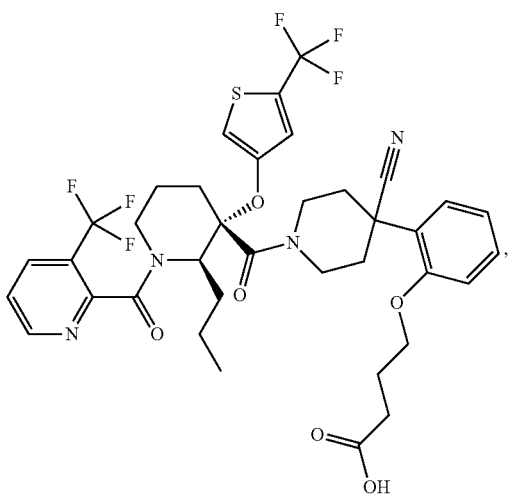
328
-continued
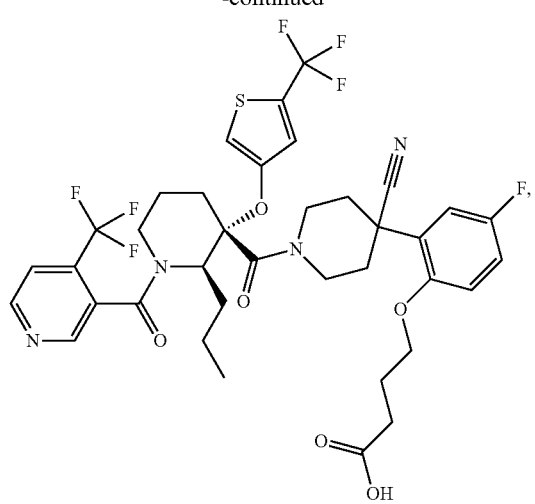
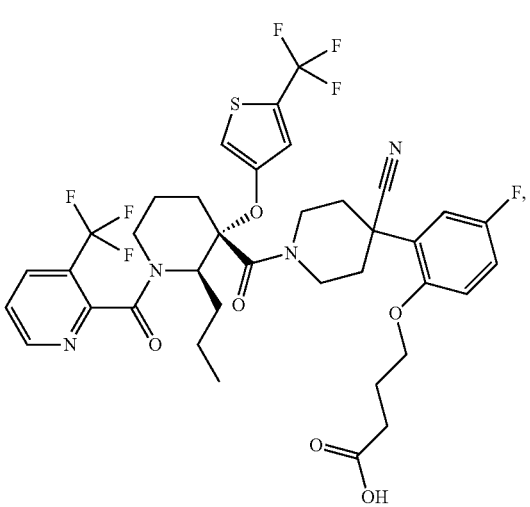
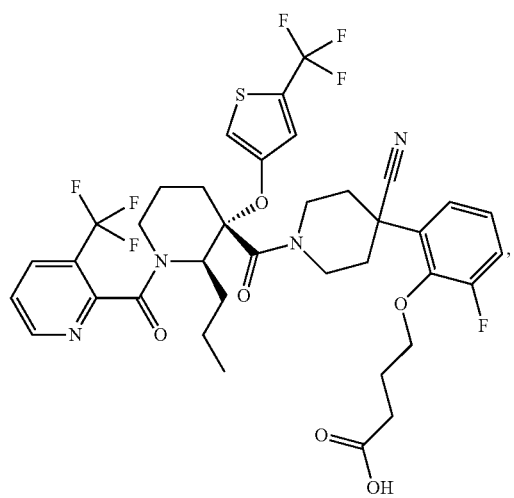

329
-continued
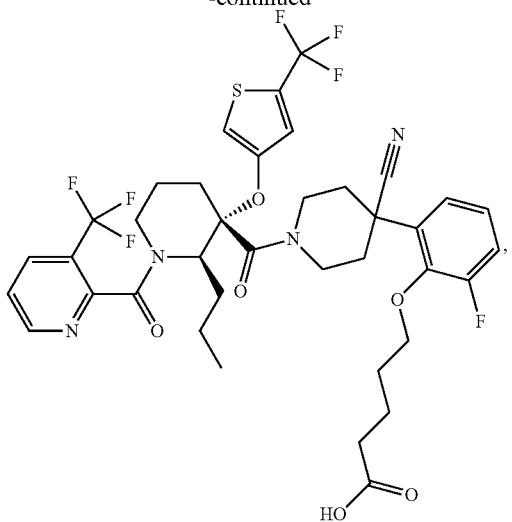
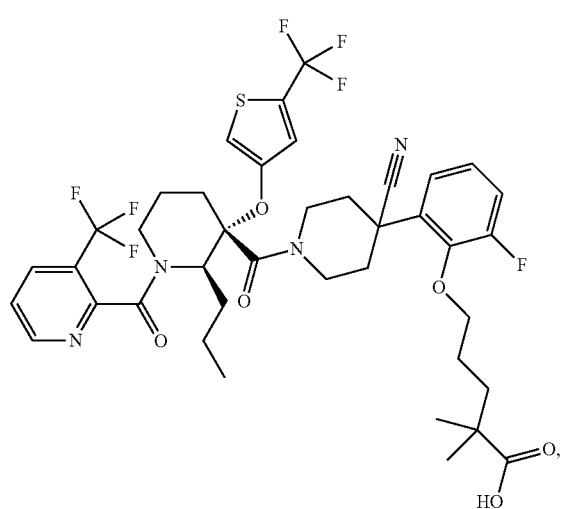
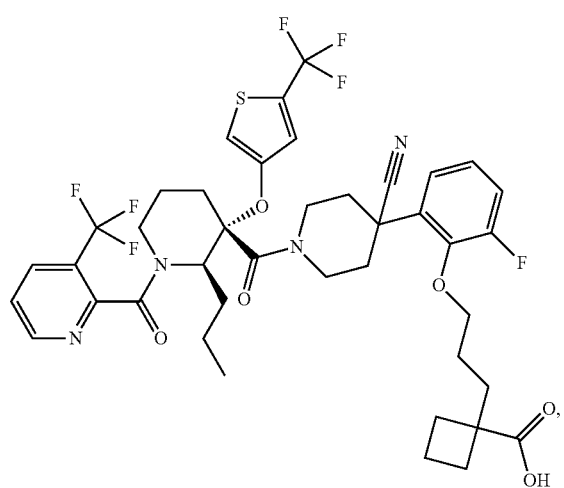
330
-continued
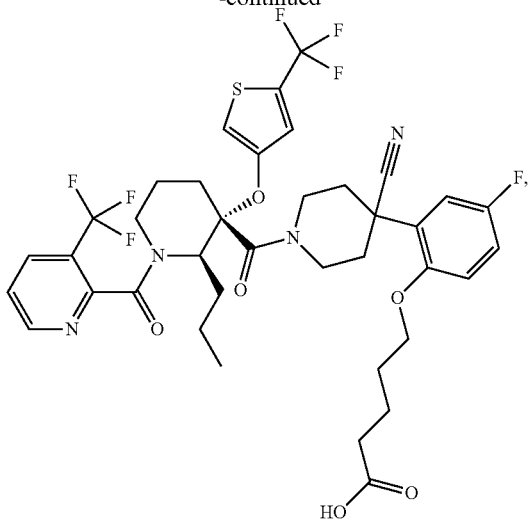
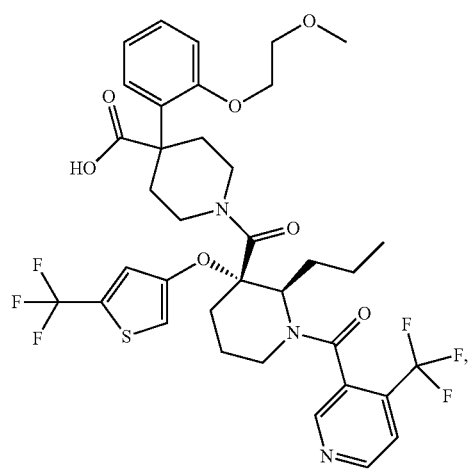
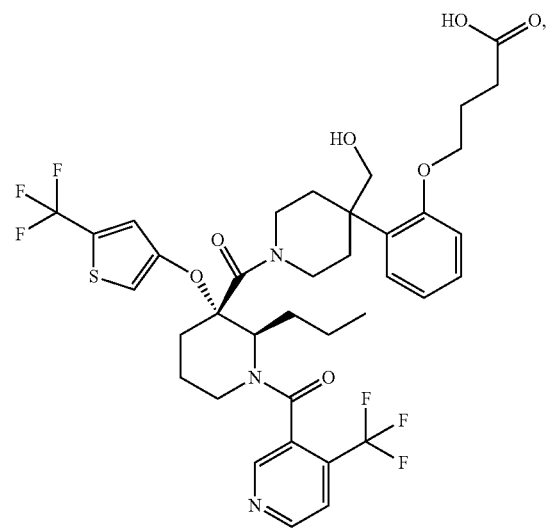

331
-continued
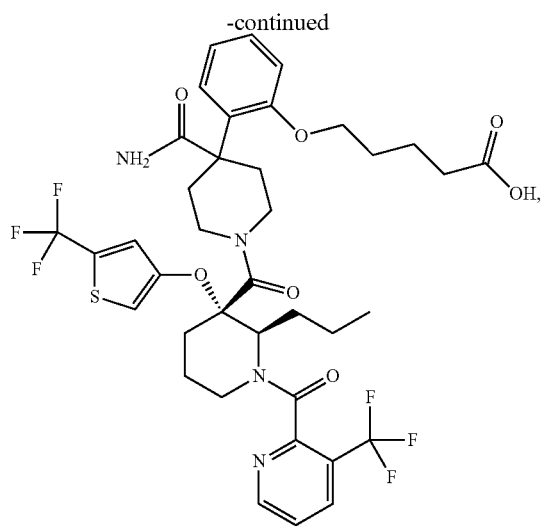
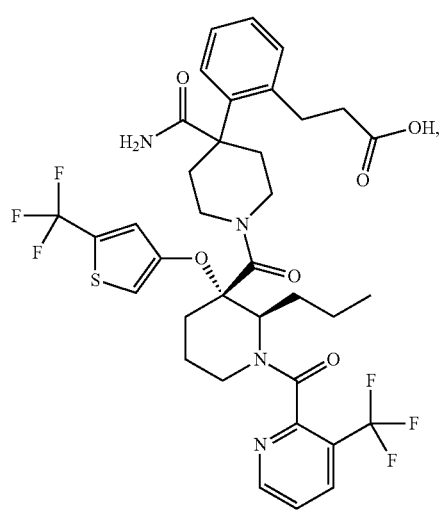
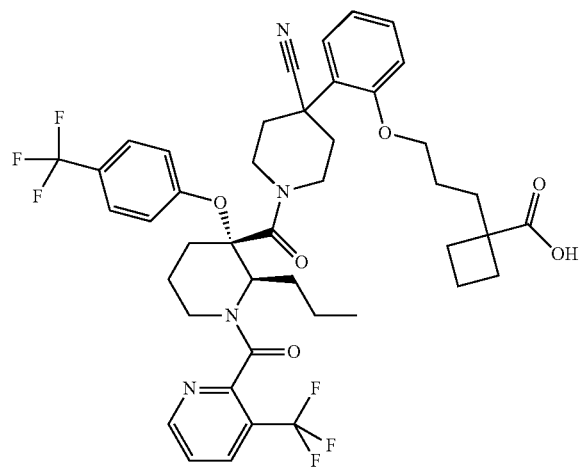
332
-continued
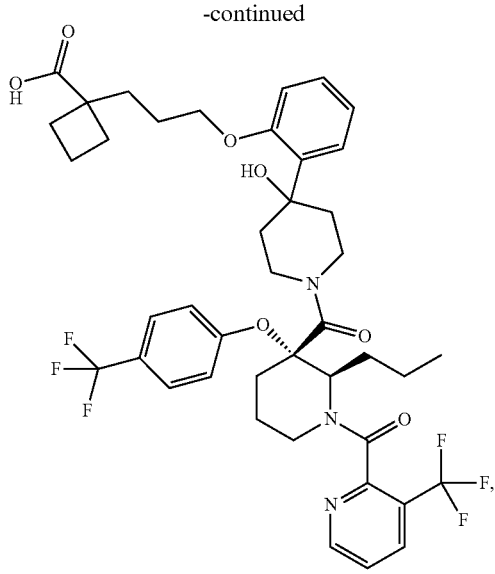
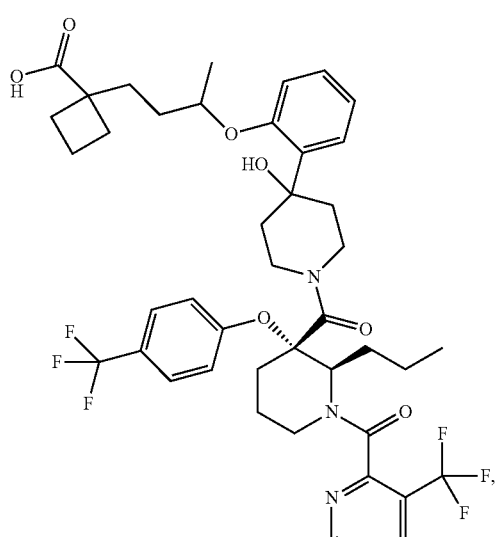
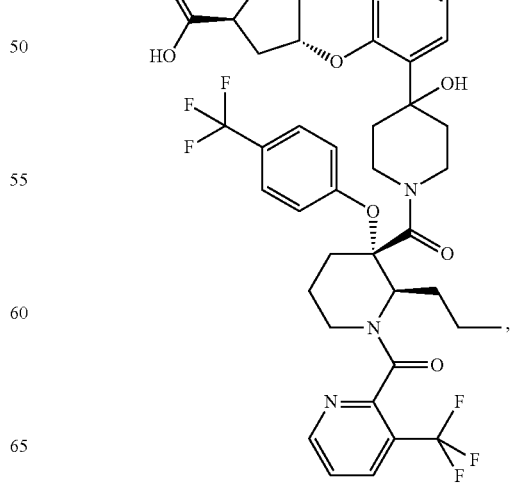

333
-continued
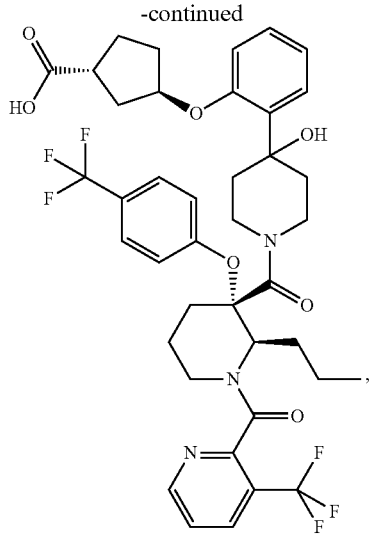
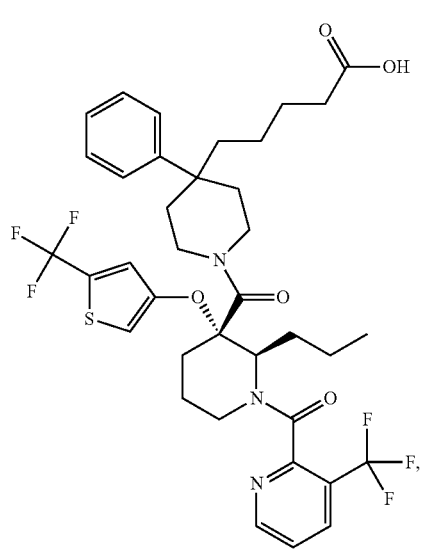
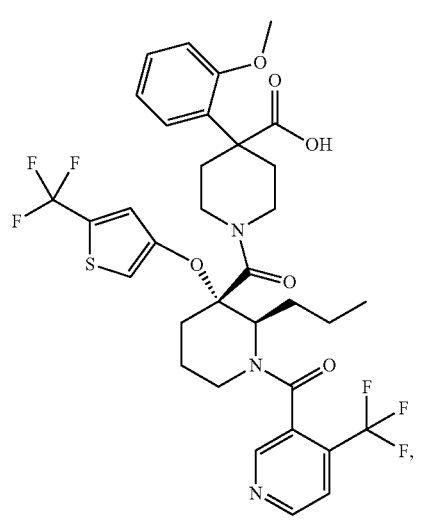
334
-continued
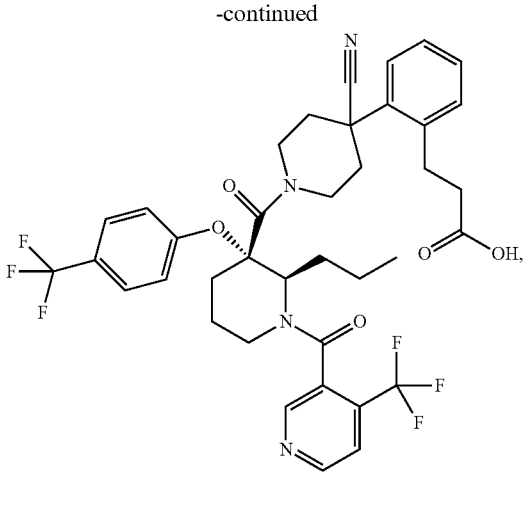
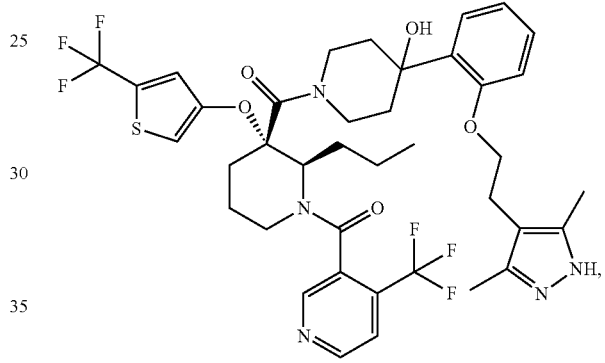
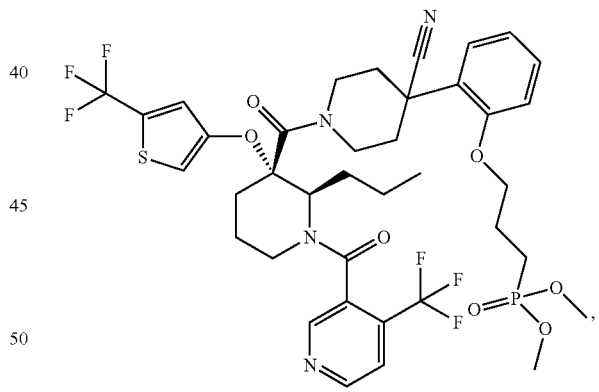
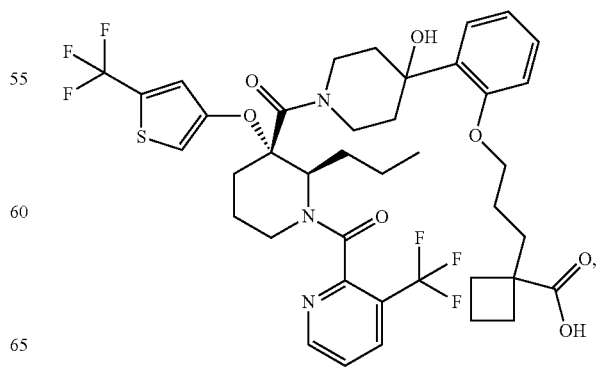

335
-continued
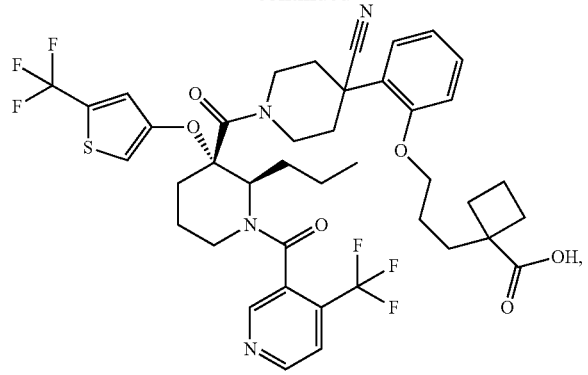
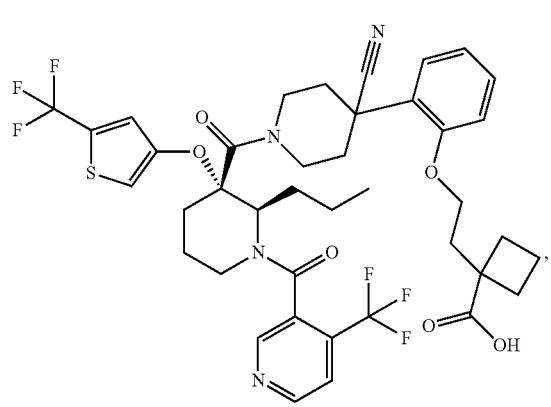
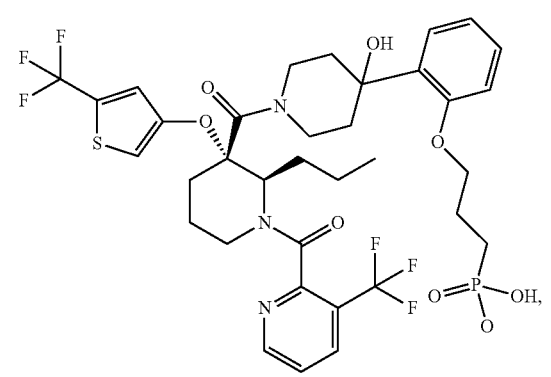
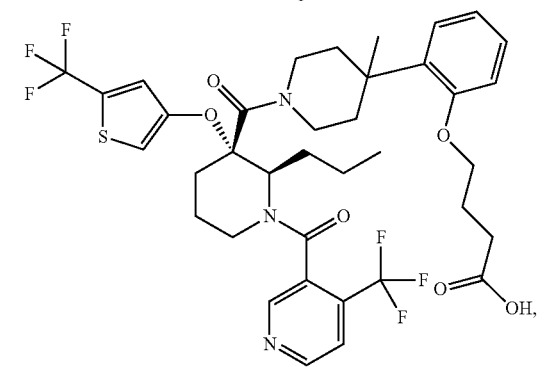
336
-continued
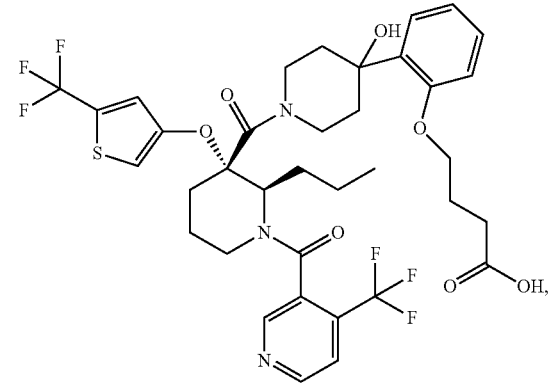
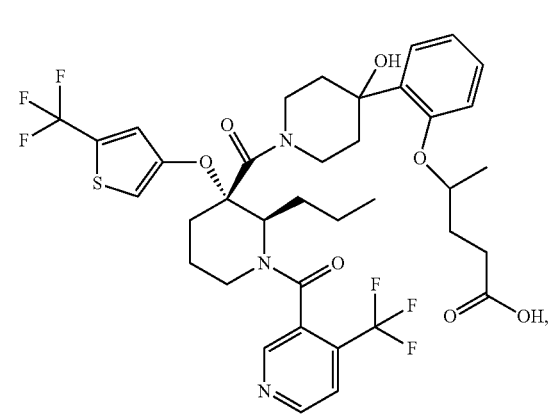
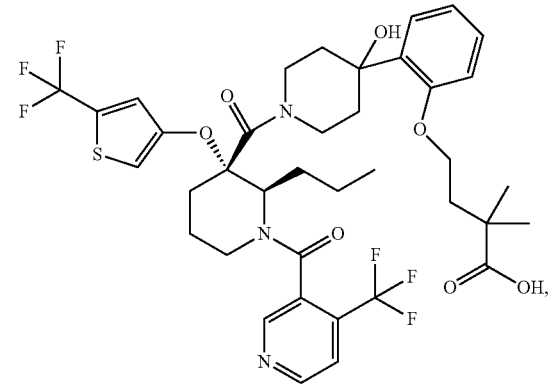
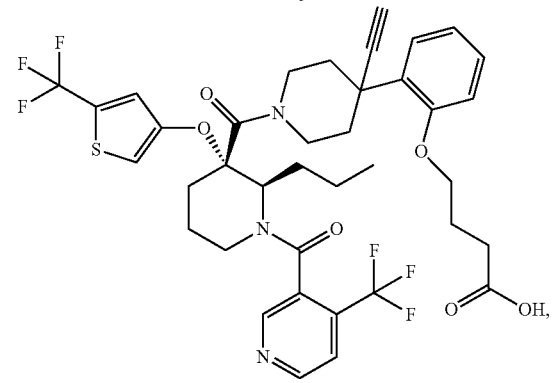

337
-continued
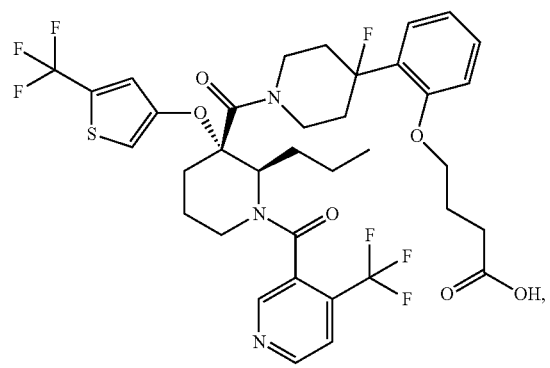
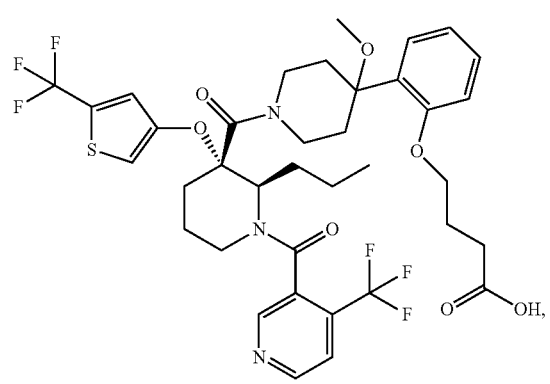
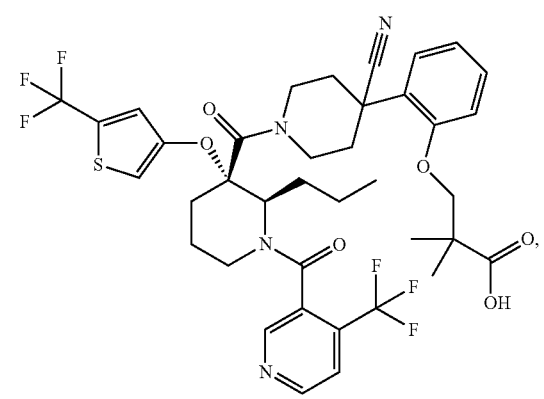
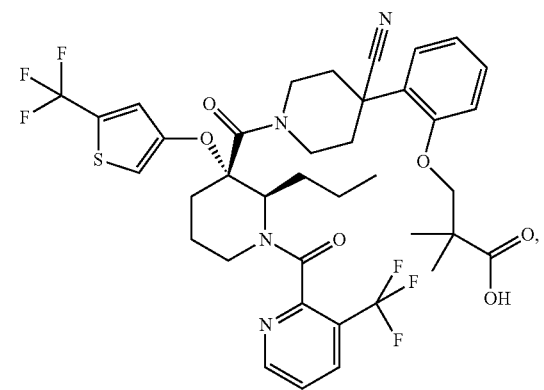
338
-continued
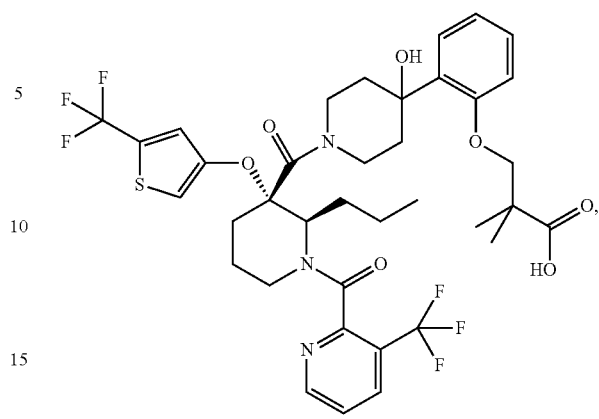
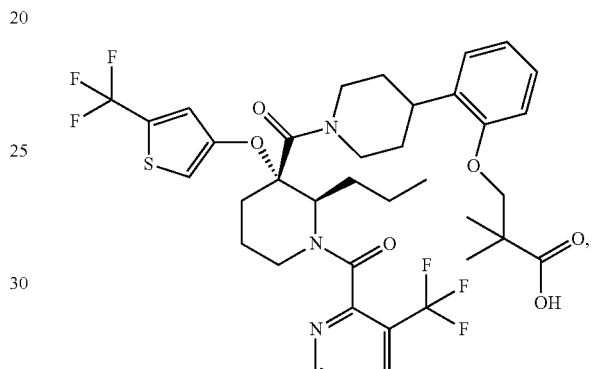
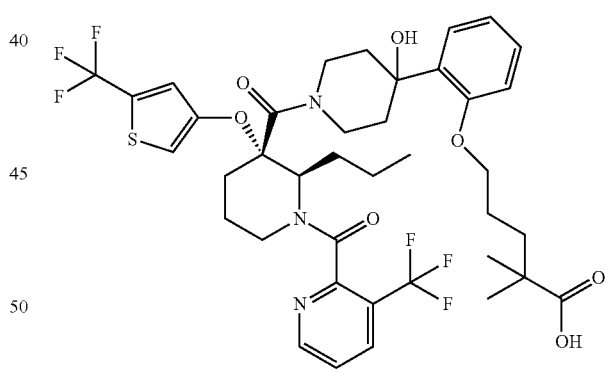
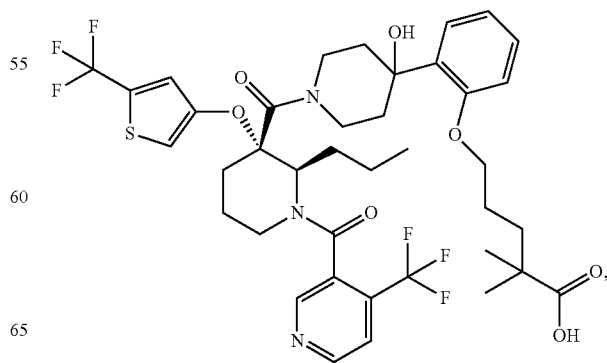

339
-continued
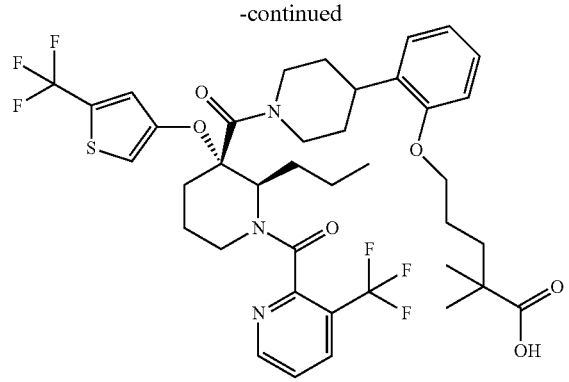
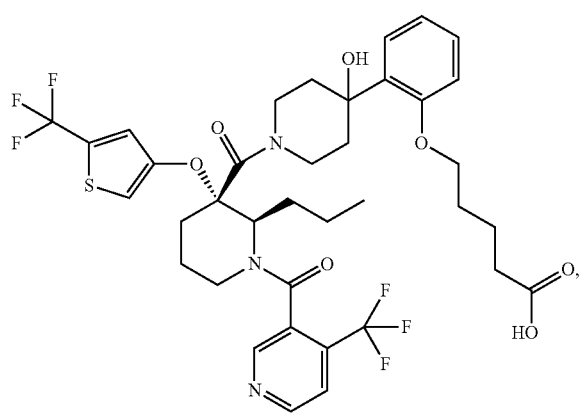
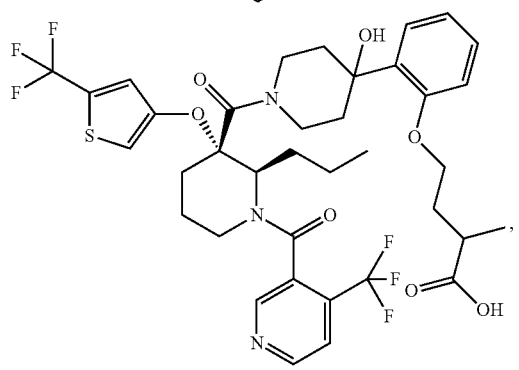
340
-continued
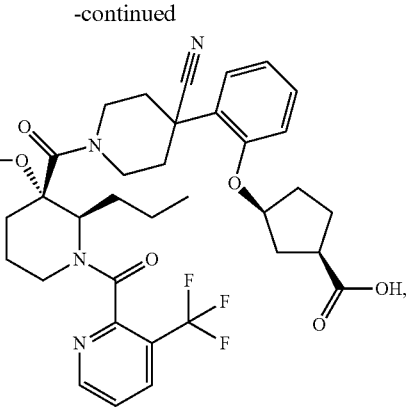
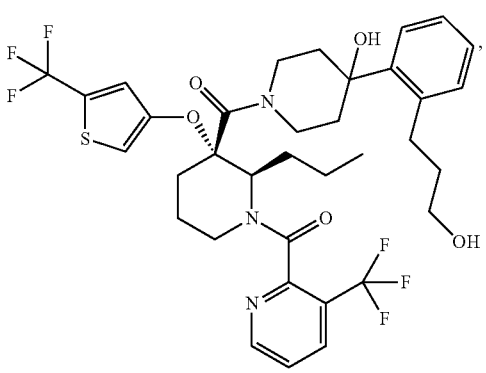
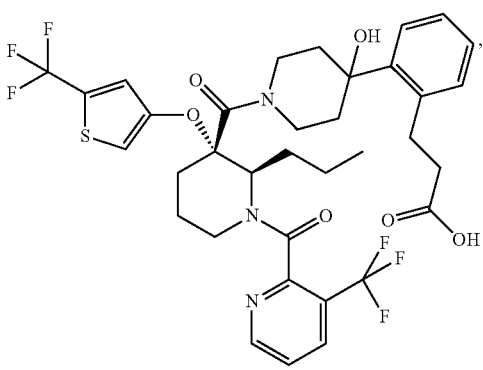

341
-continued
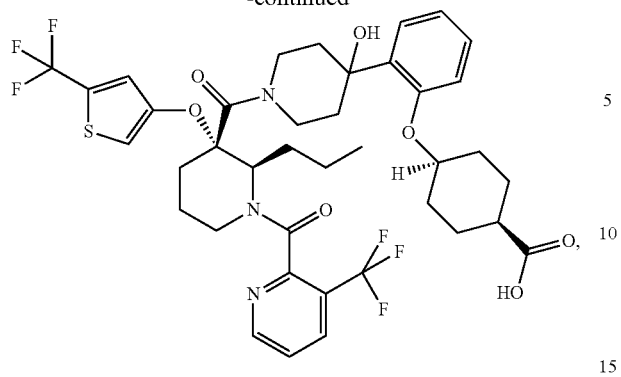
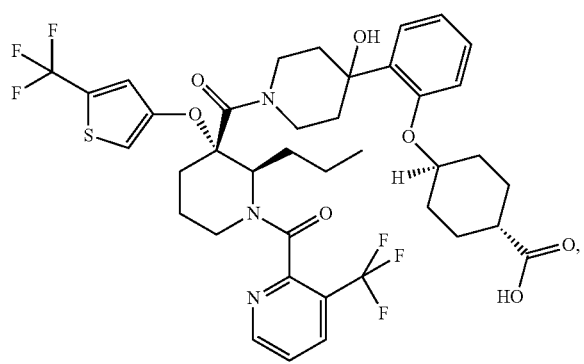
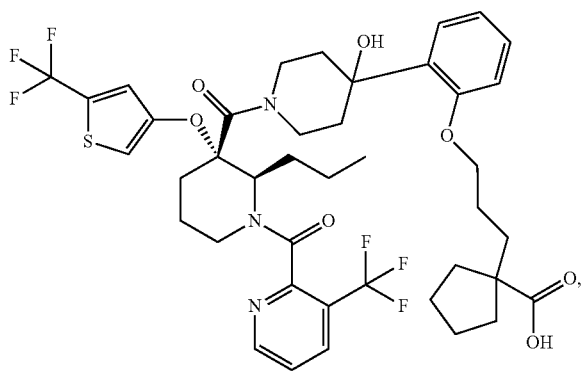
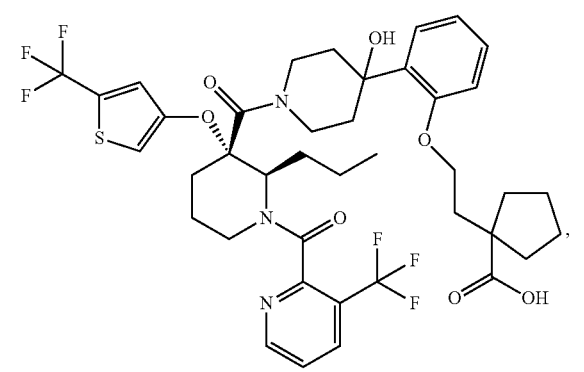
342
-continued
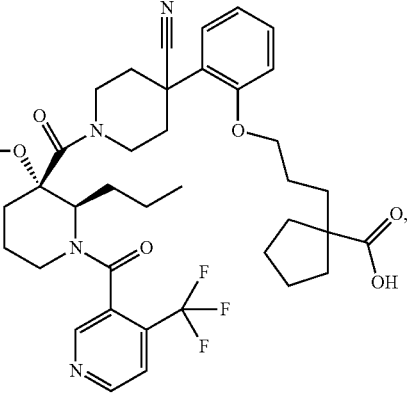
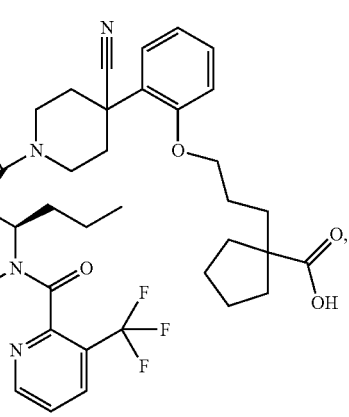
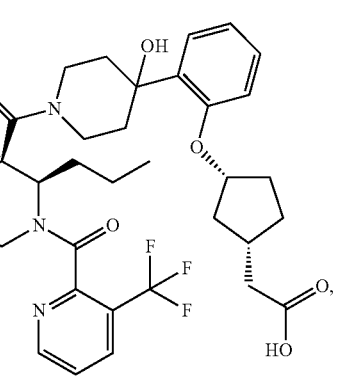
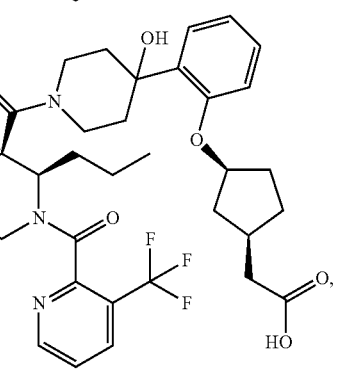

-continued
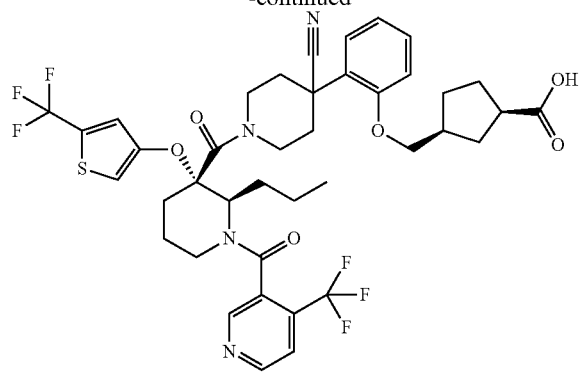
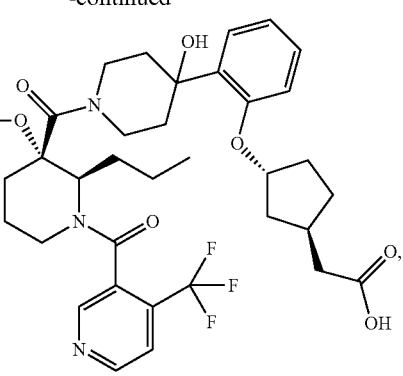
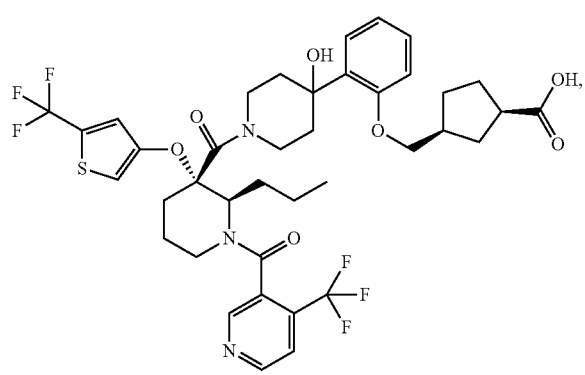
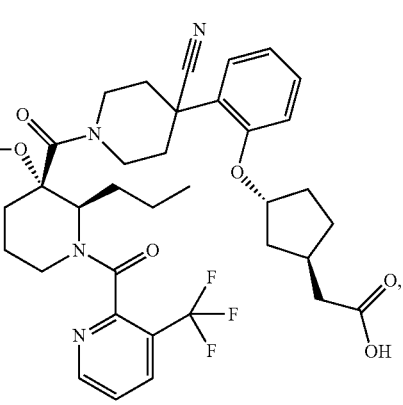
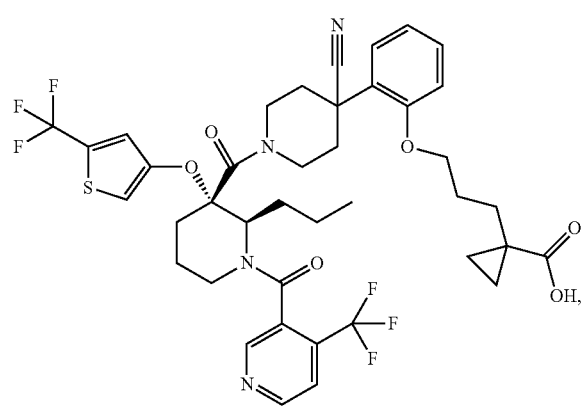
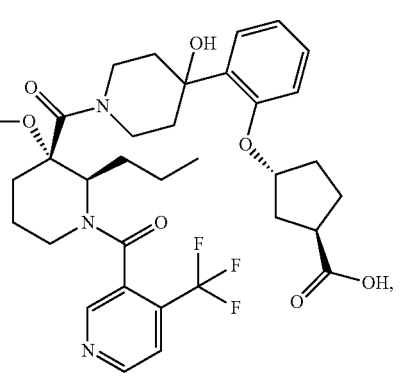
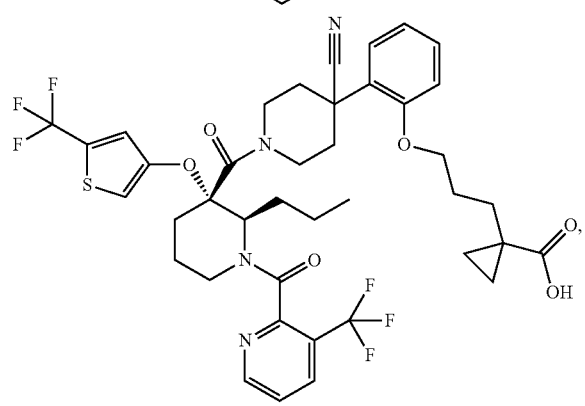
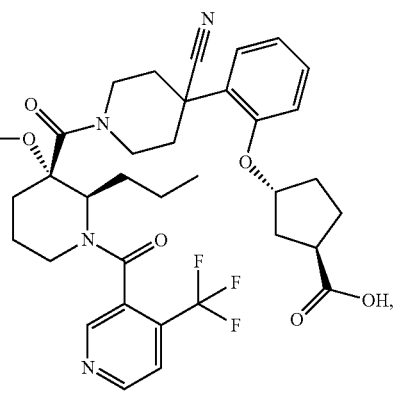

345
-continued
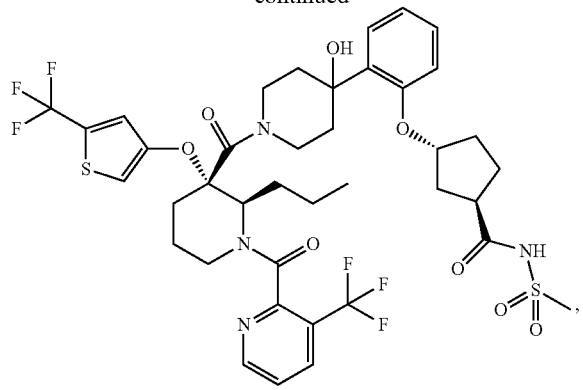
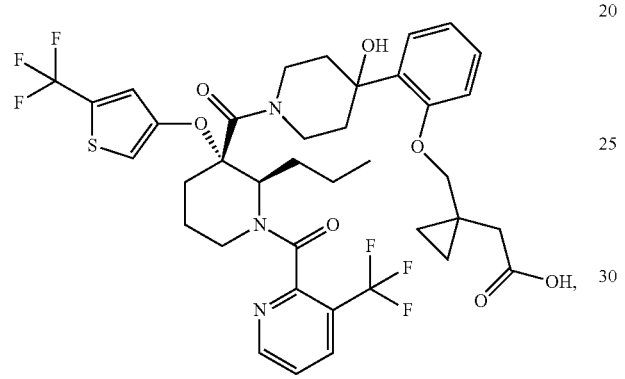
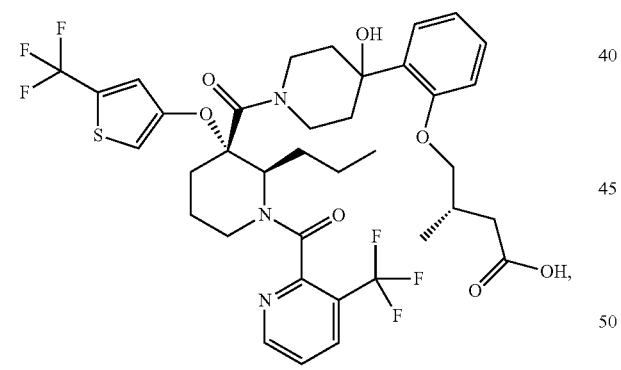
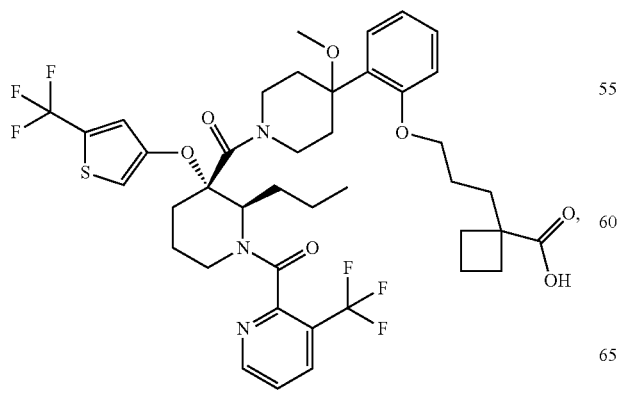
346
-continued
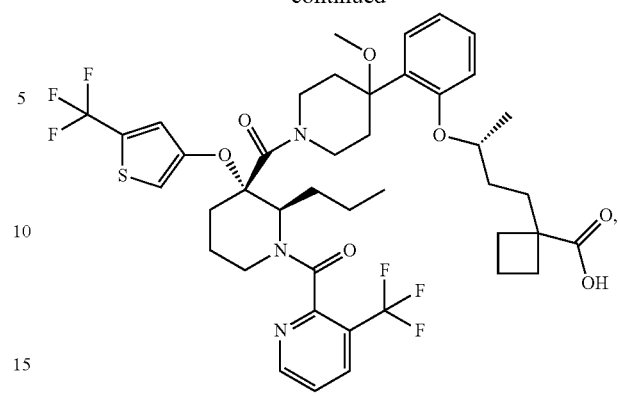
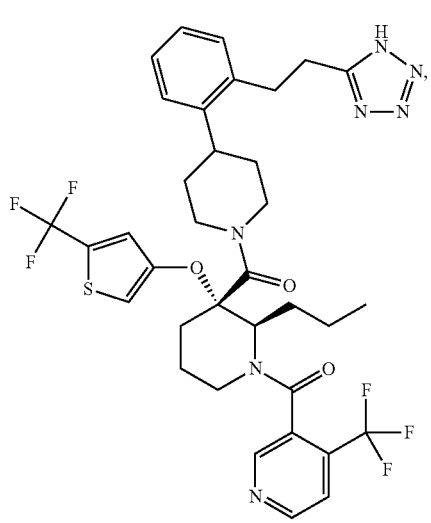
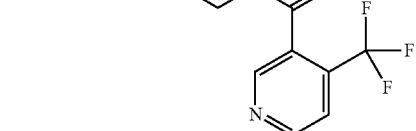
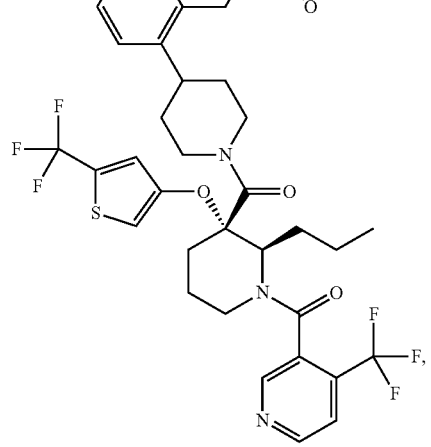

347
-continued
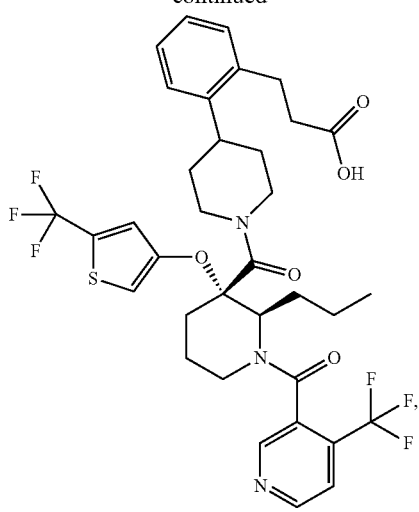
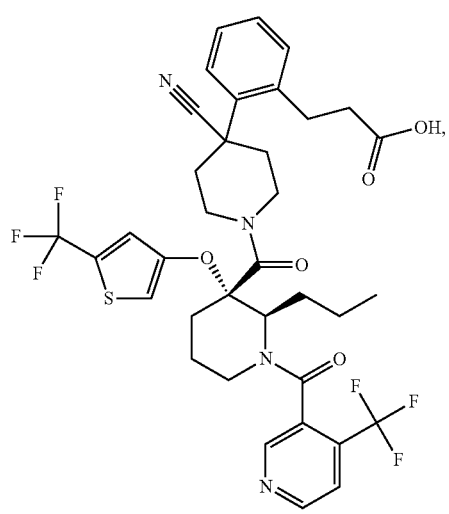
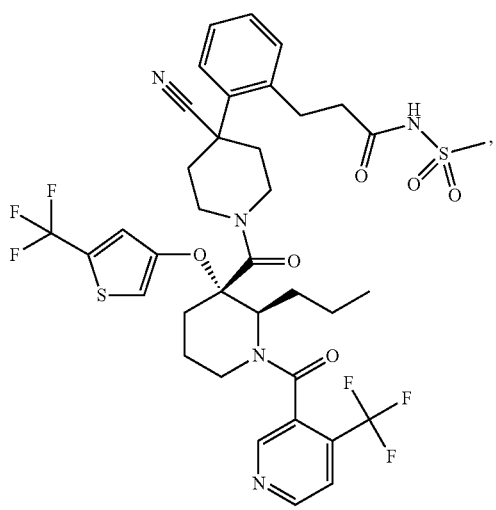
348
-continued
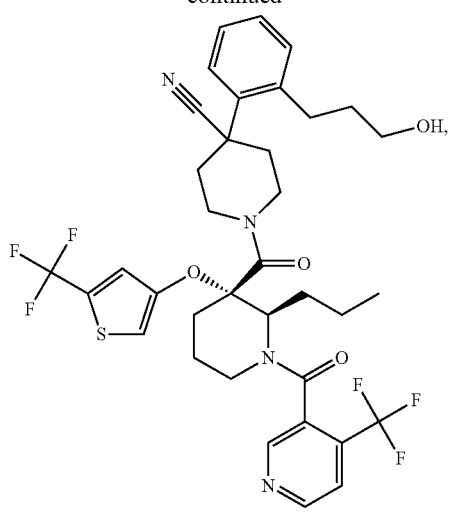
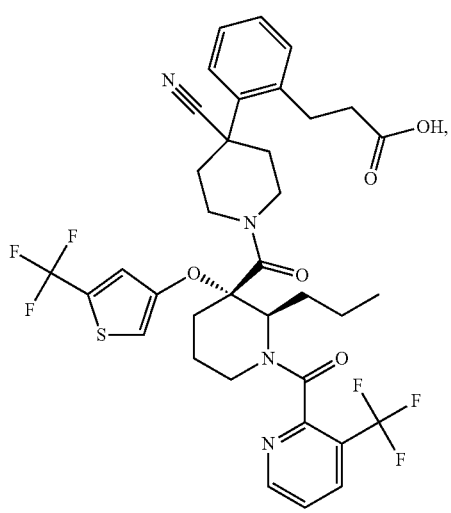
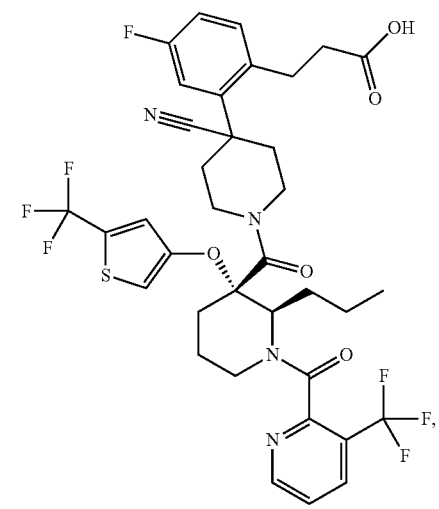

-continued

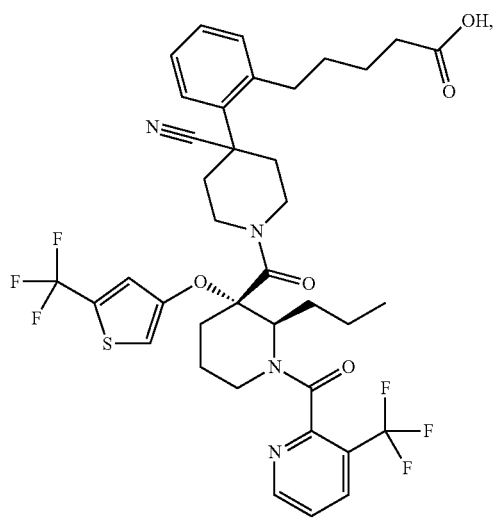

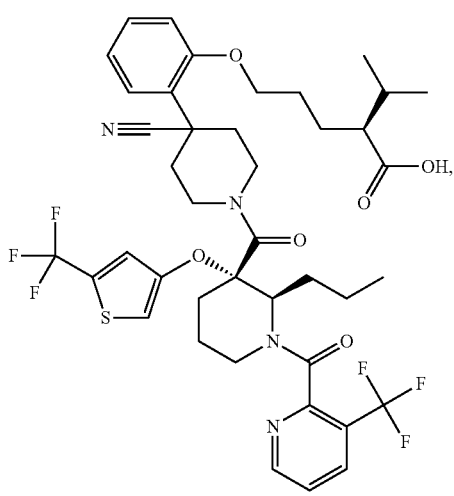

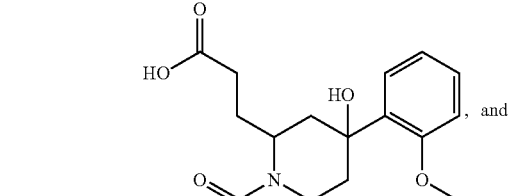

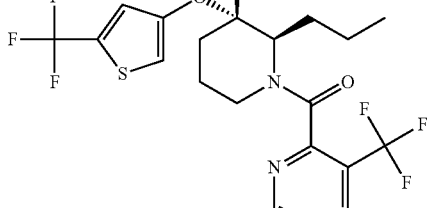

or a pharmaceutically acceptable salt thereof.

17. A pharmaceutical composition comprising at least one compound of claim 1 or a pharmaceutically acceptable salt thereof, in combination with at least one pharmaceutically acceptable carrier.

18. The compound of claim 14, wherein E is CN or OH, each J in $R^1$ is H, Y is O, and G is $(CR^8R^{8'})_n$—$(C_3\text{-}C_8)$cycloalkyl-$(CR^8R^{8'})_n$—C(O)OH.

19. The compound of claim 14, wherein E is CN or OH, each J in $R^1$ is H, Y is O, and G is selected from the group consisting of

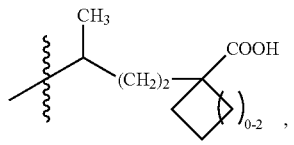

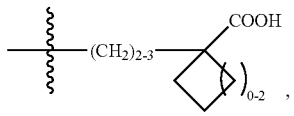

—$CH_2$-cyclopentyl-C(O)OH, -cyclobutyl-C(O)OH, -cyclopentyl-C(O)OH, -cyclohexyl-C(O)OH, and -cyclopentyl-$CH_2$—C(O)OH.

20. The compound of claim 14, wherein E is CN or OH, each J in $R^1$ is H, Y is O, and G is selected from the group consisting of —$CH(CH_3)$—$(CH_2)_{2-3}$—C(O)OH, —$(CH_2)_3$CH(CH(CH_3)_2)$—C(O)OH, —$(CD_2)_3$C(O)OH, —$(CH_2)_{1-2}$—CH(CH_3)$—$(CH_2)_{1-2}$—C(O)OH, and —$CH(CH_3)$—$(CH_2)_{2-3}$—C(O)OH.

21. The compound of claim 16 that is

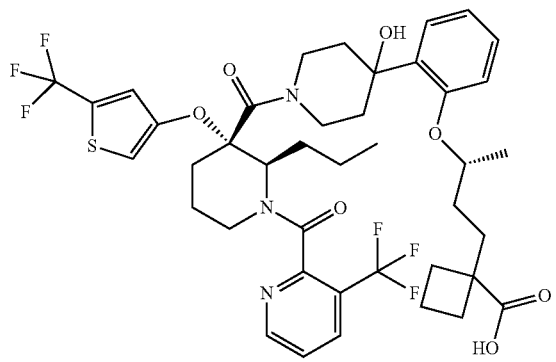 [SMILES: CCC[C@H]1N(C(=O)c2ncccc2C(F)(F)F)CCC[C@@]1(Oc1csc(C(F)(F)F)c1)C(=O)N1CCC(O)(c2ccccc2O[C@H](C)CCC2(C(=O)O)CCC2)CC1]

or a pharmaceutically acceptable salt thereof.

22. The compound of claim 16 that is

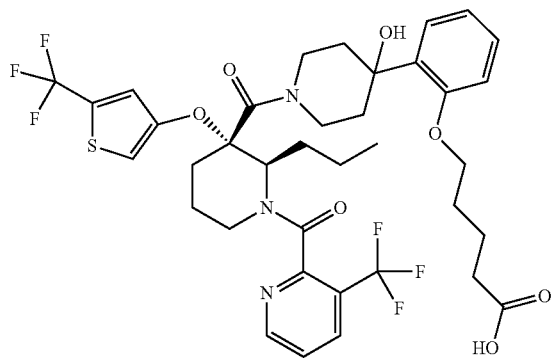 [SMILES: CCC[C@H]1N(C(=O)c2ncccc2C(F)(F)F)CCC[C@@]1(Oc1csc(C(F)(F)F)c1)C(=O)N1CCC(O)(c2ccccc2OCCCCC(=O)O)CC1]

or a pharmaceutically acceptable salt thereof.

23. The compound of claim 16 that is

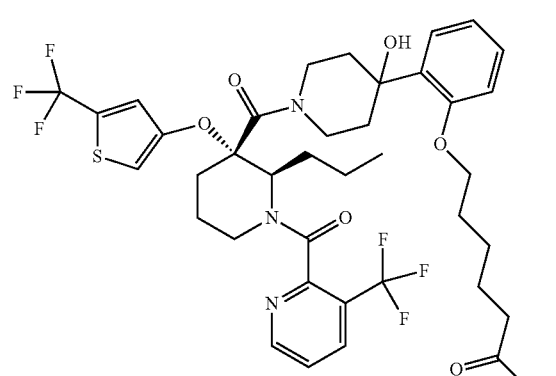

or a pharmaceutically acceptable salt thereof.

24. The compound of claim 16 that is

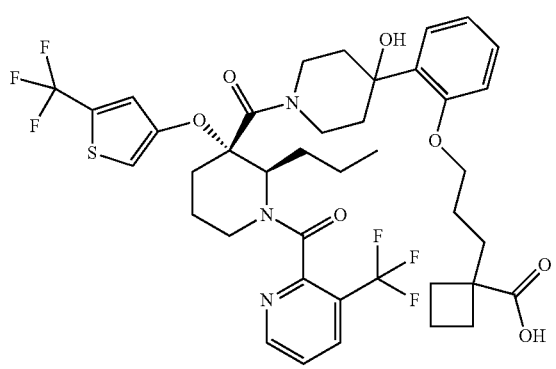 [SMILES: CCC[C@H]1N(C(=O)c2ncccc2C(F)(F)F)CCC[C@@]1(Oc1csc(C(F)(F)F)c1)C(=O)N1CCC(O)(c2ccccc2OCCCC2(C(=O)O)CCC2)CC1]

or a pharmaceutically acceptable salt thereof.

25. The compound of claim 16 that is

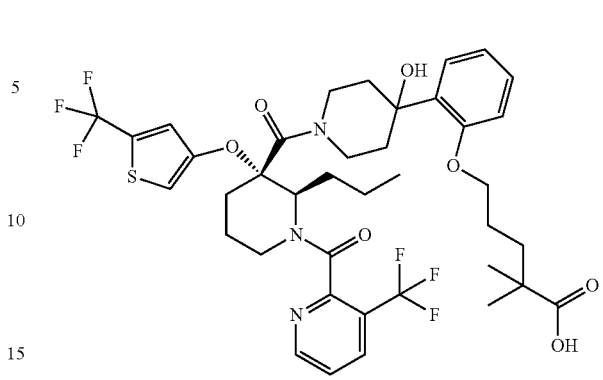

or a pharmaceutically acceptable salt thereof.

26. A pharmaceutical composition comprising the compound of claim 21 or a pharmaceutically acceptable salt thereof, in combination with at least one pharmaceutically acceptable carrier.

27. A pharmaceutical composition comprising the compound of claim 22 or a pharmaceutically acceptable salt thereof, in combination with at least one pharmaceutically acceptable carrier.

28. A pharmaceutical composition comprising the compound of claim 23 or a pharmaceutically acceptable salt thereof, in combination with at least one pharmaceutically acceptable carrier.

29. A pharmaceutical composition comprising the compound of claim 24 or a pharmaceutically acceptable salt thereof, in combination with at least one pharmaceutically acceptable carrier.

30. A pharmaceutical composition comprising the compound of claim 25 or a pharmaceutically acceptable salt thereof, in combination with at least one pharmaceutically acceptable carrier.

31. A compound that is

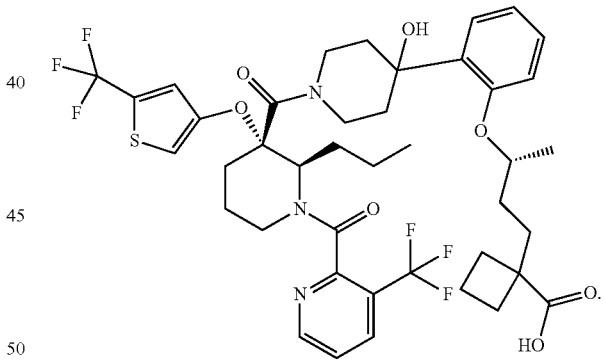

32. A compound that is

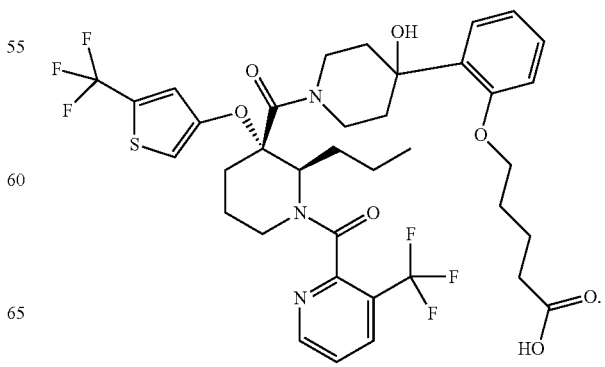

33. A compound that is

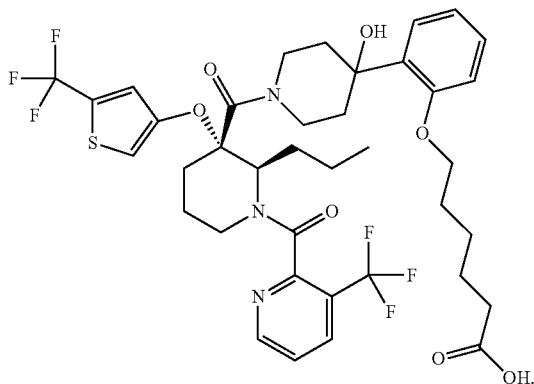 [SMILES: CCC[C@H]1N(C(=O)c2ncccc2C(F)(F)F)CCC[C@@]1(Oc1csc(C(F)(F)F)c1)C(=O)N1CCC(O)(c2ccccc2OCCCCCC(=O)O)CC1]

34. A compound that is

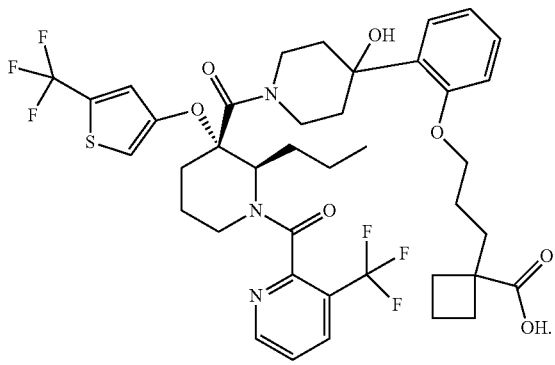 [SMILES: CCC[C@H]1N(C(=O)c2ncccc2C(F)(F)F)CCC[C@@]1(Oc1csc(C(F)(F)F)c1)C(=O)N1CCC(O)(c2ccccc2OCCCC2(C(=O)O)CCC2)CC1]

35. A compound that is

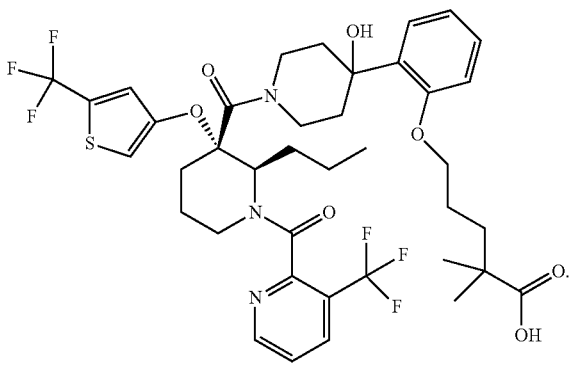 [SMILES: CCC[C@H]1N(C(=O)c2ncccc2C(F)(F)F)CCC[C@@]1(Oc1csc(C(F)(F)F)c1)C(=O)N1CCC(O)(c2ccccc2OCCCC(C)(C)C(=O)O)CC1]

36. A pharmaceutical composition comprising the compound of claim 31 in combination with at least one pharmaceutically acceptable carrier.

37. A pharmaceutical composition comprising the compound of claim 32 in combination with at least one pharmaceutically acceptable carrier.

38. A pharmaceutical composition comprising the compound of claim 33 in combination with at least one pharmaceutically acceptable carrier.

39. A pharmaceutical composition comprising the compound of claim 34 in combination with at least one pharmaceutically acceptable carrier.

40. A pharmaceutical composition comprising the compound of claim 35 in combination with at least one pharmaceutically acceptable carrier.

41. The compound of claim 1, wherein G is selected from the group consisting of —$(CR^8R^{8'})_n$—$(C_3$-$C_8)$cycloalkyl-$(CR^8R^{8'})_n$—C(O)OH and —$(CR^8R^{8'})_n$—O—$(CR^8R^{8'})_n$—$(C_3$-$C_8)$cycloalkyl-$(CR^8R^{8'})_n$—C(O)OH.

42. The compound of claim 1, wherein G is —$(CR^8R^{8'})_n$—P(O)OR$^8$OR$^{8'}$ or —$(CR^8R^{8'})_n$—S—$(CR^8R^{8'})_n$—C(O)OH.

43. The compound of claim 1, wherein R$^1$ is

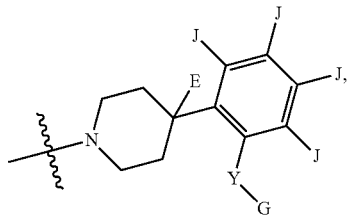

E is present, G is present and is selected from the group consisting of —$(CR^8R^{8'})_n$—C(O)OH, wherein n is 3, 4, 5 or 6, —CH(CH$_3$)—(CH$_2)_{2\text{-}3}$—C(O)OH, —(CH$_2)_3$CH(CH(CH$_3)_2$)—C(O)OH, —(CD$_2)_3$C(O)OH, —(CH$_2)_{1\text{-}2}$—CH(CH$_3$)—(CH$_2)_{1\text{-}2}$—C(O)OH, —CH(CH$_3$)—(CH$_2)_{2\text{-}3}$—C(O)OH,

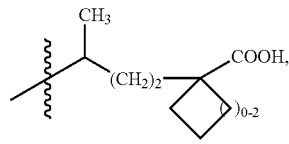

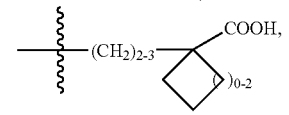

—$(CR^8R^{8'})_n$—O—$(CR^8R^{8'})_n$—C(O)OH, wherein the first n is 0 or 1, and the second n is 3, —CH$_2$—O—(CH$_2)_3$—C(O)OH, —O—(CH$_2)_2$—C(CH$_3)_2$—C(O)OH, and —O—(CH$_2)_3$—C(O)OH.

44. The compound of claim 1, wherein G is present and is selected from the group consisting of —(CH$_2)_{0\text{-}4}$CH((C$_1$-C$_6$)alkyl)-(CH$_2)_{1\text{-}5}$—C(O)OH, —(CH$_2)_{1\text{-}5}$—CH((C$_1$-C$_6$)alkyl)-C(O)OH, —(CH$_2)_{0\text{-}5}$—(C$_3$-C$_8$)cycloalkyl-C(O)OH, —(CH$_2)_{0\text{-}5}$—(C$_3$-C$_8$)cycloalkyl-(CH$_2)_{1\text{-}6}$C(O)OH,

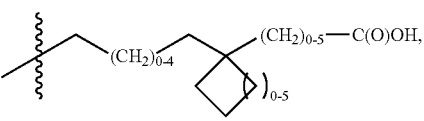

-continued
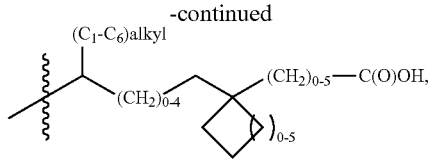
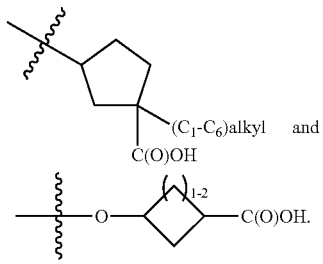
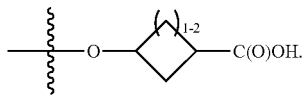
* * * * *